(12) United States Patent
Alvaro et al.

(10) Patent No.: US 8,722,695 B2
(45) Date of Patent: May 13, 2014

(54) IMIDAZOLIDINEDIONE DERIVATIVES

(75) Inventors: Giuseppe Alvaro, Verona (IT); Anne Décor, Verona (IT); Stefano Fontana, Verona (IT); Dieter Hamprecht, Verona (IT); Charles Large, Verona (IT); Agostino Marasco, Verona (IT)

(73) Assignee: Autifony Therapeutics Limited, London (GB)

( * ) Notice: Subject to any disclaimer, the term of this patent is extended or adjusted under 35 U.S.C. 154(b) by 24 days.

(21) Appl. No.: 13/515,097

(22) PCT Filed: Dec. 6, 2010

(86) PCT No.: PCT/EP2010/068946
§ 371 (c)(1),
(2), (4) Date: Jun. 11, 2012

(87) PCT Pub. No.: WO2011/069951
PCT Pub. Date: Jun. 16, 2011

(65) Prior Publication Data
US 2012/0289526 A1    Nov. 15, 2012

(30) Foreign Application Priority Data
Dec. 11, 2009    (GB) .................................. 0921760.5

(51) Int. Cl.
| A01N 43/54 | (2006.01) |
| A61K 31/505 | (2006.01) |
| C07D 239/22 | (2006.01) |
| C07D 239/47 | (2006.01) |
| C07D 213/643 | (2006.01) |

(52) U.S. Cl.
CPC ............ C07D 239/22 (2013.01); C07D 239/47 (2013.01); *C07D 213/643* (2013.01)
USPC ........... 514/274; 514/341; 514/398; 544/295; 546/274.1; 548/300.7; 548/319.1

(58) Field of Classification Search
USPC ........ 514/274, 341, 398; 544/295; 546/274.1; 548/319.1
See application file for complete search history.

(56) References Cited

U.S. PATENT DOCUMENTS

| 4,350,701 | A | | 9/1982 | Rentzea et al. |
| 4,675,403 | A | | 6/1987 | Abou-Gharbia et al. |
| 4,804,671 | A | | 2/1989 | Costin et al. |
| 5,362,878 | A | | 11/1994 | Chang et al. |
| 5,637,729 | A | * | 6/1997 | Lacroix et al. ............. 548/316.7 |
| 5,656,634 | A | | 8/1997 | Chang et al. |
| 5,703,087 | A | | 12/1997 | Perregaard et al. |
| 2003/0008884 | A1 | | 1/2003 | Gerusz et al. |
| 2003/0149061 | A1 | | 8/2003 | Nishihara et al. |
| 2005/0009817 | A1 | | 1/2005 | Savoy et al. |
| 2005/0153968 | A1 | | 7/2005 | Bi et al. |
| 2007/0004753 | A1 | | 1/2007 | Sawyers et al. |
| 2007/0254933 | A1 | | 11/2007 | Jung et al. |
| 2008/0139634 | A2 | | 6/2008 | Jung et al. |
| 2008/0261961 | A1 | | 10/2008 | Flynn et al. |
| 2010/0172975 | A1 | | 7/2010 | Sawyers et al. |
| 2010/0210665 | A1 | | 8/2010 | Sawyers et al. |
| 2011/0003839 | A1 | | 1/2011 | Jung et al. |
| 2011/0112097 | A1 | * | 5/2011 | Jaehne et al. .............. 514/236.8 |
| 2012/0190718 | A1 | | 7/2012 | Jung et al. |

FOREIGN PATENT DOCUMENTS

| DE | 3836175 | 5/1990 |
| EP | 0368008 | 5/1990 |
| EP | 0726898 | 12/2000 |
| EP | 1206935 | 5/2002 |
| GB | 2216890 | 10/1989 |
| WO | 91/04027 | 4/1991 |
| WO | 96/36229 | 11/1996 |
| WO | 96/36633 | 11/1996 |
| WO | 97/00612 | 1/1997 |
| WO | 98/05652 | 2/1998 |
| WO | 98/23155 | 6/1998 |

(Continued)

OTHER PUBLICATIONS

International Search Report for PCT/EP2010/068946 mailed Mar. 18, 2011.

(Continued)

*Primary Examiner* — Deepak Rao
*Assistant Examiner* — Alexander R Pagano
(74) *Attorney, Agent, or Firm* — Nixon & Vanderhye P.C.

(57) ABSTRACT

The invention provides a compound of formula (Ia), and pharmaceutically acceptable salts thereof. The invention also provides use of the compounds or salts as modulators of Kv3.1 and/or Kv3.2, and in the treatment of diseases or disorders where a modulator of Kv3.1 and/or Kv3.2 is required, such as depression and mood disorders, hearing disorders, schizophrenia, substance abuse disorders, sleep disorders or epilepsy.

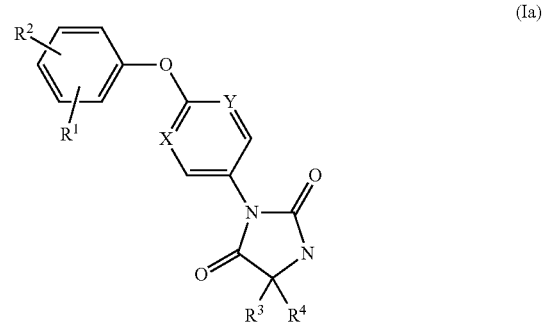

(Ia)

16 Claims, 6 Drawing Sheets

(56) References Cited

FOREIGN PATENT DOCUMENTS

| WO | 98/23156 | 6/1998 |
|---|---|---|
| WO | 98/33382 | 8/1998 |
| WO | 01/76582 | 10/2001 |
| WO | 03/048134 | 6/2003 |
| WO | 03/066050 | 8/2003 |
| WO | 2004/099159 | 11/2004 |
| WO | 2005/000309 | 1/2005 |
| WO | 2005/049580 | 6/2005 |
| WO | 2006/071471 | 7/2006 |
| WO | 2006/124118 | 11/2006 |
| WO | 2007/126765 | 11/2007 |
| WO | 2007/127010 | 11/2007 |

OTHER PUBLICATIONS

Written Opinion of the International Searching Authority mailed Mar. 18, 2011.
Rudy and McBain, Kv3 channels: voltage-gated K+channels designed for high-frequency repetitive firing, Trends in Neurosciences, 24, 517-526, 2001.
Weiser et al., Differential Expression of Shaw-related K+Channels in the Rat Central Nervous System, J.Neurosci., 14, pp. 949-972, 1994.
Chow et al., J.Neurosci., K+Channel Expression Distinguishes Subpopulations of Parvalbumin-and Somatostatin-Containing Neocortical Interneurons, 19, pp. 9332-9345, 1999.
Martina et al., Functional and Molecular Differences between Voltage-Gated K+Channels of Fast-spiking Interneurons and Pyramidal Neurons of Rat Hippocampus, J.Neurosci., 18, pp. 8111-8125, 1998.
McDonald and Mascagni, Differential Expression of Kv3.1b and Kv3.2 Potassium Channel Subunits in Interneurons of the Basolateral Amygdala, J. Neurosci., 138, pp. 537-547, 2006.
International Search Report and Written Opinion for PCT/EP2010/068946.
Chang et al., Distribution of Kv3.3 Potassium Channel Subunits in Distinct Neuronal Populations of Mouse Brain, J. Comp. Neurol., 502, pp. 953-972, 2007.
Kasten et al., Differential regulation of action potential firing in adult murine thalamocortical neurons by Kv3.2, Kv1 and SK potassium and N-type calcium channels, J.Physiol., 584, pp. 565-582, 2007.
Sacco et al., Properties and expression of Kv3 channels is cerebellar Purkinje cells, Mol. Cell. Neurosci., 33, pp. 170-179, 2006.
Li et al., Localization of Two High-Threshold Potassium Channel Subunits in the Rat Auditory System, J. Comp. Neurol., 437, pp. 196-218, 2001.
Joho et al., Increased γ- and Decreased δ-Oscillations in a Mouse Deficient for a Potassium Channel Expressed in Fast-Spiking Interneurons, J.Neurophysiol., 82, pp. 1855-1864, 1999.
Lau et al., Impaired Fast-Spiking, Suppressed Cortical Inhibition, and Increased Susceptibility to Seizures in Mice Lacking Kv3.2 K+Channel Proteins, J.Neurosci., 20, pp. 9071-9085, 2000.
McMahon et al., Allele-dependent changes of olivocerebellar circuit properties in the absence of the voltage-gated potassium channels Kv3.1 and Kv3.3, Eur. J.Neurosci., 19, pp. 3317-3327, 2004.
Espinosa et al., Alcohol Hypersensitivity, Increased Locomotion, and Spontaneous Myoclonus in Mice Lacking the Potassium Channels Kv3.1 and Kv3.3, J.Neurosci., 21, pp. 6657-6665, 2001.
Espinosa et al., Ablation of Kv3.1 and Kv3.3 Potassium Channels Disrupts Thalamocortical Oscillations In Vitro and In Vivo, J.Neurosci., 28, pp. 5570-5581, 2008.

Diochot et al., Sea Anemone Peptides with a Specific Blocking Activity against the Fast Inactivating Potassium Channel Kv3.4, J. Biol. Chem., 273, pp. 6744-6749, 1998.
Yeung et al., Modulation of Kv3 Subfamily Potassium Currents by the Sea Anemone Toxin BDS: Significance for CNS and Biophysical Studies, J.Neurosci., 25, pp. 8735-8745, 2005.
Atzori et al., $H_2$ histamine receptor-phosphorylation of Kv3.2 modulates interneuron fast spiking, Nat. Neurosci., 3, pp. 791-798, 2000.
Song et al., Acoustic environment determines phosphorylation state of the Kv3.1 potassium channel in auditory neurons, Nat Neurosci., 8, pp. 1335-1342, 2005.
Reynolds et al., Calcium Binding Protein Markers of GABA Deficits in Schizophrenia—Post Mortem Studies and Animal Models, Neurotox. Res., 6, pp. 57-61, 2004.
Benes et al., Circuitry based gene expression profiles in GABA cells of the trisynaptic pathway in schizophrenics versus bipolars, PNAS, 105, pp. 20935-20940, 2008.
Spencer et al., Neural synchrony indexes disordered perception and cognition in schizophrenia, PNAS, 101, pp. 17288-17293, 2004.
Schulz and Steimer, Neurobiology of Circadian Systems, CNS Drugs, 23 Suppl 2, pp. 3-13, 2009.
Goldman and Holme, Hearing loss and tinnitus—the hidden healthcare time bomb, Drug Discovery Today, 15, pp. 253-255, 2010.
B. Shield, Evaluation of the social and economic costs of hearing impairment, A report for Hear-It AISBL: www.hear-it.org/multimedia/Hear_It_Report_October_2006.pdf, 2006.
von Hehn et al., Loss of Kv3.1 Tonotopicity and Alterations in cAMP Response Element-Binding Protein Signaling in Central Auditory Neurons of Hearing Impaired Mice, J. Neurosci., 24, pp. 1936-1940, 2004.
Jung et al., Age-related changes in the distribution of Kv1.1 and Kv3.1 in rat cochlear nuclei, Neurol. Res., 27, pp. 436-440, 2005.
Kaczmarek et al., Regulation of the timing of MNTB neurons by short-term and long-term modulation of potassium channels, Hearing Res., 206, pp. 133-145, 2005.
Strumbos et al., Specific and Rapid Effects of Acoustic Stimulation on the Tonotopic Distribution of Kv3.1b Potassium Channels in the Adult Rat, J. Neuroscience, 167, pp. 567-572, 2010.
Strumbos et al., Fragile X Mental Retardation Protein Is Required for Rapid Experience-Dependent Regulation of Potassium Channel Kv3.1b, J. Neuroscience, 167, pp. 10263-10271, 2010.
Berge et al., Pharmaceutical Salts, J. Pharm. Sci., 66, pp. 1-19, 1977.
Zhang et al., Total synthesis and reassignment of stereochemistry of obyanamide, Tetrahedron, 62(42), pp. 9966-9972, 2006.
Stean TO, et al., Postsynaptic 5-$HT_{1B}$ receptors modulate electroshock-induced generalised seizures in rats, Br J Pharmacol., 144(5):628-35, 2005.
Costall, B. et al., A Primate Model for the Assessment of Anxiolytic Drug Action, Br. J. Pharmac., 1988, 95, pp. 475P, 1988.
Brambilla et al., GABAergic dysfunction in mood disorders, Mol. Psychiatry, 8, pp. 721-737, 2003.
Aroniadou-Anderjaska et al., Mechanisms regulating GABAergic inhibitory transmission in the basolateral amygdala: implications for epilepsy and anxiety disorders, Amino Acids, 32, pp. 305-315, 2007.
Ben-Ari, Seizures Beget Seizures: The Quest for GABA as a Key Player, Crit. Rev. Neurobiol., 18, pp. 135-144, 2006.
Markram et al., Interneurons of the Neocortical Inhibitory System, Nat.Rev.Neurosci., 5, pp. 793-807, 2004.
Fisahn, Kainate receptors and rhythmic activity in neuronal networks: hippocampal gamma oscillations as a tool, J.Physiol, 562, pp. 65-72, 2005.
Engel et al., Dynamic Predictions: Oscillations and Synchrony in Top-Down Processing, Nat.Rev.Neurosci., 2, pp. 704-716, 2001.

* cited by examiner

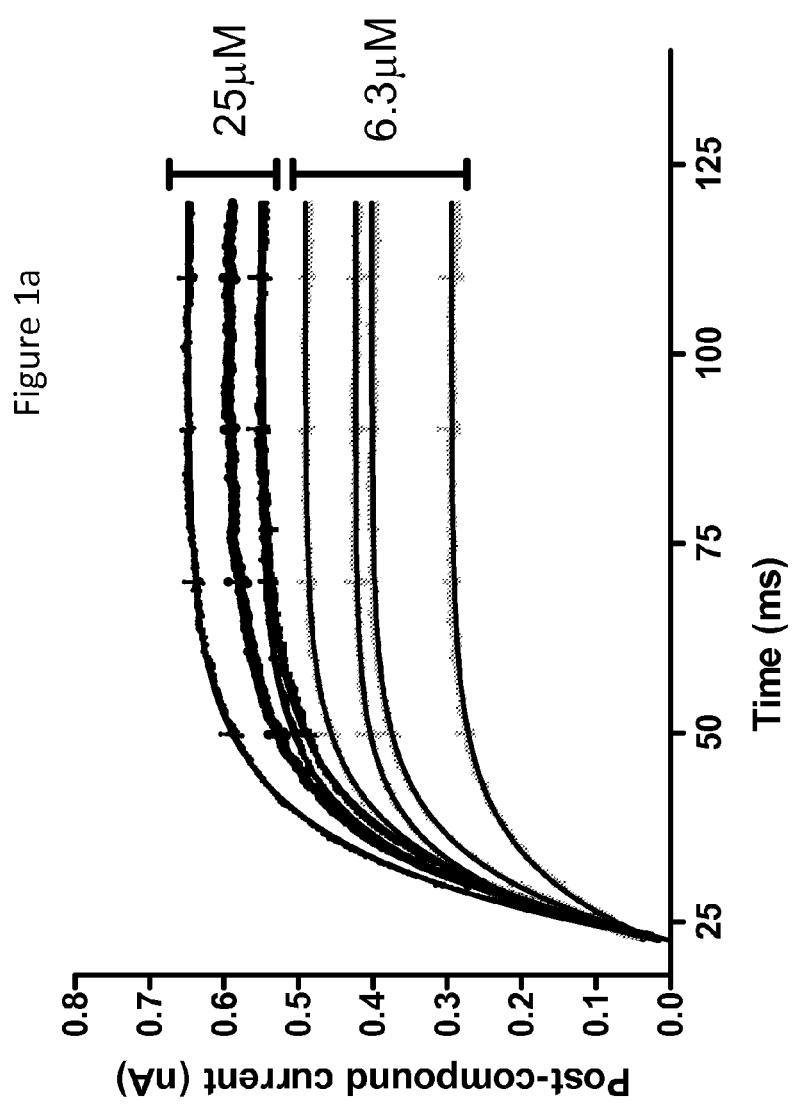
Figure 1a: hKv3.2 currents recorded using the assay described in Example 89, at two concentrations of the compound of Example 19

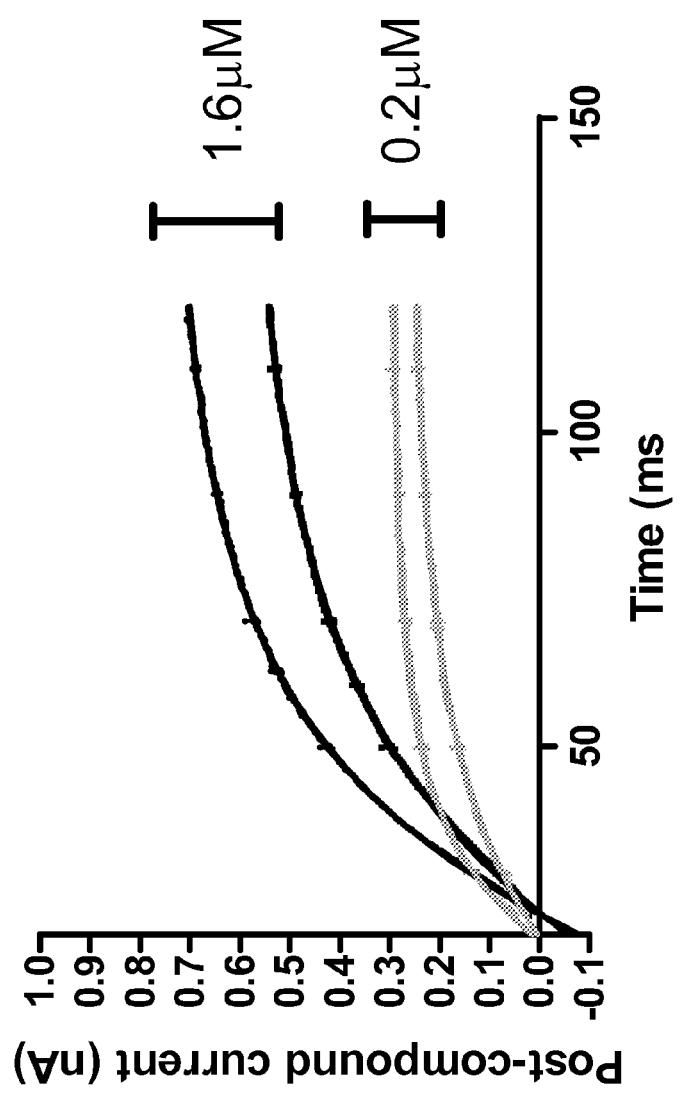
Figure 1b: hKv3.2 currents recorded using the assay described in Example 89, at two concentrations of the compound of Example 71

IMIDAZOLIDINEDIONE DERIVATIVES

This application is the U.S. national phase of International Application No. PCT/EP2010/068946 filed 6 Dec. 2010 which designated the U.S. and claims priority to GB 0921760.5 filed 11 Dec. 2009 and GB 1012924.5 filed 30 Jul. 2010, the entire contents of each of which are hereby incorporated by reference.

This invention relates to novel compounds, pharmaceutical compositions containing them and their use in therapy, in particular as antipsychotic agents.

BACKGROUND TO THE INVENTION

The Kv3 voltage-gated potassium channel family includes four members, Kv3.1, Kv3.2, KV3.3, and Kv3.4. Genes for each of these subtypes can generate multiple isoforms by alternative splicing, producing versions with different C-terminal domains. Thirteen isoforms have been identified in mammals to date, but the currents expressed by these variants appear identical (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (e.g. Sacco et al., 2006, Mol. Cell. Neurosci. 33, 170-179), and auditory brain stem nuclei (Li et al., 2001, J. Comp. Neurol. 437, 196-218).

Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999, J. Neurophysiol. 82, 1855-1864). The deletion of Kv3.2 leads to a reduction in seizure threshold and altered cortical electroencephalographic activity (Lau et al., 2000, J. Neurosci. 20, 9071-9085). Deletion of Kv3.3 is associated with mild ataxia and motor deficits (McMahon et al., 2004, Eur. J. Neurosci. 19, 3317-3327). Double deletion of Kv3.1 and Kv3.3 gives rise to a severe phenotype characterised by spontaneous seizures, ataxia, and an increased sensitivity to the effects of ethanol (Espinosa et al., 2001, J. Neurosci. 21, 6657-6665; Espinosa et al., 2008, J. Neurosci. 28, 5570-5581).

The known pharmacology of Kv3 channels is limited. Tetraethylammonium (TEA) has been shown to inhibit the channels at low millimolar concentrations (Rudy and McBain, 2001, Trends in Neurosci. 24, 517-526), and blood-depressing substance (BDS) toxins from the sea anemone, *Anemonia sulcata* (Diochot et al., 1998, J. Biol. Chem. 273, 6744-6749), have been shown to selectively inhibit Kv3 channels with high affinity (Yeung et al., 2005, J. Neurosci. 25, 8735-8745). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000, Nat. Neurosci. 3, 791-798; Song et al., 2005, Nat. Neurosci. 8, 1335-1342); these studies suggest that PKA and PKC can specifically phosphorylate Kv3 channels in a neuron-specific manner, causing a reduction in Kv3-mediated currents. There are no descriptions in the literature of compounds or biochemical mechanisms that positively modulate or activate Kv3 channels.

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004, Neurotox. Res. 6, 57-61; Benes et al., 2008, PNAS, 105, 20935-20940; Brambilla et al., 2003, Mol. Psychiatry. 8, 721-37, 715; Aroniadou-Anderjaska et al., 2007, Amino Acids 32, 305-315; Ben-Ari, 2006, Crit. Rev. Neurobiol. 18, 135-144). Parvalbumin positive basket cells that express Kv3 channels in the cortex and hippocampus play a key role in generating feedback inhibition within local circuits (Markram et al., 2004, Nat. Rev. Neurosci. 5, 793-807). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005, J. Physiol 562, 65-72; Engel et al., 2001, Nat. Rev. Neurosci. 2, 704-716). Notably, a reduction in gamma oscillations has been observed in patients with schizophrenia (Spencer et al., 2004, PNAS 101, 17288-17293). Consequently, positive modulators of Kv3 channels might be expected to enhance the firing capabilities of specific groups of fast-firing neurons in the brain. These effects may be beneficial in disorders associated with abnormal activity of these neuronal groups.

In addition, Kv3.2 channels have been shown to be expressed by neurons of the superchiasmatic nucleus (SCN) the main circadian pacemaker in the CNS (Schulz and Steimer, 2009, CNS Drugs 23 Suppl 2, 3-13). We have shown that the expression of Kv3.2 channels varies over a 24 hour period; thus Kv3.2 channel expression may contribute to changes in the firing properties of neurons in the SCN and thus influence circadian rhythm. Consequently, drugs that modulate the activity of Kv3.2 channels could influence circadian rhythm and thus be useful in the treatment of related disorders.

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www-.hear-it.org/multimedia/Hear It Report October 2006.pdf). As life expectancy continues to increase, so too will the number of people suffering from hearing disorders. Furthermore, it is believed that modern lifestyles may exacerbate this burden as the younger generation ages. Hearing conditions, including tinnitus have a profound effect on the quality of life, causing social isolation, depression, work and relationship difficulties, low self-esteem, and prejudice. Voltage-gated ion channels of the Kv3 family are expressed at high levels in auditory brainstem nuclei (Li et al., 2001, J. Comp. Neurol. 437, 196-218) where they permit the fast firing of neurons that transmit auditory information from the cochlear to higher brain regions. Loss of Kv3.1 channel expression in central auditory neurons is observed in hearing impaired mice (von Hehn et al., 2004, J. Neurosci. 24, 1936-1940), and a decline in Kv3.1 expression may be associated with loss of hearing in aged mice (Jung et al. 2005 Neurol. Res. 27, 436-440). Furthermore, pathological plasticity of auditory brainstem networks is likely to contribute to symptoms of tinnitus that are experienced by many people suffering from hearing loss of different types. Recent studies have shown that regulation of Kv3.1 channel function and expression has a major role in controlling auditory neuron excitability (Kaczmarek et al., 2005, Hearing Res. 206, 133-145), suggesting that this mechanism could account for some of the plastic changes that give rise to tinnitus. Finally, Fraglie X syndrome and autism are frequently associated with hypersensitivity to sensory input, including auditory stimuli. Recent findings suggest that the protein coded by the FMR-I gene, whose mutation or absence gives rise to Fragile X syndrome, may directly regulate the expression of Kv3.1 channels in the auditory brainstem nuclei (Strumbos et al., 2010, J. Neuroscience, in press), suggesting that mis-regulation of Kv3.1 channels could give rise to hyperacusis in patients suffering from Fragile X or autism. Consequently, we propose that small molecule modulators of Kv3 channels in auditory brainstem nuclei could have a benefit in the treatment of disorders of hearing, including tinnitus and auditory hyper-acuity associated with Fragile X syndrome and autism.

In a first aspect therefore, the invention provides a compound of formula (Ia)

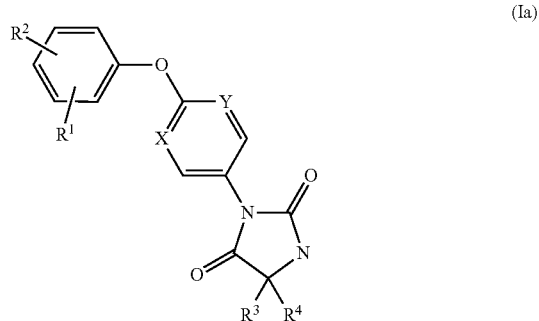

wherein:
$R^1$ is halo, $C_{1-4}$ alkyl, $C_{1-4}$ alkoxy, halo-$C_{1-4}$ alkyl, halo-$C_{1-4}$alkoxy, or cyano;
$R^2$ is H, halo, cyano, $C_{1-4}$ alkyl or $C_{1-4}$ alkoxy; with the proviso that when $R_2$ is H, $R_1$ is not in the para position;
X is C or N;
Y is C or N;
$R^3$ is $C_{1-4}$ alkyl;
$R^4$ is H, deuterium, or $C_{1-4}$alkyl; or $R_3$ and $R_4$ can be fused to form a $C_{3-4}$ spiro carbocyclyl group;
or a pharmaceutically acceptable salt thereof.

In a second aspect the invention provides a compound of formula (Ib)

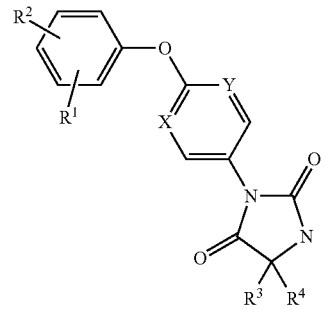

wherein:
$R^1$ is halo, $C_{1-4}$ alkyl or $C_{1-4}$ alkoxy, halo-$C_{1-4}$alkoxy, cyano;
$R^2$ is H, halo, $C_{1-4}$ alkyl and $C_{1-4}$ alkoxy; with the proviso that when $R_2$ is H, $R_1$ is not in the para position;
X is C or N;
Y is C or N;
$R^3$ is $C_{1-4}$ alkyl;
$R^4$ is H, deuterium, $C_{1-4}$ alkyl; or $R_3$ and $R_4$ can be fused to form a $C_{3-4}$ spiro carbocycly group;
or a pharmaceutically acceptable salt thereof.

In a third aspect therefore, the invention provides a compound of formula (Ic)

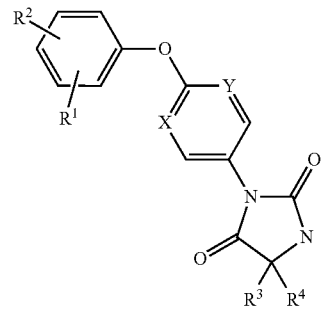

wherein:
$R^1$ is halo, $C_{1-4}$ alkyl or $C_{1-4}$ alkoxy;
$R^2$ is H, halo, $C_{1-4}$ alkyl and $C_{1-4}$ alkoxy; with the proviso that when $R_2$ is H, $R_1$ is not in the para position;
X is C or N;
Y is C or N;
$R^3$ is $C_{1-4}$ alkyl;
$R^4$ is H, deuterium, $C_{1-4}$ alkyl; or $R_3$ and $R_4$ can be fused to form a $C_{3-4}$ spiro carbocycly group;
or a pharmaceutically acceptable salt thereof.

As used herein below, "Formula (I)" means any one of Formula (Ia), (Ib), or (Ic).

In one embodiment of the invention $R^1$ is $C_{1-4}$ alkoxy. In another embodiment of the invention $R^1$ is methoxy.

In one embodiment of the invention $R^1$ is $C_{1-4}$ alkyl. In another embodiment of the invention $R^1$ is methyl. In a further embodiment of the invention $R^1$ is ethyl. In a yet further embodiment of the invention $R^1$ is propyl. In a yet further embodiment of the invention $R^1$ is butyl.

In one embodiment of the invention $R^1$ is halo. In another embodiment of the invention $R^1$ is chloro. In a further embodiment of the invention $R^1$ is fluoro.

In one embodiment of the invention $R^1$ is halo-$C_{1-4}$alkoxy. In another embodiment of the invention $R^1$ is trifluoromethoxy.

In one embodiment of the invention $R^1$ is halo-$C_{1-4}$alkyl. In another embodiment of the invention $R^1$ is trifluoromethyl.

In one embodiment of the invention $R^1$ is cyano.

In one embodiment of the invention, $R^2$ is H.

In one embodiment of the invention $R^2$ is $C_{1-4}$ alkyl. In another embodiment of the invention $R^2$ is methyl.

In one embodiment of the invention $R^2$ is halo. In another embodiment of the invention, $R^2$ is chloro. In a further embodiment of the invention $R^2$ is fluoro.

In one embodiment of the invention $R^2$ is $C_{1-4}$ alkyl.

In one embodiment of the invention $R^2$ is cyano.

In one embodiment of the invention X is C and Y is C.

In one embodiment of the invention X is N and Y is C.

In one embodiment of the invention X is N and Y is N.

In one embodiment of the invention $R^3$ is methyl. In another embodiment of the invention $R^3$ is ethyl. In a further embodiment of the invention $R^3$ is propyl. In a yet further embodiment of the invention $R^3$ is butlyl.

In one embodiment of the invention $R^4$ is H.

In one embodiment of the invention $R^4$ is deuterium.

In one embodiment of the invention $R^4$ is $C_{1-4}$ alkyl. In another embodiment of the invention $R^4$ is methyl.

In one embodiment of the invention $R^3$ and $R^4$ together form a $C_{3-4}$ spiro carbocyl.

In another embodiment of the invention $R^3$ and $R^4$ together form a $C_3$ spiro carbocycyl. In a further embodiment of the invention $R^3$ and $R^4$ together form a $C_4$ spiro carbocycyl.

In one embodiment of the invention $R^3$ is $C_{1-4}$ alkyl, $R^4$ is H and the absolute configuration of the stereogenic centre is R.

In one embodiment of the invention $R^1$ is $C_{1-4}$alkyl, $C_{1-4}$ alkoxy, or halo-$C_{1-4}$ alkoxy;

$R^2$ is H, cyano or alkyl; X is N, Y is N or C, $R_3$ is $C_{1-4}$ alkyl, and $R^4$ is $C_{1-4}$ alkyl or H; or a pharmaceutically acceptable salt thereof.

In one embodiment of the invention $R_1$ is propyl, butyl, methoxy, propoxy, or trifluoromethoxy; $R^2$ is H, cyano or methyl; X is N, Y is N or C, $R^3$ is ethyl, and $R^4$ is methyl or H; or a pharmaceutically acceptable salt thereof.

In one embodiment of the invention $R^1$ is methoxy and $R^2$ is methyl. In another embodiment of the invention $R^1$ is methoxy in the meta position and $R^2$ is methyl in the para position. In a further embodiment of the invention $R^1$ is methoxy in the meta position, $R^2$ is methyl in the para position, $R^3$ is $C_{1-4}$ alkyl, $R^4$ is H, $R^3$ is in the R configuration. In a yet further embodiment of the invention $R^1$ is methoxy in the meta position, $R^2$ is methyl in the para position, X is N, Y is C, $R^3$ is $C_{1-4}$ alkyl, $R^4$ is H and the absolute configuration of the stereogenic centre is R. In a still further embodiment of the invention $R^1$ is methoxy in the meta position, $R^2$ is methyl in the para position, X is N, Y is C, $R^3$ is ethyl, $R^4$ is H and the absolute configuration of the stereogenic centre is R.

In one embodiment of the invention the compound is selected from the group consisting of:

(5R)-5-methyl-3-{4-[(3-methylphenyl)oxy]phenyl}-2,4-imidazolidinedione;

(5R)-5-methyl-3-(4-{[3-(methyloxy)phenyl]oxy}phenyl)-2,4-imidazolidinedione;

(5R)-3-(4-{[3-(ethyloxy)phenyl]oxy}phenyl)-5-methyl-2,4-imidazolidinedione;

(5R)-3-{4-[(3-chloro-5-fluorophenyl)oxy]phenyl}-5-methyl-2,4-imidazolidinedione;

(5R)-3-{4-[(3-chloro-4-fluorophenyl)oxy]phenyl}-5-methyl-2,4-imidazolidinedione;

(5S)-3-{4-[(3-chloro-4-fluorophenyl)oxy]phenyl}-5-methyl-2,4-imidazolidinedione;

(5R)-5-methyl-3-(4-{[2-methyl-5-(methyloxy)phenyl]oxy}phenyl)-2,4-imidazolidinedione;

(5R)-5-methyl-3-(4-{[4-methyl-3-(methyloxy)phenyl]oxy}phenyl)-2,4-imidazolidinedione;

(5R)-5-methyl-3-(6-{[3-(1-methylethyl)phenyl]oxy}-3-pyridinyl)-2,4-imidazolidinedione;

(5R)-5-methyl-3-[6-({3-[(1-methylethyl)oxy]phenyl}oxy)-3-pyridinyl]-2,4-imidazolidinedione;

(5R)-3-{6-[(2,5-dimethylphenyl)oxy]-3-pyridinyl}-5-methyl-2,4-imidazolidinedione;

(5R)-3-{6-[(2,3-dimethylphenyl)oxy]-3-pyridinyl}-5-methyl-2,4-imidazolidinedione;

(5R)-3-{6-[(2,6-dimethylphenyl)oxy]-3-pyridinyl}-5-methyl-2,4-imidazolidinedione;

(5R)-3-{6-[(2-ethylphenyl)oxy]-3-pyridinyl}-5-methyl-2,4-imidazolidinedione;

(5R)-5-methyl-3-(6-{[4-methyl-3-(methyloxy)phenyl]oxy}-3-pyridinyl)-2,4-imidazolidinedione;

(5R)-5-methyl-3-(6-{[2-methyl-5-(methyloxy)phenyl]oxy}-3-pyridinyl)-2,4-imidazolidinedione;

(5R)-5-methyl-3-(6-{[2-methyl-3-(methyloxy)phenyl]oxy}-3-pyridinyl)-2,4-imidazolidinedione;

(5R)-5-ethyl-3-(4-{[3-(methyloxy)phenyl]oxy}phenyl)-2,4-imidazolidinedione;

(5R)-5-ethyl-3-(6-{[4-methyl-3-(methyloxy)phenyl]oxy}-3-pyridinyl)-2,4-imidazolidinedione;

(5S)-5-ethyl-3-(6-{[4-methyl-3-(methyloxy)phenyl]oxy}-3-pyridinyl)-2,4-imidazolidinedione;

(5R)-5-ethyl-3-(6-{[3-(1-methylethyl)phenyl]oxy}-3-pyridinyl)-2,4-imidazolidinedione;

5,5-dimethyl-3-(4-{[3-(methyloxy)phenyl]oxy}phenyl)-2,4-imidazolidinedione;

3-{4-[(2,3-dimethylphenyl)oxy]phenyl}-5,5-dimethyl-2,4-imidazolidinedione;

3-{6-[(2-ethylphenyl)oxy]-3-pyridinyl}-5,5-dimethyl-2,4-imidazolidinedione;

3-{6-[(2,6-dimethylphenyl)oxy]-3-pyridinyl}-5,5-dimethyl-2,4-imidazolidinedione;

(5R)-5-(1-methylethyl)-3-(4-{[4-methyl-3-(methyloxy)phenyl]oxy}phenyl)-2,4-imidazolidinedione;

(5R)-5-methyl-3-(2-{[3-(1-methylethyl)phenyl]oxy}-5-pyrimidinyl)-2,4-imidazolidinedione;

(5R)-5-ethyl-3-(2-{[3-(ethyloxy)-4-methylphenyl]oxy}-5-pyrimidinyl)-2,4-imidazolidinedione;

(5R)-5-(1,1-dimethylethyl)-3-(6-{[4-methyl-3-(methyloxy)phenyl]oxy}-3-pyridinyl)-2,4-imidazolidinedione;

(5R)-5-ethyl-5-methyl-3-(6-{[4-methyl-3-(methylaxy)phenyl]oxy}-3-pyridinyl)-2,4-imidazolidinedione;

7-(6-{[4-methyl-3-(methyloxy)phenyl]oxy}-3-pyridinyl)-5,7-diazaspiro[3.4]octane-6,8-dione;

6-(6-{[4-methyl-3-(methyloxy)phenyl]oxy}-3-pyridinyl)-4,6-diazaspiro[2.4]heptane-5,7-dione;

4-{[5-(4,4-dimethyl-2,5-dioxo-1-imidazolidinyl)-2-pyridinyl]oxy}-2-(1-methylethyl)benzonitrile;

4-{[5-(4,4-dimethyl-2,5-dioxo-1-imidazolidinyl)-2-pyridinyl]oxy}-2-[(trifluoromethyl)oxy]benzonitrile;

3-{6-[(4-fluoro-3-methylphenyl)oxy]-3-pyridinyl}-5,5-dimethyl-2,4-imidazolidinedione;

3-{6-[(4-fluoro-2-methylphenyl)oxy]-3-pyridinyl}-5,5-dimethyl-2,4-imidazolidinedione;

5,5-dimethyl-3-(6-{[4-methyl-3-(methyloxy)phenyl]oxy}-3-pyridinyl)-2,4-imidazolidinedione;

(5R)-5-(1-methylethyl)-3-(6-{[4-methyl-3-(methyloxy)phenyl]oxy}-3-pyridinyl)-2,4-imidazolidinedione;

3-(6-{[2-(1,1-dimethylethyl)phenyl]oxy}-3-pyridinyl)-5,5-dimethyl-2,4-imidazolidinedione;
3-(2-{[2-(1,1-dimethylethyl)phenyl]oxy}-5-pyrimidinyl)-5,5-dimethyl-2,4-imidazolidinedione;
(5R)-5-ethyl-5-methyl-3-(2-{[4-methyl-3-(methylaxy)phenyl]oxy}-5-pyrimidinyl)-2,4-imidazolidinedione;
(5R)-5-ethyl-3-(2-{[3-(ethyloxy)-4-methylphenyl]oxy}-5-pyrimidinyl)-5-methyl-2,4-imidazolidinedione;
5,5-dimethyl-3-[6-({3-[(trifluoromethyl)oxy]phenyl}oxy)-3-pyridinyl]-2,4-imidazalidinedione;
4-{[5-(4,4-dimethyl-2,5-dioxo-1-imidazolidinyl)-2-pyridinyl]oxy}-3-ethylbenzonitrile;
2-chloro-4-{[5-(4,4-dimethyl-2,5-dioxo-1-imidazolidinyl)-2-pyridinyl]oxy}benzonitrile;
5,5-dimethyl-3-[6-({4-methyl-3-[(trifluoromethyl)oxy]phenyl}oxy)-3-pyridinyl]-2,4-imidazolidinedione;
4-{[5-(4,4-dimethyl-2,5-dioxo-1-imidazolidinyl)-2-pyridinyl]oxy}-2-(methyloxy)benzonitrile;
4-{[5-(4,4-dimethyl-2,5-dioxo-1-imidazolidinyl)-2-pyridinyl]oxy}-3-methylbenzonitrile;
4-{[5-(4,4-dimethyl-2,5-dioxo-1-imidazolidinyl)-2-pyridinyl]oxy}-3-(trifluoromethyl)benzonitrile;
4-{[5-(4,4-dimethyl-2,5-dioxo-1-imidazolidinyl)-2-pyridinyl]oxy}-2-ethylbenzonitrile;
4-{[5-(4,4-dimethyl-2,5-dioxo-1-imidazolidinyl)-2-pyrimidinyl]oxy}-2-ethylbenzonitrile;
3-cyclopropyl-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-3-(1,1-dimethylethyl)benzonitrile;
2-[(cyclopropylmethyl)oxy]-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-2-(ethyloxy)benzonitrile;
2-cyclopropyl-4-{[5-(4,4-dimethyl-2,5-dioxo-1-imidazolidinyl)-2-pyridinyl]oxy}benzonitrile;
5,5-dimethyl-3-[2-({4-methyl-3-[(trifluoromethyl)oxy]phenyl}oxy)-5-pyrimidinyl]-2,4-imidazolidinedione;
4-{[5-(4,4-dimethyl-2,5-dioxo-1-imidazolidinyl)-2-pyrimidinyl]oxy}-3-(1,1-dimethylethyl)benzonitrile;
4-{[5-(4,4-dimethyl-2,5-dioxo-1-imidazolidinyl)-2-pyridinyl]oxy}-2-[(1-methylethyl)oxy]benzonitrile;
4-({5-[(4R)-4-ethyl-4-methyl-2,5-dioxo-1-imidazolidinyl]-2-pyridinyl}oxy)-2-[(1-methylethyl)oxy]benzonitrile;
3-cyclopropyl-4-({5-[(4R)-4-ethyl-4-methyl-2,5-dioxo-1-imidazolidinyl]-2-pyridinyl}oxy)benzonitrile;
4-({5-[(4R)-4-ethyl-4-methyl-2,5-dioxo-1-imidazolidinyl]-2-pyridinyl}oxy)-2-[(trifluoromethyl)oxy]benzonitrile;
2-cyclopropyl-4-({5-[(4R)-4-ethyl-4-methyl-2,5-dioxo-1-imidazolidinyl]-2-pyridinyl}oxy)benzonitrile;
(5R)-5-ethyl-5-methyl-3-[2-({4-methyl-3-[(trifluoromethyl)oxy]phenyl}oxy)-5-pyrimidinyl]-2,4-imidazolidinedione;
3-(1,1-dimethylethyl)-4-({5-[(4R)-4-ethyl-4-methyl-2,5-dioxo-1-imidazolidinyl]-2-pyrimidinyl}oxy)benzonitrile;
3-(1,1-dimethylethyl)-4-({5-[(4R)-4-ethyl-4-methyl-2,5-dioxo-1-imidazolidinyl]-2-pyridinyl}oxy)benzonitrile;
4-{[4-(4,4-dimethyl-2,5-dioxo-1-imidazolidinyl)phenyl]oxy}-2-(methyloxy)benzonitrile;
4-{[4-(4,4-dimethyl-2,5-dioxo-1-imidazolidinyl)phenyl]oxy}-2-(ethyloxy)benzonitrile;
4-({4-[(4R)-4-ethyl-2,5-dioxo-1-imidazolidinyl]phenyl}oxy)-2-(ethyloxy)benzonitrile;
3-cyclopropyl-4-({5-[(4R)-4-ethyl-2,5-dioxo-1-imidazolidinyl]-2-pyridinyl}oxy)benzonitrile;
3-(1,1-dimethylethyl)-4-({5-[(4R)-4-ethyl-2,5-dioxo-1-imidazolidinyl]-2-pyridinyl}oxy)benzonitrile;
4-({5-[(4R)-4-ethyl-2,5-dioxo-1-imidazolidinyl]-2-pyridinyl}oxy)-2-(methyloxy)benzonitrile;
4-({4-[(4R)-4-ethyl-2,5-dioxo-1-imidazolidinyl]phenyl}oxy)-2-(methyloxy)benzonitrile;
2-[(cyclopropylmethyl)oxy]-4-({5-[(4R)-4-ethyl-2,5-dioxo-1-imidazolidinyl]-2-pyridinyl}oxy)benzonitrile;
(5R)-5-ethyl-3-[6-({4-methyl-3-[(trifluoromethyl)oxy]phenyl}oxy)-3-pyridinyl]-2,4-imidazolidinedione;
2-cyclopropyl-4-({5-[(4R)-4-ethyl-2,5-dioxo-1-imidazolidinyl]-2-pyridinyl}oxy)benzonitrile;
4-({5-[(4R)-4-ethyl-2,5-dioxo-1-imidazolidinyl]-2-pyridinyl}oxy)-2-(1-methylethyl)benzonitrile;
4-({5-[(4R)-4-ethyl-2,5-dioxo-1-imidazolidinyl]-2-pyridinyl}oxy)-2-(1-methylethyl)benzonitrile;
(5R)-5-ethyl-3-[2-({4-methyl-3-[(trifluoromethyl)oxy]phenyl}oxy)-5-pyrimidinyl]-2,4-imidazolidinedione;
4-({5-[(4R)-4-ethyl-2,5-dioxo-1-imidazolidinyl]-2-pyridinyl}oxy)-2-[(1-methylethyl)oxy]benzonitrile;
4-({5-[(4R)-4-ethyl-2,5-dioxo-1-imidazolidinyl]-2-pyridinyl}oxy)-3-methylbenzonitrile;
4-({5-[(4R)-4-ethyl-2,5-dioxo-1-imidazolidinyl]-2-pyridinyl}oxy)-2-[(trifluoromethyl)oxy]benzonitrile;
3-ethyl-4-({5-[(4R)-4-ethyl-2,5-dioxo-1-imidazolidinyl]-2-pyrimidinyl}oxy)benzonitrile;
4-({5-[(4R)-4-ethyl-2,5-dioxo-1-imidazolidinyl]-2-pyrimidinyl}oxy)-3-methylbenzonitrile;
3-(1,1-dimethylethyl)-4-({5-[(4R)-4-ethyl-2,5-dioxo-1-imidazolidinyl]-2-pyrimidinyl}oxy)benzonitrile and 4-({5-[(4R)-4-ethyl-4-methyl-2,5-dioxo-1-imidazolidinyl]-2-pyridinyl}oxy)-2-(1-methylethyl)benzonitrile or
a pharmaceutically acceptable salt thereof.

In one embodiment of the invention, the compound is selected from the group consisting of:
(5R)-5-ethyl-3-(6-{[4-methyl-3-(methyloxy)phenyl]oxy}-3-pyridinyl;
(5R)-5-ethyl-5-methyl-3-(6-{[4-methyl-3-(methyloxy)phenyl]oxy}-3-pyridinyl)-2,4-imidazolidinedione;
4-({5-[(4R)-4-ethyl-4-methyl-2,5-dioxo-1-imidazolidinyl]-2-pyridinyl}oxy)-2-[(trifluoromethyl)oxy]benzonitrile;
(5R)-5-ethyl-5-methyl-3-[2-({4-methyl-3-[(trifluoromethyl)oxy]phenyl}oxy)-5-pyrimidinyl]-2,4-imidazolidinedione;
3-(1,1-dimethylethyl)-4-({5-[(4R)-4-ethyl-4-methyl-2,5-dioxo-1-imidazolidinyl]-2-pyridinyl}oxy)benzonitrile;
(5R)-5-ethyl-3-[6-({4-methyl-3-[(trifluoromethyl)oxy]phenyl}oxy)-3-pyridinyl]-2,4-imidazolidinedione;
4-({5-[(4R)-4-ethyl-2,5-dioxo-1-imidazolidinyl]-2-pyridinyl}oxy)-2-(1-methylethyl)benzonitrile;
4-({5-[(4R)-4-ethyl-2,5-dioxo-1-imidazolidinyl]-2-pyridinyl}oxy)-2-(1-methylethyl)benzonitrile;
(5R)-5-ethyl-3-[2-({4-methyl-3-[(trifluoromethyl)oxy]phenyl}oxy)-5-pyrimidinyl]-2,4-imidazolidinedione;
4-({5-[(4R)-4-ethyl-2,5-dioxo-1-imidazolidinyl]-2-pyridinyl}oxy)-2-[(1-methylethyl)oxy]benzonitrile;
4-({5-[(4R)-4-ethyl-2,5-dioxo-1-imidazolidinyl]-2-pyridinyl}oxy)-2-[(trifluoromethyl)oxy]benzonitrile;
3-(1,1-dimethylethyl)-4-({5-[(4R)-4-ethyl-2,5-dioxo-1-imidazolidinyl]-2-pyrimidinyl}oxy)benzonitrile;
or a pharmaceutically acceptable salt thereof.

For the avoidance of doubt, the embodiments of any one feature of the compounds of the invention may be combined with any embodiment of another feature of compounds of the invention to create a further embodiment.

The term 'halo' or 'halogen' as used herein, refers to a fluorine, chlorine, bromine or iodine atom.

When the compound contains a $(C_{1-4})$alkyl group, whether alone or forming part of a larger group, e.g. $(C_{1-4})$alkoxy, the alkyl group may be straight chain, branched, cyclic, or a combination thereof. Examples of $(C_{1-4})$alkyl are methyl, ethyl, n-propyl, isopropyl, n-butyl, isobutyl, sec-butyl, tert-butyl, cyclopropyl and cyclobutyl. An example of $(C_{1-4})$ alkoxy is methoxy. An example of halo-$C_{1-4}$ alky is trifluoromethyl. An example of halo-$C_{1-4}$alkoxy is trifluoromethoxy.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, eg. as the hydrate. This invention includes within its scope stoichiometric solvates (eg. hydrates) as well as compounds containing variable amounts of solvent (eg. water).

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further aspect of the present invention there is provided a process for the preparation of compounds of formula (I) and derivatives thereof. The following schemes detail some synthetic routes to compounds of the invention. In the following schemes reactive groups can be protected with protecting groups and deprotected according to well established techniques.

In general, the compounds of formula (I) may be made according to the organic synthesis techniques known to those skilled in this field, as well as by the representative methods set forth in the Examples.

Compounds of formula (I), and salts and solvates thereof, may be prepared by the general methods outlined hereinafter. In the following description, the groups $R_1$, $R_2$, X, Y, $R_3$, $R_4$ have the meanings as previously defined for compounds of formula (I) unless otherwise stated.

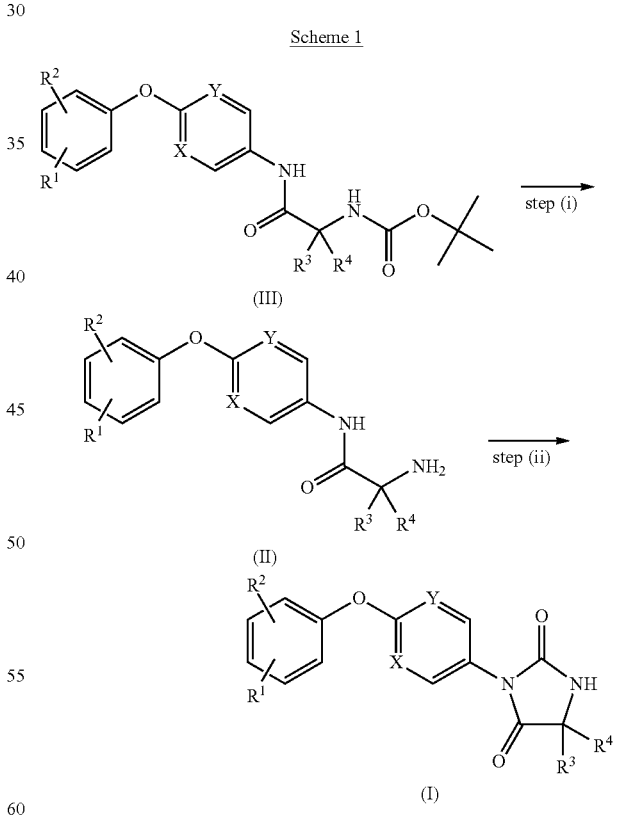

Scheme 1

Step (ii):
Compounds of formula (I) can be prepared by cyclization of compounds of formula (II) in a solvent e.g. dichloromethane with a carbonylating agent e.g. triphosgene preferentially prediluted in the same solvent and added in a second time at 0° C. in presence of a base e.g. triethylamine. In some cases ethyl acetate could be used as a solvent. Optionally a catalytic amount of DMAP can be added.

Step (i):

Compounds of formula (II) can be prepared from compounds of formula (III) by removal of the BOC protective group in acidic conditions e.g. TFA in a solvent e.g. dichloromethane e.g. at 0° C., RT.

Scheme 2

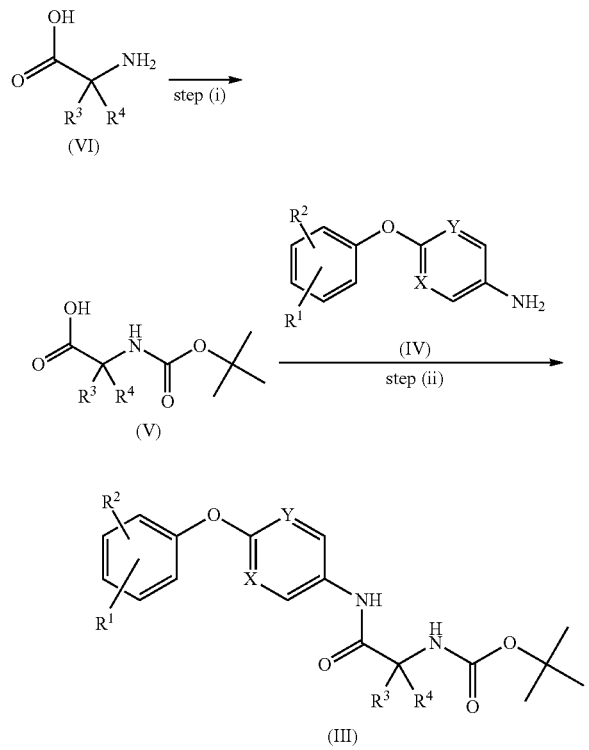

Step (ii):

Compounds of formula (III) can be prepared from anilines of formula (IV) and N-protected amino acids of formula (V) by amidic coupling in presence of a base e.g. DIPEA and of a coupling agent e.g. HATU, TBTU, HBTU in a solvent such as N,N-dimethylformamide.

Step (i):

Some N-Boc protected amino acids of formula (V) are commercially available e.g. N-{[(1,1-dimethylethyl)oxy]carbonyl}-2-methylalanine from for example Aldrich, N-{[(1,1-dimethylethyl)oxy]carbonyl}-D-alanine from for example Aldrich, (2R)-2-({[(1,1-dimethylethyl)oxy]carbonyl}amino)butanoic acid from for example Bachem UK Ltd, N-{[(1,1-dimethylethyl)oxy]carbonyl}-D-isovaline from for example Nagase & Co Ltd. N-protected amino acids of formula (V) can also be prepared from compounds of formula (VI) for example with Boc-anhydride in presence of a base e.g. aqueous NaHCO$_3$, aqueous sodium hydroxide in a solvent such as THF, methanol, dioxane. Many descriptions are available in the literature (for example Tetrahedron, 2006, 62(42), 9966-9972)

Scheme 3

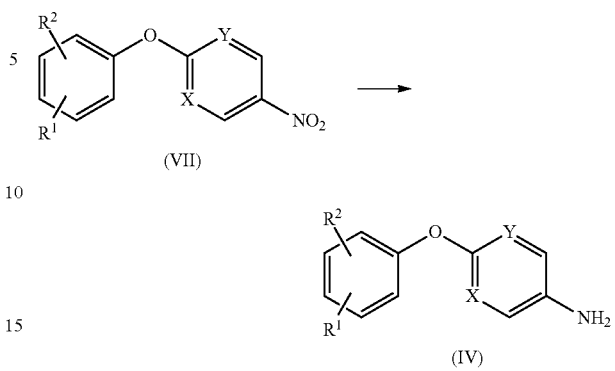

Some anilines (IV) are commercially available, e.g. 4-{[3-(methyloxy)phenyl]oxy}aniline for example from ChemBridge Corporation.

Other anilines can be prepared from the nitro compounds (VII). Suitable reactions conditions to transform (VII) into (IV) are for example:

reduction in presence of Fe powder and ammonium chloride in a solvent such as ethanol or a mixture THF/water with heating or not reduction in presence of Zn powder and ammonium chloride in a solvent such as ethanol or a mixture THF/water with heating or not reduction with tin chloride hydrate in a solvent such as ethyl acetate, ethanol with heating for example at reflux Scheme 4

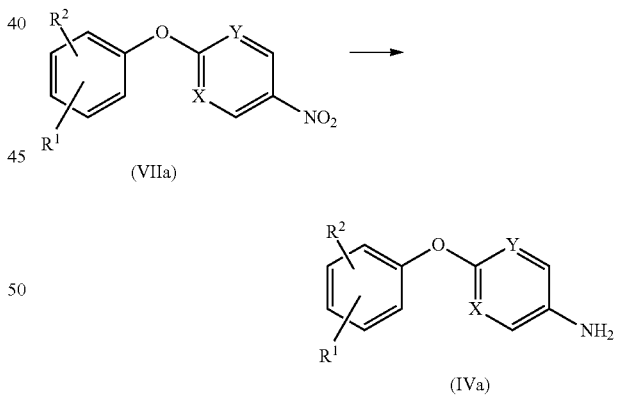

Anilines of formula (IVa), wherein R$^1$ is (C$_{1-4}$ alkyl or C1-4 alkoxy), R$^2$ is (H, C1-4 alkyl or C$_{1-4}$ alkoxy) and (X,Y)≠(N, N) can be prepared from the nitro compounds (VIIa) with the conditions described on scheme 3 or with the following conditions:

hydrogenation with H$_2$ with a catalyst such as Pd/C in a solvent such as methanol, ethanol, THF, a mixture methanol/ethyl acetate with heating or not reduction with hydrazine hydrate and a catalytic amount of Pd/C in a solvent such as ethanol with heating

Scheme 5

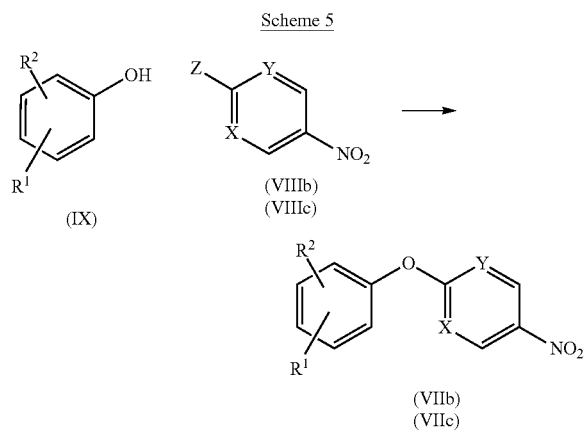

(VIIb), (VIIIb): X = Y = C or (X = C, Y = N) or (X = N, Y = C)
(VIIc), (VIIIc): X = Y = N

Compounds of formula (VIIb) wherein X=Y=C or (X=C, Y=N) or (X=N, Y=C) can be prepared by nucleophilic aromatic substitution. In this reaction are used a nitro derivative of formula (VIIIb) wherein Z=F (usually when [X=C, Y=C]) or Z=Cl (usually when [X=N, Y=C] or [X=C, Y=N]) and a phenol of formula (IX) in presence of a base in a solvent such as

- potassium carbonate e.g. in N,N-dimethylformamide or in acetonitrile with regular heating or microwave one
- potassium tertiary-butoxide e.g. in DMSO,
- sodium hydride e.g. in N,N-dimethylformamide with a regular heating e.g. at reflux or with a microwave irradiation. Optionally, before addition of the nitro derivative (VIII), the phenol (IX) can be pre-stirred in presence of the solvent and the base.

Compounds of formula (VIIc) wherein X=Y=N can be prepared by nucleophilic aromatic substitution from phenol (IX) and nitro compound (VIIIc) wherein usually Z=Cl. The base use is for example

- potassium carbonate e.g. in N,N-dimethylformamide or acetonitrile at room temperature
- triethylamine e.g. in acetonitrile at reflux

Scheme 6

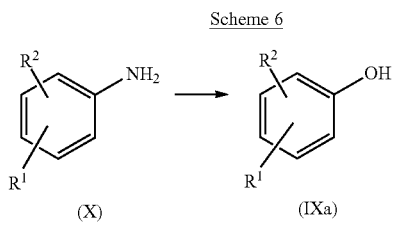

Phenols of formula (IXa), wherein $R^1$ and $R^2$ are groups compatible with typical nitrosation conditions, can be prepared using the corresponding anilines (X) with sodium nitrite in presence of an excess of acid such as sulphuric acid in a solvent such as water, at 0° C. or 0° C.-50° C. in a first time and under heating in a second time e.g. at 40° C.-90° C.

Scheme 7

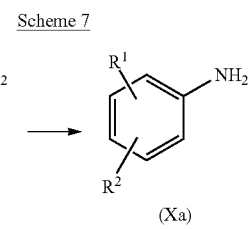

Anilines of formula (Xa) (wherein $R^1$ and $R^2$ are groups non sensitive to typical nitrosation conditions) can be prepared from the nitro derivatives of formula (XI) (wherein $R^1$ and $R^2$ are groups non sensitive to typical nitrosation conditions) using usual reduction conditions for example

- hydrogenation with H2 in a solvent, such as methanol in presence of a metal catalyst such as Raney Nickel or Pd/C typically at room temperature.
- reduction in presence of Fe powder and ammonium chloride in a solvent such as a mixture THF water or ethanol for example at room temperature.

Scheme 8

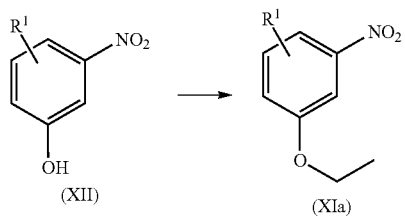

Some nitro derivatives of formula (XI) are commercially available.

Some other nitro derivatives such as the compound of formula (XIa) wherein $R^2$ is an ethoxy group can be prepared from the corresponding nitro-phenol derivative of formula (XII) by alkylation with for example ethyl iodide in presence of a base such as potassium carbonate in acetone with heating e.g. at reflux.

Scheme 9

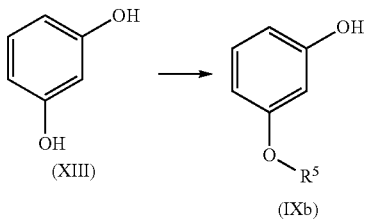

Phenols of formula (IXb), wherein $R^1$ is H and $R^2$ is a $C_{1-4}$ alkoxy group ($R^5$ is a $C_{1-4}$ alkyl group) can be prepared by monoalkylation from the compounds of formula (XIII) using for example the suitable iodo-alkyl in presence of a base such as potassium hydroxide in a solvent such as ethanol.

Scheme 10

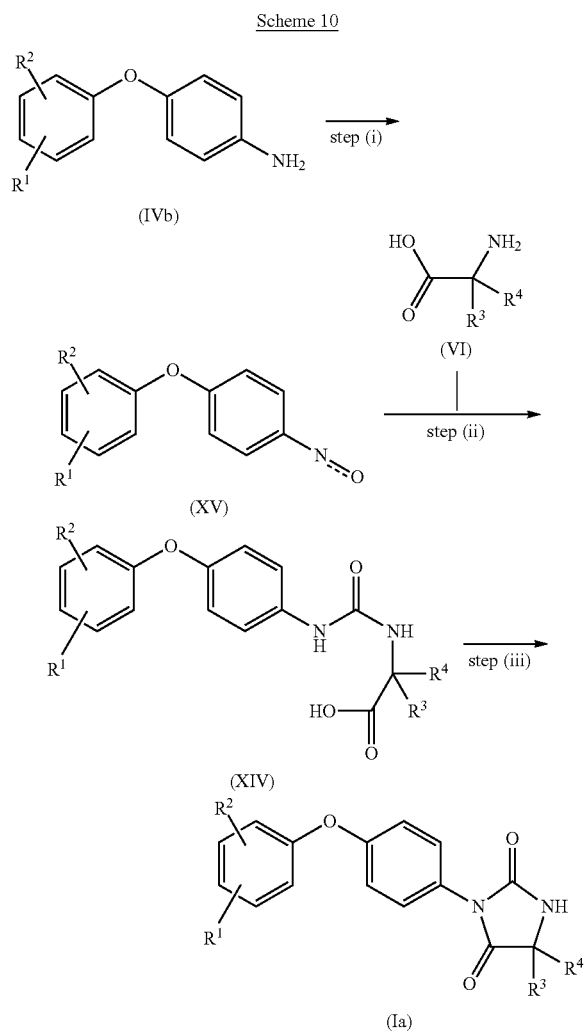

Step (iii):
Compounds of formula (Ia), corresponding to compounds of formula (I) wherein X=C, Y=C can be prepared from compounds of formula (XIV) by heating e.g. at 100° C. in aqueous HCl.

Step (ii):
Compounds of formula (XIV) can be prepared from isocyanates of formula (XV) wherein X=C, Y=C by addition of aminoacids of formula (VI) in presence of a base e.g. DIPEA in a solvent e.g. THF for example at room temperature.

Step (i):
Some isocyanates of formula (XV) are commercially available, other ones can be prepared from anilines of formula (IVb) using triphosgene and optionally triethylamine in a solvent such as dichloromethane at room temperature. Anilines (IVb) corresponding to anilines of formula (IV) with X=C, Y=C can be prepared with similar conditions to the ones described previously.

Optionally the two steps (ii) and (iii) can be performed in a one pot fashion; in a first time, an addition of isocyanates (XV) over aminoacides of formula (VI) in presence of a base e.g. pyridine or trietylamine in a solvent e.g. N,N-dimethylformamide or a mixture dichloromethane/DMF (e.g. at 35° C.), then in a second time addition of HCl with heating (e.g. at 100° C.). Isocyanates can be prediluted in a solvent or not e.g. in THF.

Scheme 11

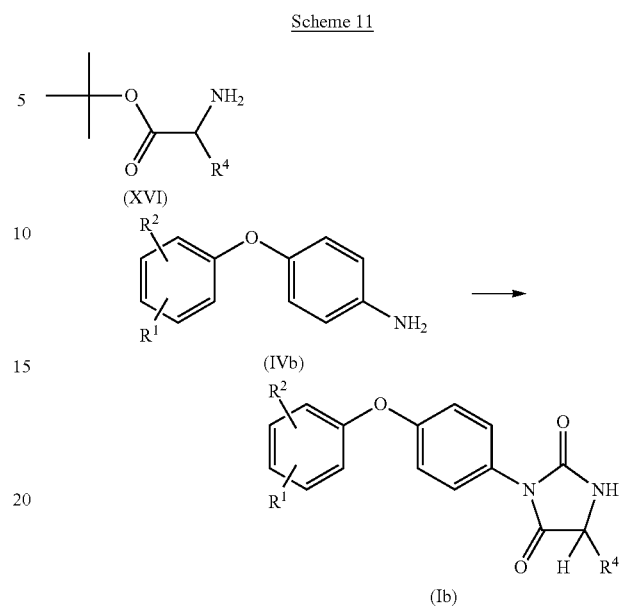

Compounds of formula (Ib) corresponding to compounds of formula (I) wherein X=C, Y=C and R$^3$=H can be prepared from anilines (IVb) [corresponding to anilines of formula (IV) wherein X=C, Y=C] in a one pot protocol.

In a first time, amino ester of formula (XVI) can be N-protected by a Boc group by reaction with Boc-anhydride in presence of a base e.g. DMAP in a solvent e.g. dichloromethane.

In a second time, this solution can react with anilines (IVb) with heating e.g. at 35° C. and in a third time the cyclization can be promoted by addition of HCl and heating e.g. at 100° C.

Scheme 12

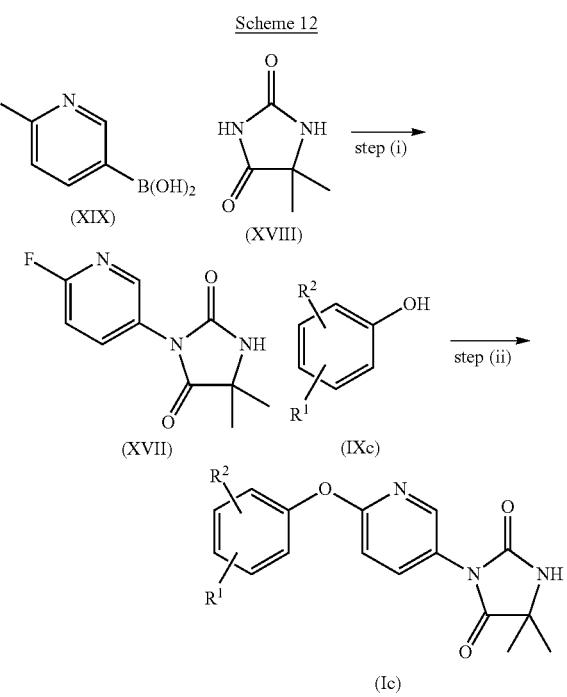

Step (ii):

A nucleophilic substitution can be used to prepare compounds of formula (Ic) corresponding to compounds of formula (I) wherein X=N, Y=C R$^3$=R$^4$=Me and (R$^1$, R$^2$) are combinations of groups such as for example (p-CN, m-iPr), (H, m-OCF$_3$), (p-F, m-CH$_3$), (p-F, o-CH$_3$), (p-CN, m-Cl), (p-CN, o-Et), (p-Me, m-OCF$_3$), (p-CN, m-OMe). This reaction uses the corresponding phenol of formula (IXc), a fluoro compound of formula (XVII) in presence of a base e.g. potassium carbonate heating e.g. at 120° C. in a high boiling point solvent e.g. DMF.

Step (i):

Fluoro compound of formula (XVII) can be prepared by N-arylation of 5,5-dimethyl-2,4-imidazolidinedione (XVIII) with the arylboronic acid (XIX), promoted for example by copper (II) acetate using a base e.g. pyridine and a solvent such as dichloromethane e.g. at room temperature, open to air.

Step (ii):

Compounds of formula (Id) corresponding to compounds of formula (I) wherein X=N, Y=C or X=C, Y=C or X=N, Y=N and R$^3$=R$^4$=Me can be prepared from ureas of formula (XXa) by cyclization in presence of a base e.g. sodium methoxide heating e.g. at 65° C. in solvent such as methanol.

Step (i):

Ureas of formula (XXa) can be prepared by addition of a solution containing an aniline of formula (IVc) (corresponding to anilines of formula IV wherein X=N, Y=C or X=C, Y=C or X=N, Y=N) and a base such as triethylamine in a solvent such as EtOAc to a solution of a carbonylating agent such as triphosgene in a solvent such as EtOAc e.g. at 0° C., followed by addition of triethylamine and ester (XXIa).

Optionally, the ester (XXIa) can be pre-dissolved in a solvent such as EtOAc, the triethylamine being added to this pre-solution. Optionally some additional triethylamine and ester (XXIa) or some additional triphosgene can be added. The needed ester (XXIa) can be prepared from the corresponding aminoacid, using methanol, heating the reaction mixture e.g. at reflux, after thionyl chloride addition.

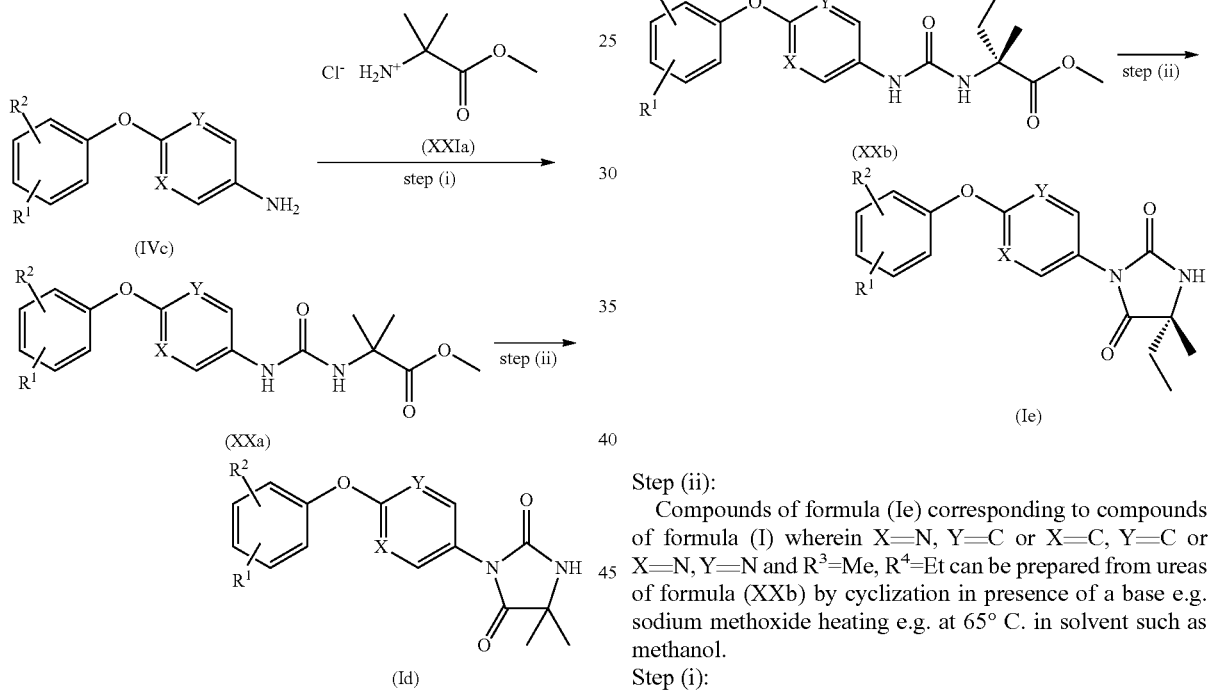

Scheme 14

Step (ii):

Compounds of formula (Ie) corresponding to compounds of formula (I) wherein X=N, Y=C or X=C, Y=C or X=N, Y=N and R$^3$=Me, R$^4$=Et can be prepared from ureas of formula (XXb) by cyclization in presence of a base e.g. sodium methoxide heating e.g. at 65° C. in solvent such as methanol.

Step (i):

Ureas of formula (XXb) can be prepared by addition of a solution containing an aniline of formula (IVc) (corresponding to anilines of formula IV wherein X=N, Y=C or X=C, Y=C or X=N, Y=N) and a base such as triethylamine or diisopropylethylamine in a solvent such as EtOAc or dichloromethane to a solution of a carbonylating agent such as triphosgene in a solvent such as EtOAc or dichloromethane e.g. at 0° C., followed by addition of triethylamine or diisopropylethylamine and ester (XXIb). Optionally, the ester (XXIb) can be pre-dissolved in a solvent such as EtOAc or dichloromethane, the triethylamine or diisopropylethylamine being added to this pre-solution. Optionally some additional triethylamine or diisopropylethylamine and ester (XXIb) or some additional triphosgene can be added. The needed ester (XXIb) can be prepared from the corresponding aminoacid, using methanol, heating the reaction mixture e.g. at reflux, after thionyl chloride addition.

Scheme 15

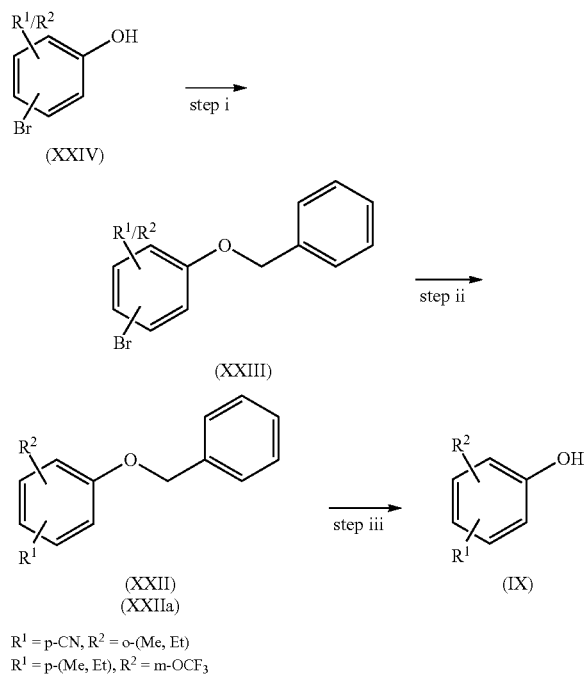

R¹ = p-CN, R² = o-(Me, Et)
R¹ = p-(Me, Et), R² = m-OCF₃

Step (iii):

Phenols of formula (IX) can be prepared from compounds of formula (XXII) by removal of the benzyl group for example in presence of hydrogen (e.g. P=1 atm) with a catalyst such as Pd/C in a solvent such as methanol, a mixture of ethylacetate/ethanol etc.

Step (ii):

Compounds of formula (XXIIa) corresponding to compounds of formula (XXII) wherein [R¹; R²] are for example [(p-CN; o-Me or o-Et) or (p-Me or p-Et; m-OCF₃)] can be prepared by Negishi coupling using the suitable pre-formed organozinc intermediate in solution (e.g. in THF) then Pd(tBu₃P)₂ and the corresponding bromo compound (XXIII) in a solvent such as THF. The organozinc intermediate can be prepared by addition of a solution of zinc dichloride on the suitable alkyl magnesium bromide solution or by reverse addition of the alkyl magnesium bromide solution on the zinc dichloride solution e.g. at −15° C., 0° C. or r.t. in solvents such as THF, diethyl ether. A solution of the bromo compound (XXIII) e.g. in THF can be added e.g. at 0° C. to the organozinc intermediate or reversely the organozinc intermediate solution can be added to a solution of the bromo compound (XXIII) pre-warmed e.g. at 60° C. Optionally some additional Pd(tBu₃P)₂ or some additionnal pre-formed organozinc intermediate can be added.

Step (i):

Bromo compound of formula (XXIII) can be prepared from compounds of formula (XXIV) by benzylation with benzylhalide e.g. benzyl bromide in presence of a base e.g. potassium carbonate, in a solvent such as acetone heating e.g. at 50° C.

Scheme 16

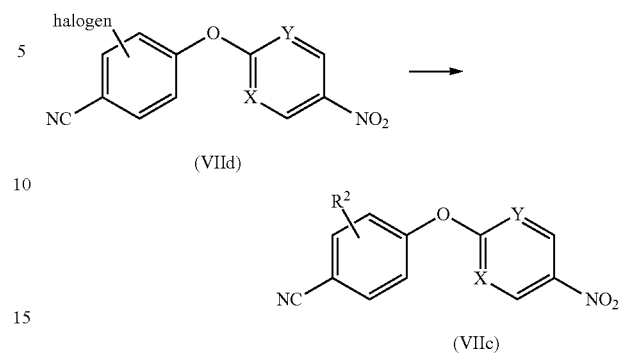

Compounds of formula (VIIc) [corresponding to compounds of formula (VII) wherein X=N, Y=C or X=N, Y=N, R¹=CN and R²=meta- or ortho-(Me, Et or cyclopropyl)] can be prepared by Negishi coupling using the suitable pre-formed organozinc intermediate in solution (e.g. in THF) then Pd(tBu₃P)₂ and the corresponding halo compounds (VIIId) [corresponding to compounds of formula (VII) wherein R¹=CN and R²=meta- or ortho-halogen such as bromine and iodine)] in a solvent such as THF. The organozinc intermediate can be prepared by addition of a solution of zinc dichloride on the suitable alkyl magnesium bromide solution or by reverse addition of the alkyl magnesium bromide solution on the zinc dichloride solution e.g. at −15° C., 0° C. or room temperature in solvents such as THF, diethyl ether. A solution of the halo compound (VIIId) e.g. in THF can be added e.g. at 0° C. to the organozinc intermediate or reversely the organozinc intermediate solution can be added to a solution of the halo compound (VIId) pre-warmed e.g. at 60° C. Optionally some additional Pd(tBu₃P)₂ or some additionnal pre-formed organozinc intermediate can be added.

Scheme 17

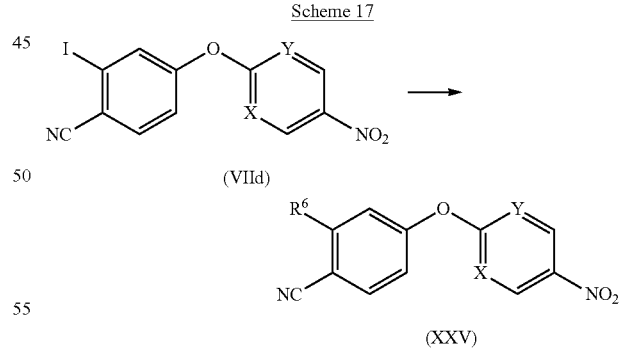

Compounds of formula (XXV) wherein X=N, Y=C, R¹=para-CN and R⁵=meta-(cyclopropyl), meta-isopropenyl] can be prepared by Suzuki coupling using the corresponding boronic acid or boronic ester, a base such as potassium triphosphate, a system containing a palladium catalyst and a ligand such as (Pd(OAc)₂/PCy₃) or (Pd(tBu₃)₂, in a solvent such as DMF, a mixture (toluene/water) etc heating e.g. at 110° C. optionally under microwave irradiation.

Scheme 18

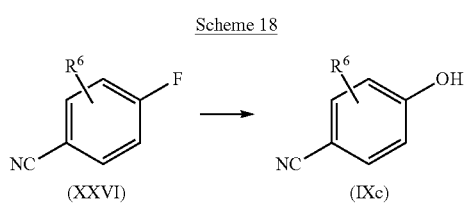

Phenol of formula (IXc) [corresponding to compound of formula (IX) wherein $R^1$=para-CN and $R^6$=meta-I or ortho-Me]can be prepared from fluoroaromatics of formula (XXVI), using potassium trimethylsilanolate and heating e.g. at a temperature ranging from r.t. to 70° C. in a solvent such as acetonitrile.

Scheme 19

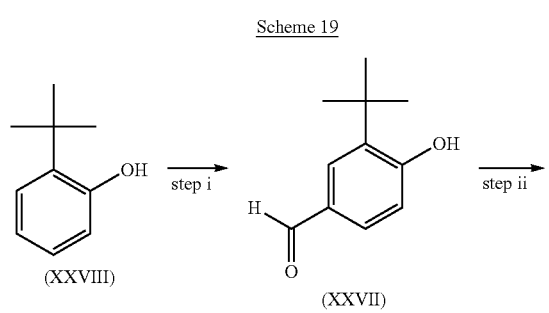

Step ii:

Phenol of formula (IXd) [corresponding to compound of formula (IX) wherein $R^1$=para-CN and $R^2$=ortho-tBu]can be prepared from compounds of formula (XXVII) using hydroxylamine hydrochloride in acetic acid, heating e.g. at reflux.

Step i:

Compound of formula (XXVII) can be prepared by a Reimer-Tiemann formylation starting from compound of formula (XXVIII) in a solvent such as a mixture MeOH/water, using an hydroxide base such as sodium hydroxide in water, heating e.g. at 60° C. and adding chloroform.

Scheme 20

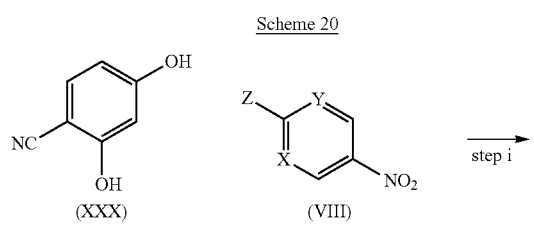

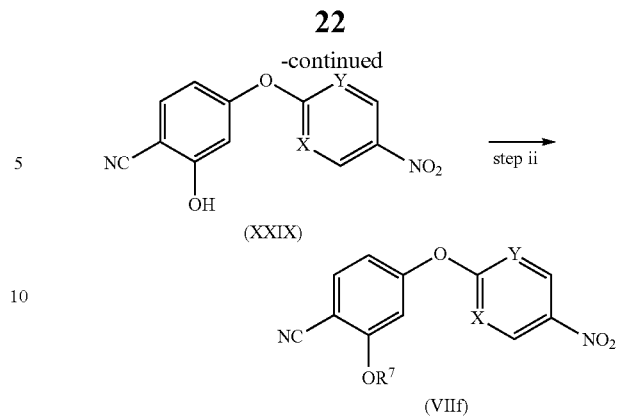

Step ii:

Compounds of formula (VIIf) [corresponding to compounds of formula (VII) wherein X=C, Y=N or X=C, Y=C and $R^1$=para-CN and $R^2$=$OR^7$ with $R^7$=$C_{1-4}$alkyl] can be prepared from compounds of formula (XXIX) using as alkylating agent a suitable halo derivative, a base such as potassium carbonate in a solvent such as DMF e.g. at temperature ranging from r.t. to 60°

Step i:

Compounds of formula (XXIX) can be prepared from compounds of formula (XXX) and electrophiles (VIII), wherein Z=F or Cl in a similar manner to the one described in scheme 5.

Scheme 21

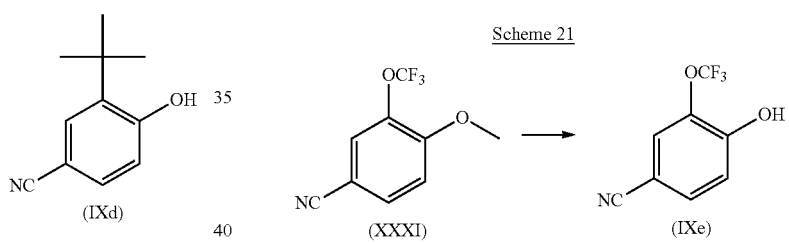

Phenol of formula (IXe) can be prepared from compound of formula (XXXI), using a demethylating agent such a $BBr_3$, in a solvent such as dichlorometane or dichloroethane at a suitable temperature ranging from r.t. to 100° C. optionally under microwave irradiation.

Scheme 22

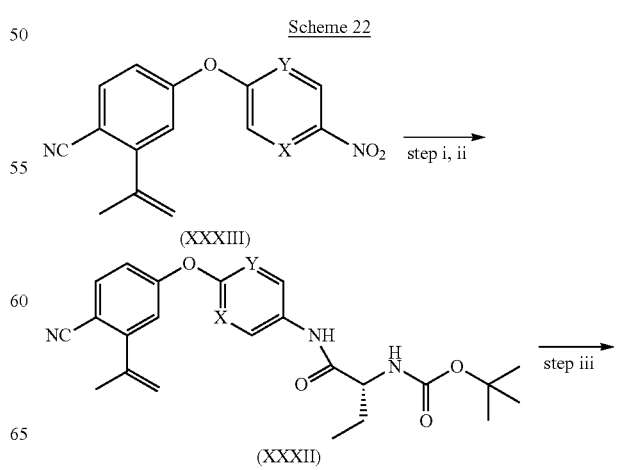

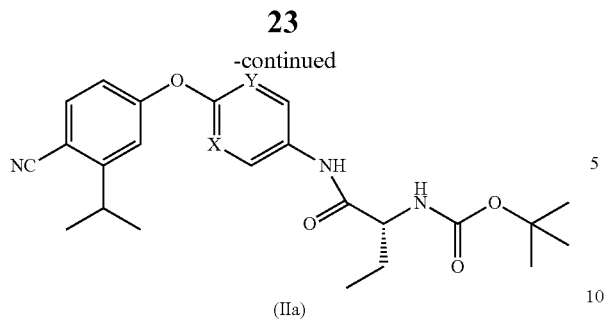

(IIa)

(Ie)

Step iii:

Compounds of formula (IIIa) [corresponding to compounds of formula (III) wherein X=C, Y=N and $R^1$=para-CN and $R^2$=iPr] can be prepared from compounds of formula (XXXII) by reduction with hydrogen (P=1 atm) in presence of a catalyst such as Pd/C, in a solvent such as methanol.

Step ii, i:

Compounds of formula (XXXII) can be prepared in 2 steps from nitro compounds of formula (XXXIII) using a similar way to the one described on schemes 3, 2 (e.g. reduction with Fe/ammonium chloride and coupling).

Scheme 23

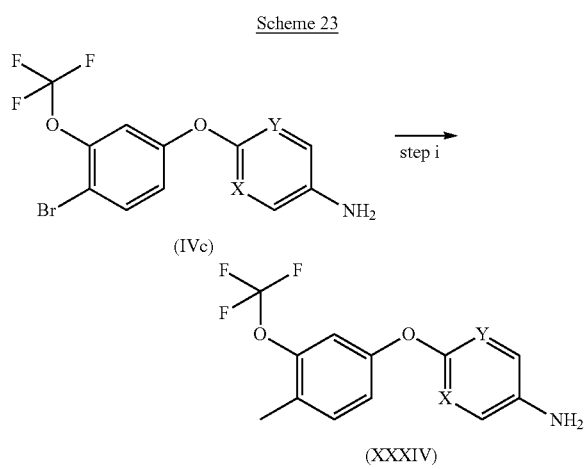

(IVc)

(XXXIV)

Step i:

Compounds of formula (XXXIV) wherein X=N, Y=N can be prepared by Suzuki coupling using the methyl boronic acid, a base such as potassium triphosphate, a system containing a palladium catalyst and a ligand such as (Pd(OAc)$_2$/PCy$_3$) or (Pd(tBu$_3$)$_2$) in a solvent such as DMF heating e.g. at 110° C. optionally under microwave irradiation.

Scheme 24

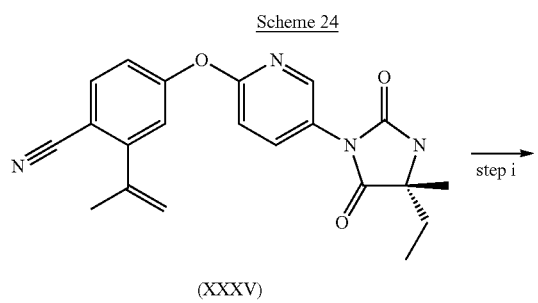

(XXXV)

Step i:

Compounds of formula (Ie) can be prepared from compounds of formula (XXXV) by reduction with hydrogen (P=1 atm) in presence of a catalyst such as Pd/C, in a solvent such as methanol.

The present invention provides compounds of formula (I) or a pharmaceutically acceptable salt thereof for use in therapy.

The compounds of formula (I) or their pharmaceutically acceptable salts may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv 3.1 and Kv3.2 is a compound which alters the properties of these channels, either positively or negatively.

Diseases or conditions that may be mediated by modulation of Kv3.1 and/or Kv3.1 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

The compounds of formula (I) or their pharmaceutically acceptable salts may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts may be of use for the treatment or prophylaxis of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

The compounds of formula (I) or their pharmaceutically acceptable salts may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

The compounds of formula (I) or their pharmaceutically acceptable salts may be of use for the treatment or prophylaxis of enhancement of cognition including the treatment of cognition impairment in other diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

The compounds of formula (I) or their pharmaceutically acceptable salts may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

The compounds of formula (I) or their pharmaceutically acceptable salts may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

The compounds of formula (I) or their pharmaceutically acceptable salts may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts may be of use for the treatment or prophylaxis of Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts may be of use for the treatment or prophylaxis of hearing disorders including auditory neuropathy, auditory processing disorder, hearing loss, which includes sudden hearing loss, noise induced hearing loss, substance-induced hearing loss, and hearing loss in adults over 60 (presbycusis), and tinnitus.

The compounds of formula (I) or their pharmaceutically acceptable salts may be of use for the treatment or prophylaxis of Ménière's disease, disorders of balance, and disorders of the inner ear.

The compounds of formula (I) or their pharmaceutically acceptable salts may be of use for the treatment or prophylaxis of hyperacusis and disturbances of loudness perception, including Fragile-X syndrome and autism.

The compounds of formula (I) or their pharmaceutically acceptable salts may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomalies associated with seizures or epilepsy such as Partial monosomy (15Q)/Angelman syndrome) and the like.

In one embodiment of the invention, there is provided a compound of formula (I) or a pharmaceutically acceptable salt thereof for the treatment or prophylaxis of depression and mood disorders, hearing disorders, schizopherenea, substance abuse disorders, sleep disorders or epilepsy.

In one embodiment of the invention, there is provided a compound of formula (I) or a pharmaceutically acceptable salt thereof for the treatment or prophylaxis of bipolar disorder or mania.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

The invention also provides a method of treating or preventing a disease or disorder where a modulator of Kv3 is required, for example those diseases and disorders mentioned hereinabove, which comprises administering to a subject in need thereof an effective amount of a compound of formula (I) or a pharmaceutically acceptable salt thereof.

The invention also provides a compound of formula (I), or a pharmaceutically acceptable salt thereof, for use in the treatment or prophylaxis of a disease or disorder where a modulator of Kv3 is required, for example those diseases and disorders mentioned hereinabove.

The invention also provides the use of a compound of formula (I), or a pharmaceutically acceptable salt thereof, in the manufacture of a medicament for the treatment or prophylaxis of a disease or disorder where a modulator of Kv3 is required, for example those diseases and disorders mentioned hereinabove.

The invention also provides a method of treating depression and mood disorders, schizopherenea, substance abuse disorders, sleep disorders or epilepsy, for example for those indications mentioned hereinabove, which comprises administering to a subject in need thereof an effective amount of a Kv3 modulator or a pharmaceutically acceptable salt thereof.

For use in therapy the compounds of the invention are usually administered as a pharmaceutical composition. The invention also provides a pharmaceutical composition comprising a compound of formula (I), or a pharmaceutically acceptable salt thereof, and a pharmaceutically acceptable carrier.

The compounds of formula (I) or their pharmaceutically acceptable salts may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable derivative thereof together with a further therapeutic agent or agents.

When the compounds are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The present invention also provides Kv3 modulators, or their pharmaceutically acceptable salts, for use in the treatment or prophylaxis of depression and mood disorders, hearing disorders, schizopherenea, substance abuse disorders, sleep disorders or epilepsy.

In particular Kv3 modulators or their pharmaceutically acceptable salts may be particularly useful in the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90), Seasonal affective disorder The invention also provides a method of treating depression and mood disorders, hearing disorders, schizopherenea, substance abuse disorders, sleep disorders or epilepsy, including for example those disorders mentioned hereinabove, which comprises administering to a subject in need thereof an effective amount of Kv3 modulator or a pharmaceutically acceptable salt thereof.

The invention also provides a Kv3 modulator, or a pharmaceutically acceptable salt thereof, for use in the treatment or prophylaxis of depression and mood disorders, hearing disorders, schizopherenea, substance abuse disorders, sleep disorders or epilepsy, including for example those disorders mentioned hereinabove.

The invention also provides the use of a Kv3 modulator, or a pharmaceutically acceptable salt thereof, in the manufacture of a medicament for the treatment or prophylaxis of depression and mood disorders, hearing disorders, schizopherenea, substance abuse disorders, sleep disorders or epilepsy, including for example those disorders mentioned hereinabove.

For use in therapy the Kv3 modulators are usually administered as a pharmaceutical composition for example a composition comprising a Kv3 modulator or a pharmaceutically acceptable salt thereof, and a pharmaceutically acceptable carrier. Examples of such compositions, and methods of administration thereof, which compositions comprise a compound of formula (I) or a pharmaceutically acceptable salt thereof, are described hereinabove. Such compositions and methods of administration may also be used for other Kv3 modulators or pharmaceutically acceptable salts thereof, in the treatment of depression and mood disorders, hearing disorders, schizopherenea, substance abuse disorders, sleep disorders or epilepsy, including for example those disorders mentioned hereinabove.

All publications, including but not limited to patents and patent applications, cited in this specification are herein incorporated by reference as if each individual publication were specifically and individually indicated to be incorporated by reference herein as though fully set forth.

BRIEF DESCRIPTION OF THE DRAWINGS

The present invention is illustrated, by way of example only, with reference to the following figures in which:

FIG. 1a hKv3.2 currents recorded using the assay described in Example 89. Data shown are the individual currents over the period of the depolarising voltage step to −15 mV recorded from 4 different cells at two concentrations of the compound of Example 19. The data are fitted by a single exponential curve (solid lines) using the fitting procedure in Prism version 5 (Graphpad Software Inc).

FIG. 1b hKv3.2 currents recorded using the assay described in Example 89. Data shown are the individual currents over the period of the depolarising voltage step to −15 mV recorded from 2 different cells at two concentrations of compound of Example 71. The data are fitted by a single exponential curve (solid lines) using the fitting procedure in Prism version 5 (Graphpad Software Inc).

EXPERIMENTAL

Figure 2:
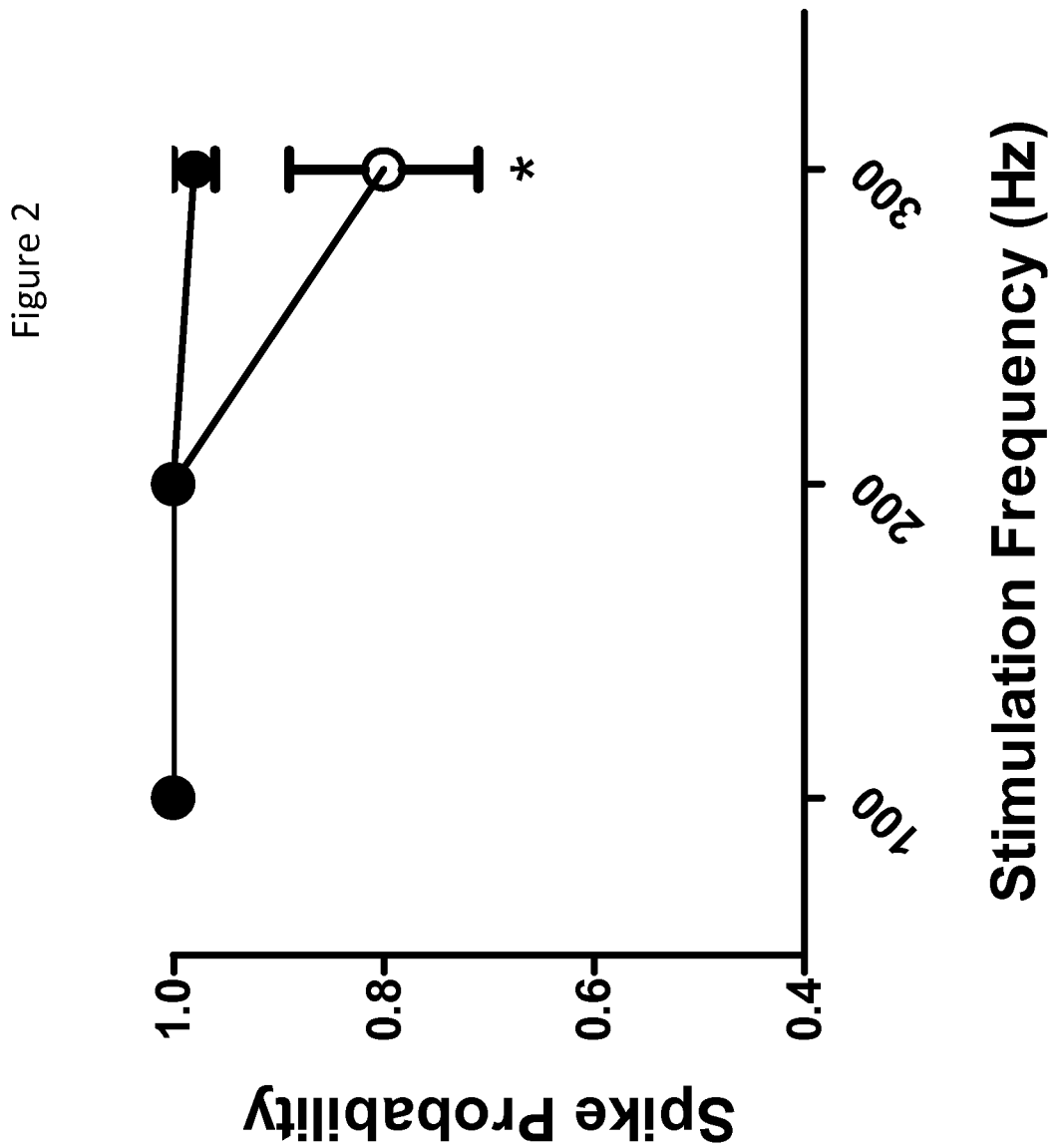
FIG. 2 Recordings made from identified "fast-firing" interneurons in the somatosensory cortex of the mouse.

The invention is illustrated by the Compounds described below. In the procedures that follow, after each starting material, reference to a description is typically provided. This is provided merely for assistance to the skilled chemist. The starting material may not necessarily have been prepared from the Description referred to.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 30° C.

Direct infusion Mass spectra (MS) were run on an Agilent 1100 Series LC/MSD Mass Spectrometer, operating in ES (+) and ES (−) ionization mode [ES (+): Mass range: 100-1000 amu. Infusion solvent: water+0.1% HCO2H/CH3CN 50/50. ES (−): Mass range: 100-1000 amu. Infusion solvent: water+0.05% NH4OH/CH3CN 50/50]. The use of this methodology is indicated by "MS_1 (ESI)" in the analytic characterization of the described compounds. Alternatively, Mass spectra (MS) were run on a mass spectrometer, operating in ES (+) and ES (−) ionization mode coupled with an HPLC instrument Agilent 1100 Series [LC/MS-ESI(+) analyses were performed on a Supelcosil ABZ+Plus (33×4.6 mm, 3 μm) (mobile phase: from 10%[$CH_3CN$+0.05% TFA] to 90% [$CH_3CN$+0.05% TFA] and 10% [water] in 2.2 min, under these conditions for 2.8 min. T=45° C., flux=0.9 mL/min)]. The use of this methodology is indicated by "MS_2 (ESI)" in the analytic characterization of the described compounds.

HPLC-Mass spectra (HPLC-MS) were taken on an Agilent 1100 Series LC/MSD Mass Spectrometer coupled with HPLC instrument Agilent 1100 Series, operating in positive or negative electrospray ionization mode and in both acidic and basic gradient conditions.

Acidic Gradient:

LC/MS-ES (+ or −) analyses were performed on a Supelcosil ABZ+Plus column (33×4.6 mm, 3 μm). Mobile phase: A: (water+0.1% HCO2H)/B: CH3CN. Gradient (standard method): t=0 min 0% (B), from 0% (B) to 95% (B) in 5 min lasting for 1.5 min, from 95% (B) to 0% (B) in 0.1 min, stop time 8.5 min. Column T=r.t. Flow rate=1 ml/min. The use of this methodology is indicated by "LC-MS_A" in the analytic characterization of the described compounds.

Ultra Performance Liquid Chromatography with an Acidic Gradient:

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS-ES (+ or −): analyses were performed using an Acquity™ UPLC BEH C18 column (50×2.1 mm, 1.7 μm particle size).

General Method:

Mobile phase: A: (water+0.1% HCO2H)/B: (CH3CN+0.06% HCO2H). Gradient: t=0 min 3% (B), t=0.05 min 6% (B), t=0.57 min 70% (B), t=1.06 min 99% (B) lasting for 0.389 min, t=1.45 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC" in the analytic characterization of the described compounds.

$1^{st}$ Focussed Method: Mobile phase: A: (water+0.1% HCO2H)/B: (CH3CN+0.1% HCO2H). Gradient: t=0 min 3% (B), t=1.06 min 99% (B), t=1.45 min 99% (B), t=1.46 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_s" in the analytic characterization of the described compounds.

$2^{nd}$ Focussed Method:

Mobile phase: A: (water+0.1% HCO2H)/B: (CH3CN+0.1% HCO2H). Gradient: t=0 min 3% (B), t=1.5 min 100% (B), t=1.9 min 100% (B), t=2 min 3% (B), stop time 2 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_ipqc" in the analytic characterization of the described compounds.

Ultra Performance Liquid Chromatography with a Basic Gradient:

Total ion current (TIC) and DAD UV chromatographic traces together with MS and UV spectra associated with the peaks were taken on a UPLC/MS Acquity™ system equipped with PDA detector and coupled to a Waters SQD mass spectrometer operating in positive and negative alternate electrospray ionisation mode [LC/MS-ES+/−: analyses were performed using an Acquity™ UPLC BEH C18 column (50×2.1 mm, 1.7 μm particle size). Mobile phase: A: (10 mM aqueous solution of NH4HCO3 (adjusted to pH 10 with ammonia))/B: CH3CN. Gradient: t=0 min 3% (B), t=1.06 min 99% (B) lasting for 0.39 min, t=1.46 min 3% (B), stop time 1.5 min. Column T=40° C. Flow rate=1.0 mL/min. Mass range: ES (+): 100-1000 amu. ES (−): 100-1000 amu. UV detection range: 220-350 nm. The use of this methodology is indicated by "UPLC_B" in the analytic characterization of the described compounds.

For reactions involving microwave irradiation, a Personal Chemistry Emrys™ Optimizer was used or a Biotage Initiator In a number of preparations, purification was performed using Biotage manual flash chromatography (Flash+), Biotage automatic flash chromatography (Horizon, SP1 and SP4), Companion CombiFlash (ISCO) automatic flash chromatography, Flash Master Personal or Vac Master systems.

Flash chromatographies were carried out on silica gel 230-400 mesh (supplied by Merck AG Darmstadt, Germany) or on silica gel 300-400 mesh (supplied by Sinopharm Chemical Reagent Co., Ltd.), Varian Mega Be—Si pre-packed cartridges, pre-packed Biotage silica cartridges (e.g. Biotage SNAP cartridge), KP-NH prepacked flash cartridges, ISOLUTE $NH_2$ prepacked cartridges or ISCO RediSep Silica cartridges.

SPE-Si cartridges are silica solid phase extraction columns supplied by Varian.

In a number of preparations, purification was performed on a Mass-Directed Autopurification (MDAP) system Fractionlynx™ equipped with Waters 2996 PDA detector and coupled with ZQ™ mass spectrometer (Waters) operating in positive and negative electrospray ionisation mode ES+, ES− (mass range 100-1000 or 100-900)

A set of semi-preparative gradients have been used:
Method A: Chromatographic Basic Conditions
Column: XTerra Prep MS C18 OBD (150 mm×30 mm 10 μm particle size) at room temperature
Mobile phase: A: (water+10 mM aqueous solution of ammonium bicarbonate (adjusted to
pH 10 with ammonia)), B: acetonitrile
Flow rate: 40 ml/min
Gradient: 10% (B) for 0.5 min, from 10% (B) to 95% (B) in 12.5 min, from 95% (B) to 100% (B) in 3 min
Method B: Chromatographic Basic Conditions
Column: XTerra Prep MS C18 OBD (150 mm×30 mm 10 μm particle size) at room temperature
Mobile phase: A: water+10 mM aqueous solution of ammonium bicarbonate (adjusted to pH 10 with ammonia), B: acetonitrile
Flow rate: 40 ml/min Gradient: from 20% to 25% (B) in 1 min, from 25% (B) to 65% (B) in 12 min, from 65% (B) to 100% (B) in 0.5 min Method C: Chromatographic Basic Conditions
Column: Waters Xbridge C18 OBD (50 mm×19 mm 5 μm particle size) at room temperature
Mobile phase: A: water+10 mM aqueous solution of ammonium bicarbonate (adjusted to pH 10 with ammonia), B: acetonitrile
Flow rate: 17 ml/min
Gradient: from 20% (B) to 25% (B) in 1 min, from 25% (B) to 55% (B) in 9 min, from 55% (B) to 100% (B) in 2 min, return to 20% (B) in 0.1 min Method D: Chromatographic Acidic Conditions
Column: Waters Xbridge C18 OBD (50 mm×19 mm 5 μm particle size) at room temperature
Mobile phase: A: (water+0.1% formic acid in water); B: acetonitrile
Flow rate: 17 ml/min
Gradient: from 20% (B) to 25% B in 1 min, from 25% (B) to 55% (B) in 9 min, from 55% (B) to 100% (B) in 2 min, return to 20% (B) in 0.1 min Method E: Chromatographic Basic Conditions
Column: Waters Xbridge C18 OBD (50 mm×19 mm 5 μm particle size) at room temperature
Mobile phase: A: (water+10 mM aqueous solution of ammonium bicarbonate (adjusted to pH 10 with ammonia)), B: acetonitrile
Flow rate: 17 ml/min
Gradient: from 10% (B) to 15% (B) in 1 min, from 15% (B) to 70% (B) in 7 min, from 70% (B) to 100% (B) in 1 min, 100% (B) for 2 min, return to 10% (B) in 0.1 min Method F: Chromatographic Basic Conditions
Column: Phenomenex Gemini AXIA C18 (50×21.2 mm 5 μm particle size)
Mobile phase: A: water+10 mM aqueous solution of ammonium bicarbonate (adjusted to pH 10 with ammonia), B: acetonitrile
Flow rate: 17 ml/min
Gradient: from 10% (B) to 15% (B) in 1 min, from 15% (B) to 65% (B) in 8 min, from 65% (B) to 100% (B) in 1 min, return to 10% (B) in 1 min.

Method G: Chromatographic Basic Conditions
Column: Phenomenex Gemini AXIA C18 (50×21.2 mm 5 μm particle size)
Mobile phase: A: water+10 mM aqueous solution of ammonium bicarbonate (adjusted to pH 10 with ammonia), B: acetonitrile
Flow rate: 17 ml/min
Gradient: from 10% (B) to 15% (B) in 1 min, from 15% (B) to 70% (B) in 7 min, from 70% (B) to 100% (B) in 1 min, 100% (B) during 2 min, return to 10% (B) in 0.1 min.

Method H: Chromatographic Acidic Conditions
Column: Waters Xbridge C18 OBD (100 mm×19 mm 5 μm particle size) at room temperature
Mobile phase: A: (water+0.1% formic acid in water); B: acetonitrile
Flow rate: 17 ml/min
Gradient: 5% (B) during 1 min, from 5% (B) to 90% (B) in 9 min, from 90% (B) to 100% (B) in 0.1 min, 100% (B) during 0.8 min, return to 5% (B) in 0.1 min Method I: Chromatographic Acidic Conditions
Column: Waters Sunfire OBD (100 mm×19 mm, 5 μm particle size) at room temperature
Mobile phase: A: (water+0.1% formic acid in water); B: acetonitrile
Flow rate: 17 ml/min
Gradient: from 30% (B) to 70% (B) in 9 min, from 70% (B) to 100% (B) in 1 min, return to 30% (B) then 30% (B) during 1 min Method J: Chromatographic Acidic Conditions
Column: Waters Sunfire OBD (100 mm×19 mm, 5 μm particle size) at room temperature
Mobile phase: A: (water+0.1% formic acid in water); B: acetonitrile
Flow rate: 17 mL/min
Gradient: 10% (B) during 1 min, from 10% (B) to 95% (B) in 10 min, 95% (B) during 1.5 min, return to 10% (B) in 0.1 min.

SPE-SCX cartridges are ion exchange solid phase extraction columns supplied by Varian. The eluent used with SPE-SCX cartridges is DCM and MeOH or MeCN or MeOH followed by ammonia solution in MeOH (typically 2 N). The collected fractions are those eluted with the ammonia solution in MeOH unless otherwise stated.

ABBREVIATIONS

Boc t-butyloxycarbonyl
$CDCl_3$ deutrated chloroform
$CH3CN$ acetonitrile
$(CH_2O)_n$ paraformaldehyde
cHex cyclohexane
CV column volume
$(Cy)_3P$ Tricyclohexylphosphine
DCM dichloromethane
DIPEA N,N-diisopropylethylamine
DMAP 4-dimethylaminopyridine
DMF N,N-dimethylformamide
DMSO dimethylsulfoxide
DMSO-$d_6$ deutrated dimethylsulfoxide
EDC.HCl N-(3-dimethylaminopropyl)-N'-ethylcarbodiimide hydrochloride
$Et_2O$ diethyl ether
EtOAc ethyl acetate
h hours
$H_2$ gaseous hydrogen
HATU (O-7-azabenzotriazol-1-yl)-N,N,N',N'-tetramethyluroniumhexafluoro phosphate)
HBTU O-benzotriazol-1-yl-tetramethyluronium hexafluoro-phosphate
$HCO2H$ formic acid
HCl hydrogen chloride
$HNO_3$ nitric acid
HOBt.$H_2O$ 1-hydroxybenzyltriazole hydrate
$H_2SO_4$ sulfuric acid
$K_2CO_3$ potassium carbonate
KOH potassium hydroxide
MeCN/$CH_3$CN acetonitrile
MeOH methanol
methanol-$d_4$ deutrated methanol
MDAP mass-directed autopurification
$N_2$ gaseous nitrogen
$NaBH(OAc)_3$ sodium triacethoxyborohydride
$NaHCO_3$ sodium hydrogenocarbonate
$NaNO_2$ sodium nitrite
$Na_2CO_3$ sodium carbonate
NaOH sodium hydroxide
NH4OH ammonium hydroxide
NH4 HCO3H ammonium bicarbonate
NMR Nuclear Magnetic Resonance
Pd/C palladium on charcoal
Pd(OAc)$_2$ Palladium(II) acetate
Pd(tBu$_3$P)$_2$ Palladium (0) bis(Tri-Tert-Butylphosphine)

PE petroleum ether
r.t. room temperature
tBuOK potassium tert-butoxide
TBTU o-Benzotriazol-1-yl-n,n,n',n'-tetramethyluronium tetrafluoroborate
TEA triethylamine
TFA trifluoroacetic acid
THF tetrahydrofuran
TsOH*H$_2$O 4-methylbenzenesulfonic acid hydrate, p-toluenesulfonic acid hydrate

SUPPORTING EXAMPLES AND INTERMEDIATES

Intermediate 1

1,1-dimethylethyl{(1R)-1-methyl-2-[(4-{[3-(methyloxy)phenyl]oxy}phenyl)amino]-2-oxoethyl}carbamate

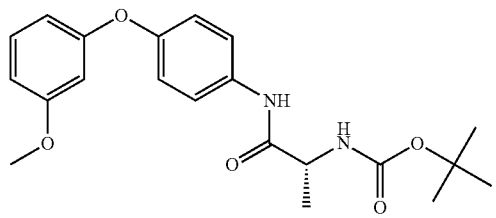 [SMILES: COc1cccc(Oc2ccc(NC(=O)[C@@H](C)NC(=O)OC(C)(C)C)cc2)c1]

To a solution of N-{[(1,1-dimethylethyl)oxy]carbonyl}-D-alanine (250 mg, 1.321 mmol) in dry N,N-dimethylformamide (5 mL), DIPEA (0.346 mL, 1.982 mmol) and then TBTU (467 mg, 1.453 mmol) were added and the reaction mixture was stirred for 15 minutes at room temperature. (4-{[3-(methyloxy)phenyl]oxy}phenyl)amine (313 mg, 1.453 mmol) was then added and the reaction mixture was stirred for 30 minutes at room temperature. The reaction was quenched with brine (10 mL), diluted with water (5 mL) and extracted with diethyl ether (3 times 20 mL). The organic layer was dried over sodium sulphate, filtered and evaporated and the residue was purified by silica gel chromatography (Biotage system, 25 g, SNAP column) using as eluents a gradient cyclohexane/ethyl acetate from 100/0 to 70/30 to afford the title compound (440 mg) as a light yellow gum.

$^1$H-NMR (400 MHz, DMSO-d$_6$) δ ppm: 9.96 (1H, s), 7.62 (2H, m), 7.25 (1H, t), 7.04-7.11 (1H, m), 7.01 (2H, m), 6.68 (1H, dd), 6.44-6.55 (2H, m), 4.04-4.16 (1H, m), 3.70-3.76 (3H, m), 1.29-1.46 (9H, m), 1.19-1.29 (3H, m); UPLC: 0.76 min, 387 [M+H]+.

Intermediate 2

N$^1$-(4-{[3-(methyloxy)phenyl]oxy}phenyl)-D-alaninamide

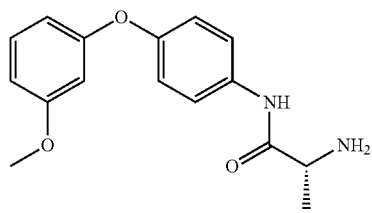 [SMILES: COc1cccc(Oc2ccc(NC(=O)[C@@H](C)N)cc2)c1]

To a solution of 1,1-dimethylethyl{(1R)-1-methyl-2-[(4-{[3-(methyloxy)phenyl]oxy}phenyl)amino]-2-oxoethyl}carbamate (Intermediate 1, 435 mg) in dry dichloromethane (6 mL), TFA (2 mL, 26.0 mmol) was added and the reaction mixture was stirred for 1 hour at room temperature. The solvent and the excess of TFA were evaporated and the residue was purified by SCX cartridge to afford the title compound as a yellow gum (320 mg).

$^1$H-NMR (400 MHz, DMSO-d$_6$) δ ppm: 7.67 (2H, m), 7.25 (1H, t), 7.00 (2H, m), 6.68 (1H, dd), 6.53 (1H, t), 6.49 (1H, dd), 3.73 (3H, s), 3.39-3.46 (1H, m), 1.22 (3H, d); UPLC: 0.51 min, 287 [M+H]+.

Intermediate 3

1-(ethyloxy)-3-[(4-nitrophenyl)oxy]benzene

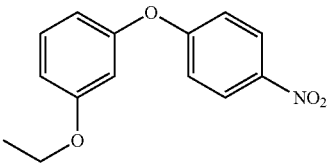 [SMILES: CCOc1cccc(Oc2ccc([N+](=O)[O-])cc2)c1]

The two reactions were performed in parallel. Two microwave vials were set up in parallel. In a large 30 mL microwave vial, 3-(ethyloxy)phenol (2 times 1.25 g, 9.045 mmol) was dissolved in 6 mL of dimethylformamide. 1-Fluoro-4-nitrobenzene (2 times 1.28 g, 9.045 mmol) and potassium carbonate (2 times 3.75 g, 27.15 mmol) were added. The reaction mixture was heated under microwave irradiation during 1 hour at 120° C. The combined reaction mixtures were filtered. The filtrated solid was washed with dichloromethane. The volatiles were evaporated under vacuum. Some dichloromethane and brine were added to this crude. The compound was extracted with dichloromethane (2 times) and ethyl acetate (2 times). The combined organic phases were dried over sodium sulphate. This afforded the title compound (4 g).

$^1$H NMR (400 MHz, methanol-d$_4$): δ ppm 8.38-8.05 (2H, m), 7.46-7.31 (1H, m), 7.20-7.05 (2H, m), 6.94-6.81 (1H, m), 6.77-6.63 (2H, m), 4.08 (2H, q), 1.42 (3H, t); UPLC: 0.89 min, 260 [M+H]+.

Intermediate 4

4-{[3-(ethyloxy)phenyl]oxy}aniline

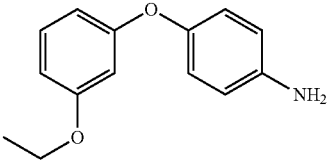

A solution of 1-(ethyloxy)-3-[(4-nitrophenyl)oxy]benzene (Intermediate 3, 4 g) and tin chloride monohydrate (28.8 g, 139 mmol) in ethyl acetate (200 mL) was heated at reflux overnight (15 hours). The reaction mixture was cooled down. It was then diluted with ethyl acetate (50 mL), washed with saturated NaHCO3 (100 mL), brine (100 mL) and dried over sodium sulphate. After evaporation of the volatiles, the residue was purified by an SCX (wash of the column with methanol, adsorption of the compound, wash with methanol (3CV), desorption with 2N methanolic ammonia (3CV)). Evaporation afforded the title compound (2.9 g).

$^1$HNMR (400 MHz, CDCl$_3$): δ ppm 6.50 (1H, t), 6.21 (2H, d), 6.06 (2H, d), 5.91-5.84 (3H, m), 3.34-3.29 (4H, m), 0.72 (3H, t); UPLC: 0.89 min, 260 [M+H]+.

Intermediate 5

3-chloro-5-fluorophenyl 4-nitrophenyl ether

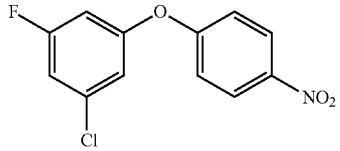

To a solution of 3-chloro-5-fluorophenol (1.46 g, 10 mmol) and 1-fluoro-4-nitrobenzene (1.41 g, 10 mmol) in acetonitrile (40 mL) was added potassium carbonate (2.76 g, 20 mmol) and the reaction mixture was heated to reflux for 4 hours. After filtration, the solvent was removed. The residue obtained was washed with n-hexane (2 times 15 mL) and dried to afford the title compound (2.38 g) which was directly used in the next step.

Intermediate 6

4-[(3-chloro-5-fluorophenyl)oxy]aniline

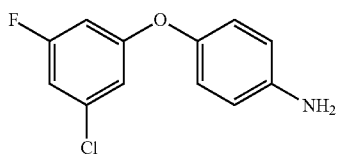 [SMILES: Nc1ccc(Oc2cc(F)cc(Cl)c2)cc1]

To a solution of 3-chloro-5-fluorophenyl 4-nitrophenyl ether (Intermediate 5, 2.38 g) in THF (40 mL) and water (10 mL) was added Fe power (11.2 g, 200 mmol) and ammonium chloride (10.7 g, 200 mmol). The reaction mixture was heated at reflux for 4 hours. After filtration, the solvent was concentrated to give a residue and poured into 50 mL of water. The mixture was extracted with ethyl acetate (3 times 50 mL) and the combined organic phases were washed and dried over magnesium sulphate. Removal of the solvent afforded the title compound (2.02 g) which was directly used in the next step.

Intermediate 7

3-chloro-4-fluorophenyl 4-nitrophenyl ether

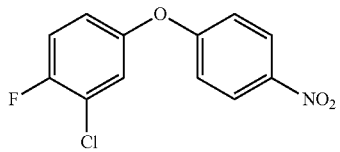 [SMILES: Nc1ccc(Oc2ccc(F)c(Cl)c2)cc1]

To a solution of 3-chloro-4-fluorophenol (1.46 g, 10 mmol) and 1-fluoro-4-nitrobenzene (1.41 g, 10 mmol) in acetonitrile (40 mL) was added potassium carbonate (2.76 g, 20 mmol). The reaction mixture was heated at reflux for 4 hours. After filtration, the solvent was removed to give a residue. The residue was washed with n-hexane (2 times 15 mL) and dried to afford the title compound (2.48 g) which was directly used in the next step.

Intermediate 8

4-[(3-chloro-4-fluorophenyl)oxy]aniline

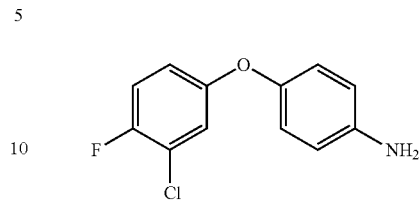

To a solution of 3-chloro-4-fluorophenyl 4-nitrophenyl ether (Intermediate 7, 2.48 g) in THF/water (40 mL/10 mL) was added Fe power (11.2 g, 200 mmol) and ammonium chloride (10.7 g, 200 mmol and the mixture was heated at reflux for 4 hours. After filtration, the solvent was concentrated to give a residue and poured into 50 mL of water. The mixture was extracted with ethyl acetate (3 times 50 mL) and the combined organic phases were washed and dried over magnesium sulphate. Removal of the solvent afforded the title compound (2.15 g) which was directly used in the next step.

Intermediate 9

N-[({4-[(3-chloro-4-fluorophenyl)oxy] phenyl}amino)carbonyl]-D-alanine

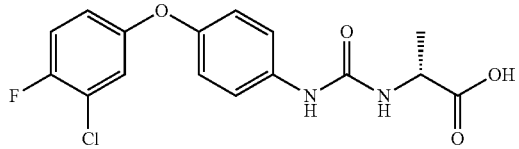 [SMILES: C[C@@H](NC(=O)Nc1ccc(Oc2ccc(F)c(Cl)c2)cc1)C(=O)O]

To a solution of 4-[(3-chloro-4-fluorophenyl)oxy]aniline (Intermediate 8, 237 mg) and triphosgene (99 mg, 0.33 mmol) in 15 mL of dichloromethane was added DIPEA (155 mg, 1.2 mmol) and the mixture was stirred at room temperature for 2 hours. Then the solvent was evaporated to give a residue. The residue was dissolved in 5 mL of THF and was transferred to a mixture of DIPEA (65 mg, 0.5 mmol, Acros) and D-Alanine (89 mg, 1 mmol) in 5 mL of THF. The whole reaction mixture was stirred at room temperature for 16 hours. Removal of the solvent afforded the title compound (352 mg) which was directly used in the next step.
MS_2 (ESI): 353 [M+H]+

Intermediate 10

N-[({4-[(3-chloro-4-fluorophenyl)oxy] phenyl}amino)carbonyl]-L-alanine

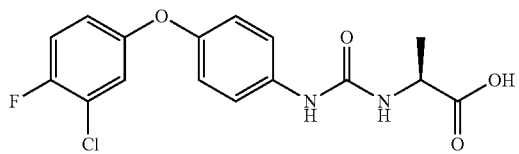 [SMILES: C[C@H](NC(=O)Nc1ccc(Oc2ccc(F)c(Cl)c2)cc1)C(=O)O]

The title compound was made in a similar fashion to the preparation of intermediate 9 replacing D-alanine with L-alanine (89 mg, 1 mmol) to afford the title compound (325 mg), which was used directly in the next step.

MS_2 (ESI): 353 [M+H]+

Intermediate 11

2-methyl-5-(methyloxy)aniline

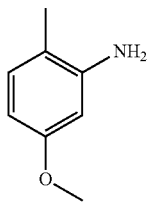

A suspension of 1-methyl-4-(methyloxy)-2-nitrobenzene (20.0 g, 119.8 mmol) and Pd/C (10%, 3 g) in methanol (100 mL) was stirred under H2 atmosphere at room temperature overnight. The mixture was filtered through a pad of celite and the filtrate was evaporated under vacuum to afford the title compound as a solid (16.1 g).

MS_2 (ESI): 138 [M+H]+.

Intermediate 12

2-methyl-5-(methyloxy)phenol

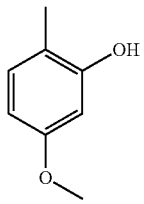

To a solution of 2-methyl-5-(methyloxy)aniline (Intermediate 11, 6.0 g) in H2SO4 (5 M, 20 mL) was added portionwise NaNO2 (3.4 g, 49.3 mmol) at 0-5° C. The mixture was stirred at 50° C. for 1 hour and extracted with ethyl acetate (4 times 30 mL). The combined ethyl acetate layers were dried over sodium sulphate and concentrated under vacuum to give a residue, which was purified by column chromatography on silica gel (with EtOAc:PE=1:20 as eluents) to afford the title compound as a solid.

MS_2 (ESI): 139 [M+H]+.

Intermediate 13

1-methyl-4-(methyloxy)-2-[(4-nitrophenyl)oxy]benzene

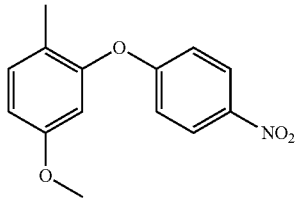

To a solution of 2-methyl-5-(methyloxy)phenol (Intermediate 12, 1.5 g) and 1-fluoro-4-nitrobenzene (1.4 g, 10.0 mmol) in acetonitrile (100 mL) was added potassium carbonate (2.1 g, 15.2 mmol) and the mixture was stirred at reflux for 5 hours. The resulting mixture was concentrated and partitioned between ethyl acetate (3 times 30 mL) and water (100 mL). The combined ethyl acetate layers were dried over sodium sulphate, filtered and concentrated under vacuum. The crude product thus obtained was purified by column chromatography on silica gel (EtOAc:PE=1:20) to afford the title compound as a solid (2.5 g).

Intermediate 14

4-{[2-methyl-5-(methyloxy)phenyl]oxy}aniline

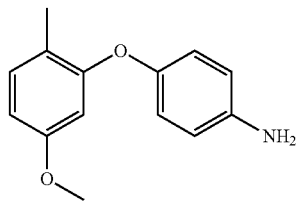 [SMILES: COc1ccc(C)c(Oc2ccc(N)cc2)c1]

A suspension of 1-methyl-4-(methyloxy)-2-[(4-nitrophenyl)oxy]benzene (Intermediate 13, 2.5 g) and Pd/C (10%, 1 g) in MeOH (100 mL) was stirred under H2 atmosphere for overnight at room temperature and filtered through a pad of celite. The filtrate was evaporated to afford the title compound as a solid (2.0 g).

$^1$HNMR (400 MHz, CDCl$_3$): δ ppm 7.14-7.12 (1H, d), 6.85-6.82 (2H, d), 6.68-6.66 (2H, d), 6.59-6.56 (1H, d), 6.40 (1H, s), 3.74-3.71 (5H, m), 2.25 (3H, s); MS_2 (ESI): 230 [M+H]+

Intermediate 15

1,1-dimethylethyl{(1R)-1-methyl-2-[(4-{[2-methyl-5-(methyloxy)phenyl]oxy}phenyl)amino]-2-oxoethyl}carbamate

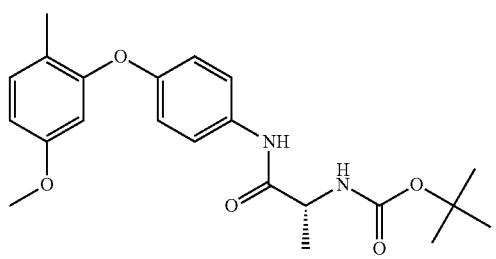 [SMILES: COc1ccc(C)c(Oc2ccc(NC(=O)[C@@H](C)NC(=O)OC(C)(C)C)cc2)c1]

To a solution of N-{[(1,1-dimethylethyl)oxy]carbonyl}-D-alanine (89 mg, 0.471 mmol) in dry N,N-dimethylformamide (5 mL), DIPEA (0.103 mL, 0.589 mmol) then HATU (179 mg, 0.471 mmol) were added and the reaction mixture was stirred for 15 minutes at room temperature under argon. Then 4-{[2-methyl-5-(methyloxy)phenyl]oxy}aniline (Intermediate 14, 90 mg) was added and the reaction mixture was stirred at 60° C. under argon for 1 hour 30 min. The reaction mixture was evaporated. The residues obtained was purified by silica gel chromatography (Companion instrument, 40 g silica cartridge) eluting with a gradient cHex/EtOAc 100/0 to 75/25 during 15 min and then 75/25 during 30 min to afford the title compound (155 mg).

$^1$H-NMR (400 MHz, methanol-d$_4$): δ ppm 7.52 (2H, d), 7.13 (1H, d), 6.85 (2H, d), 6.64 (1H, dd), 6.42 (1H, d), 4.22

(1H, dd), 3.57-3.78 (3H, m), 2.12 (3H, s), 1.46 (9H, s), 1.41 (3H, d); UPLC_B: 1.04 min, 401 [M+H]+.

Intermediate 16

N¹-(4-{[2-methyl-5-(methyloxy)phenyl]oxy}phenyl)-D-alaninamide

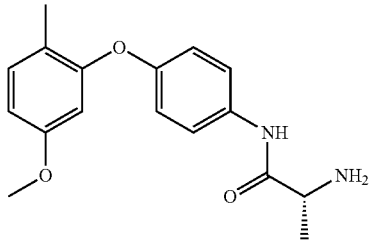 [SMILES: COc1ccc(C)c(Oc2ccc(NC(=O)[C@@H](C)N)cc2)c1]

1,1-dimethylethyl{(1R)-1-methyl-2-[(4-{[2-methyl-5-(methyloxy)phenyl]oxy}phenyl)amino]-2-oxoethyl}carbamate (Intermediate 15, 150 mg) was dissolved in 3 mL of dry dichloromethane. To this solution at 0° C. under argon was added dropwise 30 equivalents of TFA (0.866 mL, 11.24 mmol). The reaction was stirred at 0° C. for 4 hours. The reaction mixture was evaporated. The residue obtained was purified with an SCX cartridge (the cartridge was washed with 3 CV of methanol, then the compound was adsorbed on the cartridge, washed with 5 CV of methanol and desorbed with 2 CV of methanolic ammonia (1N)). Evaporation of the volatiles, afforded the title compound (129 mg).

¹H-NMR (400 MHz, methanol-$d_4$): δ ppm 7.48 (2H, m), 7.10 (1H, d), 6.81 (2H, m), 6.60 (1H, dd), 6.36 (1H, d), 3.64 (3H, s), 3.54 (1H, m), 2.06 (3H, s), 1.33 (3H, d); UPLC_B: 0.77 min, 301 [M+H]+.

Intermediate 17

4-methyl-3-(methyloxy)aniline

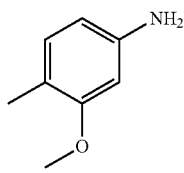

To a solution of 1-methyl-2-(methyloxy)-4-nitrobenzene (2.5 g, 14.96 mmol) in methanol (50 mL) Ni-Raney (~2 g) was added and the reaction mixture was stirred overnight at room temperature under H2 atmosphere (1 atm). The catalyst was filtered off and the residue was purified by SCX cartridge (50 g) to afford the title compound (1.86 g) as a colourless oil.

¹H-NMR (400 MHz, DMSO-$d_6$) δ ppm: 6.73 (1H, d), 6.19 (1H, d), 6.05 (1H, dd), 4.85 (2H, s), 3.68 (3H, s), 1.97 (3H, s); UPLC_B: 0.62 min, 138 [M+H]+.

Intermediate 18

4-methyl-3-(methyloxy)phenol

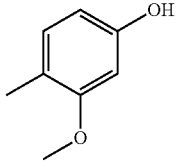

To a suspension of 4-methyl-3-(methyloxy)aniline (Intermediate 17, 1.86 g) in water (100 mL)/H2SO4 (30 mL, 563 mmol) at 0° C. a solution of sodium nitrite (1.029 g, 14.91 mmol) in water (10 mL) was slowly added and the reaction mixture was stirred for 30 minutes at 0° C. The reaction mixture was slowly added to a solution of H2SO4 98% (20 mL) in Water (80 mL) pre-heated at 90° C. and stirred at this temperature for 1 h. After cooling the mixture was extracted with Et2O (2×200 mL), the organic layer was dried on sodium sulphate, filtered and evaporated to afford the title compound (1.86 g) as a red/brown oil.

¹H-NMR (400 MHz, DMSO-$d_6$) δ ppm: 9.14 (1H, br.s), 6.87 (1H, d), 6.35 (1H, d), 6.24 (1H, dd), 3.71 (3H, s), 2.01 (3H, s); UPLC_B: 0.63 min, 137 [M−H]−.

Intermediate 19

1-methyl-2-(methyloxy)-4-[(4-nitrophenyl)oxy]benzene

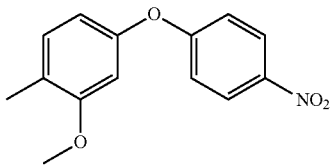

To a solution of 4-methyl-3-(methyloxy)phenol (Intermediate 18, 0.800 g) in dry acetonitrile (60 mL) potassium carbonate (1.600 g, 11.58 mmol) and then 1-fluoro-4-nitrobenzene (817 mg, 5.79 mmol) were added and the reaction mixture was refluxed for 6 hours. The solid was filtered off and the solvent evaporated affording the title compound (1.43 g) as an orange solid.

¹H-NMR (400 MHz, DMSO-$d_6$) δ ppm: 8.24 (2H, m), 7.23 (1H, d), 7.11 (2H, m), 6.82 (1H, d), 6.66 (1H, dd), 3.78 (3H, s), 2.16 (3H, s); UPLC_B: 1.03 min, 260 [M+H]+.

Intermediate 20

4-{[4-methyl-3-(methyloxy)phenyl]oxy}aniline

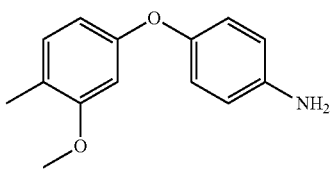 [SMILES: COc1cc(Oc2ccc([N+](=O)[O-])cc2)ccc1C]

To a solution of 1-methyl-2-(methyloxy)-4-[(4-nitrophenyl)oxy]benzene (Intermediate 19, 1.43 g) in tetrahydrofuran (65 mL)/water (32.5 mL) iron (1.540 g, 27.6 mmol) and then ammonium chloride (1.475 g, 27.6 mmol) were added and the reaction mixture was stirred for 5 hours at room temperature. The catalyst was filtered off and the solution was diluted with a saturated solution of Na2CO3 (10 mL) and extracted with ethyl acetate (2 times 60 mL). Combined organic layers were dried over sodium sulphate, filtered and evaporated to the title compound (1.25 g) as a brown/red solid.

$^1$H-NMR (400 MHz, DMSO-$d_6$) δ ppm: 7.00 (1H, d), 6.77-6.70 (2H, m), 6.60-6.51 (3H, m), 6.24 (1H, dd), 4.94 (2H, br. s), 3.71 (3H, s), 2.06 (3H, s); UPLC_B: 0.86 min, 230 [M+H]+.

Intermediate 21

1,1-dimethylethyl{(1R)-1-methyl-2-[(4-{[4-methyl-3-(methyloxy)phenyl]oxy}phenyl)amino]-2-oxoethyl}carbamate

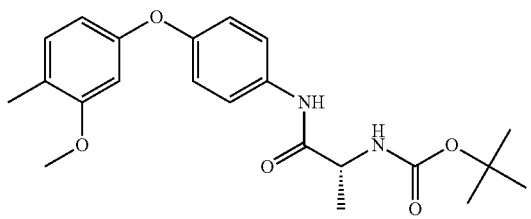 [SMILES: COc1cc(Oc2ccc(NC(=O)[C@@H](C)NC(=O)OC(C)(C)C)cc2)ccc1C]

To a solution of N-{[(1,1-dimethylethyl)oxy]carbonyl}-D-alanine (182 mg, 0.960 mmol) in dry N,N-Dimethylformamide (DMF) (4 mL) DIPEA (0.305 mL, 1.745 mmol) and then TBTU (336 mg, 1.047 mmol) were added and the reaction mixture was stirred for 15 minutes at r.t. 4-{[4-methyl-3-(methyloxy)phenyl]oxy}aniline (Intermediate 20, 200 mg) was then added and the reaction mixture was stirred for 1 hour at the same temperature. The reaction was quenched with water (2 mL), diluted with brine (10 mL) and extracted with ethyl acetate (2 times 20 mL). Organic layer was dried over sodium sulphate, filtered and evaporated and the residue was purified by flash chromatography (Biotage system, 10 g SNAP column) using as eluent a gradient cyclohexane/ethyl acetate from 100/0 to 80/20 to afford the title compound as a yellow pale solid (304 mg).

$^1$H-NMR (400 MHz, DMSO-$d_6$) δ ppm: 9.93 (s, 1H), 7.60 (m, 2H), 7.09 (d, 2H), 6.97 (m, 2H), 6.63 (d, 1H), 6.39 (dd, 1H), 4.15-4.03 (m, 1H), 3.74 (s, 3H), 2.10 (s, 3H), 1.39 (s, 9H), 1.26 (d, 3H), UPLC_B: RT 0.96 min, m/z 401 [M+H]+.

Intermediate 22

N$^1$-(4-{[4-methyl-3-(methyloxy)phenyl]oxy}phenyl)-D-alaninamide

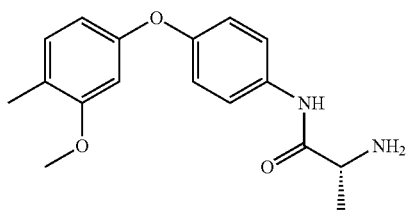 [SMILES: COc1cc(Oc2ccc(NC(=O)[C@@H](C)N)cc2)ccc1C]

To a solution of 1,1-dimethylethyl{(1R)-1-methyl-2-[(4-{[4-methyl-3-(methyloxy)phenyl]oxy}phenyl)amino]-2-oxoethyl}carbamate (Intermediate 21, 300 mg) in dry dichloromethane (7.5 mL) TFA (2.5 mL, 32.4 mmol) was slowly added and the reaction mixture was stirred for 1.5 hours at room temperature. The solvent and the excess of TFA were evaporated and the residue was purified by SCX cartridge (10 g) to afford the title compound as an orange oil (219 mg).

$^1$H-NMR (400 MHz, DMSO-$d_6$) δ ppm: 7.64 (2H, m), 7.08 (1H, s), 6.96 (2H, m), 6.63 (1H, d), 6.39 (1H, dd), 3.74 (3H, s), 3.41 (1H, q), 2.10 (3H, s), 1.21 (3H, d); UPLC_B: 0.80 min, 301 [M+H]+.

Intermediate 23

2-{[3-(1-methylethyl)phenyl]oxy}-5-nitropyridine

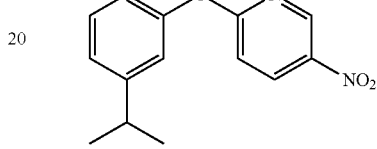

In a 30 mL large microwave vial, 2-chloro-5-nitropyridine (1.041 g, 6.57 mmol, 1 equiv) was dissolved in 5.5 mL of dimethylformamide. 3-(1-methylethyl)phenol (0.90 mL, 6.57 mmol, 1 equiv) and potassium carbonate (4.54 g, 32.8 mmol, 5 equiv) were added. The reaction mixture was heated under microwave irradiation for 1 hour at 110° C. (Biotage Initiator). The reaction mixture was filtered. The filtrated solid was washed with dichloromethane (30 mL). The volatiles were evaporated under vacuum. The crude compound was dissolved in dichoromethane (20 mL) and brine was added (20 mL). The compound was extracted 2 times with dichloromethane (2×20 mL) and 2 times with ethyl acetate (2×20 mL). The organic phase was dried over sodium sulphate. Evaporation afforded the title compound (1.402 g).

$^1$HNMR (400 MHz, methanol-$d_4$): δ ppm 8.94 (1H, d), 8.52 (1H, dd), 7.33 (1H, t), 7.15 (1H, d), 7.06 (1H, d), 7.02 (1H, t), 6.90-6.97 (1H, m), 2.81 (3H, s); UPLC: 0.93 min, 259 [M+H]+.

Intermediate 24

6-{[3-(1-methylethyl)phenyl]oxy}-3-pyridinamine

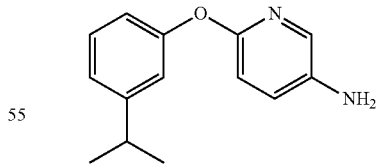

2-{[3-(1-methylethyl)phenyl]oxy}-5-nitropyridine (Intermediate 23, 1.39 g) was dissolved in ethanol (25 mL). Hydrazine monohydrate (0.524 mL, 1076 mmol) and palladium on carbon (401 mg, 0.377 mmol) were added. The reaction mixture was heated at reflux under argon for 1 hour. The reaction was cooled down and then filtered on celite. The organic phase was evaporated under vacuum. The residue was purified by flash chromatography on silica (Companion instrument, 120 g silica cartridge, gradient cyclohexane/ethylacetate from 100/0 to 30/70 in 15 min then 30/70 during 30 min). Evaporation afforded the title compound as a yellow oil (821 mg).

¹HNMR (400 MHz, methanol-d₄): δ ppm 7.65 (1H, d), 7.29-7.15 (2H, m), 6.99 (1H, d), 6.81-6.86 (1H, m), 6.68-6.78 (2H, m), 2.97-2.75 (1H, m), 1.23 (3H, s), 1.22 (3H, s); UPLC: 0.70 min, 229 [M+H]+.

Intermediate 25

1,1-dimethylethyl{(R)-1-methyl-2-[(6-{[3-(1-methylethyl)phenyl]oxy}-3-pyridinyl)amino]-2-oxoethyl}carbamate

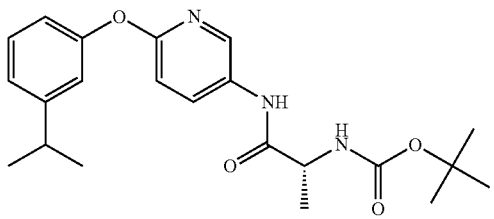 [SMILES: CC(C)c1cccc(Oc2ccc(NC(=O)[C@@H](C)NC(=O)OC(C)(C)C)cn2)c1]

To a solution of N-{[(1,1-dimethylethyl)oxy]carbonyl}-D-alanine (69.6 mg, 0.368 mmol) in dry N,N-dimethylformamide (4 mL), DIPEA (0.080 mL, 0.460 mmol), HATU (140 mg, 0.368 mmol) were added and the reaction mixture was stirred for 15 minutes at room temperature under argon. Then 6-{[3-(1-methylethyl)phenyl]oxy}-3-pyridinamine (Intermediate 24, 70 mg) was added and the reaction mixture was stirred overnight at 60° C. under argon. The reaction mixture was evaporated. The residue obtained was purified by silica gel chromatography (Companion system, 12 g cartridge) with a gradient cyclohexane/ethyl acetate from 100/0 to 65/35 to afford the title compound (59 mg).

¹HNMR (400 MHz, methanol-d₄): δ ppm 8.33 (1H, d), 8.05 (1H, dd), 7.30 (1H, t), 7.08 (1H, d), 6.92-6.98 (1H, m), 6.83-6.91 (2H, m), 4.12-4.29 (1H, m), 2.79-2.97 (1H, m), 1.45 (9H, s), 1.38 (3H, d), 1.25 (6H, d); UPLC: 0.85 min, 400 [M+1]+

Intermediate 26

N¹-(6-{[3-(1-methylethyl)phenyl]oxy}-3-pyridinyl)-D-alaninamide

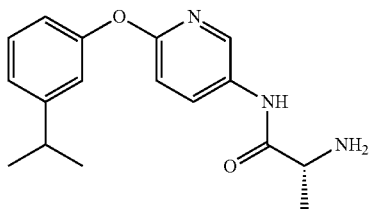 [SMILES: CC(C)c1cccc(Oc2ccc(NC(=O)[C@@H](C)N)cn2)c1]

1,1-dimethylethyl{(1R)-1-methyl-2-[(6-{[3-(1-methylethyl)phenyl]oxy}-3-pyridinyl)amino]-2-oxoethyl}carbamate (Intermediate 25, 56 mg) was dissolved in 3 mL of dry dichloromethane. To this solution at 0° C. were added dropwise 30 equivalents of TFA (0.324 mL). The reaction was stirred at 0° C. for 3 hours. The reaction mixture was evaporated. The crude obtained was purified by SCX on a 5 g cartridge. 3 CV of methanol were used first, then the residue was adsorbed on the cartridge, washed with 5 CV of methanol and desorbed with 2 CV of methanolic ammonia (1N). Evaporation of the volatiles, afforded the title compound (38 mg).

¹HNMR (400 MHz, methanol-d₄): δ ppm 8.40 (1H, d), 8.10 (1H, dd), 7.33 (1H, t), 7.10 (1H, d), 6.98 (1H, t), 6.85-6.92 (2H, m), 3.52-3.69 (1H, m), 2.78-3.02 (1H, m), 1.39 (3H, d), 1.27 (6H, d); UPLC: 0.59 min, 300 [M+1]+

Intermediate 27

3-[(1-methylethyl)oxy]phenol

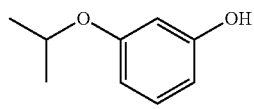

To a solution of 1,3-benzenediol (8 g, 72.7 mmol) and 2-iodopropane (12 g, 70.6 mmol) in ethanol (100 mL preheated at reflux) was added a solution of KOH (83%, 5.3 g, 77.6 mmol) in water (20 mL) over a period of 30 minutes. The mixture was refluxed for 3 hours and poured into NaOH (1 N, 100 mL). The resulting mixture was extracted with ethyl acetate (3 times 50 mL) and the aqueous layer was acidified with 10% HCl to adjust the pH=5 and extracted with ethyl acetate (3 times 50 mL). The combined extracts were washed with brine (50 mL), dried and concentrated under vacuum. The residue was purified by column chromatography on silica gel (PE:EtOAc=5:1) to afford the title compound as a colourless oil (2.1 g).

MS 1 (ESI): 151 [M−H]−

Intermediate 28

2-({3-[(1-methylethyl)oxy]phenyl}oxy)-5-nitropyridine

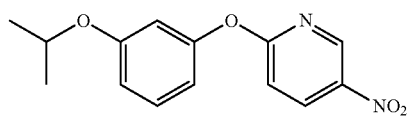 [SMILES: CC(C)Oc1cccc(Oc2ccc([N+](=O)[O-])cn2)c1]

To a solution of 3-[(1-methylethyl)oxy]phenol (Intermediate 27, 456 mg) in DMSO (8 mL) was added t-BuOK (336 mg, 3 mmol, Acros). The reaction mixture was stirred at 20° C. for 30 minutes. 2-chloro-5-nitropyridine (474 mg, 3 mmol, Aldrich) was added and the resulting mixture was stirred at 120° C. for 2 hours. The reaction mixture was cooled to room temperature, poured into ice-water (50 mL) and extracted with dichloromethane (3 times 50 mL). The combined organic layers were dried over sodium sulphate, filtered and concentrated. The residue was purified by column chromatography on silica gel eluting with (PE:EtOAc=50:1) to afford the title compound as a light yellow solid (670 mg).

MS 1 (ESI): 275 [M+H]+

Intermediate 29

6-(3-[(1-methylethyl)oxy]phenyloxy)-3-pyridinamine

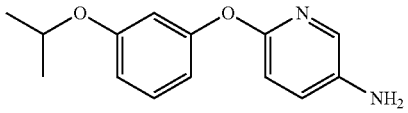

To a solution of 2-({3-[(1-methylethyl)oxy]phenyl}oxy)-5-nitropyridine (Intermediate 28, 670 mg, 2.45 mmol) in methanol (50 mL) was added Pd/C (10%, 100 mg, 0.1 wet. e.q.) and the flask was filled in with $H_2$. The resulting mixture was stirred at room temperature under $H_2$ atmosphere overnight and filtered. The filtrate was concentrated under vacuum to afford the title compound as a brown solid (560 mg).
MS 1 (ESI): 245 [M+H]+

Intermediate 30

N-{[(1,1-dimethylethyl)oxy]carbonyl}-D-alanine

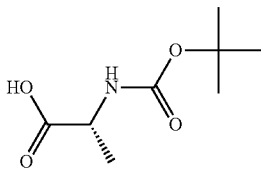

To a solution of D-alanine (4.45 g, 50 mmol) in THF (100 mL) and water (50 mL) was added a solution of NaHCO3 (4.2 g, 50 mmol) in water (30 mL). After stirring for 15 minutes, a solution of Boc-anhydride (16.35 g, 75 mmol) in THF (20 mL) was added and the mixture was stirred at room temperature for 4 hours. The solvent was evaporated and 2N HCl was used to adjust the pH=3-4. The mixture was extracted with ethyl actetate (3 times 200 mL) and the combined ethyl acetate layers were washed with brine (50 mL), dried and concentrated. The residue was recrystallized with ethyl acetate/hexane to afford the title compound as a white solid (5 g).
$^1$HNMR (DMSO-$d_6$): δ ppm 12.38 (1H, s), 7.11-7.09 (1H, d), 3.94-3.88 (1H, m), 1.38 (9H, s), 1.22-1.21 (3H, d).

Intermediate 31

1,1-dimethylethyl((R)-1-methyl-2-{[6-({3-[(1-methylethyl)oxy]phenyl}oxy)-3-pyridinyl]amino}-2-oxoethyl)carbamate

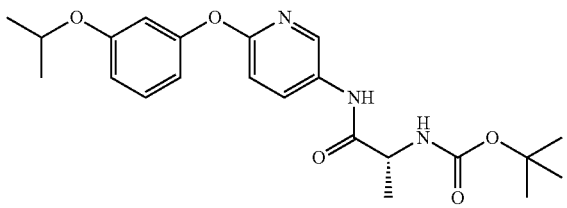 [SMILES: CC(C)Oc1cccc(Oc2ccc(NC(=O)[C@@H](C)NC(=O)OC(C)(C)C)cn2)c1]

A solution of 6-({3-[(1-methylethyl)oxy]phenyl}oxy)-3-pyridinamine (Intermediate 29, 244 mg, 1 mmol), N-{[(1,1-dimethylethyl)oxy]carbonyl}-D-alanine (Intermediate 30, 284 mg), HBTU (567 mg, 1.5 mmol) and DIPEA (194 mg, 1.5 mmol, Acros) in DMF (8 mL) was heated under microwave (Biotage instrument) at 110° C. for 3 hours. The solvent was distilled off to afford the title compound as a brown oil, which was used directly in the next step (400 mg, 96% yield).
MS_2 (ESI): 416 [M+H]+

Intermediate 32

$N^1$-[6-({3-[(1-methylethyl)oxy]phenyl}oxy)-3-pyridinyl]-D-alaninamide

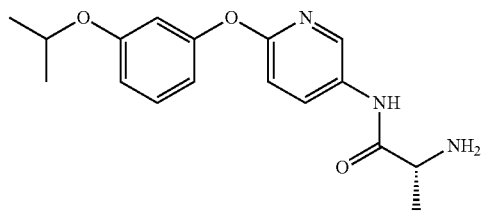 [SMILES: CC(C)Oc1cccc(Oc2ccc(NC(=O)[C@@H](C)N)cn2)c1]

To a solution of 1,1-dimethylethyl((1R)-1-methyl-2-{[6-({3-[(1-methylethyl)oxy]phenyl}oxy)-3-pyridinyl]amino}-2-oxoethyl)carbamate (Intermediate 31, 400 mg, 0.96 mmol) in dichloromethane (14 mL) was added TFA (6 mL) portionwise during 15 minutes at 0° C. The resulting mixture was stirred at room temperature for 2 hours. The solvent was distilled off to afford the title compound (260 mg, 85%) as a grey oil.
MS 1 (ESI): 316 [M+H]+

Intermediate 33

2-[(2,5-dimethylphenyl)oxy]-5-nitropyridine

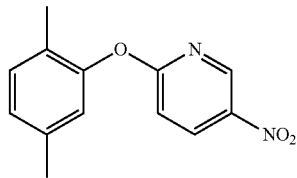 [SMILES: Cc1ccc(C)c(Oc2ccc([N+](=O)[O-])cn2)c1]

In a microwave vial, 2-chloro-5-nitropyridine (80 mg, 0.505 mmol) was dissolved in 2 mL of dry dimethylformamide. 2,5-dimethylphenol (80 mg, 0.505 mmol, 1 equiv) and potassium carbonate (418 mg, 3.03 mmol, 6 equiv) were added. The reaction mixture was heated under microwave irradiation for 1 hour at 110° C. (Biotage Initiator). The reaction mixture was filtered. The filtrated solid was washed with dichloromethane (5 mL). The volatiles were evaporated. The residue was dissolved in dichoromethane (10 mL) and brine was added (10 mL). The organic layer was extracted 2 times with dichloromethane (2×15 mL) and 2 times with ethylacetate (2×15 mL). The organic phase was dried over sodium sulphate. The solvent was removed to afford the title compound (112 mg)
$^1$HNMR (400 MHz, methanol-$d_4$): δ ppm 8.97 (1H, d), 8.58 (1H, dd), 7.20-6.90 (4H, m), 2.32 (3H, s), 2.07 (3H, s); UPLC: 0.87 mins, 245 [M+H]+.

Intermediate 34

6-[(2,5-dimethylphenyl)oxy]-3-pyridinamine

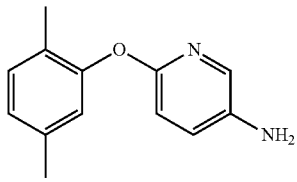 [SMILES: Cc1ccc(C)c(Oc2ccc(N)cn2)c1]

2-[(2,5-dimethylphenyl)oxy]-5-nitropyridine (Intermediate 33, 140 mg, 0.450 mmol) was dissolved in ethanol (3 mL). Hydrazine hydrate (83 μL, 0.884 mmol) and palladium on carbon (47 mg, 0.044 mmol) were added. The reaction mixture was heated at reflux under argon. After overnight heating, the reaction was cooled down. The reaction mixture was filtered. The organic phase was evaporated under vacuum. The residue was purified by SCX (wash with MeOH, desorbed with 2N methanolic ammonia). Evaporation afforded the title compound (85 mg).

UPLC: 0.68 min, 215 [M+H]+.

Intermediate 35

1,1-dimethylethyl[(1R)-2-({6-[(2,5-dimethylphenyl)oxy]-3-pyridinyl}amino)-1-methyl-2-oxoethyl]carbamate

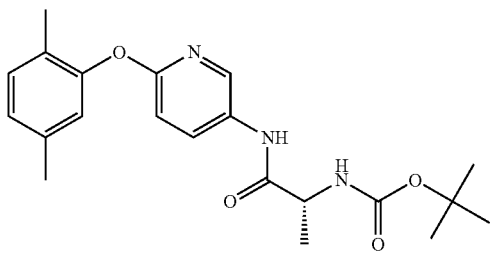 [SMILES: Cc1ccc(C)c(Oc2ccc(NC(=O)[C@@H](C)NC(=O)OC(C)(C)C)cn2)c1]

The title compound was made in a similar fashion to the preparation of Intermediate 25 replacing 6-{[3-(1-methylethyl)phenyl]oxy}-3-pyridinamine with 6-[(2,5-dimethylphenyl)oxy]-3-pyridinamine (Intermediate 34) and using the following conditions for the silica gel chromatography: Companion instrument, 12 g cartridge, a gradient cHex/EtOAc as eluent from 100/0 to 70/30. This afforded the title compound as a light brown oil (63 mg).

$^1$HNMR (400 MHz, methanol-$d_4$): δ ppm 8.31 (1H, d), 8.05 (1H, dd), 7.18 (1H, d), 6.98 (1H, d), 6.76-6.87 (2H, m), 4.02-4.34 (1H, m), 2.35 (3H, s), 2.12 (3H, s) 1.47 (9H, s) 1.41 (3H, d); UPLC: 0.84 min, 386 [M+1]+

Intermediate 36

$N^1$-{6-[(2,5-dimethylphenyl)oxy]-3-pyridinyl}-D-alaninamide

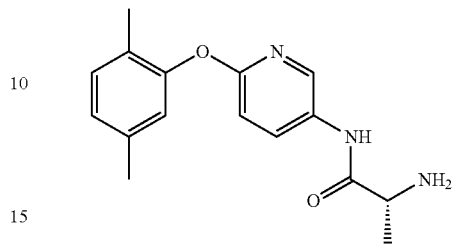

1,1-dimethylethyl[(1R)-2-({6-[(2,5-dimethylphenyl)oxy]-3-pyridinyl}amino)-1-methyl-2-oxoethyl]carbamate (Intermediate 35, 60 mg) was dissolved in 4 mL of dry dichloromethane. To this solution, at 0° C., were added dropwise 40 equivalents of TFA (0.480 mL). The reaction was stirred for 3 hours 30 at 0° C. The reaction mixture was evaporated and then purified by SCX on a 5 g cartridge. 3 CV of methanol were used first, then the residue was adsorbed on the cartridge, washed with 5 CV of methanol and desorbed with CV of methanolic ammonia (1N). Evaporation of the volatiles, afforded the title compound (49 mg)

$^1$HNMR (400 MHz, methanol-$d_4$): δ ppm 8.34 (1H, d), 8.07 (1H, dd), 7.18 (1H, d), 6.99 (1H, d), 6.69-6.90 (2H, m), 3.60 (1H, q), 2.32 (3H, s), 2.12 (3H, s), 1.39 (3H, d); UPLC: 0.54 min, 286 [M+1]+

Intermediate 37

2-[(2,3-dimethylphenyl)oxy]-5-nitropyridine

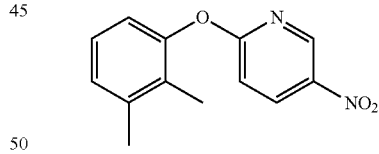

In a 20 mL microwave vial 2-chloro-5-nitropyridine (500 mg, 3.15 mmol), 2,3-dimethylphenol (385 mg, 3.15 mmol) and potassium carbonate (1308 mg, 9.46 mmol) were dissolved in N,N-Dimethylformamide (10 mL) to give a dark brown suspension. The reaction vessel was sealed and heated in Biotage Initiator at 110° C. for 1 h. After cooling the reaction was diluted with 25 mL of Et$_2$O. The organic phase was washed with 3×25 mL of water, 10 mL of brine, dried over sodium sulphate, filtered and evaporated under vacuum to afford the title compound as a pale orange oil. (640 mg). $^1$H NMR (400 MHz, CDCl$_3$): 5 ppm 9.07 (1H, d), 8.50 (1H, dd), 7.24-7.19 (1H, m), 7.18-7.14 (1H, m), 7.04 (1H, d), 6.95 (1H, d), 2.38 (3H, s), 2.09 (3H, s); UPLC: 0.81 min, 245 [M+H]+.

Intermediate 38

6-[(2,3-dimethylphenyl)oxy]-3-pyridinamine

In a 50 mL round-bottomed flask 2-[(2,3-dimethylphenyl)oxy]-5-nitropyridine (Intermediate 37, 640 mg) was dissolved in ethanol (10 mL) to give a pale yellow solution. Hydrazine hydrate (0.463 mL, 4.72 mmol) and palladium on carbon (25.10 mg, 0.236 mmol) were added. The reaction mixture was stirred at 90° C. After 1 hour, the reaction was complete. The reaction mixture was filtered and the organic phase was evaporated in vacuo affording the title compound as a pale yellow oil (573 mg).

$^1$H NMR (400 MHz, CDCl$_3$): δ ppm 7.72 (1H, d), 7.05-7.16 (2H, m), 7.01 (1H, d), 6.86 (1H, d), 6.71 (1H, d), 3.48 (2H, br. s), 2.34 (3H, s), 2.16 (3H, s); UPLC: 0.62 min, 215 [M+H]+.

Intermediate 39

1,1-dimethylethyl[(1R)-2-({6-[(2,3-dimethylphenyl)oxy]-3-pyridinyl}amino)-1-methyl-2-oxoethyl]carbamate

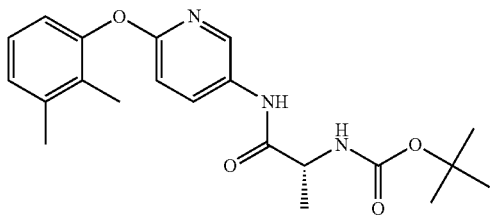 [SMILES: Cc1cccc(Oc2ccc(NC(=O)[C@@H](C)NC(=O)OC(C)(C)C)cn2)c1C]

To a solution of N-{[(1,1-dimethylethyl)oxy]carbonyl}-D-alanine (26.5 mg, 0.140 mmol) in dry N,N-dimethylformamide (4 mL), DIPEA (31 µl, 0.175 mmol, 1.5 equiv) and then HATU (53.2 mg, 0.140 mmol, 1.2 equiv) were added and the reaction mixture was stirred for 15 minutes at room temperature under argon. Then 6-[(2,3-dimethylphenyl)oxy]-3-pyridinamine (Intermediate 38, 25 mg) was added and the reaction mixture was stirred at 60° C. under argon. The reaction mixture was left overnight under heating. It was then was evaporated. The residue obtained was directly purified on silica gel chromatography (Companion instrument, 2×4 g cartridge) with a gradient cyclohexane/ethylacetate 100/0 to 70/30 during 15 min and 70/30 during 20 min. This afforded the title compound (31 mg).

$^1$HNMR (400 MHz, methanol-d$_4$): δ ppm 8.29 (1H, d), 8.02 (1H, dd), 7.20-6.99 (3H, m), 6.81 (2H, dd), 4.21 (1H, m), 2.32 (3H, s), 2.08 (3H, s), 1.45 (9H, s), 1.40 (3H, d); UPLC: 0.80 min, 386 [M+1]+

Intermediate 40

N$^1$-{6-[(2,3-dimethylphenyl)oxy]-3-pyridinyl}-D-alaninamide

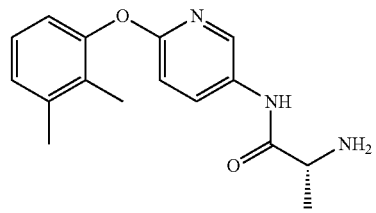 [SMILES: Cc1cccc(Oc2ccc(NC(=O)[C@@H](C)N)cn2)c1C]

1,1-dimethylethyl[(1R)-2-({6-[(2,3-dimethylphenyl)oxy]-3-pyridinyl}amino)-1-methyl-2-oxoethyl]carbamate (Intermediate 39, 29 mg) was dissoved in 3 mL of dry dichloromethane. To this solution at 0° C. under argon was added dropwise 30 equivalents of TFA (168 µl, 2.179 mmol). The reaction was stirred during 1 hour at 0° C. and 2 hours at room temperature. The reaction mixture was evaporated. The residue obtained was purified by SCX (3 CV of methanol were used first, then the residue was adsorbed on the cartridge, washed with 5 CV of methanol and desorbed with 2 CV of methanolic ammonia (1N)). Evaporation of the volatiles, afforded the title compound (21 mg).

UPLC: 0.52 min, 286 [M+1]+

Intermediate 41

2-[(2,6-dimethylphenyl)oxy]-5-nitropyridine

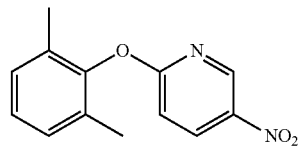 [SMILES: Cc1cccc(C)c1Oc1ccc(N)cn1]

In a 20 mL microwave vial 2-chloro-5-nitropyridine (500 mg, 3.15 mmol) was dissolved in N,N-dimethylformamide (10 mL) to give a pale yellow solution. 2,6-dimethylphenol (385 mg, 3.15 mmol) and potassium carbonate (1308 mg, 9.46 mmol) were added. The reaction vessel was sealed and heated under microwave irradiation (Biotage instrument) at 110° C. for 1 hour. The reaction mixture was quenched with 10 mL of water and diluted with 10 mL of Et$_2$O. Phases were separated through a separating funnel. The organic phase was washed with 3 times 10 mL of water, 10 mL of brine, dried over sodium sulphate, filtered and evaporated under vacuum to afford the title compound as a pale orange oil (555.9 mg).

$^1$H NMR (400 MHz, CDCl$_3$): δ ppm 9.04 (1H, d), 8.50 (1H, dd), 7.16 (3H, s), 7.03 (1H, d), 2.12 (6H, s); UPLC_B: 0.95 mins, 245 [M+H]+.

Intermediate 42

6-[(2,6-dimethylphenyl)oxy]-3-pyridinamine

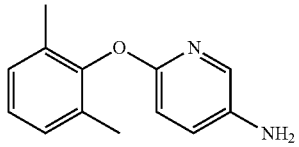

In a 50 mL round-bottomed flask 2-[(2,6-dimethylphenyl)oxy]-5-nitropyridine (Intermediate 41, 555.9 mg) was dissolved in ethanol (10 mL) to give a pale orange solution. Palladium on carbon (230 mg, 0.216 mmol) and hydrazine hydrate (0.416 mL, 4.32 mmol) were added. The reaction mixture was stirred at 90° C. After 3 hours the reaction was completed. The reaction mixture was filtered and the organic phase was evaporated under vacuum to afford 929.9 mg of a dark orange solid that was charged on a 10 g SCX cartridge. It was then flushed with 200 mL of ethanol followed by 50 mL of 2M solution of ammonia in MeOH. The ammonia eluate was evaporated under vacuum to afford the title compound as dark orange solid (447.6 mg).

$^1$H NMR (400 MHz, CDCl$_3$): d ppm 7.64 (1H, d), 7.02-7.12 (4H, m), 6.62 (1H, d), 3.50 (2H, br. s), 2.14 (6H, s); UPLC_B: 0.74 mins, 215 [M+H]+.

Intermediate 43

1,1-dimethylethyl[(1R)-2-({6-[(2,6-dimethylphenyl)oxy]-3-pyridinyl}amino)-1-methyl-2-oxoethyl]carbamate

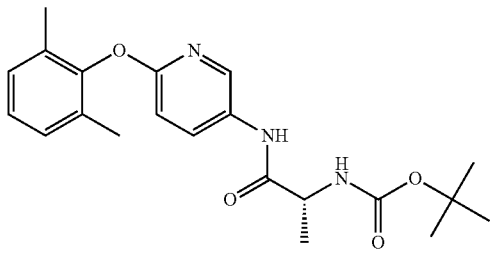 [SMILES: Cc1cccc(C)c1Oc1ccc(NC(=O)[C@@H](C)NC(=O)OC(C)(C)C)cn1]

In a 8 mL vial N-{[(1,1-dimethylethyl)oxy]carbonyl}-D-alanine (190 mg, 1.003 mmol) was dissolved in N,N-dimethylformamide (4 mL) to give a colourless solution. N-ethyl-N-(1-methylethyl)-2-propanamine (0.219 mL, 1.253 mmol) and N-[(dimethylamino)(3H-[1,2,3]triazolo[4,5-b]pyridin-3-yloxy)methylidene]-N-methylmethanaminium hexafluorophosphate (381 mg, 1.003 mmol) were added. The reaction mixture immediately became yellow and was stirred at room temperature for minutes. 6-[(2,6-dimethylphenyl)oxy]-3-pyridinamine (Intermediate 42, 223.8 mg) was added and the reaction mixture was warmed to 60° C. After 4 hours the solvent, was evaporated under vacuum using the Genevac affording a dark brown oil. This residue was purified by silica gel chromatography (Biotage instrument, 25 g SNAP Silica column) eluting with Cyclohexane/EtOAc from 3:1 Cyclohexane/EtOAc to 1:1 Cyclohexane/EtOAc in 10 CV; then 1:1 Cyclohexane/EtOAc for CV. The collected fractions afforded the title compound as a pale orange oil (282 mg).

$^1$H NMR (400 MHz, DMSO-d$_6$) d ppm 10.03 (1H, br. s), 8.22 (1H, d), 8.07 (1H, dd), 7.02-7.19 (4H, m), 6.97 (1H, dd), 4.03-4.18 (1H, m), 2.04 (6H, s), 1.40 (9H, s), 1.27 (3H, d); UPLC_B: 0.89 min, 386 [M+H]+.

Intermediate 44

N$^1$-{6-[(2,6-dimethylphenyl)oxy]-3-pyridinyl}-D-alaninamide

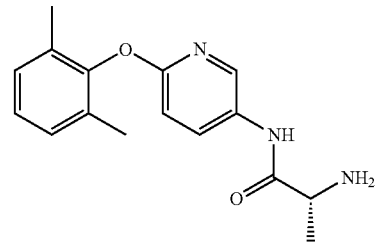 [SMILES: Cc1cccc(C)c1Oc1ccc(NC(=O)[C@@H](C)N)cn1]

In a 50 mL round-bottomed flask 1,1-dimethylethyl[(1R)-2-({6-[(2,6-dimethylphenyl)oxy]-3-pyridinyl}amino)-1-methyl-2-oxoethyl]carbamate (Intermediate 43, 282 mg) was dissolved in dichloromethane (2 mL) to give a yellow solution. Trifluoroacetic acid (2 mL, 26.0 mmol) was added. The reaction mixture was stirred at room temperature. After 20 min, the solvent was evaporated under vacuum affording a yellow oil that was charged on a 5 g SCX cartridge. It was then flushed with 25 mL of MeOH followed by 25 mL of 2M solution of ammonia in MeOH. The ammonia eluate was evaporated under vacuum to afford the title compound as a yellow oil which solidified (173.8 mg).

$^1$H NMR (400 MHz, CDCl$_3$) d ppm 9.51 (1H, br. s), 8.23-8.12 (2H, m), 7.17-7.01 (3H, m), 6.85-6.75 (1H, m), 3.64 (1H, q), 2.13 (6H, s), 1.83 (2H, br. s), 1.44 (3H, d); UPLC_B: 0.70 mins, 286 [M+H]+.

Intermediate 45

2-[(2-ethylphenyl)oxy]-5-nitropyridine

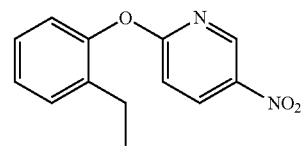 [SMILES: CCc1ccccc1Oc1ccc(N)cn1]

In a 20 mL microwave vial 2-chloro-5-nitropyridine (500 mg, 3.15 mmol) was dissolved in N,N-dimethylformamide (10 mL) to give a light brown solution. 2-ethylphenol (0.378 mL, 3.15 mmol) and K$_2$CO$_3$ (1308 mg, 9.46 mmol) were added. The reaction vessel was sealed and heated in Biotage Initiator at 110° C. for 1 hour. After cooling the reaction was complete. The reaction mixture was quenched with 10 mL of water and diluted with 10 mL of Et$_2$O. Phases were separated through a separating funnel. The organic phase was washed with 3×10 mL of water, 10 mL of brine, dried over sodium sulphate, filtered and evaporated under vacuum to give the title compound as a pale orange oil. (623 mg).

¹H NMR (400 MHz, CDCl₃) δ ppm 9.06 (1H, d), 8.49 (1H, dd), 7.40-7.34 (1H, m), 7.33-7.28 (2H, m), 7.10-7.05 (1H, m), 7.04 (1H, d), 2.55 (2H, q), 1.18 (3H, t); UPLC_B: 0.95 min, 245 [M+H]+.

Intermediate 46

6-[(2-ethylphenyl)oxy]-3-pyridinamine

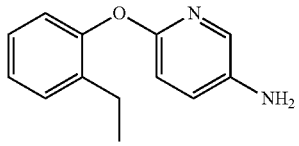

In a 50 mL round-bottomed flask 2-[(2-ethylphenyl)oxy]-5-nitropyridine (Intermediate 45, 623 mg) was dissolved in ethanol (10 mL) to give a pale orange solution. Palladium on carbon (244 mg, 0.230 mmol) and hydrazine hydrate (0.442 mL, 4.59 mmol) were added. The reaction mixture was stirred at 90° C. After 3 hours the reaction was completed. The reaction mixture was filtered and the organic phase was evaporated under vacuum affording 1.1408 g of a dark orange solid that was charged on a 10 g SCX cartridge. It was then flushed with 200 mL of ethanol followed by 50 mL of 2M solution of ammonia in MeOH. The ammonia eluate was evaporated under vacuum to afford the title compound as dark orange solid (456.1 mg).

¹H NMR (400 MHz, CDCl₃) δ ppm 7.71 (d, 1H), 7.26-7.31 (m, 1H), 7.16-7.22 (m, 1H), 7.10-7.15 (m, 1H), 7.07 (dd, 1H), 6.96 (dd, 1H), 6.70 (d, 1H), 3.52 (br. s., 2H), 2.64 (q, 2H), 1.20 (t, 3H); UPLC_B: 0.75 mins, 215 [M+H]+.

Intermediate 47

1,1-dimethylethyl[(1R)-2-({6-[(2-ethylphenyl)oxy]-3-pyridinyl}amino)-1-methyl-2-oxoethyl]carbamate

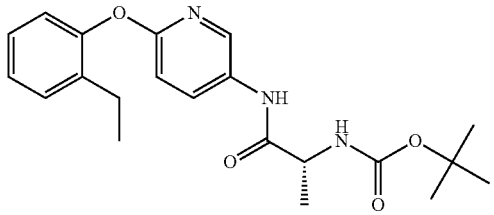 [SMILES: CCc1ccccc1Oc1ccc(NC(=O)[C@@H](C)NC(=O)OC(C)(C)C)cn1]

In a 8 mL vial N-{[(1,1-dimethylethyl)oxy]carbonyl}-D-alanine (193 mg, 1.022 mmol) was dissolved in N,N-dimethylformamide (4 mL) to give a colorless solution. N-ethyl-N-(1-methylethyl)-2-propanamine (0.223 mL, 1.277 mmol) and N-[(1H-1,2,3-benzotriazol-1-yloxy)(dimethylamino)methylidene]-N-methylmethanaminium tetrafluoroborate (328 mg, 1.022 mmol) were added. The reaction mixture was stirred at room temperature for 15 min. 6-[(2-ethylphenyl)oxy]-3-pyridinamine (Intermediate 46, 228 mg) was added and the reaction mixture was warmed to 60° C. for 32 hours. The solvent was evaporated under vacuum using the Genevac affording a dark brown oil, which was purified by silica gel chromatography (Biotage system, 25 g SNAP column) eluting with a gradient Cyclohexane/EtOAc from 3:1 C to 1:1 in 10 CV; then 1:1 for 5V. The collected fractions afforded the title compound (251.1 mg).

¹H NMR (400 MHz, CDCl₃): δ ppm 8.70 (1H, br. s), 8.17 (1H, d), 8.05 (1H, dd), 7.31 (1H, dd), 7.14-7.27 (2H, m), 7.02 (1H, dd), 6.82 (1H, d), 5.11 (1H, d), 4.22-4.52 (1H, m), 2.60 (2H, q), 1.47 (9H, s), 1.44-1.46 (3H, m), 1.18 (3H, t); UPLC_B: 0.90 min, 386 [M+H]+.

Intermediate 48

N¹-{6-[(2-ethylphenyl)oxy]-3-pyridinyl}-D-alaninamide

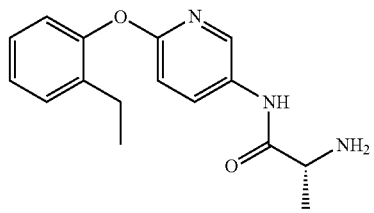 [SMILES: CCc1ccccc1Oc1ccc(NC(=O)[C@@H](C)N)cn1]

In a 50 mL round-bottomed flask 1,1-dimethylethyl[(1R)-2-({6-[(2-ethylphenyl)oxy]-3-pyridinyl}amino)-1-methyl-2-oxoethyl]carbamate (Intermediate 47, 251.1 mg) was dissolved in dichloromethane (2 mL) to give a pale orange solution. Trifluoroacetic acid (2 mL, 26.0 mmol) was added. The reaction mixture was stirred at room temperature. After 20 minutes the solvent was evaporated under vacuum affording a yellow oil which was charged on a 5 g SCX cartridge and flushed with 25 mL of MeOH followed by 25 mL of 2M solution of ammonia in MeOH. The ammonia eluate was evaporated under vacuum to afford the title compound as a yellow oil which solidified (170.0 mg).

¹H NMR (400 MHz, CDCl₃): δ ppm 9.58 (1H, br. s), 8.24 (1H, d), 8.20 (1H, dd), 7.30-7.35 (1H, m), 7.15-7.27 (2H, m), 7.03 (1H, dd), 6.85 (1H, d), 3.69 (1H, q), 2.61 (2H, q), 2.31 (2H, br. s), 1.46 (3H, d), 1.20 (3H, t); UPLC_B: 0.71 mins, 286 [M+H]+.

Intermediate 49

2-{[4-methyl-3-(methyloxy)phenyl]oxy}-5-nitropyridine

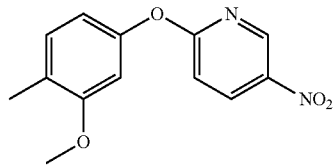

To a solution of 4-methyl-3-(methyloxy)phenol (Intermediate 18, 400 mg) in dry N,N-dimethylformamide (15 mL), potassium carbonate (1200 mg, 8.69 mmol) and then 2-chloro-5-nitropyridine (551 mg, 3.47 mmol) were added and the reaction mixture was stirred for 2 hours at 115° C. The reaction was quenched with water (10 mL), diluted with brine (20 mL) and extracted with ethyl acetate (3 times 30 mL). The organic layer was washed with ice cold brine (2 times 30 mL), dried over sodium sulphate, filtered and evaporated. The residue was purified by silica gel chromatography (Biotage system, 100 g SNAP column) with a gradient cyclohexane/ethyl acetate from 10/0 to 8/2. Evaporation afforded the to title compound as a light yellow oil (570 mg).

¹H-NMR (400 MHz, DMSO-d₆) δ ppm: 2.16 (3H, s), 3.76 (3H, s), 6.68-6.73 (1H, m), 6.83-6.86 (1H, m), 7.24-7.18 (2H, m), 8.64-8.58 (1H, m), 9.08-9.02 (1H, m); UPLC_B: 0.93 min, 261 [M+H]+.

Intermediate 50

6-{[4-methyl-3-(methyloxy)phenyl]oxy}-3-pyridinamine

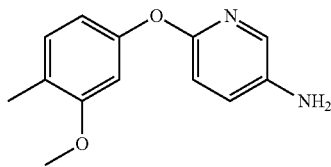 [SMILES: COc1cc(Oc2ccc([N+](=O)[O-])cn2)ccc1C]

To a solution of 2-{[4-methyl-3-(methyloxy)phenyl]oxy}-5-nitropyridine (Intermediate 49, 568 mg) in tetrahydrofuran (25 mL)/water (12.50 mL), iron (609 mg, 10.91 mmol) and then ammonium chloride (584 mg, 10.91 mmol) were added and the reaction mixture was stirred for 8 hours at room temperature. The catalyst was filtered off and the solution was diluted with an aqueous saturated solution of Na2CO3 (5 mL) and extracted with ethyl acetate (2 times 40 mL). Combined organic layers were dried over sodium sulphate, filtered and evaporated and the residue was purified by silica gel chromatography (Biotage system with a 50 g SNAP column) using a as eluent a gradient cyclohexane/ethyl acetate from 8/2 to 1/1. Evaporation afforded the title compound as light yellow oil (465 mg).

¹H-NMR (400 MHz, DMSO-d₆) δ ppm: 7.54 (1H, d), 7.06 (2H, ddd), 6.72 (1H, d), 6.59 (1H, d), 6.38 (1H, dd), 5.07 (2H, s), 3.73 (3H, s), 2.10 (3H, s); UPLC_B: 0.72 min, 231 [M+H]+.

Intermediate 51

1,1-dimethylethyl{(1R)-1-methyl-2-[(6-{[4-methyl-3-(methyloxy)phenyl]oxy}-3-pyridinyl)amino]-2-oxoethyl}carbamate

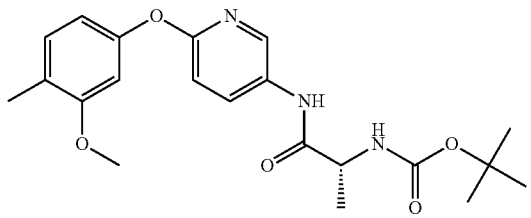 [SMILES: COc1cc(Oc2ccc(NC(=O)[C@@H](C)NC(=O)OC(C)(C)C)cn2)ccc1C]

To a solution of N-{[(1,1-dimethylethyl)oxy]carbonyl}-D-alanine (181 mg, 0.955 mmol) in dry N,N-dimethylformamide (3 mL), DIPEA (0.303 mL, 1.737 mmol) and then TBTU (335 mg, 1.042 mmol) were added and the reaction mixture was stirred for 15 minutes at room temperature. 6-{[4-methyl-3-(methyloxy)phenyl]oxy}-3-pyridinamine (Intermediate 50, 200 mg) was then added and the reaction mixture was stirred for 1 hour at the same temperature. The reaction was quenched with water (2 mL), diluted with brine (10 mL) and extracted with ethyl acetate (2×20 mL). The organic layer was dried over sodium sulphate, filtered and evaporated and the residue was purified by silica gel chromatography (Biotage system, 10 g SNAP column) using a gradient cHex/EtOAc as eluent from 100/0 to 70/30. This afforded the title compound (350 mg)

¹H NMR (400 MHz, DMSO-d₆) d ppm 10.09 (1H, br. s), 8.38-8.29 (1H, m), 8.09-8.03 (1H, m), 7.12 (2H, d), 6.97 (1H, d), 6.70 (1H, d), 6.57-6.51 (1H, m), 4.16-4.04 (1H, m), 3.74 (3H, s), 2.13 (3H, s), 1.39 (9H, s), 1.26 (3H, d); UPLC_B: 0.87 min, 402 [M+H]+

Intermediate 52

N-(6-{[4-methyl-3-(methyloxy)phenyl]oxy}-3-pyridinyl)-D-alaninamide

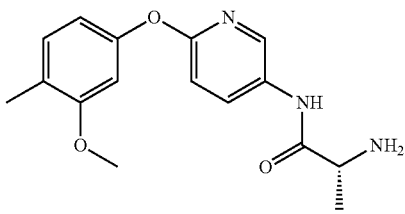 [SMILES: COc1cc(Oc2ccc(NC(=O)[C@@H](C)N)cn2)ccc1C]

To a solution of 1,1-dimethylethyl{(1R)-1-methyl-2-[(6-{[4-methyl-3-(methyloxy)phenyl]oxy}-3-pyridinyl)amino]-2-oxoethyl}carbamate (Intermediate 51, 350 mg) in dry dichloromethane (7.5 mL), TFA (2.5 mL, 32.4 mmol) was slowly added and the reaction mixture was stirred for 1.5 hours at room temperature. The solvent and the excess of TFA were evaporated and the residue was purified with an SCX cartridge (10 g) to afford the title compound as a colourless oil (258 mg).

¹H NMR (400 MHz, DMSO-d₆) d ppm 8.40 (1H, d), 8.11 (1H, dd), 7.13 (1H, d), 6.96 (1H, d), 6.70 (1H, d), 6.54 (1H, dd), 3.75 (3H, s), 3.44 (1H, q), 3.33 (2H, br. s), 2.13 (3H, s), 1.22 (3H, d); UPLCB: 0.70 min, 302 [M+H]+

Intermediate 53

2-{[2-methyl-5-(methyloxy)phenyl]oxy}-5-nitropyridine

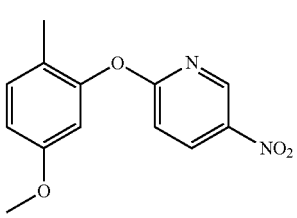 [SMILES: COc1ccc(C)c(Oc2ccc([N+](=O)[O-])cn2)c1]

To a solution of 2-methyl-5-(methyloxy)phenol (Intermediate 12, 2 g) and 2-chloro-5-nitropyridine (2.1 g, 13.2 mmol) in DMF (50 mL) was added potassium carbonate (2.76 g, 20 mmol) and the reaction mixture was stirred at 100° C. overnight. The mixture was evaporated under vacuum and water (100 mL) was added. It was extracted with ethyl acetate (3 times 100 mL) and the combined organic layers were dried

Intermediate 54

6-{[2-methyl-5-(methyloxy)phenyl]oxy}-3-pyridinamine

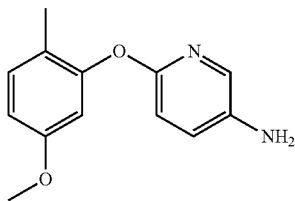

To a solution of 2-{[2-methyl-5-(methyloxy)phenyl]oxy}-5-nitropyridine (Intermediate 53, 1.5 g) in ethanol (100 mL) was added Pd/C (5%, 200 mg) and the mixture was stirred at room temperature under H$_2$ atmosphere overnight. The mixture was filtered through a pad of celite and the filtrate was evaporated to afford a yellow oil, which was purified by column chromatography on silica gel (mobile phase: EtOAc/PE=1/5-1/2). This afforded the title compound (850 mg).

$^1$HNMR (400 MHz, CDCl$_3$): δ 7.70 (1H, s), 7.12 (1H, d), 7.05-7.08 (1H, d), 6.69 (1H, d), 6.63-6.66 (1H, d), 6.54 (1H, s), 3.74 (3H, s), 3.45 (2H, s), 2.12 (3H, s); MS_2 (ESI): 231 [M+H]+

Intermediate 55

1,1-dimethylethyl{(1R)-1-methyl-2-[(6-{[2-methyl-5-(methyloxy)phenyl]oxy}-3-pyridinyl)amino]-2-oxoethyl}carbamate

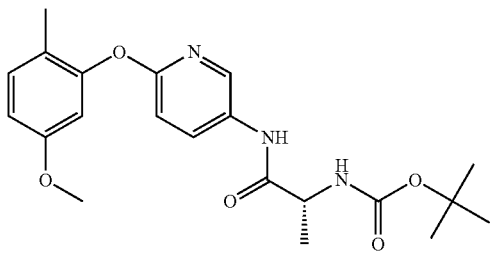 [SMILES: COc1ccc(C)c(Oc2ccc(NC(=O)[C@@H](C)NC(=O)OC(C)(C)C)cn2)c1]

The title compound was made in a similar fashion to the preparation of Intermediate 15 replacing 4-{[2-methyl-5-(methyloxy)phenyl]oxy}aniline with 6-{[2-methyl-5-(methyloxy)phenyl]oxy}-3-pyridinamine (Intermediate 54, 90 mg) to afford the title compound (152 mg).

$^1$H NMR (400 MHz, methanol-d$_4$): δ ppm 8.32 (1H, d), 8.05 (1H, d), 7.18 (1H, d), 6.86 (1H, d), 6.76 (1H, d), 6.61 (1H, d), 4.25 (1H, m), 3.13 (3H, s), 2.08 (3H, s), 1.46 (9H, s), 1.41 (3H, d); UPLC_B: 0.85 min, 402 [M+H]+

Intermediate 56

N$^1$-(6-{[2-methyl-5-(methyloxy)phenyl]oxy}-3-pyridinyl)-D-alaninamide

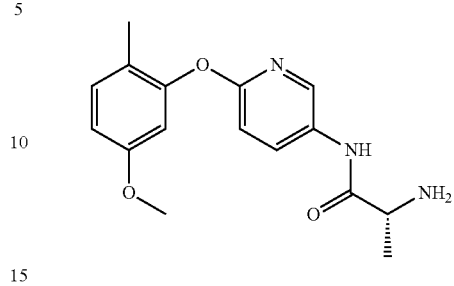

The title compound was made in a similar fashion to the preparation of Intermediate 16 replacing {(1R)-1-methyl-2-[(4-{[2-methyl-5-(methyloxy)phenyl]oxy}phenyl)amino]-2-oxoethyl}carbamate with 1,1-dimethylethyl{(1R)-1-methyl-2-[(6-{[2-methyl-5-(methyloxy)phenyl]oxy}-3-pyridinyl)amino]-2-oxoethyl}carbamate (Intermediate 55, 150 mg) to afford the title compound (120 mg).

$^1$H NMR (400 MHz, methanol-d$_4$): δ ppm 8.32 (1H, d), 8.05 (1H, dd), 7.17 (1H, d), 6.83 (1H, d), 6.73 (1H, d), 6.58 (1H, d), 3.74 (3H, s), 3.63-3.50 (1H, m), 2.06 (3H, s), 1.36 (3H, d); UPLC_B: 0.66 min, 302 [M+H]+

Intermediate 57

2-methyl-1-(methyloxy)-3-nitrobenzene

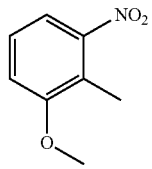

To a solution of 2-methyl-3-nitrophenol (15.3 g, 100 mmol) in DMF (150 mL) was added sodium hydride (60% in mineral oil, 2.6 g, 110 mmol) at 0° C. and the mixture was stirred for 30 minutes at room temperature. Methyl iodide (28.4 g, 200 mmol) was added and the mixture was heated to 80° C. for 5 hours. Water (100 mL) was added and the mixture was extracted with ethyl acetate (3 times 100 mL). The combined ethyl acetate phases were dried over sodium sulphate and concentrated under vacuum to give a residue, which was purified by column chromatography on silica gel (PE:EtOAc=5:1). Evaporation afforded the title compound as a yellow solid (14.4 g).

Intermediate 58

2-methyl-3-(methyloxy)aniline

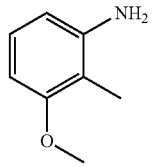

To a solution of 2-methyl-1-(methyloxy)-3-nitrobenzene (Intermediate 57, 1.67 g) in methanol (50 mL) was added Pd/C (10%, 50 mg) and the reaction mixture was stirred under

Intermediate 59

2-methyl-3-(methyloxy)phenol

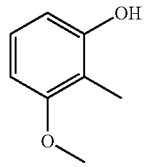

To a solution of 2-methyl-3-(methyloxy)aniline (Intermediate 58, 1.31 g) in H2SO4 (6 M, 100 mL) was added portionwise NaNO2 (794 mg, 11 mmol) at 0° C. The mixture was stirred for another 2 hours at 40° C. and water (100 mL) was added. The resulting mixture was extracted with ethyl acetate (3 times 100 mL) and the combined ethyl acetate phases were dried and evaporated. The residue was purified by silica gel column chromatography (PE:EtOAc=5:1) to afford the title compound as a solid (569 mg).

Intermediate 60

2-{[2-methyl-3-(methyloxy)phenyl]oxy}-5-nitropyridine

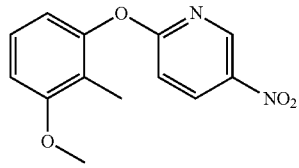 [SMILES: COc1cccc(Oc2ccc([N+](=O)[O-])cn2)c1C]

To a solution of 2-methyl-3-(methyloxy)phenol (Intermediate 59, 1.3 g) in DMF (50 mL) was added sodium hydride (60% in mineral oil, 480 mg, 0.012 mol at 0° C. and the mixture was stirred for 30 minutes. 2-Chloro-5-nitropyridine (1.9 g, 0.012 mol, Aldrich) was added and the mixture was heated at 60° C. for 3 hours. The mixture was poured into $H_2O$ (100 mL) and extracted with ethyl acetate (4 times 100 mL). The combined ethyl acetate phases were dried over sodium sulphate and concentrated under vacuum to give a residue which was purified by column chromatography on silica gel (PE:EtOAc=10:1) to afford the title compound (2.3 g) as a liquid.

MS_2 (ESI): 261 [M+H]+.

Intermediate 61

6-{[2-methyl-3-(methyloxy)phenyl]oxy}-3-pyridinamine hydrochloride salt

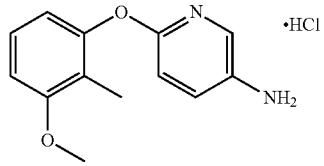 [SMILES: COc1cccc(Oc2ccc(N)cn2)c1C ; Cl]

To a solution of 2-{[2-methyl-3-(methyloxy)phenyl]oxy}-5-nitropyridine (Intermediate 60, 2.3 g) in methanol (30 mL) was added Pd/C (10%, 0.3 g) and H2 was bubbled into the mixture for 2 hours at room temperature. The reaction mixture was filtered through a pad of Celite. The filtrate was bubbled into HCl gas. The resulting mixture was concentrated to afford the title compound as a white solid (2 g).

$^1$HNMR (DMSO-d): δ ppm 10.0-8.5 (3H, m), 8.03-8.02 (1H, s), 7.73-7.71 (1H, d), 7.22-7.18 (1H, t), 7.05-7.02 (1H, d), 6.87-6.85 (1H, d), 6.65-6.63 (1H, d), 3.82 (3H, s), 1.90 (3H, s); MS_2 (ESI): 231 [M−(HCl)+H]+.

Intermediate 62

1,1-dimethylethyl{(1R)-1-methyl-2-[(6-{[2-methyl-3-(methyloxy)phenyl]oxy}-3-pyridinyl)amino]-2-oxoethyl}carbamate

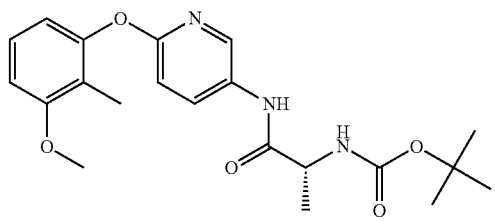 [SMILES: COc1cccc(Oc2ccc(NC(=O)[C@@H](C)NC(=O)OC(C)(C)C)cn2)c1C]

The title compound (307 mg) was made in a similar fashion to the preparation of Intermediate 25 replacing 6-{[3-(1-methylethyl)phenyl]oxy}-3-pyridinamine with 6-{[2-methyl-3-(methyloxy)phenyl]oxy}-3-pyridinamine (Intermediate 61, 201 mg).

$^1$H NMR (400 MHz, methanol-$d_4$): δ ppm 8.75 (1H, d), 8.44 (1H, dd), 7.93-8.11 (1H, m), 7.53 (1H, dd), 7.19 (1H, t), 6.83 (2H, t), 6.62 (1H, d), 4.09-4.33 (1H, m), 3.87 (3H, s), 2.02 (3H, s), 1.44-1.51 (9H, m), 1.42 (3H, d); UPLC_B: 0.86 min, 402 [M+H]+

Intermediate 63

$N^1$-(6-{[2-methyl-3-(methyloxy)phenyl]oxy}-3-pyridinyl)-D-alaninamide

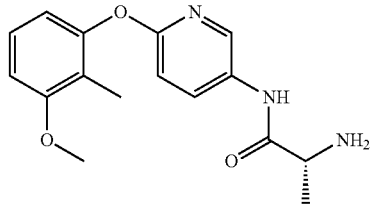 [SMILES: COc1cccc(Oc2ccc(NC(=O)[C@@H](C)N)cn2)c1C]

The title compound (268 mg) was made in a similar fashion to the preparation of Intermediate 26 replacing 1,1-dimethylethyl{(1R)-1-methyl-2-[(6-{[3-(1-methylethyl)phenyl]oxy}-3-pyridinyl)amino]-2-oxoethyl}carbamate with 1,1-dimethylethyl{(1R)-1-methyl-2-[(6-{[2-methyl-3-(methyloxy)phenyl]oxy}-3-pyridinyl)amino]-2-oxoethyl}carbamate (Intermediate 62, 304 mg). Instead of being stirred at 0° C. for 3 hours, the reaction was stirred at 0° C. for 1 hour and at room temperature for 2 hours.

$^1$H NMR (400 MHz, methanol-$d_4$): δ ppm 8.33 (1H, d), 8.03 (1H, dd), 7.18 (1H, t), 6.81 (2H, t), 6.60 (1H, d), 3.85 (3H, s), 3.66 (1H, q), 2.00 (3H, s), 1.40 (3H, d); UPLC_B: 0.67 min, 302 [M+H]+

Intermediate 64

1,1-dimethylethyl((1R)-1-{[(6-{[4-methyl-3-(methyloxy)phenyl]oxy}-3-pyridinyl)amino]carbonyl}propyl)carbamate

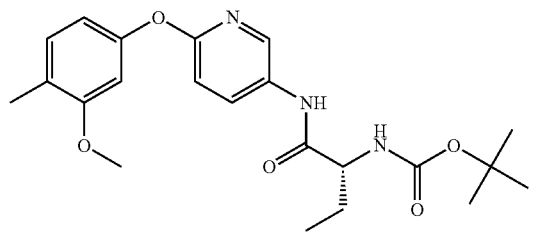 [SMILES: CC[C@@H](NC(=O)OC(C)(C)C)C(=O)Nc1ccc(Oc2ccc(C)c(OC)c2)nc1]

To a solution of (2R)-2-({[(1,1-dimethylethyl)oxy]carbonyl}amino)butanoic acid (106 mg, 0.521 mmol) in dry N,N-dimethylformamide (2 mL) DIPEA (0.152 mL, 0.869 mmol) and then TBTU (181 mg, 0.565 mmol) were added and the reaction mixture was stirred for 15 minutes at room temperature. 6-{[4-methyl-3-(methyloxy)phenyl]oxy}-3-pyridinamine (Intermediate 50, 100 mg) was then added and the reaction mixture was stirred overnight at the same temperature. The reaction was quenched with water (1 mL), diluted with brine (1 mL) and extracted with ethyl acetate (3 times mL). The organic layer was dried over sodium sulphate, filtered and evaporated and the residue was purified by silica gel chromatography (Biotage system, 10 g SNAP column) using as eluent a gradient cyclohexane/ethyl acetate from 100/0 to 70/30 to afford the title compound as a white solid (180 mg).

$^1$H NMR (400 MHz, DMSO-$d_6$) δ ppm: 10.13 (1H, br. s), 8.31-8.37 (1H, m), 8.02-8.10 (1H, m), 7.09-7.16 (1H, m), 7.01-7.08 (1H, m), 6.96 (1H, d), 6.70 (1H, d), 6.51-6.58 (1H, m), 3.91-4.03 (1H, m), 3.75 (3H, s), 2.13 (3H, s), 1.50-1.76 (2H, m), 1.39 (9H, s), 0.90 (3H, t); UPLC_B: 0.91 min, 416 [M+H]+.

Intermediate 65

(2R)-2-amino-N-(6-{[4-methyl-3-(methyloxy)phenyl]oxy}-3-pyridinyl)butanamide

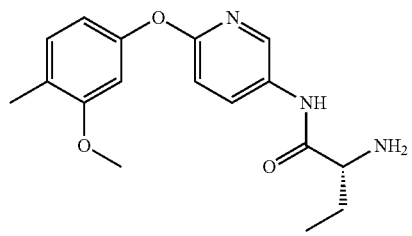 [SMILES: CC[C@@H](N)C(=O)Nc1ccc(Oc2ccc(C)c(OC)c2)nc1]

To a solution of 1,1-dimethylethyl((1R)-1-{[(6-{[4-methyl-3-(methyloxy)phenyl]oxy}-3-pyridinyl)amino]carbonyl}propyl)carbamate (Intermediate 64, 175 mg) in dry dichloromethane (DCM) (6 mL) TFA (2 mL, 26.0 mmol) was slowly added and the reaction mixture was stirred for 1 h at room temperature. The solvent and the excess of TFA were evaporated and the residue was purified by SCX cartridge (5 g) to afford the title compound as a colourless solid (122 mg).

$^1$H-NMR (400 MHz, DMSO-$d_6$) δ ppm: 8.36-8.42 (1H, m), 8.11 (1H, dd), 7.12 (1H, d), 6.95 (1H, d), 6.67-6.73 (1H, m), 6.54 (1H, dd), 3.75 (3H, s), 3.24 (1H, m), 2.13 (3H, s), 1.59-1.73 (1H, m), 1.42-1.56 (1H, m), 0.90 (3H, t); UPLC_B: 0.74 min, 316 [M+H]+.

Intermediate 65b (2HCl Salt of Intermediate 65)

(2R)-2-amino-N-(6-{[4-methyl-3-(methyloxy)phenyl]oxy}-3-pyridinyl)butanamide.2HCl

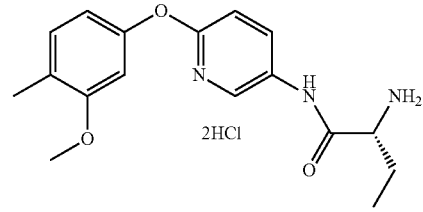 [SMILES: CC[C@@H](N)C(=O)Nc1ccc(Oc2ccc(C)c(OC)c2)nc1]

6-{[4-methyl-3-(methyloxy)phenyl]oxy}-3-pyridinamine (Intermediate 50, 500 g), (2R)-2-({[(1,1-dimethylethyl)oxy]carbonyl}amino)butanoic acid (530 g) and Et$_3$N (905 mL) are mixed together in ethyl acetate (2 L) and stirred at 0° C. until complete dissolution. ®T3P (2.15 L) was added dropwise in 30 minutes maintaining the temperature at ~0° C. Ethyl acetate (500 mL) was added for washing the line. Work-up: 10% w/w sodium carbonate aqueous solution (2.5 L) was added and the mixture was stirred for 20 minutes. Then water (1.5 L) and ethyl acetate (1 L) were added and the two phases separated. The organic layer was washed with 10% w/w sodium carbonate aqueous solution (2.5 L), stirring the mixture for 10 minutes before separation of phases, then with 28% malic acid aqueous solution (2.5 L) and finally with 20% NaCl aqueous solution (2.5 L). The organic solution was concentrated to the lowest volume (<2 L), acetonitrile (5 L) was added, the solution was concentrated to the lowest volume (<2 L) and acetonitrile was added up to 12.5 L (it is a solution of Intermediate 64 in acetonitrile). To this solution, 5-6N HCl solution in Isopropanol (2.5 L) was added at 20° C. and the resulting reaction mixture was stirred at 45° C. for 1.5 hours. The obtained suspension was cooled to 20° C., stirred for 1 hour and then filtered. The collected solid was washed with 5/1 acetonitrile/Isopropanol (3×1.5 L), then dried under vacuum at 40° C., until constant weight, obtaining the title compound (817 g).

$^1$H-NMR (400 MHz, DMSO-$d_6$): δ ppm 11.13 (1H, s), 8.30-8.50 (m, 4H), 8.07 (1H, dd), 7.10 (1H, d), 6.98 (1H, d), 6.69 (1H, d), 6.53 (1H, dd), 3.99 (1H, m), 3.72 (3H, s), 2.10 (3H, s), 1.80-1.95 (2H m), 0.92 (3H, t).

A generic Ion Chromatography method was used in order to determine the amount of Chloride. Method Conditions: Equipment Dionex ICS2000, Column type Dionex AS18 2 mm×250 mm; Mobile Phase KOH 41 mM; Flow rate 0.47 mL/min; Conductimetric Detection. Result: Chloride 17.5% w/w. From this result Intermediate 65b was confirmed being a di-hydrochloride salt.

Intermediate 66

1,1-dimethylethyl((1S)-1-{[(6-{[4-methyl-3-(methyloxy)phenyl]oxy}-3-pyridinyl)amino]carbonyl}propyl)carbamate

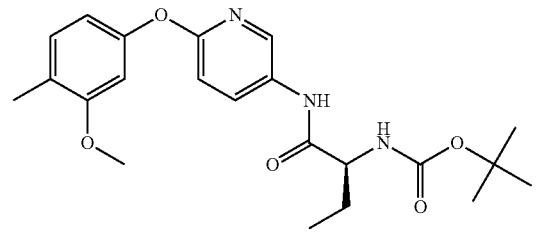 [SMILES: CC[C@H](NC(=O)OC(C)(C)C)C(=O)Nc1ccc(Oc2ccc(C)c(OC)c2)nc1]

To a solution of (2S)-2-({[(1,1-dimethylethyl)oxy]carbonyl}amino)butanoic acid (66.2 mg, 0.326 mmol) in dry N,N-dimethylformamide (1 mL), DIPEA (0.095 mL, 0.543 mmol) and then TBTU (112 mg, 0.347 mmol) were added and the reaction mixture was stirred for 15 minutes at room temperature. 6-{[4-methyl-3-(methyloxy)phenyl]oxy}-3-pyridinamine (Intermediate 50, 50 mg) was then added and the reaction mixture was stirred at room temperature overnight. The mixture was diluted with ethyl acetate (10 mL) and washed with brine (3 times 8 mL). The organic phase was separated, dried over sodium sulphate, filtered and evaporated. The residue was purified by flash chromatography on silica gel using a column SNAP 10 g and cyclohexane/ethyl acetate from 100/0 to 60/40 as eluent. This afforded the title compound as a white solid (73 mg).

1H NMR (400 MHz, DMSO): δ ppm 10.13 (1H, s), 8.33 (1H, d), 8.06 (1H, dd), 7.11 (1H, d), 7.05 (1H, d), 6.95 (1H, d), 6.69 (1H, d), 6.53 (1H, dd), 4.00-3.91 (1H, m), 3.73 (3H, s), 2.13 (3H, s), 1.74-1.51 (2H, m), 1.38 (9H, s), 0.89 (3H, t); UPLC_B: 0.92 min, 414 [M−H]−

Intermediate 67

(2S)-2-amino-N-(6-{[4-methyl-3-(methyloxy)phenyl]oxy}-3-pyridinyl)butanamide

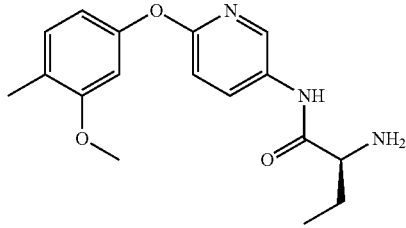 [SMILES: CC[C@H](N)C(=O)Nc1ccc(Oc2ccc(C)c(OC)c2)nc1]

To a solution of 1,1-dimethylethyl((1S)-1-{[(6-{[4-methyl-3-(methyloxy)phenyl]oxy}-3-pyridinyl)amino]carbonyl}propyl)carbamate (Intermediate 66, 70 mg) in dichlorometane (2.5 mL) cooled down to 0° C. TFA (0.779 mL, 10.11 mmol) was added dropwise. The reaction mixture was stirred at 0° C. for 1.5 hours and then evaporated. The residue was diluted with dichloromethane (10 mL) and neutralized with a saturated aqueous solution of NaHCO3 (15 mL). The organic phase was separated, dried over sodium sulphate, filtered and evaporated to afford the title compound as a yellow pale oil (53.1 mg).

1H NMR (400 MHz, DMSO): δ ppm 8.39 (1H, d), 8.11 (1H, dd), 7.12 (1H, d), 6.95 (1H, d), 6.70 (1H, d), 6.54 (1H, dd), 3.74 (3H, s), 3.52-3.21 (1H, m), 2.12 (3H, s), 1.71-1.44 (2H, m), 0.89 (3H, t). UPLC_B: 0.75 min, 314 [M−H]−

Intermediate 68

(2R)-2-({[(1,1-dimethylethyl)oxy]carbonyl}amino)butanoic acid

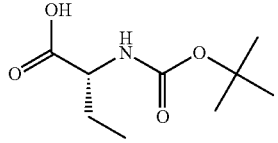

To a solution of (2R)-2-aminobutyric acid 5 (1.95 g, 18.91 mmol) in 19 mL of 1 M aqueous sodium hydroxide and 13 mL of methanol was added Boc-anhydride (4.95 g, 22.69 mmol) at 0° C. The reaction mixture was warmed to room temperature and stirred for 12 hours. After most of the methanol was evaporated, the solution was acidified to pH 2 with 1 M HCl and extracted with ethyl acetate (3 times 60 mL). The organic extracts were combined and washed with brine (2 times 12 mL). Evaporation of the solvent afforded the title compound (3.48 g).

1H-NMR (400 MHz, DMSO-d6): δ ppm 12.35 (1H, s), 7.02 (1H, d), 3.71-4.07 (1H, m), 1.47-1.79 (2H, m), 1.38 (9H, s), 0.88 (3H, t); UPLC: 0.60 min, 204 [M+H]]+.

Intermediate 69

1,1-dimethylethyl{(1R)-1-methyl-2-[(6-{[3-(1-methylethyl)phenyl]oxy}-3-pyridinyl)amino]-2-oxoethyl}carbamate

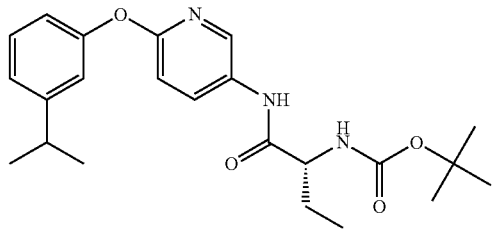 [SMILES: CC[C@@H](NC(=O)OC(C)(C)C)C(=O)Nc1ccc(Oc2cccc(C(C)C)c2)nc1]

To a solution of (2R)-2-({[(1,1-dimethylethyl)oxy]carbonyl}amino)butanoic acid (Intermediate 68, 875 mg) in dry N,N-dimethylformamide (50 mL), DIPEA (0.935 mL, 5.36 mmol, 1.5 equiv) and then HATU (1.629 g, 4.28 mmol, 1.2 equiv) were added and the reaction mixture was stirred for 15 minutes at room temperature under argon.

Then (4-{[3-(methyloxy)phenyl]oxy}phenyl)amine 4-{[3-(methyloxy)phenyl]oxy}aniline (Intermediate 24, 815 mg) was added and the reaction mixture was stirred at 63° C. under argon. The reaction was left under heating 17 hours. After evaporation, the residue obtained was purified by silica gel chromatography (Companion system, 120 g cartridge) with a gradient cyclohexane/ethyl acetate from 100/0 to 70/30. The title compound was obtained as a yellow powder (1.282 g)

1H NMR (400 MHz, methanol-d4): δ ppm 8.37 (1H, d), 8.10 (1H, dd), 7.34 (1H, t), 7.13 (1H, d), 6.98 (1H, t), 6.92 (2H, m), 4.11 (1H, t), 2.94-2.89 (1H, m), 2.02-1.77 (1H, m), 1.75-1.72 (1H, m), 1.48 (9H, s), 1.27 (6H, d), 1.04 (3H, t); UPLC: 0.91 min, 414 [M+1]+

Intermediate 70

(2R)-2-amino-N-(6-{[3-(1-methylethyl)phenyl]oxy}-3-pyridinyl)butanamide

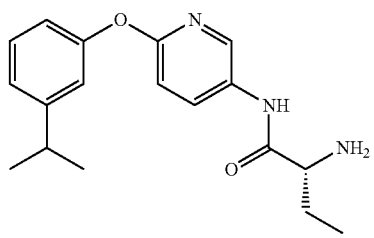 [SMILES: CC[C@@H](N)C(=O)Nc1ccc(Oc2cccc(C(C)C)c2)nc1]

1,1-dimethylethyl((1R)-1-{[(6-{[3-(1-methylethyl)phenyl]oxy}-3-pyridinyl)amino]carbonyl}propyl)carbamate (Intermediate 69, 1.28 g) was dissolved in 18 mL of dry dichloromethane. To this solution at 0° C. under argon was added dropwise 30 equivalents of TFA (7.15 mL, 93 mmol). The reaction was stirred during 3 hours at 0° C. The reaction mixture was evaporated. The residue obtained was purified by SCX on a 50 g cartridge. The cartridge was washed with 3 CV of methanol, then the compound was adsorbed on the cartridge, washed with 5 CV of methanol and desorbed with 2 CV of methanolic ammonia (1N). After evaporation of the volatiles, the title compound was obtained (932 mg).

$^1$H NMR (400 MHz, methanol-$d_4$): δ ppm 8.36 (1H, d), 8.08 (1H, dd), 7.30 (1H, t), 7.08 (1H, d), 6.98-6.78 (3H, m), 3.39 (1H, t), 2.94-2.84 (1H, m), 2.81 (2H, s), 1.87-1.74 (1H, m), 1.73-1.59 (1H, m), 1.25 (6H, d), 1.00 (3H, t); UPLC: 0.60 min, 314 [M+1]+

Intermediate 71

1,1-dimethylethyl {1,1-dimethyl-2-[(4-{[3-(methyloxy)phenyl]oxy}phenyl)amino]-2-oxoethyl}carbamate

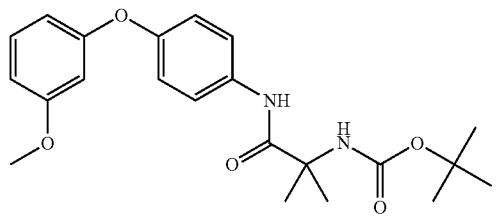 [SMILES: COc1cccc(Oc2ccc(NC(=O)C(C)(C)NC(=O)OC(C)(C)C)cc2)c1]

To a solution of N-{[(1,1-dimethylethyl)oxy]carbonyl}-2-methylalanine (1.7 g, 8.36 mmol) in dry N,N-dimethylformamide (35 mL), DIPEA (2.434 mL, 13.94 mmol) and then TBTU (2.80 g, 8.71 mmol) were added and the reaction mixture was stirred for 15 minutes at room temperature. (4-{[3-(methyloxy)phenyl]oxy}phenyl)amine (1.5 g, 6.97 mmol) was then added and the reaction mixture was stirred overnight at the same temperature. The reaction was quenched with brine (100 mL) and extracted with ethyl acetate (twice 150 mL). The organic layer was washed with ice cold brine (3 times 100 mL), dried over sodium sulphate, filtered and evaporated. The residue was purified by silica gel chromatography (Biotage system, 100 g SNAP column) using as eluent a gradient and cyclohexane/ethyl acetate from 100/0 to 70/30 to afford the title compound as a white solid (1.90 g).

$^1$H NMR (400 MHz, DMSO-$d_6$) d ppm 9.47 (1H, br. s), 7.50-7.76 (2H, m), 7.24 (1H, t), 6.97 (3H, d), 6.67 (1H, dd), 6.44-6.55 (2H, m), 3.72 (3H, s), 1.25-1.47 (15H, m); UPLC_B: 0.91 min, 401 [M+1]+.

Intermediate 72

2-methyl-N$^1$-(4-{[3-(methyloxy)phenyl]oxy}phenyl)alaninamide

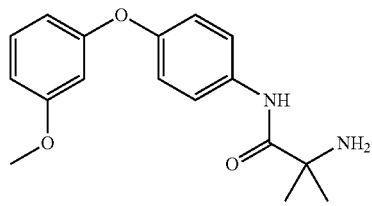 [SMILES: COc1cccc(Oc2ccc(NC(=O)C(C)(C)N)cc2)c1]

To a solution of 1,1-dimethylethyl {1,1-dimethyl-2-[(4-{[3-(methyloxy)phenyl]oxy}phenyl)amino]-2-oxoethyl}carbamate (Intermediate 71, 1.89 g) in dry dichloromethane (60 mL) at 0° C. TFA (20 mL, 260 mmol) was added dropwise and the reaction mixture was stirred for 2 hours at the same temperature. The solvent and the excess of TFA were evaporated and the residue was purified by SCX cartridge (50 g) to afford the title compound as a light brown oil (1.34 g).

$^1$H NMR (400 MHz, DMSO-$d_6$): δ ppm 7.73-7.64 (2H, m), 7.25 (1H, t), 6.95-7.03 (2H, m), 6.64-6.70 (1H, m), 6.45-6.55 (2H, m), 3.72 (3H, s), 1.28 (6H, s); UPLC_B: 0.79 min, 301 [M+1]+

Intermediate 73

2,3-dimethylphenyl 4-nitrophenyl ether

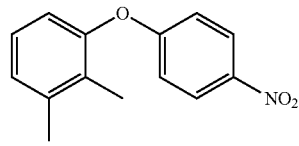 [SMILES: Cc1cccc(Oc2ccc([N+](=O)[O-])cc2)c1C]

In a microwave vial 1-fluoro-4-nitrobenzene (500 mg, 3.54 mmol) was dissolved in N,N-Dimethylformamide (10 mL) to give a pale yellow solution. Potassium carbonate (1469 mg, 10.63 mmol) and 2,3-dimethylphenol (433 mg, 3.54 mmol) were added. The reaction vessel was sealed and heated in Biotage Initiator at 100° C. for 1 hour. After cooling the reaction was diluted with 25 mL of Et$_2$O. The organic phase was washed with 3 times 25 mL of water, 10 mL of saturated brine, dried over sodium sulphate, filtered and evaporated under vacuum to afford the title compound as a yellow solid (865.1 mg).

$^1$H NMR (400 MHz, CDCl$_3$): δ ppm 8.25-8.14 (2H, m), 7.17 (1H, t), 7.13-7.08 (1H, m), 6.96-6.83 (3H, m), 2.36 (3H, s), 2.10 (3H, s); UPLC: 0.90 min, 244 [M+H]+.

Intermediate 74

4-[(2,3-dimethylphenyl)oxy]aniline

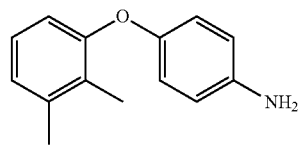 [SMILES: Cc1cccc(Oc2ccc(N)cc2)c1C]

2,3-dimethylphenyl 4-nitrophenyl ether (Intermediate 73, 865 mg) was dissolved in ethanol (10 mL) to give a pale yellow solution. Hydrazine hydrate 50% (0.698 mL, 7.1 mmol) and Pd/C (37.8 mg, 0.36 mmol) were added. The reaction mixture was stirred at 90° C. for 1 hour. The reaction mixture was filtered and the organic phase was evaporated under vacuum to afford the title compound as a pale yellow oil (796 mg).

$^1$H-NMR (400 MHz, CDCl$_3$): δ ppm 7.07-6.96 (1H, m), 6.90 (1H, d), 6.83-6.73 (2H, m), 6.72-6.61 (3H, m), 2.33 (3H, s), 2.22 (3H, s); UPLC: 0.60 min, 214 [M+H]+.

Intermediate 75

1,1-dimethylethyl[2-({4-[(2,3-dimethylphenyl)oxy]phenyl}amino)-1,1-dimethyl-2-oxoethyl]carbamate

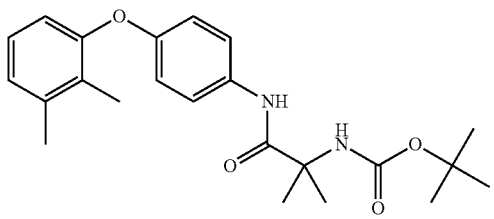 [SMILES: Cc1cccc(Oc2ccc(NC(=O)C(C)(C)NC(=O)OC(C)(C)C)cc2)c1C]

4-[(2,3-dimethylphenyl)oxy]aniline (Intermediate 74, 200 mg) was dissolved in 5.0 mL of DMF. Then DIPEA (0.246 mL, 1.41 mmol) and HATU (428 mg, 1.13 mmol) were added. After stirring for minutes, N-{[(1,1-dimethylethyl)oxy]carbonyl}-2-methylalanine (229 mg, 1.13 mmol) was added and the reaction mixture was stirred at 40° C. overnight. After removal of the volatiles, the crude was purified by silica gel chromatography eluting with a gradient cHex/EtOAc from 100/0 to 0/100 to afford the title compound (109 mg).

$^1$H NMR (400 MHz, CDCl$_3$): δ ppm 7.51-7.41 (2H, m), 7.12-6.95 (2H, m), 6.93-6.84 (2H, m), 6.82-6.73 (1H, m), 2.35 (3H, s), 2.19 (3H, s), 1.60 (3H, s), 1.57 (3H, s), 1.49 (9H, s); UPLC: 0.83 min, 399 [M+H]+.

Intermediate 76

N$^1$-{4-[(2,3-dimethylphenyl)oxy]phenyl}-2-methylalaninamide

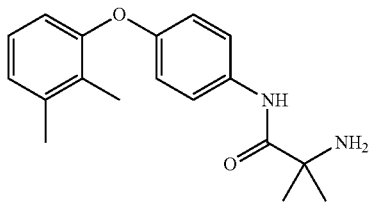 [SMILES: Cc1cccc(Oc2ccc(NC(=O)C(C)(C)N)cc2)c1C]

1,1-dimethylethyl[2-({4-[(2,3-dimethylphenyl)oxy]phenyl}amino)-1,1-dimethyl-2-oxoethyl]carbamate (Intermediate 75, 109 mg) was dissolved in 4.0 mL of dichloromethane and then TFA (1.0 mL) was added. The reaction mixture was stirred at room temperature for 1 hour. After the removal of the volatiles, the residue was charged on a SCX cartridge and eluted with DCM/MeOH/NH3 (2.0 M solution in MeOH). Evaporation afforded 68 mg of the title compound.

$^1$H NMR (400 MHz, DMSO-d$_6$): δ ppm 7.62 (2H, d), 7.17-6.96 (2H, m), 6.84 (2H, d), 6.78-6.68 (1H, m), 2.30 (3H, s), 2.11 (3H, s), 1.29 (6H, s); UPLC: 0.57 min, 299 [M+H]+.

Intermediate 77

1,1-dimethylethyl[2-({6-[(2-ethylphenyl)oxy]-3-pyridinyl}amino)-1,1-dimethyl-2-oxoethyl]carbamate

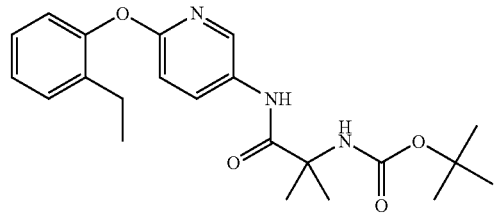 [SMILES: CCc1ccccc1Oc1ccc(NC(=O)C(C)(C)NC(=O)OC(C)(C)C)cn1]

In a 8 mL vial N-{[(1,1-dimethylethyl)oxy]carbonyl}-2-methylalanine (208 mg, 1.022 mmol) was dissolved in N,N-dimethylformamide (4 mL) to give a colourless solution. N-ethyl-N-(1-methylethyl)-2-propanamine (0.223 mL, 1.277 mmol) and N-[(1H-1,2,3-benzotriazol-1-yloxy)(dimethylamino)methyl idene]-N-methylmethanaminium tetrafluoroborate (328 mg, 1.022 mmol) were added. The reaction mixture was stirred at room temperature for 15 min. 6-[(2-ethylphenyl)oxy]-3-pyridinamine (Intermediate 46, 228 mg) was added and the reaction mixture was warmed to 60° C. After 24 hours, additional 150 mg of N-[(1H-1,2,3-benzotriazol-1-yloxy)(dimethylamino)methylidene]-N-methylmethanaminium tetrafluoroborate were added. After additional 8 hours, the solvent was evaporated under vacuum using the Genevac affording a dark brown oil which was purified by silica gel chromatography (Biotage system, 25 g SNAP column) with as eluent a gradient Cyclohexane/EtOAc from 3:1 to 1:1 in 10 CV, then 1:1 for 5 CV. The collected fractions afforded the title compound as a pale orange solid (88.6 mg).

$^1$H NMR (400 MHz, CDCl$_3$): δ ppm 9.06 (1H, br. s), 8.17-8.10 (2H, m), 7.33 (1H, dd), 7.29-7.15 (2H, m), 7.04 (1H, dd), 6.91-6.82 (1H, m), 4.91 (1H, br. s), 2.62 (2H, q), 1.60 (6H, s), 1.47 (9H, s), 1.20 (3H, t); UPLC_B: 0.92 min, 400 [M+H]+.

Intermediate 78

N$^1$-{6-[(2-ethylphenyl)oxy]-3-pyridinyl}-2-methlalaninamide

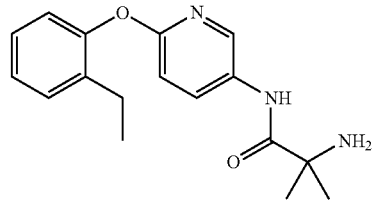 [SMILES: CCc1ccccc1Oc1ccc(NC(=O)C(C)(C)N)cn1]

In a 50 mL round-bottomed flask 1,1-dimethylethyl[2-({6-[(2-ethylphenyl)oxy]-3-pyridinyl}amino)-1,1-dimethyl-2-oxoethyl]carbamate (Intermediate 77, 88.6 mg) was dissolved in dichloromethane (2 mL) to give a yellow solution. Trifluoroacetic acid (2 mL, 26.0 mmol) was added. The reaction mixture was stirred at room temperature. After 20 minutes, the solvent was evaporated under vacuum affording a yellow oil that was charged on a 5 g SCX cartridge and was then flushed with mL of MeOH followed by 25 mL of 2M solution of ammonia in MeOH. The ammonia eluate was evaporated under vacuum to afford the title compound as a yellow oil which solidified (67.1 mg).

¹H NMR (400 MHz, CDCl₃): δ ppm 9.90 (1H, br. s), 8.18-8.27 (2H, m), 7.33 (1H, dd), 7.15-7.28 (2H, m), 7.03 (1H, dd), 6.80-6.90 (1H, m), 2.62 (2H, q), 1.84 (2H, br. s), 1.49 (6H, s), 1.20 (3H, t); UPLC_B: 0.78 min, 300 [M+H]+.

Intermediate 79

1,1-dimethylethyl[2-({6-[(2,6-dimethylphenyl)oxy]-3-pyridinyl}amino)-1,1-dimethyl-2-oxoethyl]carbamate

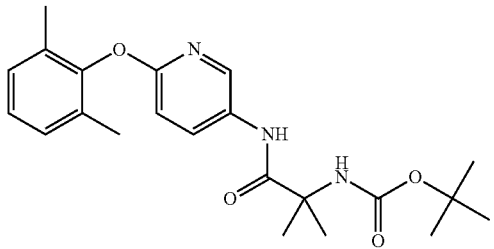 [SMILES: Cc1cccc(C)c1Oc1ccc(NC(=O)C(C)(C)NC(=O)OC(C)(C)C)cn1]

In a 8 mL vial N-{[(1,1-dimethylethyl)oxy]carbonyl}-2-methylalanine (204 mg, 1.003 mmol) and N-ethyl-N-(1-methylethyl)-2-propanamine (0.219 mL, 1.253 mmol) were dissolved in N,N-Dimethylformamide (4 mL) to give a pale yellow solution. N-[(dimethylamino)(3H-[1,2,3]triazolo[4,5-b]pyridin-3-yloxy)methylidene]-N-methylmethanaminium hexafluorophosphate (381 mg, 1.003 mmol) was added. The reaction mixture became bright yellow and was stirred at room temperature for 15 minutes. 6-[(2,6-dimethylphenyl)oxy]-3-pyridinamine (Intermediate 42, 223.8 mg) was added and the reaction mixture was warmed at 60° C. After 4 hours, the reaction was complete. The solvent was evaporated under vacuum using the Genevac affording a dark brown oil which was purified by silica gel chromatography (Biotage system, 25 g SNAP column) using as eluents a gradient Cyclohexane/EtOAc from 3:1 to 1:1 in 10 CV; then 1:1 for 5 CV. The collected fractions afforded the title compound as a pale yellow solid (202.1 mg).

¹H NMR (400 MHz, DMSO-d₆): δ ppm 9.55 (1H, br. s), 8.15-8.28 (1H, m), 7.99-8.11 (1H, m), 7.10-7.18 (2H, m), 7.04-7.10 (1H, m), 6.97-7.05 (1H, m), 6.94 (1H, d), 2.04 (6H, s), 1.38 (15H, br. s); UPLC_B: 0.91 min, 400 [M+H]+.

Intermediate 80

N¹-{6-[(2,6-dimethylphenyl)oxy]-3-pyridinyl}-2-methylalaninamide

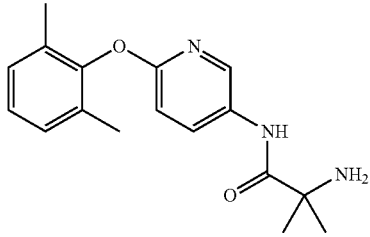 [SMILES: Cc1cccc(C)c1Oc1ccc(NC(=O)C(C)(C)N)cn1]

In a 50 mL round-bottomed flask 1,1-dimethylethyl[2-({6-[(2,6-dimethylphenyl)oxy]-3-pyridinyl}amino)-1,1-dimethyl-2-oxoethyl]carbamate (Intermediate 79, 202.1 mg) was dissolved in dichloromethane (2 mL) to give a pale yellow solution. Trifluoroacetic acid (2 mL, 26.0 mmol) was added. The reaction mixture was stirred at room temperature for 20 minutes. The solvent was evaporated under vacuum to afford a yellow oil which was charged on a 5 g SCX cartridge. It was then flushed with 25 mL of MeOH followed by 25 mL of 2M solution of ammonia in MeOH. The ammonia eluate was evaporated under vacuum to afford the title compound as a yellow oil which solidified (144.4 mg).

¹H NMR (400 MHz, CDCl₃): δ ppm 9.87 (1H, br. s), 8.21 (1H, dd), 8.17 (1H, d), 7.03-7.16 (3H, m), 6.79 (1H, d), 2.14 (6H, s), 1.85 (2H, br. s), 1.47 (6H, s). UPLC_B: 0.77 min, 300 [M+H]+.

Intermediate 81

N-{[(1,1-dimethylethyl)oxy]carbonyl}-D-valine

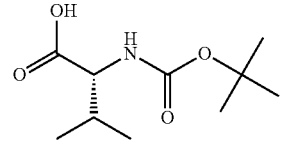

To a solution of D-valine (1 g, 8.54 mmol) in tetrahydrofuran (40 mL) a solution of NaOH (0.376 g, 9.39 mmol) in water (10 mL) was added followed by the addition of Boc-Anhydride (2.180 mL, 9.39 mmol). The reaction mixture was stirred overnight at room temperature. HCl 5% in water was added while the pH was allowed to reach ~5-6 and the mixture was extracted with ethyl acetate (50 mL). Combined organic layers were dried sodium sulphate, filtered and evaporated to afford the title compound as a colourless oil (1.85 g).

¹H-NMR (400 MHz, DMSO-d₆) δ ppm: 12.53 (1H, br.s), 6.91-6.80 (1H, m), 3.76 (1H, dd), 2.06-1.92 (1H, m), 1.38 (9H, s), 0.86 (6H, t).

Intermediate 82

1,1-dimethylethyl((1R)-2-methyl-1-{[(4-{[4-methyl-3-(methyloxy)phenyl]oxy}phenyl)amino]carbonyl}propyl)carbamate

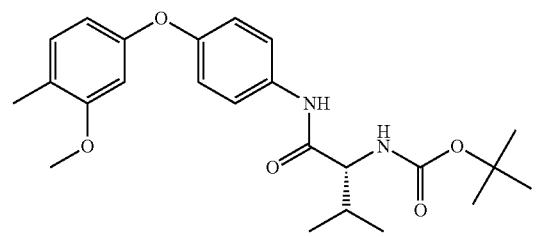 [SMILES: COc1cc(Oc2ccc(NC(=O)[C@H](NC(=O)OC(C)(C)C)C(C)C)cc2)ccc1C]

To a solution of N-{[(1,1-dimethylethyl)oxy]carbonyl}-D-valine (Intermediate 81, 120 mg) in dry N,N-dimethylformamide (1 mL), DIPEA (0.152 mL, 0.872 mmol) and then TBTU (182 mg, 0.567 mmol) were added and the reaction mixture was stirred for 5 minutes at room temperature. 4-{[4-methyl-3-(methyloxy)phenyl]oxy}aniline (Intermediate 50, 100 mg) was then added and the reaction mixture was stirred for 3 hours at the same temperature. The reaction was quenched with brine (2 mL) and extracted with ethyl acetate (3 times 3 mL), the organic layer was dried over sodium sulphate, filtered and evaporated. The residue was purified by silica gel chromatography (Biotage system, 10 g SNAP column) using as eluent a gradient cyclohexane/ethyl acetate from 100/0 to 80/20 to afford the title compound (113 mg) as a white solid.

UPLC_B: 1.04 min, 429 [M+H]+.

Intermediate 83

N$^1$-(4-{[4-methyl-3-(methyloxy)phenyl]oxy}phenyl)-D-valinamide

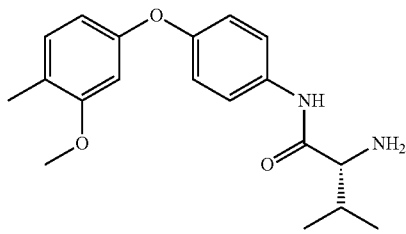 [SMILES: COc1cc(Oc2ccc(NC(=O)[C@H](N)C(C)C)cc2)ccc1C]

To a solution of 1,1-dimethylethyl((1R)-2-methyl-1-{[(4-{[4-methyl-3-(methyloxy)phenyl]oxy}phenyl)amino]carbonyl}propyl)carbamate (Intermediate 82, 110 mg) in dry dichloromethane (3 mL), TFA (1 mL, 12.98 mmol) was added and the reaction mixture was stirred for 1 hour at room temperature. The solvent and the excess of TFA were evaporated and the residue was purified by SCX cartridge (5 g) to afford the title compound as a yellow pale solid (68 mg).

$^1$H-NMR (400 MHz, DMSO-d$_6$) δ ppm: 0.89 (dd, 6H), 7.66-7.60 (2H, m), 7.12-7.06 (1H, m), 7.00-6.92 (2H, m), 6.67-6.61 (1H, m), 6.42-6.36 (1H, m), 3.74 (3H, s), 3.13-3.07 (1H, m), 2.11 (3H, s), 1.98-1.88 (1H, m); UPLC_B: 0.89 min, 329 [M+H]+.

Intermediate 84

2-{[3-(1-methylethyl)phenyl]oxy}-5-nitropyrimidine

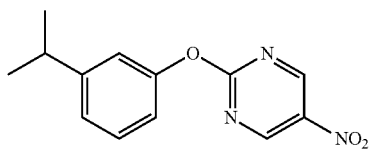 [SMILES: CC(C)c1cccc(Oc2ncc([N+](=O)[O-])cn2)c1]

To a solution of 3-(1-methylethyl)phenol (680 mg, 5 mmol, Aldrich) in acetonitrile (50 mL) were added 2-chloro-5-nitropyrimidine (800 mg, 5 mmol) and triethylamine (1.01 g, 10 mmol) and the resulting mixture was heated at reflux and stirred for 3 hours. The reaction mixture was concentrated under vacuum and water was added to the residue (80 mL). It was extracted with ethyl acetate (3 times 50 mL) and the combined organic layers were dried over sodium sulphate and evaporated to afford a brown oil, which was purified by silica gel chromatography (mobile phase: ethyl acetate: petroleum ether=0~20%) to afford the title compound (900 mg).

MS_2 (ESI): 260 [M+H]+

Intermediate 85

2-{[3-(1-methylethyl)phenyl]oxy}-5-pyrimidinamine

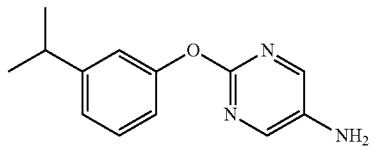 [SMILES: CC(C)c1cccc(Oc2ncc(N)cn2)c1]

To a solution of 2-{[3-(1-methylethyl)phenyl]oxy}-5-nitropyrimidine (Intermediate 84, 520 mg) in methanol (50 mL) was added Pd/C (10% wt., 100 mg) and the mixture was stirred under H$_2$ atmosphere for 3 hours. The resulting mixture was filtered through a pad of celite and the filtrate was concentrated under vacuum to afford the title compound (400 mg).

MS_2 (ESI): 230 [M+H]+

Intermediate 86

1,1-dimethylethyl{(1R)-1-methyl-2-[(2-{[3-(1-methylethyl)phenyl]oxy}-5-pyrimidinyl)amino]-2-oxoethyl}carbamate

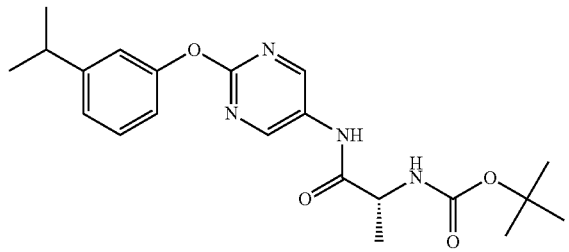 [SMILES: CC(C)c1cccc(Oc2ncc(NC(=O)[C@@H](C)NC(=O)OC(C)(C)C)cn2)c1]

To a solution of 2-{[3-(1-methylethyl)phenyl]oxy}-5-pyrimidinamine (Intermediate 85, 229 mg) in acetonitrile (20 mL) were added N-{[(1,1-dimethylethyl)oxy]carbonyl}-D-alanine (378 mg, 2 mmol), HBTU (474 mg, 1.25 mmol) and DIPEA (387 mg, 3 mmol) and the mixture was heated at reflux and stirred overnight. The resulting mixture was concentrated under vacuum and water (100 mL) was added. It was extracted with ethyl acetate (3 times 100 mL) and the combined organic layers were dried over sodium sulphate and evaporated to afford a brown oil, which was purified by silica gel chromatography (mobile phase: ethyl acetate: petroleum ether=1/5-1/2) to afford the title compound (300 mg).

Intermediate 87

N$^1$-(2-{[3-(1-methylethyl)phenyl]oxy}-5-pyrimidinyl)-D-alaninamide

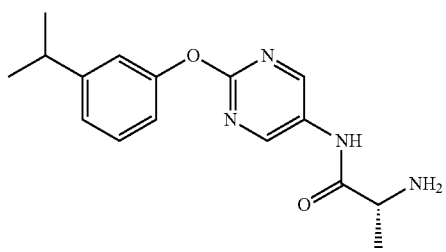 [SMILES: CC(C)c1cccc(Oc2ncc(NC(=O)[C@@H](C)N)cn2)c1]

To a solution of 1,1-dimethylethyl{(1R)-1-methyl-2-[(2-{[3-(1-methylethyl)phenyl]oxy}-5-pyrimidinyl)amino]-2-oxoethyl}carbamate (Intermediate 86, 300 mg) in ethyl acetate (50 mL) was bubbled HCl (gas). The mixture was stirred at room temperature for 1 hour. The resulting mixture was concentrated under vacuum and neutralized with an aqueous saturated solution of NaHCO$_3$ to pH=8 and extracted with dichloromethane (5 times 30 mL). The combined organic layers were dried over sodium sulphate and evaporated to afford the title compound (200 mg).

MS_2 (ESI): 301 [M+H]+

Intermediate 88 ethyl 2-methyl-5-nitrophenyl ether

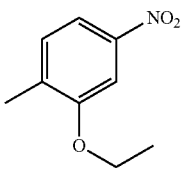

A mixture of 2-methyl-5-nitrophenol (450 mg, 2.94 mmol), ethyl iodide (356 μl, 4.41 mmol) and potassium carbonate (609 mg, 4.41 mmol) in 15 mL of acetone was heated at reflux for 2 days. The reaction mixture was filtrated, concentrated under vacuum, and the residue was partitioned between ethyl acetate and water. The organic layer was dried over sodium sulfate and concentrated under vacuum to provide the title compound (397 mg) which was directly used in the next step.

$^1$H NMR (400 MHz, methanol-d$_4$): δ ppm 7.78 (1H, dd), 7.72 (1H, d), 7.40 (1H, dd), 4.22-4.17 (2H, q), 2.35 (3H, s), 1.53 (3H, t); UPLC: 0.82 min, 182 [M+H]+.

Intermediate 89

3-(ethyloxy)-4-methylaniline

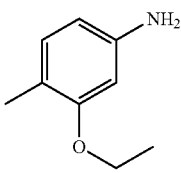

Fe powder (609 mg, 10.90 mmol) was added to a solution of ethyl 2-methyl-5-nitrophenyl ether (Intermediate 88, 395 mg) in a mixture THF/water (15 mL/5 mL) followed by ammonium chloride (583 mg, 10.90 mmol). The reaction mixture was stirred overnight under nitrogen. The reaction mixture was poured into water (20 mL) and the iron was filtrated. Ethyl acetate was used to wash the solid filtrated. The filtrate was extracted with ethyl acetate (3 times). The combined ethyl acetate layers were dried over sodium sulphate and concentrated to give the title compound (303 mg) which was directly used in the next step.

$^1$H NMR (400 MHz, CDCl$_3$): δ ppm 6.90 (1H, d), 6.35-6.02 (2H, m), 3.97 (2H, q), 2.11 (3H, s), 1.41 (3H, t); UPLC: 0.44 min, 152 [M+H]+.

Intermediate 90

3-(ethyloxy)-4-methyl phenol

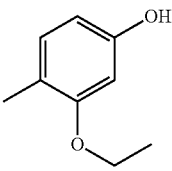

A suspension of 3-(ethyloxy)-4-methylaniline (Intermediate 89, 300 mg) in a mixture of water/concentrated sulfuric acid 98% (20 mL/7 mL) under argon was cooled at 0° C. A solution of sodium nitrite (151 mg, 2.182 mmol) in 4 mL of water was slowly added. The reaction mixture was stirred at 0° C. for 1 hour 30. The reaction mixture was then slowly added to a solution of water/concentrated sulfuric acid (18 mL/5 mL) pre-heated at 90° C. The reaction mixture was stirred at 90° C. for 1 hour 15. After cooling down, the reaction mixture was extracted with ethyl ether (4 times). The gathered organic phases were dried over sodium sulphate, filtered and concentrated under vacuum to afford tie compound (276 mg).

$^1$H NMR (400 MHz, methanol-d$_4$): δ ppm 6.87 (1H, d), 6.34 (1H, d), 6.25 (1H, dd), 3.97 (2H, q), 2.06 (3H, s), 1.40-1.37 (3H, t); UPLC: 0.66 min, 153 [M+H]+.

Intermediate 91

2-{[3-(ethyloxy)-4-methylphenyl]oxy}-5-nitropyrimidine

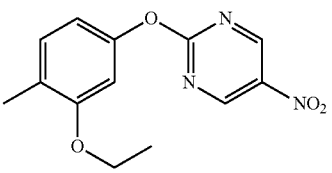 [SMILES: CCOc1cc(Oc2ncc([N+](=O)[O-])cn2)ccc1C]

2-chloro-5-nitropyridine (114 mg, 0.716 mmol, 1 equiv) was dissolved in 3 mL of dimethylformamide. 3-(ethyloxy)-4-methylphenol (Intermediate 90, 109 mg) and potassium carbonate (198 mg, 1.432 mmol) were added. The reaction mixture was stirred at room temperature 3 hours. The reaction mixture was filtered. The filtrated solid was washed with dichloromethane. The volatiles were evaporated under vacuum. Ethyl acetate and brine were added to the residue. The compound was extracted 2 times with ethyl acetate and 2 times with dichloromethane. The gathered organic phases were dried over sodium sulphate, filtered and evaporated to afford the title compound which was used directly in the next step (113 mg).

¹H NMR (400 MHz, CDCl₃): δ ppm 9.33 (2H, s), 7.21 (1H, d), 6.72-6.72 (2H, m), 4.02 (2H, q), 2.25 (3H, s), 1.44 (3H, t); UPLC: 0.79 min, 276 [M+H]+

Intermediate 92

2-{[3-(ethyloxy)-4-methylphenyl]oxy}-5-pyrimidinamine

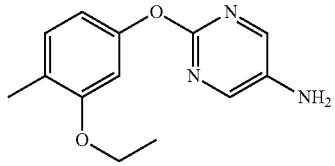 [SMILES: CCOc1cc(Oc2ncc(N)cn2)ccc1C]

Fe powder (89 mg, 1.598 mmol) was added to a solution of 2-{[3-(ethyloxy)-4-methylphenyl]oxy}-5-nitropyrimidine (Intermediate 91, 110 mg) in a mixture THF/water (9 mL/3 mL) followed by ammonium chloride (86 mg, 1.598 mmol). The reaction mixture was stirred overnight under nitrogen. The reaction mixture was poured into water and the iron was filtrated. Ethyl acetate was used to wash the solid filtrated. The filtrate was extracted with ethyl acetate (3 times). The combined ethyl acetate layers were dried over sodium sulphate and concentrated to give the title compound (94 mg) which was directly used in the next step.

UPLC: 0.64 min, 246 [M+H]+

Intermediate 93

1,1-dimethylethyl((1R)-1-{[(2-{[3-(ethyloxy)-4-methylphenyl]oxy}-5-pyrimidinyl)amino]carbonyl}propyl)carbamate

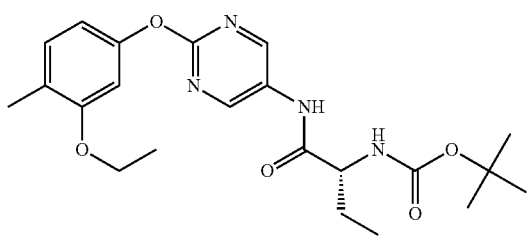 [SMILES: CCOc1cc(Oc2ncc(NC(=O)[C@@H](CC)NC(=O)OC(C)(C)C)cn2)ccc1C]

To a solution of (2R)-2-({[(1,1-dimethylethyl)oxy]carbonyl}amino)butanoic acid (90 mg, 0.445 mmol) in N,N-dimethylformamide (7 mL) DIPEA (97 µl, 0.557 mmol) and HATU (169 mg, 0.445 mmol) were added. The reaction mixture was stirred during 10 minutes at room temperature, then 2-{[3-(ethyloxy)-4-methylphenyl]oxy}-5-pyrimidinamine (Intermediate 92, 91 mg) was added. The reaction mixture was stirred for 48 hours at room temperature. The reaction mixture was evaporated and purified by silica gel chromatography (Companion system) with a gradient Cyclohexane/EtOAc from 100/0 to 40/60 in 20 minutes and then 40/60 during 15 min to afford the title compound (83 mg).

¹H NMR (400 MHz, CDCl₃): δ ppm 8.73 (2H, s), 7.13 (1H, d), 6.75-6.52 (2H, m), 4.17-4.09 (1H, m), 3.98 (2H, q), 2.20 (3H, s), 2.04-1.88 (1H, m), 1.81-1.61 (1H, m), 1.46 (9H, s), 1.40 (3H, t), 1.02 (3H, t); UPLC: 0.79 min, 431 [M+H]+

Intermediate 94

(2R)-2-amino-N-(2-{[3-(ethyloxy)-4-methylphenyl]oxy}-5-pyrimidinyl)butanamide

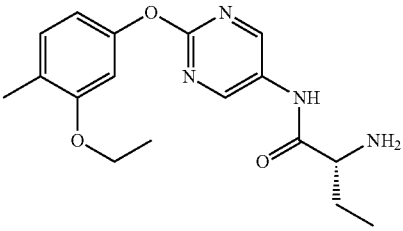 [SMILES: CCOc1cc(Oc2ncc(NC(=O)[C@H](N)CC)cn2)ccc1C]

To a solution of 1,1-dimethylethyl((1R)-1-{[(2-{[3-(ethyloxy)-4-methylphenyl]oxy}-5-pyrimidinyl)amino]carbonyl}propyl)carbamate (Intermediate 93, 80 mg) in dichloromethane (1 mL) cooled to 0° C., TFA (573 µl, 7.43 mmol) was added dropwise. The mixture reaction was stirred at 0° C. for 1.5. The solvent and the TFA were evaporated. The mixture was diluted with dichloromethane and an aqueous saturated solution of NaHCO3. The organic layer was separated, dried over sodium sulphate, filtered end evaporated to afford the title compound (65 mg) which was directly used in the next step.

¹H NMR (400 MHz, CDCl₃): δ ppm 9.39 (1H, s), 8.82 (2H, s), 7.14 (1H, d), 6.78-6.49 (2H, m), 3.98 (2H, q), 3.47 (1H, dd), 2.20 (3H, s), 2.09-1.91 (1H, m), 1.81 (2H, sb), 1.76-1.56 (1H, m), 1.02 (3H, t); UPLC: 0.54 min, 331 [M+H]+

Intermediate 95

N-{[(1,1-dimethylethyl)oxy]carbonyl}-3-methyl-D-valine

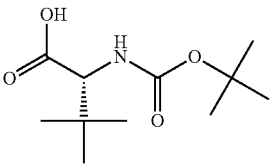 [SMILES: CC(C)(C)OC(=O)N[C@@H](C(=O)O)C(C)(C)C]

To a solution of 3-methyl-D-valine (900 mg, 6.86 mmol) in 7 mL of 1 M aqueous sodium hydroxide and 7 mL of methanol was added Boc-anhydride (1.797 g, 8.23 mmol) at 0° C. The reaction mixture was warmed to room temperature and stirred overnight. After most of the methanol was evaporated, the solution was acidified to pH 2 with an aqueous solution of HCl (1M) and extracted 3 times with ethylacetate (3×20 mL). The organic layers were combined and washed with brine (2×5 mL). Evaporation of the solvent afforded the title compound as a white solid with a 83% yield (1.36 g).

¹H NMR (400 MHz, DMSO-d₆): δ ppm 12.44 (1H, s), 6.82 (1H, d), 3.76 (1H, d), 1.38 (9H, s), 0.93 (9H, s); UPLC: 0.64 min, 232 [M+H]+

Intermediate 96

1,1-dimethylethyl((1R)-2,2-dimethyl-1-{[(6-{[4-methyl-3-(methyloxy)phenyl]oxy}-3-pyridinyl)amino]carbonyl}propyl)carbamate

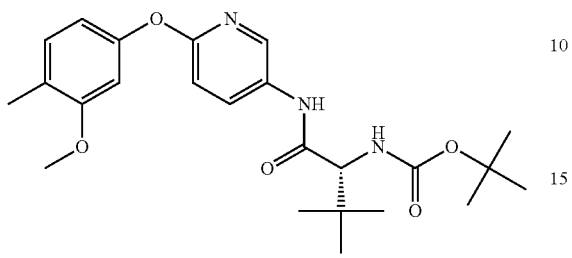

To a solution of N-{[(1,1-dimethylethyl)oxy]carbonyl}-3-methyl-D-valine (Intermediate 95, 20.1 mg) in dry N,N-dimethylformamide (1 mL), DIPEA (0.015 mL, 0.087 mmol) and then HATU (38.0 mg, 0.100 mmol) were added and the reaction mixture was stirred for 15 minutes at room temperature under argon. Then 6-{[4-methyl-3-(methyloxy)phenyl]oxy}-3-pyridinamine (Intermediate 50, 10 mg) was added and the reaction mixture was stirred at 50° C. under argon 3 hours. The reaction was left at room temperature overnight. The reaction mixture was evaporated. The residue obtained was dissolved in dichloromethane. The organic phase was washed with brine and then with a saturated aqueous solution of NaHCO3. It was then dried over sodium sulphate. The residue obtained was purified on silica gel (Companion instrument) with cyclohexane/ethylacetate as eluents from 100/0 to 70/30. This afforded the title compound (9.2 mg).

$^1$H NMR (400 MHz, CDCl$_3$): δ ppm 8.53 (1H, s), 8.21 (1H, d), 7.87 (1H, d), 7.09 (1H, d), 6.76 (1H, d), 6.59 (2H, m), 5.43 (1H, d), 4.10 (1H, d), 3.75 (3H, s), 2.17 (3H, s), 1.42 (9H, s), 1.07 (9H, s); UPLC_ipqc: 0.87 min, 444 [M+H]+

Intermediate 97

3-methyl-N$^1$-(6-{[4-methyl-3-(methyloxy)phenyl]oxy}-3-pyridinyl)-D-valinamide

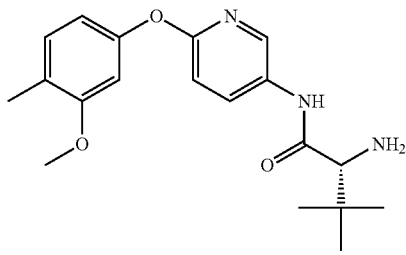 [SMILES: COc1cc(Oc2ccc(NC(=O)[C@H](N)C(C)(C)C)cn2)ccc1C]

To a solution of 1,1-dimethylethyl((1R)-2,2-dimethyl-1-{[(6-{[4-methyl-3-(methyloxy)phenyl]oxy}-3-pyridinyl)amino]carbonyl}propyl)carbamate (Intermediate 96, 8.2 mg) in dry dichloromethane (0.5 mL) cooled to 0° C., TFA (57 μl, 0.740 mmol) was added dropwise and the solution was stirred for 3 hours at that temperature. The volatiles were evaporated. The residue was dissolved with dichloromethane (2 mL) and an aqueous saturated solution of NaHCO3 was added (4 mL). The layers were separated and the aqueous layer was extracted twice with dichloromethane. The gathered organic layers were dried over sodium sulphate and evaporated to afford the title compound (6.2 mg).

$^1$H NMR (400 MHz, CDCl$_3$): δ ppm 9.13 (1H, br s), 8.18 (2H, m), 7.11 (1H, d), 6.87 (1H, d), 6.60 (2H, m), 3.78 (3H, s), 3.27 (1H, s), 2.19 (3H, s), 1.69 (2H, br s), 1.06 (9H, s); UPLC_ipqc: 0.73 min, 344 [M+H]+

Intermediate 98

1,1-dimethylethyl((1R)-1-methyl-1-{[(6-{[4-methyl-3-(methyloxy)phenyl]oxy}-3-pyridinyl)amino]carbonyl}propyl)carbamate

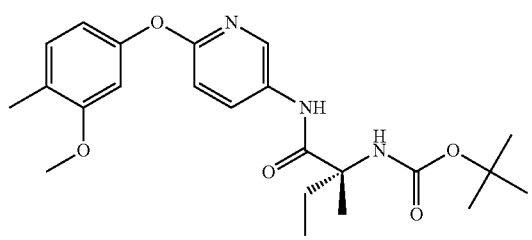 [SMILES: CC[C@@](C)(NC(=O)OC(C)(C)C)C(=O)Nc1ccc(Oc2ccc(C)c(OC)c2)nc1]

To a solution of N-{[(1,1-dimethylethyl)oxy]carbonyl}-D-isovaline (94 mg, 0.434 mmol) in dry N,N-Dimethylformamide (1 mL) DIPEA (0.114 mL, 0.651 mmol) and HATU (165 mg, 0.434 mmol) were added. The reaction was stirred at room temperature for 15 minutes. 6-{[4-methyl-3-(methyloxy)phenyl]oxy}-3-pyridinamine (Intermediate 50, 50 mg) was then added. After 1 hour of stirring at room temperature the mixture was heated at 50° C. and stirred at that temperature for 4 hours, it was then cooled down to room temperature and stirred overnight at that temperature. The mixture was quenched with brine (2 mL) and extracted with ethyl acetate (3×2 mL). Combined organic layers were dried over sodium sulphate, filtered and evaporated. The residue was purified by flash chromatography on silica gel using a 10 g SNAP column and cyclohexane/ethyl acetate as eluents from 100/0 to 60/40 (Biotage system) to afford the title compound as a white solid (65 mg).

$^1$H NMR (400 MHz, DMSO-d$_6$): δ ppm 9.60 (1H, br s), 9.10 (1H, br s), 8.31 (1H, br. s.), 8.03 (1H, br s), 7.12 (1H, d), 6.93 (1H, d), 6.69 (1H, d), 6.53 (1H, dd), 3.74 (3H, s), 2.11 (3H, s), 1.72-1.86 (1H, m), 1.60-1.72 (1H, m), 1.41 (9H, s), 1.33 (3H, s), 0.78 (3H, t); UPLC: 0.87 min, 430 [M+H]+

Intermediate 99

N-(6-{[4-methyl-3-(methyloxy)phenyl]oxy}-3-pyridinyl)-D-isovalinamide

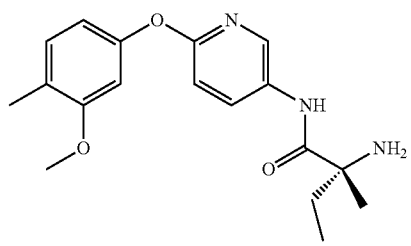 [SMILES: CC[C@@](C)(N)C(=O)Nc1ccc(Oc2ccc(C)c(OC)c2)nc1]

To a solution of 1,1-dimethylethyl((1R)-1-methyl-1-{[(6-{[4-methyl-3-(methyloxy)phenyl]oxy}-3-pyridinyl)amino]carbonyl}propyl)carbamate (Intermediate 98, 65 mg) in dry dichloromethane (3 mL) cooled to 0° C., TFA (0.700 mL, 9.08 mmol) was added dropwise. The reaction was stirred at that temperature for 2 hours. The reaction was quenched with a saturated aqueous solution of NaHCO3 (20 mL) added at 0° C., and extracted with dichloromethane (3×7 mL). The combined organic layers were dried over sodium sulphate, filtered and evaporated to afford the title compound as a white solid (44 mg).

Intermediate 100

1-({[(1,1-dimethylethyl)oxy]carbonyl}amino)cyclobutanecarboxylic acid

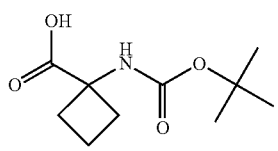

To a solution of 1-aminocyclobutanecarboxylic acid (626 mg, 5.44 mmol) in 5.6 mL of 1 M aqueous sodium hydroxide and 4 mL of methanol was added Boc-anhydride (1.425 g, 6.53 mmol) at 0° C. The reaction mixture was warmed to room temperature and stirred for 12 hours. After most of the methanol was evaporated, the solution was acidified to pH 2 with 1 M HCl and extracted with ethyl acetate. The organic extracts were combined and washed with brine. Evaporation of the solvent afforded the title compound (1.09 g).
$^1$H NMR (400 MHz, DMSO-d6): δ ppm 12.21 (1H, s), 7.44 (1H, s), 2.29-2.47 (2H, m), 2.09 (2H, q), 1.74-1.94 (2H, m), 1.36 (9H, s); UPLC: 0.56 min, 216 [M+H]+

Intermediate 101

1,1-dimethylethyl(1-{[(6-{[4-methyl-3-(methyloxy)phenyl]oxy}-3-pyridinyl)amino]carbonyl}cyclobutyl)carbamate

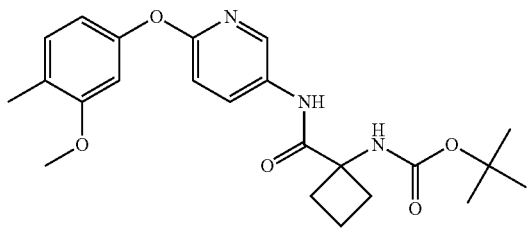 [SMILES: COc1cc(Oc2ccc(NC(=O)C3(NC(=O)OC(C)(C)C)CCC3)cn2)ccc1C]

To a solution of 1-({[(1,1-dimethylethyl)oxy]carbonyl}amino)cyclobutanecarboxylic acid (Intermediate 100, 70.1 mg) in dry N,N-dimethylformamide (2 mL) DIPEA (0.095 mL, 0.543 mmol) and TBTU (112 mg, 0.347 mmol) were added. The reaction mixture was stirred at room temperature for 15 minutes, 6-{[4-methyl-3-(methyloxy)phenyl]oxy}-3-pyridinamine (Intermediate 50, 50 mg) was then added and the mixture was stirred at room temperature for 1 day. The reaction was quenched with water (5 mL) and extracted with ethyl acetate (3×5 mL). The combined organic layer was washed with brine (3×8 mL), separated, dried over sodium sulphate, filtered and evaporated. The residue was purified by flash chromatography on silica gel using a 25 g SNAP column and cyclohexane:ethylacetate as eluents from 10:0 to 7:3. This afforded the title compound as a white powder (80 mg).
$^1$H NMR (400 MHz, DMSO-d$_6$): δ ppm 9.52 (1H, s), 8.34 (1H, s), 7.96 (1H, m), 7.51 (1H, s), 7.13 (1H, d), 6.95 (1H, d), 6.70 (1H, d), 6.54 (1H, dd), 3.75 (3H, s), 2.13 (3H, s), 2.11 (2H, br. s.), 1.76-1.97 (2H, m), 1.39 (9H, s), 1.26 (2H, s); UPLC_B: 0.93 min, 426 [M−H]−

Intermediate 102

1-amino-N-(6-{[4-methyl-3-(methyloxy)phenyl]oxy}-3-pyridinyl)cyclobutanecarboxamide

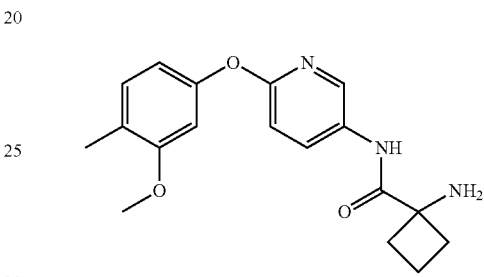

To a solution of 1,1-dimethylethyl (1-{[(6-{[4-methyl-3-(methyloxy)phenyl]oxy}-3-pyridinyl)amino]carbonyl}cyclobutyl)carbamate (Intermediate 101, 80 mg) in dry dichloromethane (2 mL) cooled to 0° C. TFA (0.865 mL, 11.23 mmol) was added dropwise. The reaction mixture was stirred at 0° C. for 2 hours, it was then allowed to reach room temperature. Dichloromethane and the excess of TFA were evaporated. The residue was diluted with dichloromethane (5 mL) and neutralized with a saturated solution of NaHCO3. The organic layer was separated, dried over sodium sulphate, filtered and evaporated to afford the title as a white solid (60 mg).
$^1$H NMR (400 MHz, CDCl$_3$) d ppm 9.43 (1H, br. s.), 8.37-7.89 (2H, m), 7.09 (1H, d), 6.85 (1H, d), 6.67-6.39 (2H, m), 3.77 (3H, s), 2.92-2.62 (2H, m), 2.18 (3H, s), 1.97-2.06 (2H, m), 1.97-1.74 (2H, m); UPLC: 0.54 min, 328 [M+H]+

Intermediate 103

1-({[(1,1-dimethylethyl)oxy]carbonyl}amino)cyclopropanecarboxylic acid

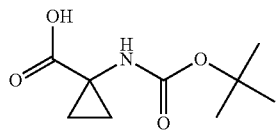

The title compound (998 mg) was made in a similar fashion to the preparation of Intermediate 100 replacing 1-aminocyclobutanecarboxylic acid with 1-aminocyclopropanecarboxylic acid (550 mg, 5.44 mmol).

¹H NMR (400 MHz, DMSO-d6): δ ppm 12.26 (1H, s), 7.40 (1H, s), 1.38 (9H, s), 1.26 (2H, m), 0.96 (2H, m); UPLC: 0.52 min, 202 [M+H]+.

Intermediate 104

1,1-dimethylethyl(1-{[(6-{[4-methyl-3-(methyloxy)phenyl]oxy}-3-pyridinyl)amino]carbonyl}cyclopropyl)carbamate

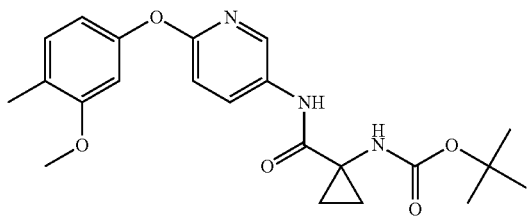 [SMILES: COc1cc(Oc2ccc(NC(=O)C3(NC(=O)OC(C)(C)C)CC3)cn2)ccc1C]

The title compound (80 mg) was made in a similar fashion to the preparation of Intermediate 101 replacing 1-({[(1,1-dimethylethyl)oxy]carbonyl}amino)cyclobutanecarboxylic acid with 1-({[(1,1-dimethylethyl)oxy]carbonyl}amino)cyclopropanecarboxylic acid (Intermediate 103, 65.5 mg).

¹H NMR (400 MHz, DMSO-d₆) d ppm 9.56-9.76 (1H, m), 8.34 (1H, d), 8.04 (1H, dd), 7.31-7.51 (1H, m), 7.13 (1H, d), 6.94 (1H, d), 6.71 (1H, d), 6.55 (1H, dd), 3.75 (3H, s), 2.13 (3H, s), 1.42 (9H, s), 1.26-1.39 (2H, m), 0.75-1.07 (2H, m); UPLC_B: 0.89 min, 412 [M−H]−

Intermediate 105

1-amino-N-(6-{[4-methyl-3-(methyloxy)phenyl]oxy}-3-pyridinyl)cyclopropanecarboxamide

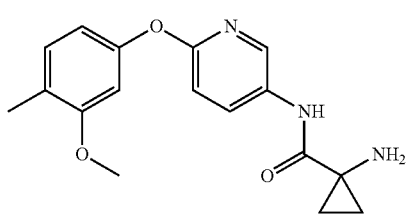 [SMILES: COc1cc(Oc2ccc(NC(=O)C3(N)CC3)cn2)ccc1C]

The title compound (58 mg) was made in a similar fashion to the preparation of Intermediate 102 replacing 1,1-dimethylethyl (1-{[(6-{[4-methyl-3-(methyloxy)phenyl]oxy}-3-pyridinyl)amino]carbonyl}cyclobutyl)carbamate with 1,1-dimethylethyl (1-{[(6-{[4-methyl-3-(methyloxy)phenyl]oxy}-3-pyridinyl)amino]carbonyl}cyclopropyl)carbamate (Intermediate 104, 80 mg)

¹H NMR (400 MHz, CDCl₃) d ppm 9.85 (1H, s), 8.23 (1H, d), 8.14 (1H, dd), 7.09 (1H, d), 6.85 (1H, d), 6.67-6.45 (2H, m), 3.77 (3H, s), 2.18 (3H, s), 1.85 (2H, br. s.), 1.47-1.57 (2H, m), 0.96-0.85 (2H, m); UPLC: 0.52 min, 314 [M+H]+

Intermediate 106

3-(6-fluoro-3-pyridinyl)-5,5-dimethyl-2,4-imidazolidinedione

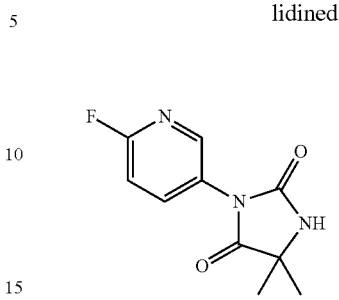

Two reactions were set up in parallel. For each of them, to a solution of 5,5-dimethyl-2,4-imidazolidinedione (1.5 g, 11.71 mmol) in dry dichloromethane (100 mL), (6-fluoro-3-pyridinyl)boronic acid (1.980 g, 14.05 mmol), copper(II) acetate (2.126 g, 11.71 mmol) and pyridine (1.420 mL, 17.56 mmol) were added. The reaction was left under stirring under air atmosphere at room temperature overnight. The two reaction mixtures were combined and the solid was filtered off. The resulting solution was washed with water (90 mL). The aqueous phase was extracted twice with dichloromethane (twice 90 mL). The organic phases were combined and washed with brine and dried over anhydrous sodium sulphate. Removal of the solvent afforded a residue which was purified by silica gel chromatography (Biotage system, 100 g SNAP column) using as eluent a gradient and cyclohexane/ethyl acetate from 65/35 to 50/50 to afford the title compound as a white solid (1.27 g).

¹H NMR (400 MHz, CDCl₃): δ ppm 8.40 (1H, m), 7.94 (1H, m), 7.06 (1H, dd), 6.18 (1H, br. s), 1.57 (6H, s); UPLC_ipqc: 0.56 min, 224 [M+H]+

Intermediate 107

2-methylalaninate hydrochloride

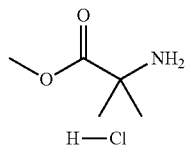

2-amine-2-methylpropionic acid (25 g, 242.43 mmol) was dissolved in methanol (150 mL). Thionyl chloride (25 mL) was added dropwise at 0° C. to the reaction mixture. The reaction was refluxed for 3 hours, evaporated and dried under vacuum. The solid was washed several times with Et₂O and dried, to afford the title compound (37 g) as a white solid.

¹H NMR (400 MHz, DMSO-d₆): δ ppm 8.71 (3H, s), 3.77 (3H, s), 1.5 (6H, s).

Intermediate 108

3-(1,1-dimethylethyl)-4-hydroxybenzaldehyde

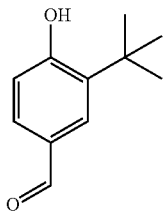

2-(1,1-dimethylethyl)phenol (10 g, 66.67 mmol) was dissolved in 40 mL of MeOH and NaOH (40 g, 1 mol) dissolved in 40 mL of water was added dropwise. Then 40 mL of CHCl₃ was added (during the course of 1 h) at 60° C. The reaction mixture was stirred at that temperature for 3 h. After cooling down to r.t., the mixture was cooled to 0° C. and 4M HCl was added until the solution reached pH 5-6. The mixture was extracted with DCM (three times) and the collected organic were dried over Na₂SO₄, filtered and evaporated. The crude was charged on a silica gel column and eluted with Cyclohexane/EtOAc (from 100:0 to 80:20 Cyclohexane/EtOAc, then plateau at 80:20) affording 766 mg of the of the title compound.

$^1$H-NMR (400 MHz, DMSO-d$_6$): δ ppm 10.62 (1H, s), 9.79 (1H, s), 7.73 (1H, br. s), 7.67-7.57 (1H, m), 7.01-6.90 (1H, m), 1.38 (9H, s); UPLC_ipqc: 0.97 min, 177 [M−H]⁻.

Intermediate 109

3-(1,1-dimethylethyl)-4-hydroxybenzonitrile

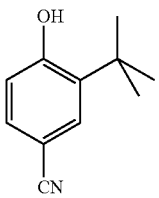

3-(1,1-dimethylethyl)-4-hydroxybenzaldehyde (Intermediate 108, 550 mg) and hydroxylamine hydrochloride (322 mg, 4.63 mmol) were stirred in 8.0 mL of acetic acid at reflux for 1 h. After cooling down to 0° C., the mixture was poured into Et₂O and washed once with water and once with NaOH (5% aqueous solution). The collected aqueous phases were extracted with Et₂O (two times) and the combined organic phases were dried over Na₂SO₄, filtered, evaporated and triturated with pentane affording 540 mg of the title compound.

$^1$H-NMR (400 MHz, DMSO-d$_6$): δ ppm 10.92 (1H, br. s), 7.53-7.45 (2H, m), 6.92 (1H, d), 1.34 (9H, s); UPLC_ipqc: 1.03 min, 174 [M−H]⁻.

Intermediate 110

3-bromo-4-[(phenylmethyl)oxy]benzonitrile

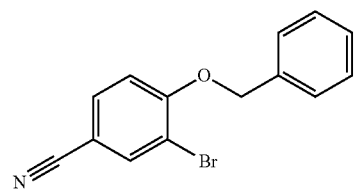 [SMILES: N#Cc1ccc(OCc2ccccc2)c(Br)c1]

3-bromo-4-hydroxybenzonitrile (5.94 g, 0.03 mol) was dissolved in 100 mL of dry acetone. Potassium carbonate (8.29 g, 0.06 mol) was added. To the reaction mixture, benzyl bromide was then added dropwise (5 g, 0.03 mol). The reaction mixture was stirred at 50° C. overnight. Then it was cooled down to room temperature, filtered and evaporated. The residue obtained was dissolved in ethyl acetate (300 mL) and water was added (200 mL). The phases were separated and the gathered organic phases were dried over sodium sulphate. Evaporation led to the title compound (7.6 g) as a light yellow solid.

$^1$H NMR (400 MHz, CDCl₃): δ ppm 7.85 (1H, d), 7.57 (1H, dd), 7.45-7.36 (5H, m), 6.99 (1H, d), 5.23 (2H, s); UPLC_ipqc: 1.24 min.

The following compounds were prepared using the foregoing methodology, replacing 3-bromo-4-hydroxybenzonitrile with the appropriately substituted phenol, as described in the foregoing Reaction Schemes.

| Int. | Structure | Name | Phenol | NMR characterization | UPLC_ipqc characterization |
|---|---|---|---|---|---|
| 111 | 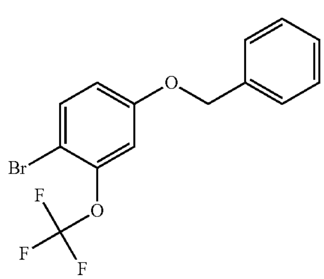 [SMILES: FC(F)(F)Oc1cc(OCc2ccccc2)ccc1Br] | 1-bromo-4-[(phenylmethyl)oxy]-2-[(trifluoromethyl)oxy]benzene | 4-bromo-3-[(trifluoromethyl)oxy]phenol | $^1$H NMR (400 MHz, CDCl₃): δ ppm 7.19-7.78 (6H, m), 6.73-7.14 (2H, m), 5.06 (2H, br. s) | 1.44 min |

Intermediate 112

3-ethyl-4-[(phenylmethyl)oxy]benzonitrile

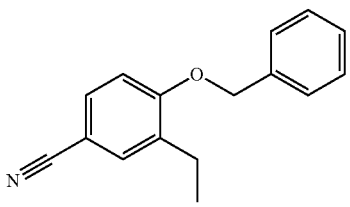 [SMILES: CCc1cc(C#N)ccc1OCc1ccccc1]

To a 1M solution of ethyl magnesium bromide (2 mL, 1.5 equiv), THF (10 mL) was added and the reaction mixture was cooled down to 0° C. A solution of 0.5 M in THF of zinc dichloride (4 mL, 1.5 equiv) was added slowly and the reaction mixture was stirred for 30 min at the same temperature. Pd(tBu$_3$P)$_2$ (102 mg, 0.1 equiv) was added followed by the addition of a solution of 3-bromo-4-[(phenylmethyl)oxy] benzonitrile (Intermediate 110, 576 mg) in THF and the reaction was allowed to reach room temperature. After stirring 30 minutes, some additional Pd(tBu$_3$P)$_2$ was added (51 mg, 0.05 equiv), then 30 min stirring, then third addition of Pd(tBu$_3$P)$_2$ (51 mg, 0.05 equiv) and stirring 30 min. The reaction mixture was quenched with an aqueous saturated solution of NH$_4$Cl (100 mL) and extracted 3 times with ethyl acetate (3×150 mL). The gathered organic phases were filtrated on celite, dried over sodium sulphate. The residue obtained was purified by chromatography on silica gel (Companion system, 40 g Si cartridge) using as eluent a gradient cyclohexane/ethyl acetate 100:0, then 100:0 to 90:10. Evaporation afforded the title compound (336 mg) as a white solid.

$^1$H NMR (400 MHz, CDCl$_3$): δ ppm 7.49-7.27 (7H, m), 6.94 (1H, d), 5.15 (2H, s), 2.72 (2H, q), 1.23 (3H, t); UPLC_ipqc: 1.30 min, 236 [M−H]−.

Intermediate 113

1-methyl-4-[(phenylmethyl)oxy]-2-[(trifluoromethyl)oxy]benzene

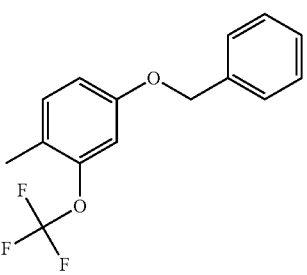 [SMILES: Cc1ccc(OCc2ccccc2)cc1OC(F)(F)F]

Preparation of organometallic solution: To a solution of 1M ZnCl$_2$ in Et$_2$O (6 mL) was slowly added at room temperature a solution of 1.4M methyl magnesium bromide solution in THF (4.3 mL) and the reaction mixture was stirred for 20 minutes at room temperature.

To a solution of 1-bromo-4-[(phenylmethyl)oxy]-2-[(trifluoromethyl)oxy]benzene (Intermediate 111, 537 mg, 1.55 mmol) and Pd(tBu$_3$P)$_2$ (208 mg, 0.4 mmol), warmed at 60° C., were added 5.15 mL of the organometallic solution previously formed and the reaction mixture was stirred for 1 hour at 60° C. Further 5.15 mL of the organometallic solution were added and the reaction mixture was stirred for 30 minutes at 60° C. After cooling the reaction was quenched with water (1 mL), diluted with an aqueous saturated solution of ammonium chloride (20 mL) and extracted with ethyl acetate (2×50 mL). The organic layer was washed with brine (2×20 mL), dried (Na$_2$SO$_4$), filtered and evaporated. The crude was purified by flash chromatography (silica, from 100:0 to 80:20 Cyclohexane/EtOAc) to give the title compound (203 mg) as solid.

$^1$H NMR (400 MHz, CDCl$_3$): δ ppm 7.30-7.49 (5H, m), 7.15 (1H, d), 6.79-6.90 (2H, m), 5.05 (2H, s), 2.25 (3H, s); UPLC_ipqc: 1.43 min, 281 [M−H]−.

The following compounds were prepared using the foregoing methodology, replacing 1-bromo-4-[(phenylmethyl) oxy]-2-[(trifluoromethyl)oxy]benzene with the appropriately substituted halo compound, as described in the foregoing Reaction Schemes.

| Int. | Structure | Name | Halo compound | NMR characterization | UPLC_ipqc characterization |
|---|---|---|---|---|---|
| 114 | 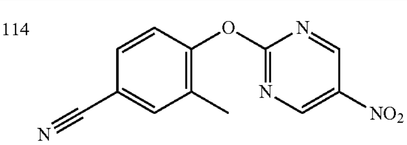 | 3-methyl-4-[(5-nitro-2-pyrimidinyl)oxy]benzonitrile | 3-bromo-4-[(5-nitro-2-pyrimidinyl)oxy]benzonitrile] (Intermediate 130) | $^1$H NMR (400 MHz, CDCl$_3$): δ ppm 9.36 (2H, s), 7.68 (1H, s), 7.64 (1H, d), 7.25 (1H, d), 2.26 (3H, s) | 0.94 min |

Intermediate 115

3-ethyl-4-hydroxybenzonitrile

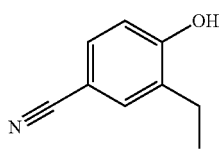

3-ethyl-4-[(phenylmethyl)oxy]benzonitrile (Intermediate 112, 334 mg) was dissolved in 15 mL of EtOAc/EtOH (2/1) and 10% mol Pd/C (0.1 equiv) was added to the solution. The resulting mixture was stirred overnight at room temperature under hydrogen gas atmosphere. The reaction mixture was filtered under argon and the solvent was removed. The residue obtained was purified by chromatography on silica gel (Companion system, 40 g Si cartridge) using as eluent a gradient cyclohexane/ethyl acetate from 100:0 to 80:20. Evaporation afforded the title compound (148 mg) as a white solid.

$^1$H NMR (400 MHz, DMSO-d$_6$): δ ppm 10.50 (1H, br s), 7.50 (2H, m), 6.92 (1H, d), 2.55 (2H, q), 1.12 (3H, t); UPLC_ipqc: 0.84 min, 146 [M–H]–

The following compounds were prepared using the foregoing methodology, replacing 3-ethyl-4-[(phenylmethyl)oxy]benzonitrile with the appropriate benzylated phenol.

Intermediate 117

4-hydroxy-2-iodobenzonitrile

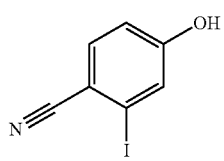

To a solution of 2-fluoro-4-iodobenzonitrile (5.0 g, 20.24 mmol) in dry acetonitrile (100 mL) potassium trimethylsilanolate (1.18 g) was added and the reaction mixture was stirred overnight at 50° C. The solvent was removed under reduced pressure and the residue was dissolved in ethyl acetate (100 mL) and an aqueous pH 3 buffer solution was added up to pH ~5. Two phases were separated and the organic layer was dried (Na$_2$SO$_4$), filtered and evaporated to afford the title compound (4.90 g) as brown solid.

$^1$H NMR (400 MHz, DMSO-d$_6$): δ ppm 10.92 (1H, s), 7.65 (1H, d), 7.39 (1H, d), 6.93 (1H, dd);

UPLC_ipqc: 0.81 min, 244 [M–H]–.

The following compounds were prepared using the foregoing methodology, replacing 4-fluoro-2-iodobenzonitrile with the appropriately substituted fluoro benzonitrile, as described in the foregoing Reaction Schemes.

| Int. | Structure | Name | Benzylated phenol | NMR characterization | UPLC_ipqc characterization |
|---|---|---|---|---|---|
| 116 | (structure: 4-methyl-3-(trifluoromethoxy)phenol) | 4-methyl-3-[(trifluoromethyl)oxy]phenol | 1-methyl-4-[(phenylmethyl)oxy]-2-[(trifluoromethyl)oxy] (Intermediate 113) | $^1$H NMR (400 MHz, DMSO-d$_6$): δ ppm 9.77 (1H, br. s.), 7.15 (1H, d), 6.63-6.75 (2H, m), 2.13 (3H, s) | 1.01 min, 192 [M – H]– |

| Int. | Structure | Name | Fluoro benzonitrile | UPLC_ipqc characterization |
|---|---|---|---|---|
| 118 | ![structure] | 4-hydroxy-3-methylbenzonitrile | 4-fluoro-3-methylbenzonitrile | 0.74 min, 134 [M + H]+, 132 [M − H]− |

Intermediate 119

4-hydroxy-2-[(trifluoromethyl)oxy]benzonitrile

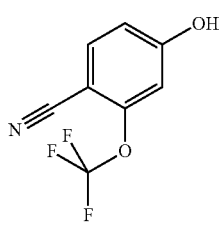 [SMILES: N#Cc1ccc(O)cc1OC(F)(F)F]

Two reactions were carried out in parallel (A and B) and then the two reaction mixtures were combined to run work-up and purification.

Reaction A: To a solution of 4-Methoxy-2-(trifluoromethoxy)benzonitrile (50 mg, 0.23 mmol) in 1,2-dichloroethane (1 mL) was added 1M BBr$_3$ solution in DCM (0.69 mL, 0.69 mmol) dropwise. The resulting reaction mixture was stirred under microwave irradiation five times (set parameters: T=100° C., t=1 hour) adding further 1M BBr$_3$ solution in DCM (1 mL) each time. The total amount of 1M BBr$_3$ solution in DCM used was 4.69 mL.

Reaction B: In a vial were added 4-Methoxy-2-(trifluoromethoxy)benzonitrile (750 mg, 3.45 mmol), 1,2-dichloroethane (5 mL) and then 1M BBr$_3$ solution in DCM (10.36 mL, 10.36 mmol) dropwise. The resulting reaction mixture was stirred under microwave irradiation for 1 hour (set T=100° C.). To the reaction mixture further 1M BBr$_3$ solution in DCM (1 mL) was added and the resulting reaction mixture was stirred under microwave irradiation three more times (set parameters: T=100° C., t=1.5 hours), adding further 1M BBr$_3$ solution in DCM (0.8 mL) each time. The total amount of 1M BBr$_3$ solution in DCM used was 13.76 mL.

The two reactions mixtures A and B were added dropwise to a NaHCO$_3$ saturated aqueous solution and the pH was adjusted to 7 with the addition of solid NaHCO$_3$. The two phases were separated and the aqueous phase was extracted with DCM (1×) and with EtOAc (2×). The combined organic phases were dried and evaporated to dryness to give the title compound in mixture with unreacted starting material (1.48 g) as a black oil. This mixture was used in the next step without further purification.

$^1$H NMR (400 MHz, DMSO-d$_6$): δ ppm 11.35 (1H, s), 7.82 (1H, d), 6.91-6.98 (2H, m); UPLC_ipqc: 0.88 min, 204 [M+H]+, 202 [M−H]−.

Intermediate 120

4-[(5-nitro-2-pyridinyl)oxy]-3-(trifluoromethyl)benzonitrile

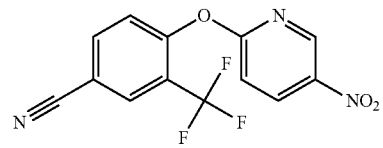

A mixture of 2-chloro-5-nitropyridine (70 mg, 0.44 mmol), 4-hydroxy-3-(trifluoromethyl)benzonitrile (91 mg, 0.49 mmol), K$_2$CO$_3$ (92 mg, 0.66 mmol) in DMF (2 mL) was stirred at 50° C. overnight. Water (4 mL) was added and a precipitate was formed. The solid was filtered-off and it was triturated with MeOH to give the title compound (85 mg) as a brownish solid.

$^1$H NMR (400 MHz, CDCl$_3$): δ ppm 8.99 (1H, d), 8.60 (1H, dd), 8.07 (1H, s), 7.95 (1H, d), 7.48 (1H, d), 7.19-7.32 (1H, m); UPLC_ipqc: 1.1 min, 310 [M+H]+.

The following compounds were prepared using the foregoing methodology, reacting the appropriate halo nitroaryl such as 2-chloro-5-nitropyridine, 2-chloro-5-nitropyrimidine, 1-fluoro-4-nitrobenzene etc. with the appropriately substituted phenol at a suitable temperature, optionally under microwave irradiation, as described in the foregoing Reaction Schemes. Some final products were purified by flash-chromatography (Silica; Cyclohexane/EtOAc or other appropriate solvent system).

| Int. | Structure | Name | Halo nitroaryl | Phenol | NMR characterization | UPLC_ipqc characterization |
|---|---|---|---|---|---|---|
| 121 | ![structure] | 2-iodo-4-[(5-nitro-2-pyrimidinyl)oxy]benzonitrile | 2-chloro-5-nitropyrimidine | 4-hydroxy-2-iodobenzonitrile (Intermediate 117) | $^1$H-NMR (400 MHz, DMSO-d$_6$): δ ppm 9.50 (2H, br. s), 8.14 (1H, br. s), 8.05-7.99 (1H, m), 7.57-7.63 (1H, m) | 1.03 min, 369 [M + H]+ |

| Int. | Structure | Name | Halo nitroaryl | Phenol | NMR characterization | UPLC_ipqc characterization |
|---|---|---|---|---|---|---|
| 122 | 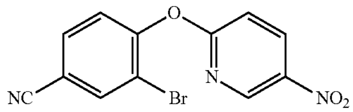 [SMILES: N#Cc1ccc(Oc2ccc([N+](=O)[O-])cn2)c(Br)c1] | 3-bromo-4-[(5-nitro-2-pyridinyl)oxy]benzonitrile | 2-chloro-5-nitropyridine | 3-bromo-4-hydroxy-benzonitrile | $^1$H-NMR (400 MHz, CDCl$_3$): δ ppm 9.01 (1 H, br. s), 8.65-8.56 (1 H, m), 8.02 (1H, s), 7.75 (1 H, d), 7.38 (1H, d), 7.25 (1H, d) | 1.08 min, 320 [M]+, Br pattern |
| 123 | 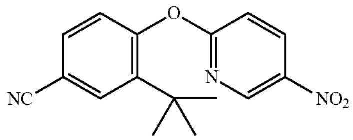 [SMILES: CC(C)(C)c1cc(C#N)ccc1Oc1ccc([N+](=O)[O-])cn1] | 3-(1,1-dimethylethyl)-4-[(5-nitro-2-pyridinyl)oxy]benzonitrile | 2-chloro-5-nitropyridine | 3-(1,1-dimethylethyl)-4-hydroxybenzonitrile (Intermediate 109) | $^1$H NMR (400 MHz, DMSO-d$_6$): δ ppm 9.09-9.04 (1H, m), 8.74-8.64 (1H, m), 7.87 (1H, br. s), 7.83-7.77 (1H, m), 7.44 (1H, d), 7.33 (1H, d), 1.32 (9H, s) | 1.23 min, 298 [M + H]$^+$ |
| 124 | 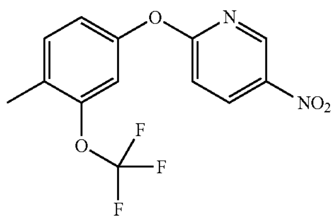 [SMILES: Cc1ccc(Oc2ccc([N+](=O)[O-])cn2)cc1OC(F)(F)F] | 2-({4-methyl-3-[(trifluoromethyl)oxy]phenyl}oxy)-5-nitropyridine | 2-chloro-5-nitropyridine | 4-methyl-3-[(trifluoromethyl)oxy]phenol | $^1$H NMR (400 MHz, CDCl$_3$): δ ppm 9.02 (1 H, d), 8.49 (1 H, dd), 7.33 (1 H, d), 6.97-7.14 (3 H, m), 2.34 (3 H, s) | 1.29 min, 315 [M + H]+. |
| 125 | 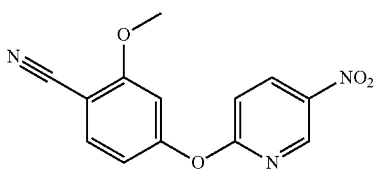 [SMILES: COc1cc(Oc2ccc([N+](=O)[O-])cn2)ccc1C#N] | 2-(methyloxy)-4-[(5-nitro-2-pyridinyl)oxy]benzonitrile | 2-chloro-5-nitropyridine | 4-hydroxy-2-(methyloxy)benzonitrile | $^1$H NMR (400 MHz, CDCl$_3$): δ ppm 9.05 (1H, dd) 8.56 (1H, dd) 7.65 (1H, d) 7.14 (1H, dd) 6.80-6.87 (2H, m) 3.94 (3H, s) | 0.99 min, 272 [M + H]+ |
| 126 | 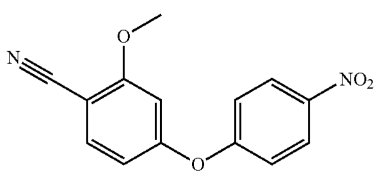 [SMILES: COc1cc(Oc2ccc([N+](=O)[O-])cc2)ccc1C#N] | 2-(methyloxy)-4-[(4-nitrophenyl)oxy]benzonitrile | 1-fluoro-4-nitrobenzene | 4-hydroxy-2-(methyloxy)benzonitrile | $^1$H NMR (400 MHz, CDCl$_3$): δ ppm 8.24-8.35 (2H, m) 7.59 (1H, d) 7.10-7.20 (2H, m) 6.69 (1H, d) 6.65 (1H, dd) 3.92 (3H, s) | 1.10 min |
| 127 | 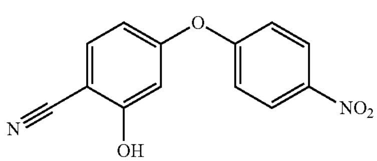 [SMILES: N#Cc1ccc(Oc2ccc([N+](=O)[O-])cc2)cc1O] | 2-hydroxy-4-[(4-nitrophenyl)oxy]benzonitrile | 1-fluoro-4-nitrobenzene | 2,4-dihydroxybenzonitrile | $^1$H NMR (400 MHz, DMSO-d$_6$): δ ppm 11.41 (1H, br. s.) 8.26-8.34 (2H, m) 7.71 (1H, d) 7.25-7.40 (2H, m) 6.69 (1H, dd) 6.67 (1H, d) | 0.97 min, 255 [M − H]− |
| 128 | 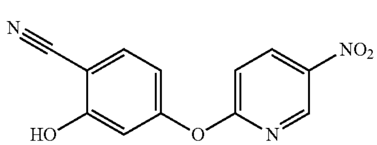 [SMILES: N#Cc1ccc(Oc2ccc([N+](=O)[O-])cn2)cc1O] | 2-hydroxy-4-[(5-nitro-2-pyridinyl)oxy]benzonitrile | 2-chloro-5-nitropyridine | 2,4-dihydroxybenzonitrile | $^1$H NMR (400 MHz, DMSO-d$_6$): δ ppm 11.45 (1H, br. s.), 9.06 (1H, d), 8.66 (1H, dd), 7.72 (1H, d), 7.34 (1H, d), 6.77-6.85 (2H, m) | 0.87 min, 256 [M − H]− |

| Int. | Structure | Name | Halo nitroaryl | Phenol | NMR characterization | UPLC_ipqc characterization |
|---|---|---|---|---|---|---|
| 129 | 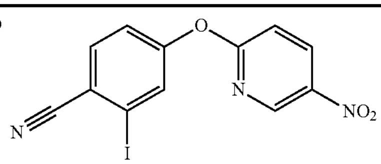 | 2-iodo-4-[(5-nitro-2-pyridinyl)oxy]benzonitrile | 2-chloro-5-nitropyridine | 4-hydroxy-2-iodobenzonitrile (Intermediate 117) | ¹H NMR (400 MHz, DMSO-d₆): δ ppm 9.08 (1H, d), 8.70 (1H, dd), 8.03 (1H, d), 7.98 (1H, d), 7.52 (1H, dd), 7.41 (1H, d) | 1.10 min |
| 130 | 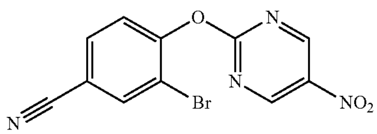 [SMILES: N#Cc1ccc(Oc2ncc([N+](=O)[O-])cn2)c(Br)c1] | 3-bromo-4-[(5-nitro-2-pyrimidinyl)oxy]benzonitrile | 2-chloro-5-nitropyrimidine | 3-bromo-4-hydroxybenzonitrile | 1H NMR (400 MHz, DMSO-d₆): δ ppm 9.51 (2H, s), 8.44-8.47 (1H, m), 8.03-8.10 (1H, m), 7.74 (1H, d). | |
| 131 | 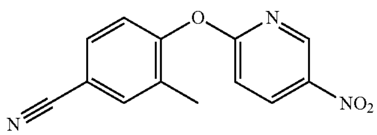 [SMILES: Cc1cc(C#N)ccc1Oc1ccc([N+](=O)[O-])cn1] | 3-methyl-4-[(5-nitro-2-pyridinyl)oxy]benzonitrile | 2-chloro-5-nitropyridine | 4-hydroxy-3-methylbenzonitrile (Intermediate 118) | ¹H NMR (400 MHz, CDCl₃): δ ppm 9.02 (1H, d), 8.57 (1H. dd), 7.50-7.71 (2H, m), 7.13-7.25 (2H, m), 2.23 (3 H, s) | 1.04 min, 256 [M + H]+. |
| 132 | 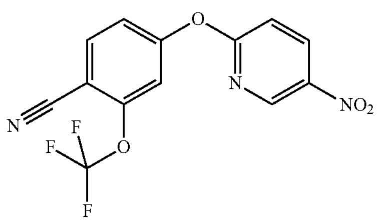 [SMILES: N#Cc1ccc(Oc2ccc([N+](=O)[O-])cn2)cc1OC(F)(F)F] | 4-[(5-nitro-2-pyridinyl)oxy]-2-[(trifluoromethyl)oxy]benzonitrile | 2-chloro-5-nitropyridine | 4-hydroxy-2-[(trifluoromethyl)oxy]benzonitrile (Intermediate 119) | ¹H NMR (400 MHz, CDCl₃): δ ppm 9.02-9.11 (1H, m), 8.55-8.65 (1H, m), 7.82 (1 H, d), 7.25-7.35 (2 H, m), 7.20 (1 H, d) | 1.14 min, 326 [M + H]+ |

Intermediate 133

2-ethyl-4-[(5-nitro-2-pyrimidinyl)oxy]benzonitrile

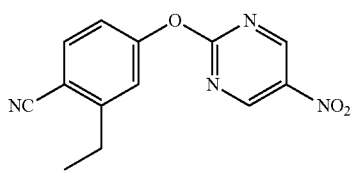 [SMILES: CCc1cc(Oc2ncc([N+](=O)[O-])cn2)ccc1C#N]

In a flamed 2-necked flask, under N₂, to a solution of ZnCl₂ (0.82 mL of a 0.5 M solution on THF, 0.41 mmol) in 1.0 mL of THF, cooled at −15° C., EtMgBr (0.41 mL of a 1.0 M solution in THF, 0.41 mmol) was slowly added and the reaction mixture was stirred at that temperature for 1 h. Then Pd(tBu₃P)₂ (7.0 mg, 0.03 mmol) was added, followed by 2-iodo-4-[(5-nitro-2-pyrimidinyl)oxy]benzonitrile (Intermediate 121, 50.0 mg) in THF (1.0 mL) and the reaction mixture was stirred at −15° C. for 1 h and then the NaCl/ice bath was removed. After 2 hours at r.t. additional 3.5 mg (0.015 mmol) of (tBu₃P)₂ were added. The reaction was quenched with NH₄Cl (saturated aqueous solution) and extracted with EtOAc (three times). The collected organic were dried over Na₂SO₄, filtered and evaporated. The residue obtained was charged on a silica gel column and eluted with Cyclohexane/EtOAc (from 100:0 to 90:10 Cyclohexane/EtOAc, plateau at 90:10) affording 25 mg of the title compound.

¹H-NMR (400 MHz, DMSO-d₆): δ ppm 9.47 (2H, br. s), 7.94 (1H, d), 7.49 (1H, br. s), 7.41-7.33 (1H, m), 2.84 (2H, q), 1.24 (3H, t); UPLC_ipqc: 1.06 min, 271 [M+H]+.

Intermediate 134

2-cyclopropyl-4-[(5-nitro-2-pyridinyl)oxy]benzonitrile

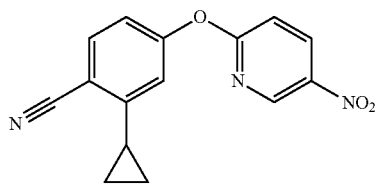 [SMILES: N#Cc1ccc(Oc2ccc([N+](=O)[O-])cn2)cc1C1CC1]

Preparation of organometallic solution: to a solution of 0.5M ZnCl₂ in THF (9 mL) a solution of 0.5M Cyclopropyl Magnesium bromide in THF (9 mL) was slowly added at r.t. and the reaction mixture was stirred for 20 minutes at r.t.

To a solution of 2-iodo-4-[(5-nitro-2-pyridinyl)oxy]benzonitrile (Intermediate 129, 550 mg) and Pd(tBu₃P)₂ (76 mg, 0.15 mmol), warmed at 60° C., were added 6 mL of the organometallic solution previously formed and the reaction mixture was stirred for 1 hour at 60° C. Further 6 mL of the organometallic solution were added and the reaction mixture was stirred for additional 1 hour at 60° C. Further 6 mL of the organometallic solution were added and the reaction mixture was stirred for additional 1 hour at 60° C. After cooling the reaction was quenched with water (1 mL), diluted with an aqueous saturated solution of ammonium chloride (20 mL) and extracted with ethyl acetate (2×50 mL). The organic layer was washed with brine (2×20 mL), dried (Na$_2$SO$_4$), filtered and evaporated and the residue was purified by flash chromatography on silica gel (SNAP 50 g), eluting from 100:0 to 80:20 n-hexane/ethyl acetate affording the title compound (400 mg) as white solid.

$^1$H NMR (400 MHz, DMSO-d$_6$): δ ppm 9.06 (1H, d), 8.67 (1H, dd), 7.88 (1H, d), 7.35 (1H, d), 7.23 (1H, dd), 7.01 (1H, dd), 2.17-2.27 (1H, m), 1.10-1.19 (2H, m), 0.82-0.90 (2H, m); UPLC_ipqc: 1.13 min, 282 [M+H]+.

The following compounds were prepared using the foregoing methodology, replacing Cyclopropyl Magnesium bromide with the appropriate Grignard reagent to form the organozinc reagent, as described in the foregoing Reaction Schemes.

$^1$H NMR (400 MHz, DMSO-d$_6$): δ ppm 9.04 (1H, br. s), 8.69 (1H, dd), 7.75 (1H, d), 7.58 (1H, s), 7.41 (2H, t), 1.90-1.80 (1H, m), 0.90-0.73 (4H, m); UPLC_ipqc: 1.12 min, 282 [M+H]+.

Intermediate 138

2-(1-methylethenyl)-4-[(5-nitro-2-pyridinyl)oxy]benzonitrile

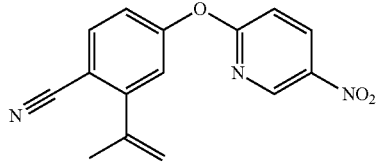

To a solution of 2-iodo-4-[(5-nitro-2-pyridinyl)oxy]benzonitrile (Intermediate 129, 5.0 g) in DMF (50 mL) were added K$_3$PO$_4$ (5.77 g, 27.24 mmol), Pd(tBu$_3$)$_2$ (696 mg, 1.36 mmol) and 4,4,5,5-tetramethyl-2-(1-methylethenyl)-1,3,2-dioxaborolane (3.84 mL, 20.43 mmol) and the reaction mixture was stirred for 4 hours at 110° C. After cooling the

| Int. | Structure | Name | Grignard reagent | NMR characterization | UPLC_ipqc characterization |
|------|-----------|------|------------------|----------------------|---------------------------|
| 135 | 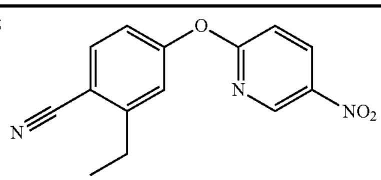 | 2-ethyl-4-[(5-nitro-2-pyridinyl)oxy]benzonitrile | Ethyl magnesium bromide | $^1$H-NMR (400 MHz, CDCl$_3$): δ ppm 9.06 (1H, d) 8.56 (1H, dd) 7.72 (1H, d) 7.18 (1H, d) 7.10-7.17 (2H, m) 2.95 (2H, q) 1.35 (3H, t) | 1.12 min, 270 [M + H]+ |
| 136 | 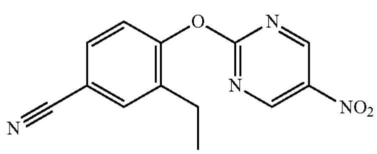 [SMILES: CCc1cc(C#N)ccc1Oc1ncc([N+](=O)[O-])cn1] | 3-ethyl-4-[(5-nitro-2-pyrimidinyl)oxy]benzonitrile | Ethyl Magnesium bromide | $^1$H NMR (400 MHz, CDCl$_3$): δ ppm 9.35 (2H, s), 7.70 (1H, s), 7.64 (1H, dd), 7.23 (1H, d), 2.62 (2H, q), 1.25 (3H, t) | 1.02 min |

Intermediate 137

3-cyclopropyl-4-[(5-nitro-2-pyridinyl)oxy]benzonitrile

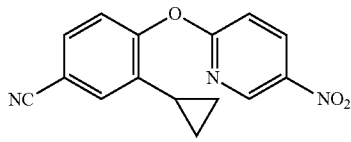

In a vial 3-bromo-4-[(5-nitro-2-pyridinyl)oxy]benzonitrile (Intermediate 122, 800 mg) was dissolved in 16.0 mL of toluene. Cyclopropylboronic acid (1073.8 mg, 12.5 mmol) was added, followed by Pd(OAc)$_2$ (56.1 mg, 0.25 mmol) and (Cy)$_3$P (70.0 mg 0.25 mmol). Then, an aqueous solution (8.0 mL of water) of K$_3$PO$_4$ (1855.0 mg, 8.75 mmol) was added. The reaction mixture was heated at 80° C. overnight. After cooling down to r.t., the mixture was partitioned between brine and EtOAc and the separated aqueous phase was extracted with EtOAc (three times). The collected organic were dried over Na$_2$SO$_4$, filtered and evaporated. The crude obtained was charged on a silica gel column and eluted with Cyclohexane/EtOAc (from 100:0 to 80:20 Cyclohexane/EtOAc) affording 634 mg of the title compound.

reaction was diluted with water (100 mL) and extracted with ethyl acetate (3×100 mL). The organic layer was washed with ice cold brine (3×50 mL), dried (Na$_2$SO$_4$), filtered and evaporated and the residue was purified by flash chromatography on silica gel (SNAP 100 g) eluting from 100:0 to 80:20 cyclohexane/ethyl acetate to afford the title compound (1.8 g) as white solid.

$^1$H-NMR (400 MHz, DMSO-d$_6$): δ ppm 9.08 (1H, d), 8.69 (1H, dd), 7.97 (1H, d), 7.47 (1H, d), 7.40 (2H, d), 5.46 (1H, s), 5.32 (1H, s), 2.16 (3H, s); UPLC_ipqc: 1.14 min, 282 [M+H]+.

Intermediate 139

2-(ethyloxy)-4-[(4-nitrophenyl)oxy]benzonitrile

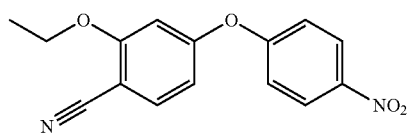 [SMILES: CCOc1cc(Oc2ccc([N+](=O)[O-])cc2)ccc1C#N]

2-hydroxy-4-[(4-nitrophenyl)oxy]benzonitrile (Intermediate 127, 87.2 mg) was dissolved in DMF (5 mL). K₂CO₃ (92.2 mg, 0.67 mmol) and iodoethane (32 μL, 0.40 mmol) were added. The reaction mixture was stirred at r.t. After 16 h, the reaction mixture was evaporated to dryness to give the crude product that was purified by silica gel chromatography (from 100:0 to 50:50 Cyclohexane/EtOAc in 10 CV; then 50:50 Cyclohexane/EtOAc for 10 CV) to obtain 84.9 mg of the title compound as a yellow solid.

¹H NMR (400 MHz, DMSO-d₆): δ ppm 8.26-8.35 (2H, m) 7.82 (1H, d) 7.26-7.35 (2H, m) 7.09 (1H, d) 6.80 (1H, dd) 4.18 (2H, q) 1.36 (3H, t); UPLC_ipqc: 1.16 min, [M+H]+.

The following compounds were prepared using the foregoing methodology, replacing 2-hydroxy-4-[(4-nitrophenyl)oxy]benzonitrile with the appropriately substituted phenol and iodoethane with the appropriate electrophile, as described in the foregoing Reaction Schemes. Some final products were purified by flash-chromatography (Silica; Cyclohexane/EtOAc or other appropriate solvent system).

tions (Set Temperature: 110° C.). The reaction mixture was diluted with Et₂O and water, acidified with aqueous 1N HCl until pH=2, the phases were separated and the organics were dried over Na₂SO₄. The solid was filtered out and the solvent was removed affording crude 2-hydroxy-4-[(5-nitro-2-pyridinyl)oxy]benzonitrile (664 mg) as a brown solid. To a solution of this crude in dry DMF (5 mL) potassium carbonate (460 mg, 3.33 mmol) and isopropyl bromide (313 μL, 3.33 mmol) were added and the reaction mixture was stirred overnight at 50° C. The reaction was diluted with brine (10 mL) and extracted with ethyl acetate (2×20 mL). The organic layer was dried (Na₂SO₄), filtered and evaporated and the residue was purified by flash chromatography on silica gel (SNAP 25 g) eluting from 100:0 to 75:25 cyclohexane/ethyl acetate affording the title compound (260 mg) as white solid.

¹H-NMR (400 MHz, CDCl₃): δ ppm 9.06 (1H, d), 8.56 (1H, dd), 7.61-7.67 (1H, m), 7.15 (1H, d), 6.76-6.84 (2H, m), 4.56-4.68 (1H, m), 1.44 (6H, d).

| Int. | Structure | Name | Phenol | Electrophile | NMR characterization | UPLC_ipqc characterization |
|---|---|---|---|---|---|---|
| 140 | 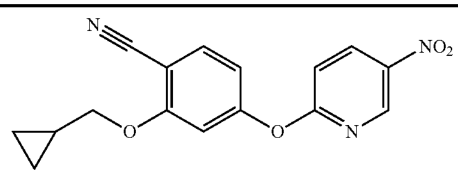 | 2-[(cyclopropylmethyl)oxy]-4-[(5-nitro-2-pyridinyl)oxy]benzonitrile (Intermediate 128) | 2-hydroxy-4-[(5-nitro-2-pyridinyl)oxy]benzonitrile | (bromomethyl)cyclopropane | ¹H NMR (400 MHz, DMSO-d₆): δ ppm 9.06 (1H, d), 8.67 (1H, dd), 7.83 (1H, d), 7.36 (1H, d), 7.19 (1H, d), 6.97 (1H, dd), 3.97 (2H, d), 1.17-1.35 (1H, m), 0.53-0.65 (2H, m), 0.29-0.40 (2H, m) | 1.14 min, 312 [M + H]+ |
| 141 | 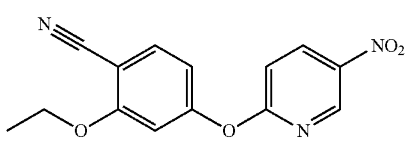 [SMILES: CCOc1cc(Oc2ccc([N+](=O)[O-])cn2)ccc1C#N] | 2-(ethyloxy)-4-[(5-nitro-2-pyridinyl)oxy]benzonitrile | 2-hydroxy-4-[(5-nitro-2-pyridinyl)oxy]benzonitrile (Intermediate 128) | iodoethane | ¹H NMR (400 MHz, DMSO-d₆): δ ppm 9.06 (1H, d), 8.67 (1H, dd), 7.83 (1H, d), 7.36 (1H, d), 7.20 (1H, d), 6.97 (1H, dd), 4.17 (2H, q), 1.35 (3H, t) | 1.06 min, 286 [M + H]+. |

Intermediate 142

2-[(1-methylethyl)oxy]-4-[(5-nitro-2-pyridinyl)oxy]benzonitrile

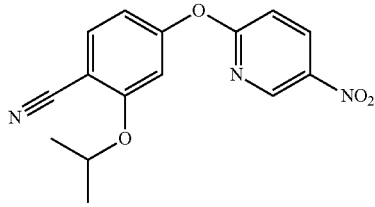

In a vial 2,4-dihydroxybenzonitrile (300 mg, 2.2 mmol), 2-chloro-5-nitropyridine (351.96 mg, 2.22 mmol) and K₂CO₃ (920 mg, 6.62 mmol) were dissolved in DMF (5 mL). The reaction was heated for 1 hour under microwave irradia- Intermediate 143

4-[(5-amino-2-pyridinyl)oxy]-3-(trifluoromethyl)benzonitrile

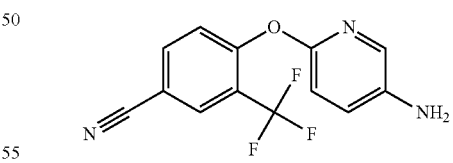

To a solution of 4-[(5-nitro-2-pyridinyl)oxy]-3-(trifluoromethyl)benzonitrile (Intermediate 120, 83 mg) in THF (3 mL)/water (1.5 mL) was added at room temperature, iron (75 mg, 1.34 mmol) and NH₄Cl (72 mg, 1.34 mmol) and the resulting reaction mixture was stirred overnight. The mixture was filtered through a small pad of celite washing with EtOAc and water. To the filtered mixture was added an aqueous NaHCO₃ saturated solution and the two phases were separated. The aqueous phase was extracted with EtOAc and the combined organic phases were dried and evaporated to dryness. The crude was purified by flash chromatography (companion system, 2×12 g Si cartridge, from 100:0 to 70:30 Cyclohexane/EtOAc) to afford the title compound (72 mg).

$^1$H NMR (400 MHz, CDCl$_3$): δ ppm 7.97 (1H, s), 7.69-7.79 (2H, m), 7.23 (1H, d), 7.16 (1H, dd), 6.93 (1H, d); UPLC_ipqc: 0.91 min, 280 [M+H]+.

The following compounds were prepared using the foregoing methodology, replacing 4-[(5-nitro-2-pyridinyl)oxy]-3-(trifluoromethyl)benzonitrile (Intermediate 120) with the appropriate nitro derivative, as described in the foregoing Reaction Schemes. Some final products were purified by flash-chromatography (Silica or NH cartridge; Cyclohexane/EtOAc or other appropriate solvent system). In some cases purification by SCX (MeOH and then 2M ammonia solution in MeOH) was run before the usual flash-chromatography.

| Int. | Structure | Name | Nitro derivative | NMR characterization | UPLC_ipqc characterization |
|---|---|---|---|---|---|
| 144 | 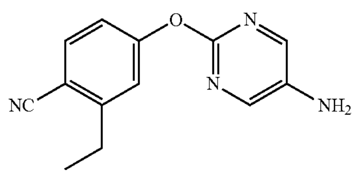 | 4-[(5-amino-2-pyrimidinyl)oxy]-2-ethylbenzonitrile | 2-ethyl-4-[(5-nitro-2-pyrimidinyl)oxy]benzonitrile (Intermediate 133) | $^1$H-NMR (400 MHz, DMSO-d$_6$): δ ppm 8.03 (2 H, br. s), 7.79 (1H, d), 7.19 (1 H, br. s), 7.07 (1H, d), 5.41 (2H, br. s), 2.80 (2H, q), 1.22 (3H, t) | 0.78 min, 241 [M + H]$^+$ |
| 145 | 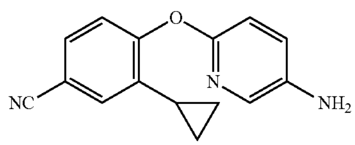 [SMILES: N#Cc1ccc(Oc2ccc(N)cn2)c(C2CC2)c1] | 4-[(5-amino-2-pyridinyl)oxy]-3-cyclopropylbenzonitrile | 3-cyclopropyl-4-[(5-nitro-2-pyridinyl)oxy]benzonitrile (Intermediate 137) | $^1$H NMR (400 MHz, DMSO-d$_6$): δ ppm 7.61-7.52 (2H, m), 7.42 (1H, s), 7.16-7.09 (1H, m), 6.89 (2H, t), 5.19 (2H, br. s), 2.14-2.04 (1H, m), 0.97-0.89 (2H, m), 0.82-0.75 (2H, m) | 0.86 min, 252 [M + H]$^+$ |
| 146 | 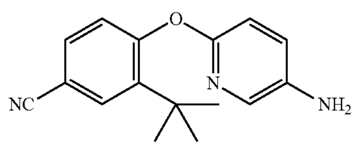 [SMILES: CC(C)(C)c1cc(C#N)ccc1Oc1ccc(N)cn1] | 4-[(5-amino-2-pyridinyl)oxy]-3-(1,1-dimethylethyl)benzonitrile | 3-(1,1-dimethylethyl)-4-[(5-nitro-2-pyridinyl)oxy]benzonitrile (Intermediate 123) | $^1$H NMR (400 MHz, DMSO-d$_6$): δ ppm 7.72 (1H, br. s), 7.65-7.57 (2H, m), 7.16-7.08 (1H, m), 6.89-6.78 (2H, m), 5.28-5.19 (2H, m), 1.39 (9H, s) | 1.02 min, 268 [M + H]$^+$ |
| 147 | 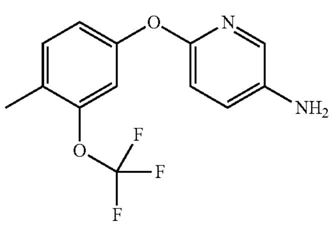 | 6-({4-methyl-3-[(trifluoromethyl)oxy]phenyl}oxy)-3-pyridinamine | 2-({4-methyl-3-[(trifluoromethyl)oxy]phenyl}oxy)-5-nitropyridine (Intermediate 124) | $^1$H NMR (400 MHz, CDCl$_3$): δ ppm 7.70 (1H, d), 7.20 (1H, d), 7.09 (1H, dd), 6.95 (1H, br. s.), 6.91 (1H, dd), 6.78 (1H, d), 2.27 (3H, s) | 1.04 min, 285 [M + H]$^+$ |
| 148 | 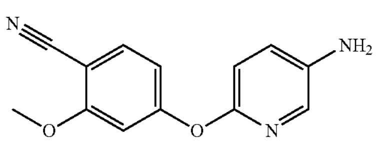 [SMILES: COc1cc(Oc2ccc(N)cn2)ccc1C#N] | 4-[(5-amino-2-pyridinyl)oxy]-2-(methyloxy)benzonitrile | 2-(methyloxy)-4-[(5-nitro-2-pyridinyl)oxy]benzonitrile (Intermediate 125) | $^1$H NMR (400 MHz, DMSO-d$_6$): δ ppm 7.64 (1H, d) 7.61 (1H, d) 7.11 (1H, dd) 6.87 (1H, d) 6.83 (1H, d) 6.52 (1H, dd) 5.27 (2H, br. s.) 3.86 (3H, s) | 0.74 min, 242 [M + H]+ |
| 149 | 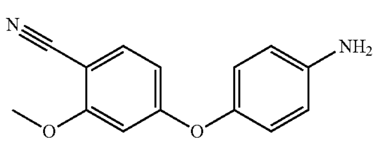 [SMILES: COc1cc(Oc2ccc(N)cc2)ccc1C#N] | 4-[(4-aminophenyl)oxy]-2-(methyloxy)benzonitrile | 2-(methyloxy)-4-[(4-nitrophenyl)oxy]benzonitrile (Intermediate 126) | $^1$H NMR (400 MHz, DMSO-d$_6$): δ ppm 7.63 (1 H, d) 6.81-6.87 (2 H, m) 6.76 (1 H, d) 6.60-6.67 (2 H, m) 6.42 (1 H, dd) 5.12 (2 H, br. s.) 3.86 (3 H, s) | 0.70 min, 241 [M + H]+ |
| 150 | 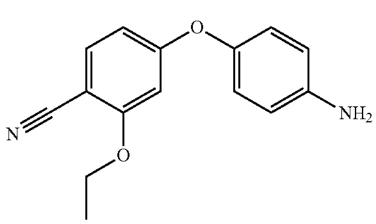 [SMILES: CCOc1cc(Oc2ccc(N)cc2)ccc1C#N] | 4-[(4-aminophenyl)oxy]-2-(ethyloxy)benzonitrile | 2-(ethyloxy)-4-[(4-nitrophenyl)oxy]benzonitrile (Intermediate 139) | $^1$H NMR (400 MHz, CDCl$_3$): δ ppm 7.42 (1H, d) 6.85-6.90 (2H, m) 6.68-6.75 (2H, m) 6.48 (1H, d) 6.44 (1H, dd) 4.04 (2H, q) 3.70 (2H, br. s.) 1.45 (3H, t) | 0.80 min, 255 [M + H]+ |

-continued

| Int. | Structure | Name | Nitro derivative | NMR characterization | UPLC_ipqc characterization |
|---|---|---|---|---|---|
| 151 | 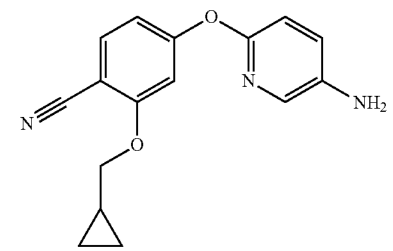 [SMILES: N#Cc1ccc(Oc2ccc(N)cn2)cc1OCC1CC1] | 4-[(5-amino-2-pyridinyl)oxy]-2-[(cyclopropylmethyl)oxy]benzonitrile | 2-[(cyclopropylmethyl)oxy]-4-[(5-nitro-2-pyridinyl)oxy]benzonitrile (Intermediate 140) | $^1$H NMR (400 MHz, CDCl$_3$): δ ppm 7.74 (1H, dd), 7.47 (1H, d), 7.13 (1H, dd), 6.83 (1H, d), 6.61 (1H, d), 6.57 (1H, dd), 3.85 (2H, d), 3.70 (2H, br. s.), 1.21-1.35 (1H, m), 0.60-0.70 (2H, m), 0.32-0.40 (2H, m) | 0.91 min, 282 [M + H]+ |
| 152 | 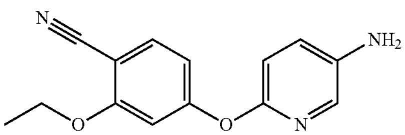 | 4-[(5-amino-2-pyridinyl)oxy]-2-(ethyloxy)benzonitrile | 2-(ethyloxy)-4-[(5-nitro-2-pyridinyl)oxy]benzonitrile (Intermediate 141) | $^1$H NMR (400 MHz, CDCl$_3$): δ ppm 7.75 (1H, dd), 7.48 (1H, d), 7.13 (1H, dd), 6.84 (1H, d), 6.63 (1H, d), 6.58 (1H, dd), 4.08 (2H, q), 3.68 (2H, br. s.), 1.46 (3H, t) | 0.81 min, 256 [M + H]+ |
| 153 | 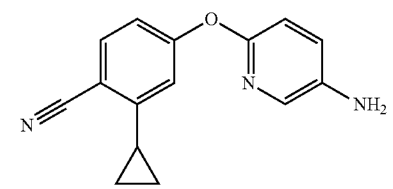 | 4-[(5-amino-2-pyridinyl)oxy]-2-cyclopropylbenzonitrile | 2-cyclopropyl-4-[(5-nitro-2-pyridinyl)oxy]benzonitrile (Intermediate 134) | $^1$H NMR (400 MHz, DMSO-d$_6$) δ ppm 7.70 (1 H, d), 7.60 (1 H, d), 7.12 (1 H, dd), 6.85 (1 H, d), 6.80 (1 H, dd), 6.65 (1 H, d), 5.26 (2 H, br. s.), 2.11-2.22 (1 H, m), 1.07-1.15 (2 H, m), 0.75-0.82 (2 H, m) | 0.86 min, 252 [M + H]+ |
| 154 | 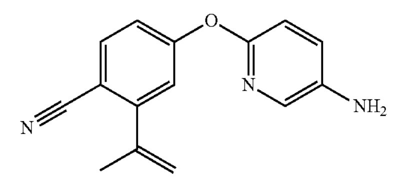 | 4-[(5-amino-2-pyridinyl)oxy]-2-(1-methylethenyl)benzonitrile | 2-(1-methylethenyl)-4-[(5-nitro-2-pyridinyl)oxy]benzonitrile (Intermediate 138) | $^1$H-NMR (400 MHz, DMSO-d$_6$): δ ppm 7.79 (1H, d), 7.62 (1H, d), 7.12 (1H, dd), 7.05 (1H, d), 6.98 (1H, dd), 6.89 (1H, d), 5.40 (1H, s), 5.28 (2H, br. s.), 5.23 (1H, s), 2.12 (3H, s) | 0.90 min, 252 [M + H]+ |
| 155 | 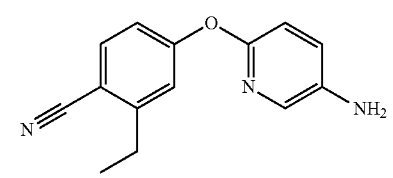 [SMILES: CCc1cc(Oc2ccc(N)cn2)ccc1C#N] | 4-[(5-amino-2-pyridinyl)oxy]-2-ethylbenzonitrile | 2-ethyl-4-[(5-nitro-2-pyridinyl)oxy]benzonitrile (Intermediate 135) | $^1$H-NMR (400 MHz, CDCl$_3$): δ ppm 7.77 (1H, d) 7.58 (1H, d) 7.15 (1H, dd) 7.00 (1H, d) 6.92 (1H, dd) 6.86 (1H, d) 3.62 (2H, br. s.) 2.86 (2H, q) 1.29 (3H, t) | 0.86 min, 240 [M + H]+ |
| 156 | 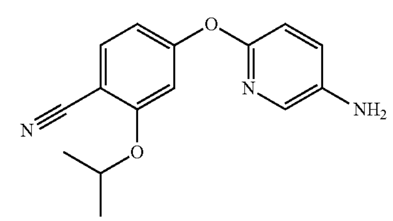 | 4-[(5-amino-2-pyridinyl)oxy]-2-[(1-methylethyl)oxy]benzonitrile | 2-[(1-methylethyl)oxy]-4-[(5-nitro-2-pyridinyl)oxy]benzonitrile (Intermediate 142) | $^1$H-NMR (400 MHz, DMSO-d$_6$): δ ppm 7.63 (1H, d), 7.61 (1H, d), 7.12 (1H, dd), 6.88 (1H, d), 6.84 (1H, d), 6.51 (1H, dd), 5.29 (2H, br. s.), 4.66-4.77 (1H, m), 1.29 (6H, d) | 0.89 min, 270 [M + H]+ |
| 157 | 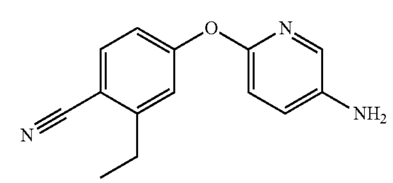 [SMILES: CCc1cc(Oc2ccc(N)cn2)ccc1C#N] | 4-[(5-amino-2-pyridinyl)oxy]-2-ethylbenzonitrile | 2-ethyl-4-[(5-nitro-2-pyridinyl)oxy]benzonitrile (Intermediate 135) | $^1$H NMR (400 MHz, DMSO-d$_6$): δ ppm 7.73 (1H, d), 7.60 (1H, m), 7.13-7.10 (1H, m), 7.02 (1H, d), 6.89-6.86 (2H, m), 5.28 (2H, br. s.), 2.79-2.73 (2H, q), 1.21-1.17 (3H, t) | 0.85 min, 240 [M + H]+ |
| 158 | 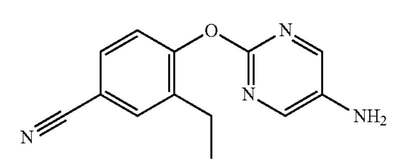 [SMILES: CCc1cc(C#N)ccc1Oc1ncc(N)cn1] | 4-[(5-amino-2-pyrimidinyl)oxy]-3-ethylbenzonitrile | 3-ethyl-4-[(5-nitro-2-pyridinyl)oxy]benzonitrile (Intermediate 136) | $^1$H NMR (400 MHz, CDCl$_3$): δ ppm 8.09 (2H, s), 7.62 (1H, s), 7.55 (1H, dd), 7.15 (1 H, d), 3.62 (2H, br. s.), 2.68 (2 H, q), 1.24 (3H, t) | 0.77 min, 241 [M + H]+ |

-continued

| Int. | Structure | Name | Nitro derivative | NMR characterization | UPLC_ipqc characterization |
|---|---|---|---|---|---|
| 159 | 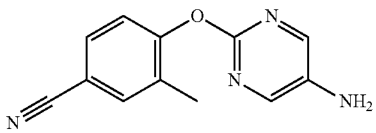 | 4-[(5-amino-2-pyrimidinyl)oxy]-3-methylbenzonitrile | 3-methyl-4-[(5-nitro-2-pyrimidinyl)oxy]benzonitrile (Intermediate 114) | $^1$H NMR (400 MHz, CDCl$_3$): δ ppm 8.08 (2H, s), 7.60 (1H, s), 7.55 (1H, d), 7.17 (1H, d), 3.59 (2H, br. s.), 2.27 (3H, s) | 0.68 min, 227 [M + H]+ |
| 160 | 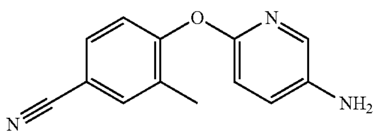 [SMILES: Cc1cc(C#N)ccc1Oc1ccc(N)cn1] | 4-[(5-amino-2-pyridinyl)oxy]-3-methylbenzonitrile | 3-methyl-4-[(5-nitro-2-pyridinyl)oxy]benzonitrile (Intermediate 131) | $^1$H NMR (400 MHz, CDCl$_3$): δ ppm 7.71 (1H, d), 7.54 (1H, s), 7.45 (1H, dd), 7.14 (1H, dd), 6.95 (1H, d), 6.83 (1 H, d), 3.61 (2H, br. s.), 2.29 (3H, s) | 0.75 min, 226 [M + H]+ |
| 161 | 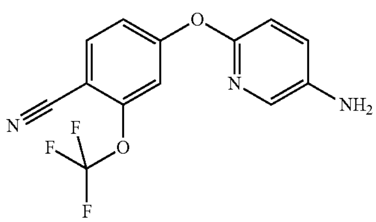 | 4-[(5-amino-2-pyridinyl)oxy]-2-[(trifluoromethyl)oxy]benzonitrile | 4-[(5-nitro-2-pyridinyl)oxy]-2-[(trifluoromethyl)oxy]benzonitrile (Intermediate 132) | $^1$H NMR (400 MHz, CDCl$_3$): δ ppm 7.77 (1H, d), 7.66 (1H, d), 7.17 (1 H, dd), 7.11 (1 H, s), 7.06 (1 H, dd), 6.89 (1 H, d) | 0.94 min, 296 [M + H]+ |

Intermediate 162

2-({4-bromo-3-[(trifluoromethyl)oxy]phenyl}oxy)-5-pyrimidinamine

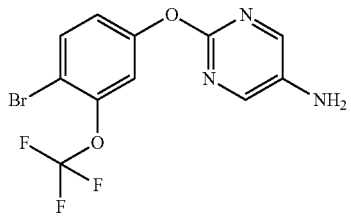 [SMILES: Nc1cnc(Oc2ccc(Br)c(OC(F)(F)F)c2)nc1]

To a solution of 4-bromo-3-[(trifluoromethyl)oxy]phenol (257 mg, 1.0 mmol) in dry DMF (4 mL) potassium carbonate (276 mg, 2 mmol) and then 2-chloro-5-nitropyrimidine (319 mg, 2.0 mmol) were added and the reaction mixture was stirred for 2 hours at r.t. The reaction was quenched with water (1 mL), diluted with brine (5 mL) and extracted with ethyl acetate (2×15 mL). The organic layer was dried (Na$_2$SO$_4$), filtered and evaporated to give crude 2-({4-bromo-3-[(trifluoromethyl)oxy]phenyl}oxy)-5-nitropyrimidine. This crude was dissolved in THF/water (2:1) (6 mL) and Iron (279 mg, 5 mmol) and NH$_4$Cl (267.5 mg, 5 mmol) were added and the reaction mixture was stirred overnight at r.t. The solid was filtered off and the solution was diluted with an aqueous saturated solution of NaHCO$_3$ (5 mL) and extracted with ethyl acetate (2×20 mL). The organic layer was dried (Na$_2$SO$_4$), filtered and evaporated and the residue was purified by flash chromatography on silica gel (SNAP 25 g) eluting from 75:25 to 40:60 cyclohexane/ethyl acetate to afford the title compound (280 mg) as light yellow solid.

$^1$H-NMR (400 MHz, DMSO-d$_6$): δ ppm 8.00 (2H, s), 7.81 (1H, d), 7.34-7.40 (1H, m), 7.14 (1H, dd), 5.37 (2H, br. s.); UPLC_ipqc: 1.02 min, 350 [M]+Br pattern.

The following compounds were prepared using the foregoing methodology, replacing 4-bromo-3-[(trifluoromethyl)oxy]phenol with the appropriately substituted phenol, as described in the foregoing Reaction Schemes.

| Int. | Structure | Name | Phenol | NMR characterization | UPLC_ipqc characterization |
|---|---|---|---|---|---|
| 163 | 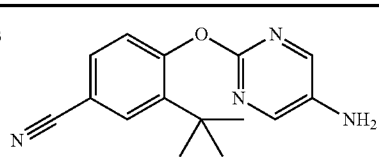 | 4-[(5-amino-2-pyrimidinyl)oxy]-3-(1,1-dimethylethyl)benzonitrile | (3-(1,1-dimethylethyl)-4-hydroxybenzonitrile (Intermediate 109) | $^1$H-NMR (400 MHz, DMSO-d$_6$): δ ppm 8.01 (2H, s) 7.76 (1H, d) 7.67 (1H, dd) 7.05 (1H, d) 5.35-5.41 (2H, m) 1.35 (9H, s) | 0.92 min, 269 [M + H]+ |

Intermediate 164

2-({4-methyl-3-[(trifluoromethyl)oxy]phenyl}oxy)-5-pyrimidinamine

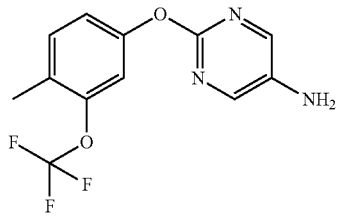

To a solution of 2-({4-bromo-3-[(trifluoromethyl)oxy]phenyl}oxy)-5-pyrimidinamine (Intermediate 162, 270 mg) in DMF (4 mL) were added $K_3PO_4$ (490 mg, 2.31 mmol), Pd(tBu$_3$)$_2$ (197 mg, 0.385 mmol) and methyl boronic acid (276 mg, 4.62 mmol) and the reaction mixture was stirred for 30 minutes at 110° C. under microwave irradiation. After cooling the reaction was diluted with water (10 mL) and extracted with ethyl acetate (3×10 mL). The organic layer was washed with ice cold brine (2×5 mL), dried (Na$_2$SO$_4$), filtered and evaporated and the residue was purified by flash chromatography on silica gel (SNAP 10 g) eluting from 80:20 to 50:50 cyclohexane/ethyl acetate to afford the title compound as white solid (135 mg).

UPLC_ipqc: 0.97 min, 286 [M+H]+.

Intermediate 165 methyl N-{[(6-{[4-cyano-2-(trifluoromethyl)phenyl]oxy}-3-pyridinyl)amino]carbonyl}-2-methylalaninate

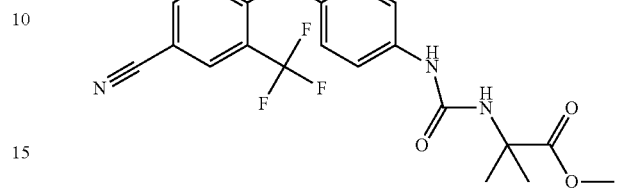

To a solution of triphosgene (32 mg, 0.11 mmol) in EtOAc (1 ml) at 0° C. was added dropwise a solution of 4-[(5-amino-2-pyridinyl)oxy]-3-(trifluoromethyl)benzonitrile (Intermediate 143, 69.8 mg) in triethylamine (60 µL)/EtOAc (4 mL) and then a suspension of methyl 2-methylalaninate hydrochloride (Intermediate 107, 46 mg) in triethylamine (120 µL)/EtOAc (4 mL). The resulting reaction mixture was stirred for 1 hour. An aqueous pH 3 buffer solution was added to the reaction mixture and the two phases were separated. The aqueous phase was extracted 3 times with EtOAc and the combined organic phases were dried over sodium sulphate and evaporated to dryness to give the title compound (49 mg) as crude. This crude was used in the next step without further purification.

UPLC_ipqc: 1.01 min, 423 [M+H]+.

The following compounds were prepared using the foregoing methodology, replacing 4-[(5-amino-2-pyridinyl)oxy]-3-(trifluoromethyl)benzonitrile (Intermediate 143) with the appropriate aniline, as described in the foregoing Reaction Schemes. Final products were isolated as crudes.

| Int. | Structure | Name | Aniline | UPLC_ipqc characterization |
|---|---|---|---|---|
| 166 | 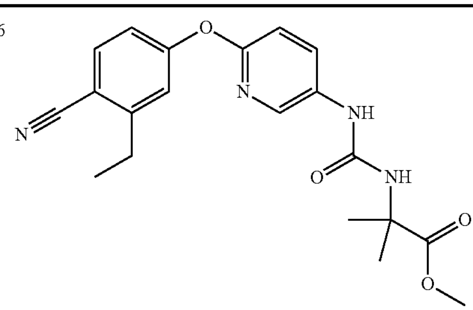 | methyl N-[({6-[(4-cyano-3-ethylphenyl)oxy]-3-pyridinyl}amino)carbonyl]-2-methylalaninate | 4-[(5-amino-2-pyridinyl)oxy]-2-ethylbenzonitrile (Intermediate 157) | 0.99 min, 383 [M + H]+ |
| 167 | 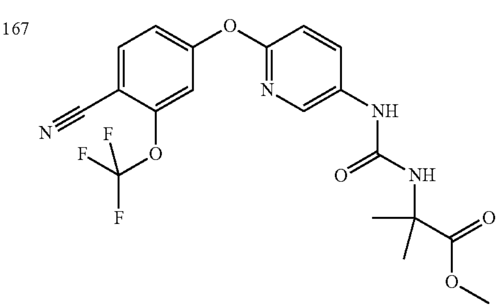 | methyl N-({[6-({4-cyano-3-[(trifluoromethyl)oxy]phenyl}oxy)-3-pyridinyl]amino}carbonyl)-2-methylalaninate | 4-[(5-amino-2-pyridinyl)oxy]-2-[(trifluoromethyl)oxy]benzonitrile (Intermediate 161) | 1.05 min, 439 [M + H]+ |

Intermediate 168

1,1-dimethylelethyl{(1R)-1-[({6-[(4-cyano-2-cyclopropylphenyl)oxy]-3-pyridinyl}amino)carbonyl]propyl}carbamate

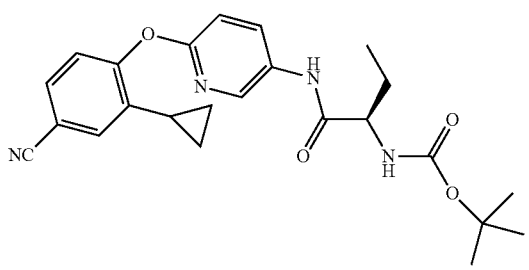 [SMILES: CC[C@@H](NC(=O)OC(C)(C)C)C(=O)Nc1ccc(Oc2ccc(C#N)cc2C2CC2)nc1]

(2R)-2-({[(1,1-dimethylethyl)oxy]carbonyl}amino)butanoic acid (121.4 mg, 0.60 mmol) was dissolved in N,N-Dimethylformamide (1 mL). N,N-Diisopropylethylamine (0.126 mL, 0.72 mmol) and O-(7-Azabenzotriazol-1-yl)-N,N,N',N'-tetramethyluronium hexafluorophosphate (227.2 mg, 0.60 mmol) were added. The reaction mixture was stirred at r.t. for 30 min. 4-[(5-amino-2-pyridinyl)oxy]-3-cyclopropylbenzonitrile (Intermediate 145, 100 mg) was dissolved in 1.0 mL of DMF and the obtained solution was added to the reaction mixture. The reaction mixture was stirred and heated at 60° C. for 2 h. After cooling down to r.t., the reaction mixture was evaporated under vacuum and the crude obtained was charged on a silica gel column and eluted with Cyclohexane/EtOAc (from 100:0 to 50:50 Cyclohexane/EtOAc, then plateau at 50:50) affording 133 mg of the title compound.

$^1$H-NMR (400 MHz, CDCl$_3$): δ ppm 8.42 (1H, br. s), 8.20-8.10 (2H, m), 7.51-7.44 (1H, m), 7.32-7.23 (1H, m), 7.08 (1H, d), 7.03-6.95 (1H, m), 4.95 (1H, br. s), 4.16-4.05 (1H, m), 2.07-1.95 (2H, m), 1.77-1.68 (1H, m), 1.47 (9H, s), 1.04 (3H, t), 0.95-0.88 (2H, m), 0.71-0.64 (2H, m); UPLC_ipqc: 1.14 min, 437 [M+H]+.

The following compounds were prepared using the foregoing methodology, replacing (2R)-2-({[(1,1-dimethylethyl)oxy]carbonyl}amino)butanoic acid with the appropriate aminoacid and 4-[(5-amino-2-pyridinyl)oxy]-3-cyclopropylbenzonitrile (Intermediate 145) with the appropriate aniline, as described in the foregoing Reaction Schemes. The reaction was carried out at a suitable temperature ranging from r.t. to high temperature. Final products were purified by flash-chromatography (Silica; Cyclohexane/EtOAc or other appropriate solvent system).

| Int. | Structure | Name | Amino acid |
|---|---|---|---|
| 169 | 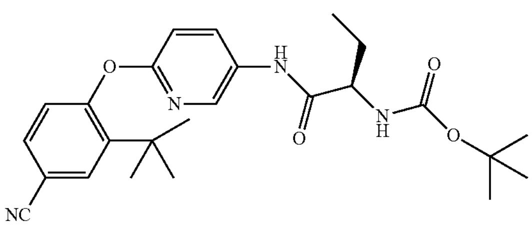 [SMILES: CC[C@@H](NC(=O)OC(C)(C)C)C(=O)Nc1ccc(Oc2ccc(C#N)cc2C(C)(C)C)nc1] | 1,1-dimethylethyl ((1R)-1-{[(6-{[4-cyano-2-{1,1-dimethylethyl)phenyl]oxy}-3-pyridinyl)amino]carbonyl}propyl)carbamate | (2R)-2-({[(1,1-dimethylethyl)oxy]carbonyl}amino)butanoic acid |
| 170 | 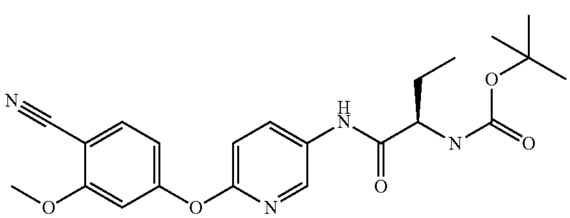 [SMILES: CC[C@@H](NC(=O)OC(C)(C)C)C(=O)Nc1ccc(Oc2ccc(C#N)c(OC)c2)nc1] | 1,1-dimethylethyl ((1R)-1-{[(6-{[4-cyano-3-(methyloxy)phenyl]oxy}-3-pyridinyl)amino]carbonyl}propyl)carbamate | (2R)-2-({[(1,1-dimethylethyl)oxy]carbonyl}amino)butanoic acid |
| 171 | 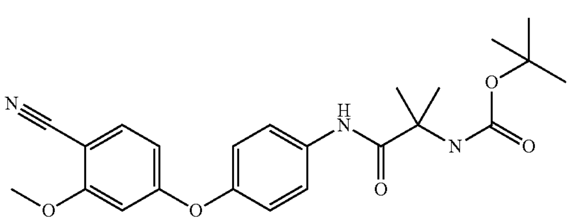 [SMILES: COc1cc(Oc2ccc(NC(=O)C(C)(C)NC(=O)OC(C)(C)C)cc2)ccc1C#N] | 1,1-dimethylethyl {2-[(4-{[4-cyano-3-(methyloxy)phenyl]oxy}phenyl)amino]-1,1-dimethyl-2-oxoethyl}carbamate | N-{[(1,1-dimethylethyl)oxy]carbonyl}-2-methylalanine |
| 172 | 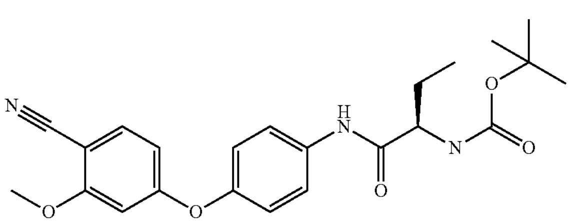 [SMILES: CC[C@@H](NC(=O)OC(C)(C)C)C(=O)Nc1ccc(Oc2ccc(C#N)c(OC)c2)cc1] | 1,1-dimethylethyl ((1R)-1-{[(4-{[4-cyano-3-(methyloxy)phenyl]oxy}phenyl)amino]carbonyl}propyl)carbamate | (2R)-2-({[(1,1-dimethylethyl)oxy]carbonyl}amino)butanoic acid |

-continued

| | | | |
|---|---|---|---|
| 173 | 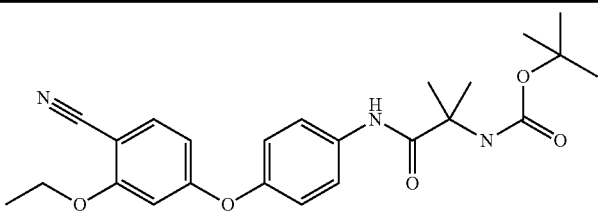 | 1,1-dimethylethyl {2-[(4-{[4-cyano-3-(ethyloxy)phenyl]oxy}phenyl)amino]-1,1-dimethyl-2-oxoethyl}carbamate | N-{[(1,1-dimethylethyl)oxy]carbonyl}-2-methylalanine |
| 174 | 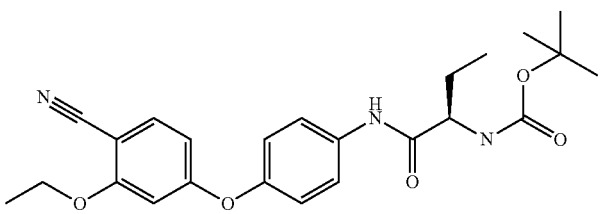 [SMILES: CCOc1cc(Oc2ccc(NC(=O)[C@@H](CC)NC(=O)OC(C)(C)C)cc2)ccc1C#N] | 1,1-dimethylethyl ((1R)-1-{[(4-{[4-cyano-3-(ethyloxy)phenyl]oxy}phenyl)amino]carbonyl}propyl)carbamate | (2R)-2-({[(1,1-dimethylethyl)oxy]carbonyl}amino)butanoic acid |
| 175 | 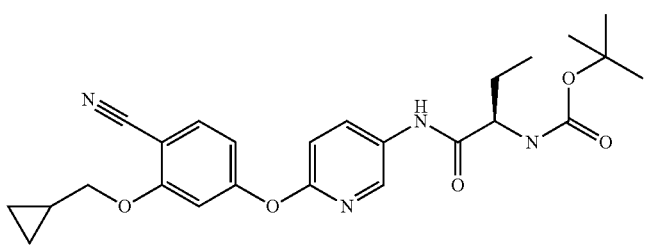 [SMILES: CC[C@@H](NC(=O)OC(C)(C)C)C(=O)Nc1ccc(Oc2ccc(C#N)c(OCC3CC3)c2)nc1] | 1,1-dimethylethyl [(1R)-1-({[6-({4-cyano-3-[(cyclopropylmethyl)oxy]phenyl}oxy)-3-pyridinyl]amino}carbonyl)propyl]carbamate | (2R)-2-({[(1,1-dimethylethyl)oxy]carbonyl}amino)butanoic acid |
| 176 | 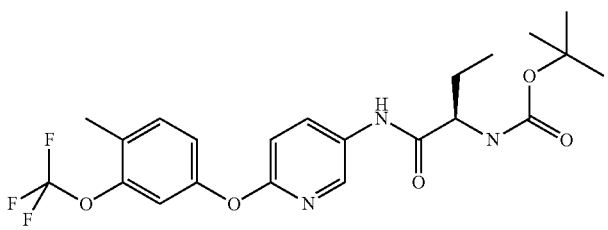 [SMILES: CC[C@@H](NC(=O)OC(C)(C)C)C(=O)Nc1ccc(Oc2ccc(C)c(OC(F)(F)F)c2)nc1] | 1,1-dimethylethyl [(1R)-1-({[6-({4-methyl-3-[(trifluoromethyl)oxy]phenyl}oxy)-3-pyridinyl]amino}carbonyl)propyl]carbamate | (2R)-2-({[(1,1-dimethylethyl)oxy]carbonyl}amino)butanoic acid |
| 177 | 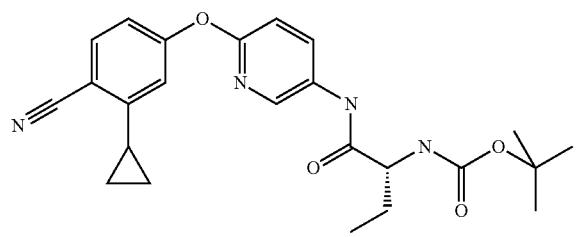 [SMILES: CC[C@@H](NC(=O)OC(C)(C)C)C(=O)Nc1ccc(Oc2ccc(C#N)c(C3CC3)c2)nc1] | 1,1-dimethylethyl {(1R)-1-[({6-[(4-cyano-3-cyclopropylphenyl)oxy]-3-pyridinyl}amino)carbonyl]propyl}carbamate | (2R)-2-({[(1,1-dimelhylethyl)oxy]carbonyl}amino)butanoic acid |
| 178 | 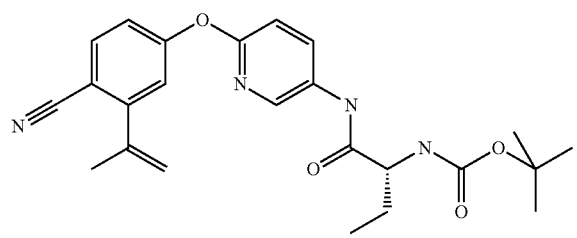 [SMILES: C=C(C)c1cc(Oc2ccc(NC(=O)[C@@H](CC)NC(=O)OC(C)(C)C)cn2)ccc1C#N] | 1,1-dimethylethyl ((1R)-1-{[(6-{[4-cyano-3-(1-methylethenyl)phenyl]oxy}-3-pyridinyl)amino]carbonyl}propyl)carbamate | (2R)-2-({[(1,1-dimethylethyl)oxy]carbonyl}amino)butanoic acid |
| 179 | 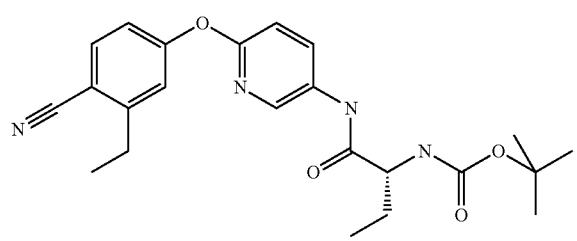 [SMILES: CCc1cc(Oc2ccc(NC(=O)[C@@H](CC)NC(=O)OC(C)(C)C)cn2)ccc1C#N] | 1,1-dimethylethyl {(1R)-1-[({6-[(4-cyano-3-ethylphenyl)oxy]-3-pyridinyl}amino)carbonyl]propyl}carbamate | (2R)-2-({[(1,1-dimethylethyl)oxy]carbonyl}amino)butanoic acid |

| | | | |
|---|---|---|---|
| 180 | 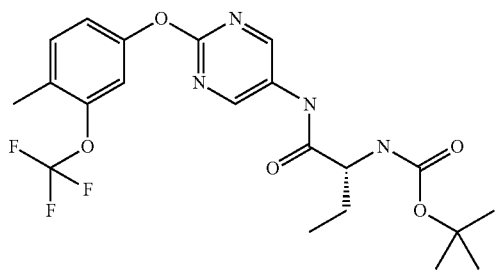 [SMILES: CC[C@@H](NC(=O)OC(C)(C)C)C(=O)Nc1cnc(Oc2ccc(C)c(OC(F)(F)F)c2)nc1] | 1,1-dimethylethyl [(1R)-1-({[2-({4-methyl-3-[(trifluoromethyl)oxy]phenyl}oxy)-5-pyrimidinyl]amino}carbonyl)propyl]carbamate | (2R)-2-({[(1,1-dimethylethyl)oxy]carbonyl}amino)butanoic acid |
| 181 | 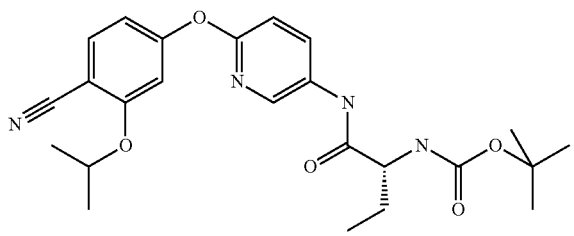 [SMILES: CC[C@@H](NC(=O)OC(C)(C)C)C(=O)Nc1ccc(Oc2ccc(C#N)c(OC(C)C)c2)nc1] | 1,1-dimethylethyl [(1R)-1-({[6-({4-cyano-3-[(1-methylethyl)oxy]phenyl}oxy)-3-pyridinyl]amino}carbonyl)propyl]carbamate | (2R)-2-({[(1,1-dimethylethyl)oxy]carbonyl}amino)butanoic acid |
| 182 | 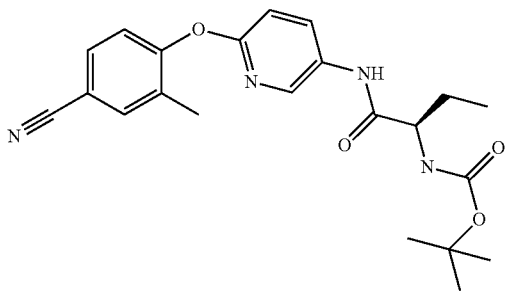 [SMILES: CC[C@@H](NC(=O)OC(C)(C)C)C(=O)Nc1ccc(Oc2ccc(C#N)cc2C)nc1] | 1,1-dimethylethyl {(1R)-1-[({6-[(4-cyano-2-methylphenyl)oxy]-3-pyridinyl}amino)carbonyl]propyl}carbamate | (2R)-2-({[(1,1-dimethylethyl)oxy]carbonyl}amino)butanoic acid |
| 183 | 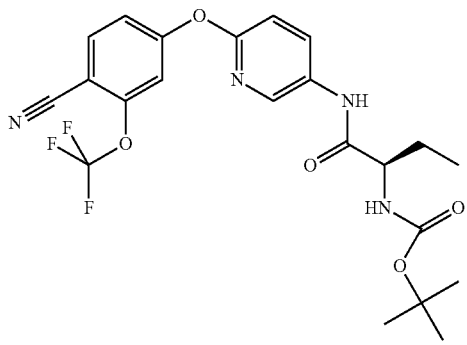 [SMILES: CC[C@@H](NC(=O)OC(C)(C)C)C(=O)Nc1ccc(Oc2ccc(C#N)c(OC(F)(F)F)c2)nc1] | 1,1-dimethylethyl [(1R)-1-({[6-[{4-cyano-3-[(trifluoromethyl)oxy]phenyl}oxy)-3-pyridinyl]amino}carbonyl)propyl]carbamate | (2R)-2-({[(1,1-dimethylethyl)oxy]carbonyl}amino)butanoic acid |
| 184 | 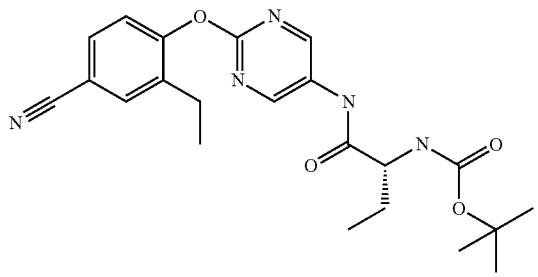 [SMILES: CCc1cc(C#N)ccc1Oc1ncc(NC(=O)[C@@H](CC)NC(=O)OC(C)(C)C)cn1] | 1,1-dimethylethyl {(1R)-1-[({2-[(4-cyano-2-ethylphenyl)oxy]-5-pyrimidinyl}amino)carbonyl]propyl}carbamate | (2R)-2-({[(1,1-dimethylethyl)oxy]carbonyl}amino)butanoic acid |

-continued

| | | | |
|---|---|---|---|
| 185 | [structure] | 1,1-dimethylethyl {(1R)-1-[({2-[(4-cyano-2-methylphenyl)oxy]-5-pyrimidinyl}amino)carbonyl]propyl} carbamate | (2R)-2-({[(1,1-dimethylethyl)oxy]carbonyl} amino) butanoic acid |
| 186 | [structure] | 1,1-dimethylethyl ((1R)-1-{[(2-{[4-cyano-2-(1,1-dimethylethyl)phenyl]oxy}-5-pyrimidinyl)amino]carbonyl} propyl) carbamate | (2R)-2-({[(1,1-dimethylethyl)oxy]carbonyl} amino) butanoic acid |

| Int. | Aniline | NMR characterization | UPLC_ipqc characterization |
|---|---|---|---|
| 169 | 4-[(5-amino-2-pyridinyl)oxy]-3-(1,1-dimethylethyl) benzonitrile (Intermediate 146) | $^1$H NMR (400 MHz, DMSO-d$_6$): δ ppm 10.20 (1H, br. s), 8.38 (1H, br. s), 8.20-8.11 (1H, m), 7.77 (1H, br. s), 7.70-7.64 (1H, m), 7.15 (1H, d), 7.05 (2H, d), 4.04-3.91 (1H, m), 1.77-1.55 (2H, m), 1.41-1.34 (18H, m), 0.93-0.87 (3H, m) | 1.25 min, 453 [M + H]$^+$. |
| 170 | 4-[(5-amino-2-pyridinyl)oxy]-2-(methyloxy) benzonitrile (Intermediate 148) | $^1$H NMR (400 MHz, CDCl$_3$): δ ppm 8.81 (1H, br. s.) 8.26 (1H, d) 8.09 (1H, br. s.) 7.46-7.62 (1H, m) 6.84-7.00 (1H, m) 6.62-6.79 (2H, m) 5.13 (1H, br. s.) 4.09-4.30 (1H, m) 3.88 (3H, s) 1.89-2.04 (1H, m) 1.73-1.81 (1H, m) 1.47 (9H, s) 0.97-1.12 (3H, m) | 1.04 min, 427 [M + H]+ |
| 171 | 4-[(4-aminophenyl)oxy]-2-(methyloxy) benzonitrile (Intermediate 149) | $^1$H NMR (400 MHz, CDCl$_3$): δ ppm 9.02 (1H, br. s.) 7.54-7.61 (2H, m) 7.45 (1H, d) 6.99-7.09 (2H, m) 6.55 (1H, d) 6.49 (1H, dd) 4.94 (1H, br. s.) 3.85 (3H, s) 1.59 (6H, s) 1.46 (9H, s) | 1.11 min, 426 [M + H]+. |
| 172 | 4-[(4-aminophenyl)oxy]-2-(methyloxy) benzonitrile (Intermediate 149) | $^1$H NMR (400 MHz, CDCl$_3$): δ ppm 8.66 (1H, br. s.) 7.50-7.59 (2H, m) 7.44 (1H, d) 6.92-7.04 (2H, m) 6.54 (1H, d) 6.42 (1H, dd) 5.04-5.25 (1H, m) 4.15-4.27 (1H, m) 3.86 (3H, s) 1.90-2.04 (1H, m) 1.73-1.82 (1H, m) 1.47 (9H, s) 1.04 (3H, t) | 1.13 min, 426 [M + H]+ |
| 173 | 4-[(4-aminophenyl)oxy]-2-(ethyloxy) benzonitrile (Intermediate 150) | $^1$H NMR (400 MHz, CDCl$_3$): δ ppm 9.05 (1H, br. s.) 7.54-7.60 (2H, m) 7.45 (1H, d) 6.97-7.09 (2H, m) 6.50-6.54 (1H, m) 6.48 (1H, dd) 4.99 (1H, br. s.) 4.05 (2H, q) 1.58 (15H, s) 1.45 (3H, t) | 1.17 min, 440 [M + H]+ |
| 174 | 4-[(4-aminophenyl)oxy]-2-(ethyloxy) benzonitrile (Intermediate 150) | $^1$H NMR (400 MHz, CDCl$_3$): δ ppm 8.56 (1H, s.), 7.51-7.59 (2H, m), 7.44 (1H, d), 6.94-7.03 (2H, m), 6.52 (1H, d), 6.43 (1H, dd), 5.02-5.18 (1H, m), 4.12-4.23 (1H, m, 4.05 (2H, q), 1.90-2.05 (1H, m), 1.69-1.81 (1H, m), 1.47 (9H, s), 1.46 (3H, t), 1.04 (3H, t) | 1.19 min, 440 [M + H]+ |
| 175 | 4-[(5-amino-2-pyridinyl)oxy]-2-[(cyclo-propylmethyl)oxy]benzonitrile (Intermediate 151) | $^1$H NMR (400 MHz, CDCl$_3$): δ ppm 8.86 (1H, br. s.), 8.25 (1H,d), 8.00-8.11 (1H,m), 7.52 (1H, d), 6.84-6.95 (1H, m), 6.68 (1H, d), 6.65 (1H, dd), 5.14 (1H, d), 4.15-4.28 (1H, m), 3.86 (2H, d), 1.88-2.03 (1H, m), 1.73 (1H, s), 1.46 (9H, s). 1.25-1.35 (1H. m), 1.04 (3H, t), 0.61-0.70 (2H, m), 0.32-0.42 (2H, m) | 1.17 min, 467 [M + H]+. |
| 176 | 6-({4-methyl-3-[(trifluoromethyl)oxy]phenyl}oxy)-3-pyridinamine (Intermediate 147) | $^1$H NMR (400 MHz, CDCl$_3$): δ ppm 884 (1H, br. s.), 8.19 (1H,d), 7.94-8.08 (1H, m), 7.22 (1H, d), 6.98-7.02 (1H, m), 6.95 (1H, dd), 6.83 (1H, d), 5.22 (1H, d), 4.08-4.33 (1H, m), 2.28 (3H, s), 1.87-2.01 (1H, m), 1.65-1.78 (1H, m), 1.45 (9H, s), 1.03 (3H, t) | 1.29 min, 470 [M + H]+ |
| 177 | 4-[(5-amino-2-pyridinyl)oxy]-2-cyclopropyl-benzonitrile (Intermediate 153) | $^1$H-NMR (400 MHz, CDCl$_3$): δ ppm 8.54 (1H, br. s.) 8.22 (1H, d) 8.15 (1H, dd) 7.60 (1H, d) 6.91-6.99 (2H, m) 6.68 (1H, d) 4.98 (1H, br. s.) 4.09-4.19 (1H, m) 2.26-2.35 (1H, m) 1.94-2.07 (1H, m) 1.69-1.80 (1H, m) 1.49 (9H, s) 1.12-1.19 (2H,m) 1.06 (3H.t) 0.75-0.82 (2H. m) | 1.15 min, 437 [M + H]+. |
| 178 | 4-[(5-amino-2-pyridinyl)oxy]-2-(1-methylethyl) benzonitrile (Intermediate 154) | $^1$H-NMR (400 MHz DMSO-d$_6$): δ ppm 10.21 (1 H, br. s.), 8.39-8.47 (1 H, m), 8.17 (1 H, dd), 7.86 (1 H, d), 7.24 (1 H, d), 7.17 (2 H, d), 7.01-7.10 (1 H, m), 5.43 (1 H, s), 5.27 (1 H, s), 3.95-4.05 (1 H, m, m), 2.14 (3 H, s), 1.57-1.79 (2 H, m), 1.40 (9 H, s), 0.92 (3 H, t) | 1.16 min, 437 [M + H]+. |
| 179 | 4-[(5-amino-2-pyridinyl)oxy]-2-ethyl-benzonitrile (Intermediate 155) | $^1$H-NMR (400 MHz, DMSO-d$_6$): δ ppm 10.25 (1H, s) 8.43 (1H, d) 8.16 (1H, dd) 7.80 (1H, d) 7.20 (1H, d) 7.15 (1H, d) 7.05-7.11 (2H, m) 3.94-4.02 (1H, m) 2.79 (2H, q) 1.53-1.76 (2H, m) 1.39 (9H, s) 1.21 (3H, t) 0.91 (3H, t) | |
| 180 | 2-({4-methyl-3-[(trifluoromethyl)oxy]phenyl}oxy)-5-pyrimidin-amine (Intermediate 164) | | 1.21 min, 471 [M + H]+. |
| 181 | 4-[(5-amino-2-pyridinyl)oxy]-2-[(1-methylethyl)oxy] benzonitrile (Intermediate 156) | $^1$H-NMR (400 MHz DMSO-d$_6$): δ ppm 10.24 (1H, br. s.), 8.42 (1H, d), 8.16 (1H, dd), 7.70 (1H, d), 7.15 (1H, d), 7.09 (1H, d), 7.02 (1H, d), 6.72 (1H, dd), 4.70-4.81 (1H, m), 3.94-4.02 (1H, m), 1.54-1.77 (2H, m), 1.39 (9H, s), 1.30 (6H, d), 0.91 (3H, t) | 1.15 min, 455 [M + H]+ |

-continued

| 182 | 4-[(5-amino-2-pyridinyl)oxy]-3-methyl-benzonitrile (Intermediate 160) | $^1$H NMR (400 MHz, CDCl$_3$): δ ppm 8.48 (1H, br. s.), 8.12-8.21 (2H, m), 7.59 (1H, s), 7.52 (1H, d), 7.09 (1H, d), 6.99 (1H, d), 4.98 (1H, br. s.), 4.07-4.20 (1H, m), 2.26 (3H, s), 1.94-2.09 (1H, m), 1.67-1.81 (1H, m), 1.42-1.66 (9H, m), 1.05 (3H, t) | 1.09 min, 411 [M + H]+, 409 [M − H]− |
| --- | --- | --- | --- |
| 183 | 4-[(5-amino-2-pyridinyl)oxy]-2-[(trifluoromethyl)oxy]benzonitrile (Intermediate 161) | $^1$H NMR (400 MHz, CDCl$_3$): δ ppm 8.64 (1H, br. s.), 8.26 (1H, d), 8.15-8.23 (1H, m), 7.70 (1H, d), 7.20 (1H, s), 7.12-7.18 (1H, m), 7.02 (1H, d), 4.93-5.06 (1H, m), 4.10-4.21 (1H, m), 1.93-2.12 (1H, m), 1.67-1.83 (1H, m), 1.49 (9H, s), 1.06 (3H, t) | 1.18 min, 481 [M + H]+, 479 [M − H]− |
| 184 | 4-[(5-amino-2-pyrimidinyl)oxy]-3-ethyl-benzonitrile (Intermediate 158) | $^1$H-NMR (400 MHz DMSO-d$_6$): δ ppm 10.38 (1H, s), 8.84 (2H, s), 7.87 (1H, d), 7.75 (1H, dd), 7.34 (1H, d), 7.14 (1H, d), 3.94-4.02 (1H, m), 2.52-2.58 (2H, m), 1.54-1.76 (2H, m), 1.39 (9H, s), 1.11 (3H, t), 0.91 (3H, t) | |
| 185 | 4-[(5-amino-2-pyrimidinyl)oxy]-3-methyl-benzonitrile (Intermediate 159) | $^1$H-NMR (400 MHz DMSO-d$_6$): δ ppm 10.38 (1H, s), 8.83 (2H, s), 7.87 (1H, d), 7.75 (1H, dd), 7.35 (1H, d), 7.14 (1H, d), 3.95-4.01 (1H, m), 2.14 (3H, s), 1.54-1.76 (2H, m), 1.39 (9H, s), 0.91 (3H, t) | |
| 186 | 4-[(5-amino-2-pyrimidinyl)oxy]-3-(1,1-dimethylethyl)benzonitrile (Intermediate 163) | | 1.17 min, 454 [M + H]+ |

Intermediate 187

1,1-dimethylethyl((1R)-1-{[(6-{[4-cyano-3-(1-methylethyl)phenyl]oxy}-3-pyridinyl)amino]carbonyl}propyl)carbamate

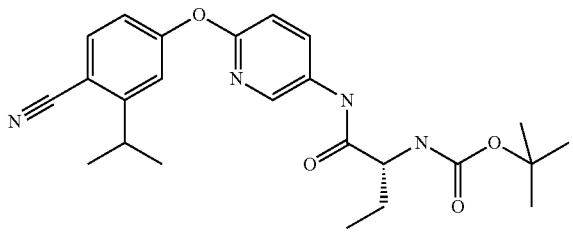 [SMILES: CC[C@@H](NC(=O)OC(C)(C)C)C(=O)Nc1ccc(Oc2ccc(C#N)c(C(C)C)c2)nc1]

To a solution of 1,1-dimethylethyl((1R)-1-{[(6-{[4-cyano-3-(1-methylethenyl)phenyl]oxy}-3-pyridinyl)amino]carbonyl}propyl)carbamate (Intermediate 178, 73 mg) in MeOH (10 mL) was added Pd 10% w/w on activated carbon (14 mg) and the reaction mixture was stirred for 30 minutes under H$_2$ atmosphere (P=1 atm). The catalyst was filtered off and the solvent removed under reduced pressure. The residue was purified by flash chromatography on silica gel (SNAP 10 g) eluting from 75:25 to 40:60 cyclohexane/ethyl acetate affording the title compound (62 mg) as white solid.

$^1$H-NMR (400 MHz, DMSO-d$_6$): δ ppm 10.24 (1H, br. s.), 8.42 (1H, d), 8.16 (1H, dd), 7.78 (1H, d), 7.24 (1H, d), 7.15 (1H, d), 7.07-7.11 (1H, m), 7.05 (1H, dd), 3.95-4.02 (1H, m), 3.19-3.27 (1H, m), 1.57-1.76 (2H, m), 1.39 (9H, s), 1.26 (6H, d), 0.91 (3H, t); UPLC_ipqc: 1.20 min, 439 [M+H]+.

Intermediate 188

(2R)-2-amino-N-{6-[(4-cyano-2-cyclopropylphenyl)oxy]-3-pyridinyl}butanamide

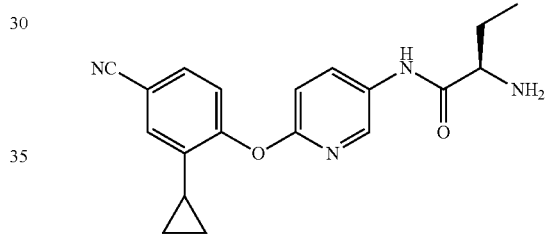

1,1-dimethylethyl{(1R)-1-[({6-[(4-cyano-2-cyclopropylphenyl)oxy]-3-pyridinyl}amino)carbonyl]propyl}carbamate (Intermediate 168, 133 mg) was dissolved in DCM (6 mL) and, at 0° C., TFA (3.0 mL) was slowly added. The reaction mixture was stirred at that temperature for 2 h. After the removal of the volatiles, the crude obtained was charged on a SCX cartridge and eluted with MeOH and then 2M NH$_3$ in MeOH affording 102 mg of the title compound.

$^1$H-NMR (400 MHz, CDCl$_3$): δ ppm 9.68 (1H, br. s), 8.32-8.18 (2H, m), 7.51-7.43 (1H, m), 7.25-7.31 (1H, m), 7.08 (1H, d), 6.99 (1H, d), 3.59-3.51 (1H, m), 2.06-1.95 (2H, m), 1.73-1.63 (1H, m), 1.03 (3H, t), 0.95-0.89 (2H, m), 0.74-0.63 (2H, m); UPLC_ipqc: 0.68 min, 337 [M+H]+.

The following compounds were prepared using the foregoing methodology, replacing 1,1-dimethylethyl{(1R)-1-[({6-[(4-cyano-2-cyclopropyl phenyl)oxy]-3-pyridinyl}amino)carbonyl]propyl}carbamate (Intermediate 168) with the appropriate N—BOC protected amine, as described in the foregoing Reaction Schemes. Final products were purified by SCX (MeOH and then 2M ammonia solution in MeOH) and fractions eluted with ammonia, containing the product, were concentrated to provide the free-base. Alternatively, after removing the volatiles, to the crude taken up with an appropriate organic solvent was added NaHCO$_3$ saturated aqueous solution, the two phases were separated and the organic layer was dried, filtered and evaporated affording the final compound as the free-base.

| Int. | Structure | Name | N-BOC Protected amine |
|---|---|---|---|
| 189 | 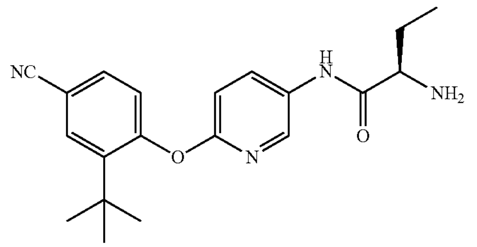 [SMILES: CC[C@@H](N)C(=O)Nc1ccc(Oc2ccc(C#N)cc2C(C)(C)C)nc1] | (2R)-2-amino-N-(6-{[4-cyano-2-(1,1-dimethylethyl)phenyl]oxy}-3-pyridinyl}butanamide | 1,1-dimethylethyl((1R)-1-{[(6-{[4-cyano-2-(1,1-dimethylethyl)phenyl]oxy}-3-pyridinyl)amino]carbonyl}propyl)carbamate (Intermediate 169) |
| 190 | 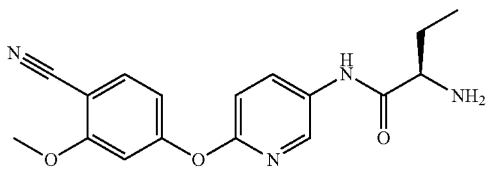 [SMILES: CC[C@@H](N)C(=O)Nc1ccc(Oc2ccc(C#N)c(OC)c2)nc1] | (2R)-2-amino-N-(6-{[4-cyano-3-(methyloxy)phenyl]oxy}-3-pyridinyl)butanamide | 1,1-dimethylethyl((1R)-1-{[(6-{[4-cyano-3-{methyloxy}phenyl]oxy}-3-pyridinyl)amino]carbonyl}propyl)carbamate (Intermediate 170) |
| 191 | 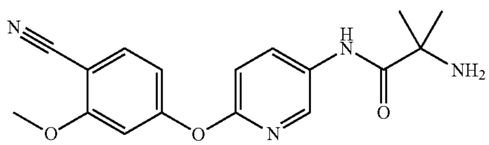 [SMILES: COc1cc(Oc2ccc(NC(=O)C(C)(C)N)cn2)ccc1C#N] | N$^1$-(4-{[4-cyano-3-(methyloxy)phenyl]oxy}phenyl)-2-methylalaninamide | 1,1-dimethylethyl{2-[(4-{[4-cyano-3-(methyloxy)phenyl]oxy}phenyl)amino]-1,1-dimethyl-2-oxoethyl}carbamate (Intermediate 171) |
| 192 | 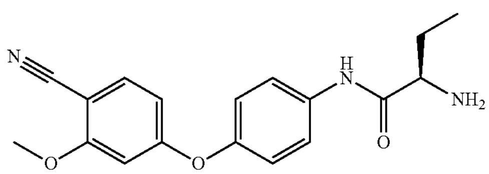 [SMILES: CC[C@@H](N)C(=O)Nc1ccc(Oc2ccc(C#N)c(OC)c2)cc1] | (2R)-2-amino-N-(4-{[4-cyano-3-(methyloxy)phenyl]oxy}phenyl)butanamide | 1,1-dimethylethyl((1R)-1-{[(4-{[4-cyano-3-(methyloxy)phenyl]oxy}phenyl)amino]carbonyl}propyl)carbamate (Intermediate 172) |
| 193 | 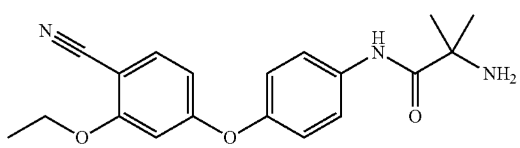 [SMILES: CCOc1cc(Oc2ccc(NC(=O)C(C)(C)N)cc2)ccc1C#N] | N$^1$-(4-{[4-cyano-3-(ethyloxy)phenyl]oxy}phenyl)-2-methylalaninamide | 1,1-dimethylethyl{2-[(4-{[4-cyano-3-(ethyloxy)phenyl]oxy}phenyl)amino]-1,1-dimethyl-2-oxoethyl}carbamate (Intermediate 173) |
| 194 | 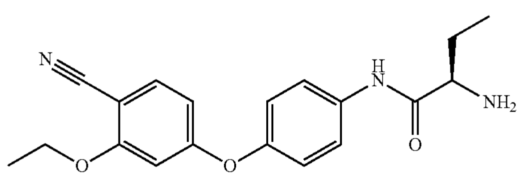 [SMILES: CCOc1cc(Oc2ccc(NC(=O)[C@H](N)CC)cc2)ccc1C#N] | (2R)-2-amino-N-(4-{[4-cyano-3-(ethyloxy)phenyl]oxy}phenyl)butanamide | 1,1-dimethylethyl((1R)-1-{[(4-{[4-cyano-3-(ethyloxy)phenyl]oxy}phenyl)amino]carbonyl}propyl)carbamate (Intermediate 174) |
| 195 | 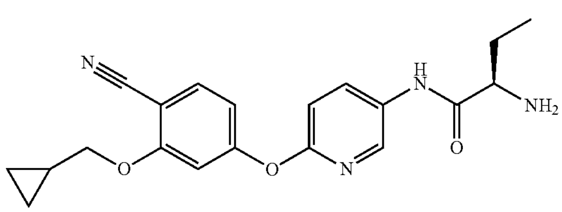 [SMILES: CC[C@@H](N)C(=O)Nc1ccc(Oc2ccc(C#N)c(OCC3CC3)c2)nc1] | (2R)-2-amino-N-[6-({4-cyano-3-[(cyclopropylmethyl)oxy]phenyl}oxy)-3-pyridinyl]butanamide | 1,1-dimethylethyl[(1R)-1-({[6-({4-cyano-3-[(cyclopropylmethyl)oxy]phenyl}oxy)-3-pyridinyl]amino}carbonyl)propyl]carbamate (Intermediate 175) |
| 196 | 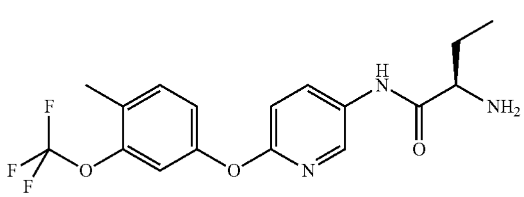 [SMILES: CC[C@@H](N)C(=O)Nc1ccc(Oc2ccc(C)c(OC(F)(F)F)c2)nc1] | (2R)-2-amino-N-[6-({4-methyl-3-[(trifluoromethyl)oxy]phenyl}oxy)-3-pyridinyl]butanamide | 1,1-dimethylethyl[(1R)-1-({[6-({4-methyl-3-[(trifluoromethyl)oxy]phenyl}oxy)-3-pyridinyl]amino}carbonyl)propyl]carbamate (Intermediate 176) |

-continued

| | | | |
|---|---|---|---|
| 197 | 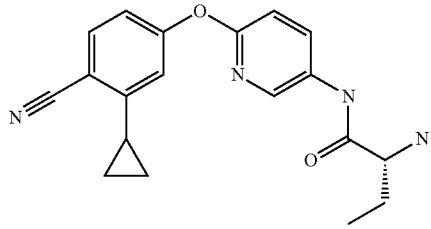 [SMILES: CC[C@@H](N)C(=O)Nc1ccc(Oc2ccc(C#N)c(C3CC3)c2)nc1] | (2R)-2-amino-N-{6-[(4-cyano-3-cyclopropylphenyl)oxy]-3-pyridinyl}butanamide | 1,1-dimethylethyl{(1R)-1-[({6-[(4-cyano-3-cyclopropylphenyl)oxy]-3-pyridinyl}amino)carbonyl]propyl}carbamate (Intermediate 177) |
| 198 | 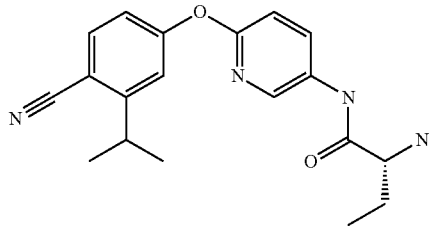 [SMILES: CC[C@@H](N)C(=O)Nc1ccc(Oc2ccc(C#N)c(C(C)C)c2)nc1] | (2R)-2-amino-N-(6-{[4-cyano-3-(1-methylethyl)phenyl]oxy}-3-pyridinyl)butanamide | 1,1-dimethylethyl((1R)-1-{[(6-{[4-cyano-3-(1-methylethyl)phenyl]oxy}-3-pyridinyl)amino]carbonyl}propyl)carbamate (Intermediate 187) |
| 199 | 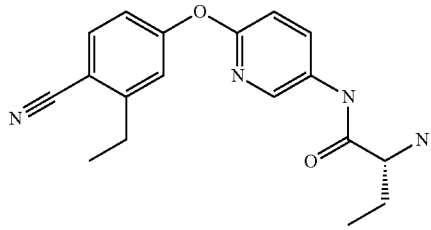 [SMILES: CCc1cc(Oc2ccc(NC(=O)[C@H](N)CC)cn2)ccc1C#N] | (2R)-2-amino-N-{6-[(4-cyano-3-ethylphenyl)oxy]-3-pyridinyl}butanamide | 1,1-dimethylethyl{(1R)-1-[({6-[(4-cyano-3-ethylphenyl)oxy]-3-pyridinyl}amino)carbonyl]propyl}carbamate (Intermediate 179) |
| 200 | 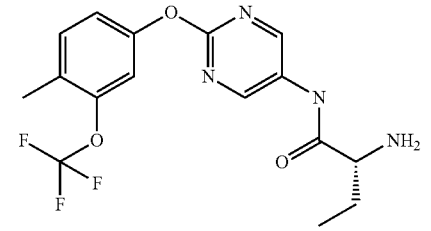 [SMILES: CC[C@@H](N)C(=O)Nc1cnc(Oc2ccc(C)c(OC(F)(F)F)c2)nc1] | (2R)-2-amino-N-[2-({4-methyl-3-[(trifluoromethyl)oxy]phenyl}oxy)-5-pyrimidinyl]butanamide | 1,1-dimethylethyl[(1R)-1-({[2-({4-methyl-3-[(trifluoromethyl)oxy]phenyl}oxy)-5-pyrimidinyl]amino}carbonyl)propyl]carbamate (Intermediate 180) |
| 201 | 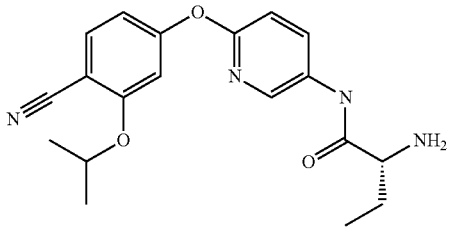 [SMILES: CC[C@@H](N)C(=O)Nc1ccc(Oc2ccc(C#N)c(OC(C)C)c2)nc1] | (2R)-2-amino-N-[6-({4-cyano-3-[(1-methylethyl)oxy]phenyl}oxy)-3-pyridinyl]butanamide | 1,1-dimethylethyl[(1R)-1-({[6-({4-cyano-3-[(1-methylethyl)oxy]phenyl}oxy)-3-pyridinyl]amino}carbonyl)propyl]carbamate (Intermediate 181) |
| 202 | 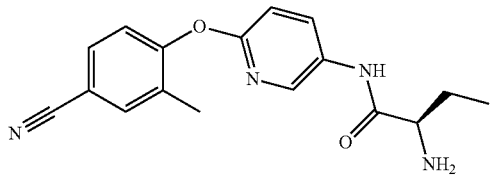 [SMILES: CC[C@@H](N)C(=O)Nc1ccc(Oc2ccc(C#N)cc2C)nc1] | (2R)-2-amino-N-(6-({4-cyano-2-methylphenyl)oxy]-3-pyridinyl}butanamide | 1,1-dimethylethyl{(1R)-1-[({6-[(4-cyano-2-methylphenyl)oxy]-3-pyridinyl}amino)carbonyl]propyl}carbamate (Intermediate 182) |
| 203 | 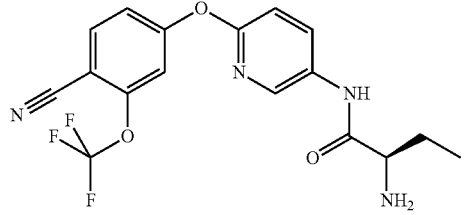 [SMILES: CC[C@@H](N)C(=O)Nc1ccc(Oc2ccc(C#N)c(OC(F)(F)F)c2)nc1] | (2R)-2-amino-N-[6-({4-cyano-3-[(trifluoromethyl)oxy]phenyl}oxy)-3-pyridinyl]butanamide | 1,1-dimethylethyl[(1R)-({[6-({4-cyano-3-[(trifluoromethyl)oxy]phenyl}oxy)-3-pyridinyl]amino}carbonyl)propyl]carbamate (Intermediate 183) |

-continued

| | | | | |
|---|---|---|---|---|
| 204 | 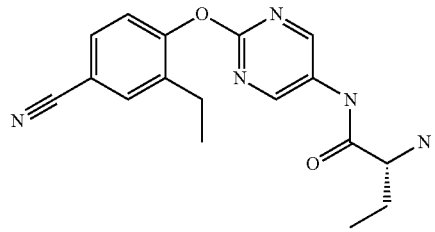 [SMILES: CCc1cc(C#N)ccc1Oc1ncc(NC(=O)[C@H](N)CC)cn1] | | (2R)-2-amino-N-{2-[(4-cyano-2-ethylphenyl)oxy]-5-pyrimidinyl}butanamide | 1,1-dimethylethyl{(1R)-1-[({2-[(4-cyano-2-ethylphenyl)oxy]-5-pyrimidinyl}amino)carbonyl]propyl}carbamate (Intermediate 184) |
| 205 | 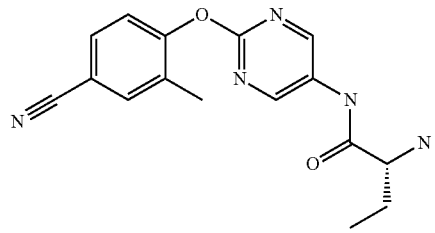 [SMILES: CC[C@@H](N)C(=O)Nc1cnc(Oc2ccc(C#N)cc2C)nc1] | | (2R)-2-amino-N-{2-[(4-cyano-2-methylphenyl)oxy]-5-pyrimidinyl}butanamide | 1,1-dimethylethyl{(1R)-1-[({2-[(4-cyano-2-methylphenyl)oxy]-5-pyrimidinyl}amino)carbonyl]propyl}carbamate (Intermediate 185) |
| 206 | 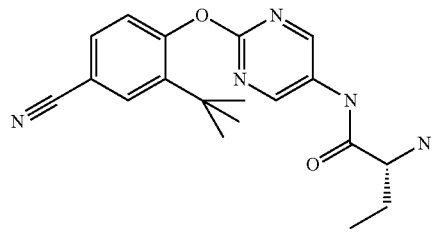 [SMILES: CC[C@@H](N)C(=O)Nc1cnc(Oc2ccc(C#N)cc2C(C)(C)C)nc1] | | (2R)-2-amino-N-(2-{[4-cyano-2-(1,1-dimethylethyl)phenyl]oxy}-5-pyrimidinyl)butanamide | 1,1-dimethylethyl((1R)-1-{[(2-{[4-cyano-2-{1,1-dimethylethyl)phenyl]oxy}-5-pyrimidinyl)amino]carbonyl}propyl)carbamate (Intermediate 186) |

| Int. | NMR characterization | UPLC_ipqc characterization |
|---|---|---|
| 189 | $^1$H NMR (400 MHz, DMSO-d$_6$): δ ppm 8.43 (1H, br. s), 6.25-8.15 (1H, m), 7.78 (1H, br. s), 7.70-7.65 (1H, m), 7.14 (1H, d), 7.05 (1H, d), 3.20-3.15 (1H, m), 1.74-1.61 (1H, m), 1.57-1.45 (1H, m), 1.36 (9H, s), 0.93 (3H, t) | 0.79 min, 353 [M + H]$^+$ |
| 190 | $^1$H NMR (400 MHz, CDCl$_3$): δ ppm 9.67 (1H, br. s.) 8.25-8.39 (2H, m) 7.53 (1H, d) 7.00 (1H, d) 6.63-6.85 (2H, m) 3.89 (3H, s) 3.40-3.57 (1H, m) 1.94-2.10 (1H, m) 1.66-1.75 (1H, m) 1.04 (3H, t) | 0.61 min. 327 [M + H]+ |
| 191 | $^1$H NMR (400 MHz, CDCl$_3$): δ ppm 9.96 (1 H, br. s.) 7.62-7.71 (2 H, m) 7.45 (1 H, d) 6.99-7.09 (2 H, m) 6.54 (1 H, d) 6.49 (1 H, dd) 3.85 (3 H, s) 1.47 (6 H, s) | 0.65 min, 326 [M + H]+ |
| 192 | $^1$H NMR (400 MHz, CDCl$_3$): δ ppm 9.59 (1H, br. s.) 7.66 (2H, d) 7.44 (1H, d) 7.04 (2H, d) 6.41-6.62 (2H, m) 3.85 (3H, s) 3.41-3.54 (1H, m) 1.92-2.11 (1H, m) 1.65-1.79 (1H, m) 0.97-1.11 (3H, m) | 0.67 min, 326 [M + H]+ |
| 193 | $^1$H NMR (400 MHz, CDCl$_3$): δ ppm 9.99 (1H, br. s.) 7.61-7.74 (2H, m) 7.46 (1H, d) 7.01-7.12 (2H, m) 6.53 (1H, d) 6.49 (1H, dd) 4.06 (2H, q) 1.49 (6H, s) 1.47 (3H, t) | 0.73 min, 340 [M + H]+ |
| 194 | $^1$H NMR (400 MHz, CDCl$_3$): δ ppm 9.61 (1H, br. s.), 7.61-7.69 (2H, m), 7.45 (1H, d), 7.00-7.08 (2H, m), 6.52 (1H, d), 6.47 (1H, dd), 4.05 (2H, q), 3.48 (1H, dd), 1.95-2.07 (1H, m), 1.63-1.69 (1H, m), 1.45 (3H, t), 1.04 (3H, t) | 0.74 min, 340 [M + H]+. |
| 195 | $^1$H NMR (400 MHz, CDCl$_3$): δ ppm 9.70 (1H, br. s.), 8.27-8.34 (2H, m), 7.54 (1H, d), 7.00 (1H, d), 6.67-6.72 (2H, m), 3.89 (2H, d), 3.50 (1H, dd), 1.96-2.10 (1H, m), 1.62-1.73 (1H, m), 1.24-1.38 (1H, m), 1.06 (3H, t), 0.63-0.71 (2H, m), 0.35-0.43 (2H, m) | 0.73 min, 367 [M + H]+ |
| 196 | $^1$H NMR (400 MHz, CDCl$_3$): δ ppm 9.61 (1H, br. s.), 8.19-8.26 (2H, m), 7.24 (1H, d), 6.99-7.03 (1H, m), 6.97 (1H, dd), 6.92 (1H, d), 3.43-3.52 (1H, m), 2.29 (3H, s), 1.92-2.06 (1H, m), 1.81 (2H, br. s.), 1.59-1.73 (1H, m), 1.03 (3H, t) | 0.83 min, 370 [M + H]+. |
| 197 | $^1$H NMR (400 MHz, DMSO-d$_6$): δ ppm 8.46 (1H, d), 8.21 (1H, dd), 7.77 (1H, d), 7.11 (1H, d), 7.00 (1H, dd), 6.81 (1H, d), 3.23-3.29 (1H, m), 2.14-2.24 (1H, m), 1.63-1 75 (1H, m), 1.45-1.57 (1H, m), 1.09-1.16 (2H, m), 0.92 (3H, t), 0.79-0.87 (2H, m) | 0.71 min, 337 [M + H]+ |
| 198 | $^1$H-NMR (400 MHz, DMSO-d$_6$): δ ppm 8.48 (1H, d) 8.22 (1H, dd) 7.79 (1H, d) 7.24 (1H, d) 7.15 (1H, d) 7.05 (1H, dd) 3.19-3.30 (2H, m) 1.61-1.74 (1H, m) 1.45-1.56 (1H, m) 1.26 (6H, d) 0.91 (3H, t) | 0.76 min, 339 [M + H]+ |
| 199 | $^1$H-NMR (400 MHz, DMSO-d$_6$): δ ppm 8.48 (1H, d) 8.22 (1H, dd) 7.80 (1H, d) 7.19 (1H, d) 7.15 (1H, d) 7.07 | |
| 200 | (1H, dd) 3.22-3.29 (1H, m) 2.79 (2H, q) 1.60-1.74 (1H, m) 1.44-1.56 (1H, m) 1.21 (3H, t) 0.91 (3H, t) | 0.78 min, 371 [M + H]+. |
| 201 | $^1$H-NMR (400 MHz, CDCl$_3$): δ ppm 9.70 (1H, br. s.), 8.26-8.38 (2H, m), 7.54 (1H, d), 7.01 (1H, d), 6.74 (1H, d), 6.68 (1H, dd), 4.52-4.66 (1H, m), 3.45-3.54 (1H, m), 1.97-2.10 (1H, m), 1.65-1.76 (1H, m), 1.41 (6H, d), 1.06 (3H, t) | |
| 202 | $^1$H NMR (400 MHz, DMSO-d$_6$): δ ppm 8.35-8.41 (1H, m), 8.15-8.25 (1H, m), 7.84 (1H, s), 7.69 (1H, d), 7.14 (2H, t), 3.23-3.39 (1H, m), 2.16 (3H, s), 1.58-1.75 (1H, m), 1.43-1.58 (1H,m), 0.90 (3 H, t) | 0.63 min, 311 [M + H]+, 309 [M − H]−. |
| 203 | $^1$H NMR (400 MHz, CDCl$_3$): δ ppm 9.76 (1H, s), 8.25-8.43 (2H, m), 7.70 (1H, d), 7.20 (1H, s), 7.16 (1H, dd), 7.06 (1H,d), 3.44-3.59 (1H, m), 1.53-2.12 (2H, m), 1.07 (3H, t) | 0.72 min, 381 [M + H]+, 379 [M − H]−. |
| 204 | $^1$H-NMR (400 MHz, DMSO-d$_6$): δ ppm 8.90 (2H, s) 7.87 (1H, d) 7.75 (1H, dd) 7.34 (1H, d) 4.72 (2H, br. s.) 3.24-3.30 (1H, m) 2.52-2.58 (2H, m) 1.62-1.75 (1H, m) 1.45-1.57 (1H, m) 1.11 (3H, t) 0.91 (3H, t) | |

| 205 | ¹H-NMR (400 MHz, DMSO-d₆): δ ppm 8.90 (2H, s) 7.87 (1H, d) 7.75 (1H, dd) 7.35 (1H, d) 4.71 (2H, br. s.) 3.23-3.30 (1H, m) 2.14 (3H, s) 1.62-1.75 (1H, m) 1.44-1.57 (1H, m) 0.91 (3H, t) | |
|---|---|---|
| 206 | | 0.73 min, 354 [M + H]⁺. |

Intermediate 207

4-({5-[(4R)-4-ethyl-4-methyl-2,5-dioxo-1-imidazolidinyl]-2-pyridinyl}oxy)-2-(1-methylethenyl)benzonitrile

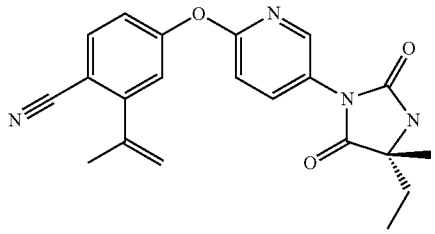 [SMILES: C=C(C)c1cc(Oc2ccc(N3C(=O)N[C@](C)(CC)C3=O)cn2)ccc1C#N]

To a solution of triphosgene (118 mg, 0.40 mmol) in dry DCM (3 mL) at 0° C. DIPEA (0.695 ml, 4.0 mmol) was added followed by a solution of 4-[(5-amino-2-pyridinyl)oxy]-2-(1-methylethenyl)benzonitrile (Intermediate 154, 100 mg) in dry DCM (6 mL) slowly added (5 minutes). After that (2R)-2-methyl-1-(methyloxy)-1-oxo-2-butanaminium chloride (268 mg, 1.6 mmol) dissolved in dry DCM (3 mL) was added at the same temperature and the reaction mixture was stirred for 45 minutes at 0° C. The reaction was quenched with water and aqueous buffer (pH 3) was added while the pH was allowed to reach ~5-6. Ethyl acetate (40 ml) was added and two phases were separated. The organic layer was washed with brine (2×10 ml), dried (Na2SO4), filtered and evaporated affording the urea intermediate as yellow foam. This urea was dissolved in MeOH (10 mL), NaOMe (10 mg) was added and the reaction mixture was refluxed for 45 minutes under stirring. After cooling the mixture was quenched with an aqueous saturated solution of ammonium chloride (10 mL) and diluted with ethyl acetate (20 mL). Two phases were separated and the organic layer was dried (Na2SO4), filtered and evaporated and the residue was purified by flash chromatography on silica gel (SNAP 10 g) eluting from 75:25 to 50:50 cyclohexane/ethyl acetate affording the title compound as a white solid (100 mg).

¹H NMR (400 MHz, CDCl₃) δ ppm 8.31 (1H, d), 7.87 (1H, dd), 7.71 (1H, d), 7.14-7.20 (2H, m), 7.12 (1H, d), 5.94 (1H, br. s.), 5.42 (1H, s), 5.34 (1H, s), 2.20 (3H, s), 1.95-2.05 (1H, m), 1.79 (1H, dd), 1.56 (3H, s), 1.00 (3H, t); UPLC_ipqc: 1.04 min, 377 [M+H]+.

Example 1

(5R)-5-methyl-3-{4-[(3-methylphenyl)oxy]phenyl}-2,4-imidazolidinedione

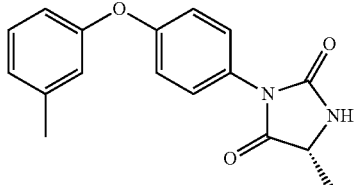

To Boc-anhydride (0.522 g, 2.394 mmol) in dichloromethane (4 mL) was added DMAP (0.248 g, 2.033 mmol) followed by slow addition via syringe of a solution of D-Alanine tertbutyl ester in dichloromethane (4 mL) (prepared from D-Alanine tertbutyl ester HCl salt) (0.410 g) that was partitioned between DCM and an aqueous solution of Na2CO3. The organic layer was dried (K2CO3), volatiles were evaporated under vacuum and re-dissolved in dichloromethane. The mixture was stirred for 10 minutes and split into three equal aliquots (solution 1).

To 4-[(3-methylphenyl)oxy]aniline (90 mg, 0.45 mmol) in dichloromethane (1 mL) was added with shaking at 35° C. an aliquot of approximately 1/3 of solution 1 slowly via syringe (over ca. 1 min). After 30 min, HCl (ca. 0.8 mL) was added and the heterogeneous mixture was heated at 100° C. for 2 hours with shaking, allowing the dichloromethane to distill off through a glass capillary. After cooling to room temperature the aqueous HCl was pipetted off and the residue dried under vacuum. The residue was purified by silica gel chromatography (Biotage instrument, 10 g column) eluting with 0-100% EtOAc/cHex to give after drying the title compound as a solid (30 mg).

¹H NMR (400 MHz, CDCl₃): δ ppm 7.40-7.34 (2H, m), 7.28-7.22 (1H, m), 7.12-7.05 (2H, m), 6.98 (1H, d), 6.91-6.84 (2H, m), 5.75 (1H, br. s), 4.28 (1H, m), 2.34-2.39 (3H, s), 1.59 (3H, m); LC-MS_A: 2.44 min, 295 [M–H]–

Example 2

(5R)-5-methyl-3-(4-(4-{[3-(methyloxy)phenyl]oxy}phenyl)-2,4-imidazolidinedione

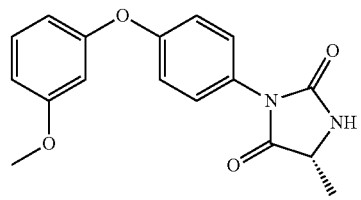 [SMILES: COc1cccc(Oc2ccc(N3C(=O)N[C@H](C)C3=O)cc2)c1]

To a solution of N1-(4-{[3-(methyloxy)phenyl]oxy}phenyl)-D-alaninamide (Intermediate 2, 315 mg) and triethyl amine (0.307 mL, 2.200 mmol) in dry ethyl acetate (5 mL), triphosgene (163 mg, 0.550 mmol) was added and the reaction mixture was stirred for 5 minutes. DMAP (67.2 mg, 0.550 mmol) was then added and the reaction mixture was stirred for further 10 minutes. The reaction was quenched with a saturated solution of sodium carbonate (5 mL), diluted with water (10 mL) and extracted with ethyl acetate (3 times 20 mL). The organic layer was dried over sodium sulphate, filtered and evaporated. The residue was purified by silica gel chromatography (Biotage system, 10 g SNAP column) eluting with a gradient cyclohexane/ethyl acetate from 100/0 to 60/40 to afford the title compound as a white solid (115 mg).

¹H-NMR (400 MHz, DMSO-d₆) δ ppm: 8.46 (1H, s), 7.27-7.42 (3H, m), 7.09 (2H, d), 6.77 (1H, dd), 6.65 (1H, t), 6.60 (1H, dd), 4.26 (1H, m), 3.76 (3H, s), 1.36 (3H, d); LC-MS_A: 2.31 min, 311 [M−H]−

Example 3

(5R)-3-(4-{[3-(ethyloxy)phenyl]oxy}phenyl)-5-methyl-2,4-imidazolidinedione

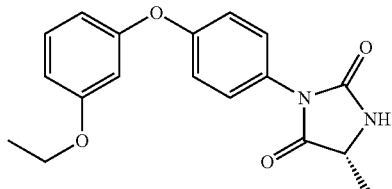

The title compound was made in a similar fashion to the preparation of Example 1 replacing 4-[(3-methylphenyl)oxy]aniline with 4-[(3-ethyloxyphenyl)oxy]aniline (Intermediate 4, 0.104 g). After silica gel chromatography a brown gum was obtained and triturated with Et2O:cHex (ca. 1:2, ca. 1.5 mL). This afforded after drying, the title compound as a faint brown solid (9 mg).

¹H NMR (400 MHz, CDCl₃): δ ppm 7.38 (2H, m), 7.28-7.22 (1H, m), 7.14-7.07 (2H, m), 6.73-6.67 (1H, m), 6.66-6.60 (2H, m), 5.56 (1H, br. s), 4.29 (1H, m), 4.02 (2H, q), 1.61-1.57 (3H, m), 1.47-1.39 (3H, m); LC-MS_A: 2.46 min, 325 [M−H]−

Example 4

(5R)-3-{4-[(3-chloro-5-fluorophenyl)oxy]phenyl}-5-methyl-2,4-imidazolidinedione

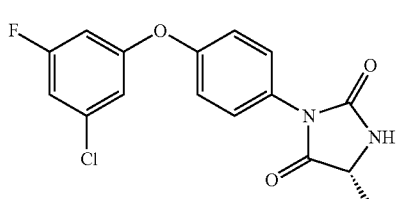

To triphosgene (0.052 g, 0.177 mmol) was added a solution of 4-[(3-chloro-5-fluorophenyl)oxy]aniline (Intermediate 6, 0.12 g) in toluene (1 mL) and triethylamine (0.16 g) with shaking. A thick slurry immediately formed and additional toluene (1 mL) was added. The mixture was stirred for 3 hours at room temperature and then D-alanine (0.067 g, 0.757 mmol) in N,N-dimethylformamide (2 mL) and water (ca. 2 mL) (barely dissolved) was rapidly added via pipette. A two-layer system formed that was vigorously stirred for 2 hours and kept overnight at room temperature. Volatiles were evaporated, hydrochloric acid (2 mL, 24.35 mmol) added and the heterogeneous mixture heated at 100° C. for 2 hours, then allowed to cool to room temperature. After cooling to room temperature the aqueous HCl was pipetted off and the residue dried under vacuum. The residue was purified by silica gel chromatography (Biotage instrument, 10 g column) eluting with 0-100% EtOAc/cHex to give the title compound as colourless solid (7 mg).

1H NMR (400 MHz, CDCl₃): δ ppm 7.52-7.41 (2H, m), 7.21-7.11 (2H, m), 6.92-6.79 (2H, m), 6.72-6.58 (1H, m), 5.57 (1H, s), 4.31 (1H, dd), 1.61 (3H, d); LC-MS_A: 2.58 min, 333 [M−H]−

Example 5

(5R)-3-{4-[(3-chloro-4-fluorophenyl)oxy]phenyl}-5-methyl-2,4-imidazolidinedione

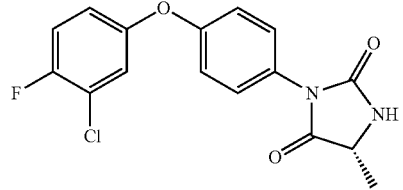 [SMILES: C[C@H]1NC(=O)N(c2ccc(Oc3ccc(F)c(Cl)c3)cc2)C1=O]

A mixture of N-[({4-[(3-chloro-4-fluorophenyl)oxy]phenyl}amino)carbonyl]-D-alanine (Intermediate 9, 352 mg) in 15 mL of 3N HCl was heated at 100° C. for 16 hours. Then sodium carbonate was added and the mixture was adjusted to pH=8. The mixture was extracted with ethyl acetate (3 times 50 mL) and the combined organic phases were washed with brine and dried over magnesium sulphate. Removal of the solvent afforded a residue which was purified by column chromatography (MeOH/DCM=1/50) to give 42 mg of the title compound as a white solid.

¹HNMR (300 MHz, DMSO): δ ppm 8.47 (1H, s), 7.50-7.45 (1H, t), 7.38-7.36 (3H, m), 7.13-7.09 (3H, m), 4.28-4.23 (1H, q), 1.36-1.34 (3H, d); MS_2 (ESI): 335 [M+H]+

Example 6

(5S)-3-{4-[(3-chloro-4-fluorophenyl)oxy]phenyl}-5-methyl-2,4-imidazolidinedione

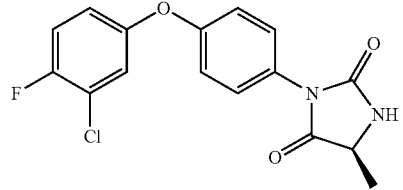 [SMILES: C[C@@H]1NC(=O)N(c2ccc(Oc3ccc(F)c(Cl)c3)cc2)C1=O]

A mixture of N-[({4-[(3-chloro-4-fluorophenyl)oxy]phenyl}amino)carbonyl]-L-alanine (Intermediate 10, 352 mg) in 15 mL of 3N HCl was heated at 100° C. for 16 hours. Then sodium carbonate was added and the mixture was adjusted to pH=8. The mixture was extracted with ethyl acetate (3×50 mL). The combined organic phases were washed with brine and dried with magnesium sulphate. Removal of the solvent afforded crude compound which was purified by column chromatography (MeOH/DCM=1/50) to give 40 mg of the title compound as a white solid.

¹HNMR (300 MHz, CDCl₃): δ ppm 7.41-7.31 (2H, m), 7.15-7.09 (2H, m), 7.08-7.03 (2H, m), 6.94-6.90 (1H, m), 5.70 (1H, s), 4.30-4.25 (1H, q), 1.59-1.57 (3H, d); MS 1 (ESI): 335 [M+H]+

Example 7

(5R)-5-methyl-3-(4-{[2-methyl-5-(methyloxy)phenyl]oxy}phenyl)-2,4-imidazolidinedione

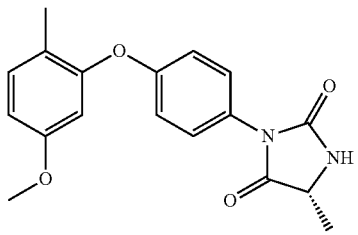 [SMILES: COc1ccc(C)c(Oc2ccc(N3C(=O)N[C@H](C)C3=O)cc2)c1]

$N^1$-(4-{[2-methyl-5-(methyloxy)phenyl]oxy}phenyl)-D-alaninamide (Intermediate 16, 118 mg) was dissolved in dry dichloromethane (18 mL). The reaction mixture was cooled down in an ice bath. Triethylamine 0.327 mL, 2.350 mmol) was added. Then a solution of triphosgene in dry dichloromethane (46.5 mg, 0.157 mmol) dissolved in 7 mL of dichloromethane was added. The reaction was stirred at 0° C. for 10 min under argon. A saturated aqueous solution of NaHCO3 was added (18 mL) and the aqueous layer was extracted with dichloromethane 4 times (4×15 mL). After drying over sodium sulphate, the solvents were removed under vacuum. The residue was purified by silica gel chromatography (Companion system, 12 g cartridge) eluting with a gradient cHex/EOAc from to 100/0 to 60/40 during 20 min and 60/40 during 30 min. This afforded the title compound (91 mg).

$^1$H NMR (400 MHz, CDCl$_3$): δ ppm 7.34-7.28 (2H, m), 7.15 (1H, d), 7.01-6.92 (2H, m), 6.68 (1H, dd), 6.53 (1H, d), 5.63 (1H, s), 4.25 (1H, dd), 3.74 (3H, s), 2.14 (3H, s), 1.56 (3H, d); UPLC_B: 0.79 min, 326 [M+1]+

Example 8

(5R)-5-methyl-3-(4-{[4-methyl-3-(methyloxy)phenyl]oxy}phenyl)-2,4-imidazolidinedione

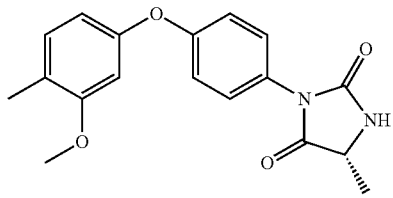 [SMILES: COc1cc(Oc2ccc(N3C(=O)N[C@H](C)C3=O)cc2)ccc1C]

To a solution of N1-(4-{[4-methyl-3-(methyloxy)phenyl]oxy}phenyl)-D-alaninamide (Intermediate 22, 215 mg) in dry dichloromethane (15 mL) triethylamine (0.499 mL, 3.58 mmol) was added and the reaction mixture was cooled to 0° C. A solution of triphosgene (96 mg, 0.322 mmol) in dry dichloromethane (5 mL) was slowly added and the reaction mixture was stirred for 30 minutes at the same temperature. The reaction was quenched with water (10 mL) and extracted with dichloromethane (20 mL). The organic layer was dried over sodium sulphate, filtered and evaporated and the residue was purified by flash chromatography (Biotage system, SNAP column) on silica gel using as eluent a gradient cyclohexane/ethyl acetate from 80/20 to 40/60 to afford the title compound as a white solid (165 mg).

$^1$H NMR (400 MHz, DMSO-d$_6$): δ ppm 8.45 (1H, s), 7.32 (2H, m), 7.16 (1H, d), 7.05 (2H, m), 6.74 (1H, d), 6.52 (1H, dd), 4.25 (1H, dd), 3.77 (3H, s), 2.14 (3H, s), 1.35 (3H, d); UPLC_B: RT 0.82 min, 327 [M+H]+

Example 9

(5R)-5-methyl-3-(6-{[3-(1-methylethyl)phenyl]oxy}-3-pyridinyl)-2,4-imidazolidinedione

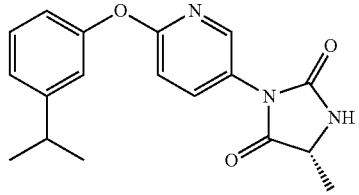 [SMILES: CC(C)c1cccc(Oc2ccc(N3C(=O)N[C@H](C)C3=O)cn2)c1]

$N^1$-(6-{[3-(1-methylethyl)phenyl]oxy}-3-pyridinyl)-D-alaninamide (Intermediate 26, 35 mg) was dissolved in dry dichloromethane (3 mL). The reaction mixture was cooled down in an ice bath. Triethylamine (98 μl, 0.701 mmol) was added. Then a solution of triphosgene in dry dichloromethane (13.88 mg, 0.047 mmol dissolved in 1 mL of dichloromethane) was added dropwise. The reaction mixture was stirred at 0° C., under argon, during 10 min. A saturated aqueous solution of NaHCO3 was added (4 mL) and the aqueous layer was extracted with dichloromethane 4 times (4×5 mL). After drying over sodium sulphate, the solvents were removed under vacuum. The residue obtained was purified by silica gel chromatography (Companion system, 2×4 g silica cartridges) with a gradient cyclohexane/ethylacetate from 100/0 to 50/50 during 10 min and 50/50 during 20 min. This afforded the title compound as a film (27 mg).

$^1$H NMR (400 MHz, CDCl$_3$): δ ppm 8.32 (1H, d), 7.78-7.75 (1H, dd), 7.36 (1H, t), 7.14 (1H, d), 7.05 (1H, t), 7.01-6.99 (2H, m), 6.55 (1H, s), 4.27 (1H, q), 2.96 (1H, m), 1.59 (3H, d), 1.30 (6H, d); UPLC: 0.78 min, 326 [M+1]+

Example 10

(5R)-5-methyl-3-[6-({3-[(1-methylethyl)oxy]phenyl}oxy)-3-pyridinyl]-2,4-imidazolidinedione

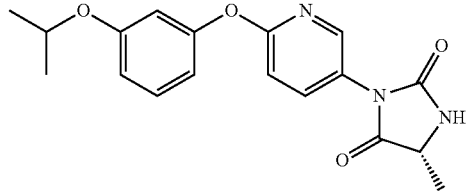 [SMILES: CC(C)Oc1cccc(Oc2ccc(N3C(=O)N[C@H](C)C3=O)cn2)c1]

To a solution of $N^1$-[6-({3-[(1-methylethyl)oxy]phenyl}oxy)-3-pyridinyl]-D-alaninamide (Intermediate 32, 229 mg) and triethylamine (442 mg, 4.38 mmol) in dichloromethane (20 mL) was added a solution of triphosgene (216 mg, 0.73 mmol) in dichloromethane (10 mL) dropwise at 0° C. during 5 minutes. The resulting mixture was stirred at room temperature for 2 hours. The solvent was distilled off and the residue was partitioned between dichloromethane (3 times 50 mL) and water (50 mL). The combined organic layers were washed with brine (3 times 10 mL), dried over sodium sulphate, filtered and concentrated to afford a grey solid, which was purified by silica gel chromatography (PE: EtOAc=2:1) to afford the title compound as a white solid (120 mg).

$^1$H NMR (300 MHz, DMSO-d$_6$): δ ppm 8.54 (1H, s), 8.15-8.14 (1H, d), 7.86-784 (1H, dd), 7.33-7.28 (1H, t), 7.13-7.10 (1H, d), 6.80-6.77 (1H, dd), 6.71-6.67 (2H, m), 4.64-4.58 (1H, m), 4.30-4.25 (1H, q), 1.37-1.35 (3H, d), 1.27-1.25 (6H, d).

MS 1 (ESI): 342 [M+H]+

Example 11

(5R)-3-{6-[(2,5-dimethylphenyl)oxy]-3-pyridinyl}-5-methyl-2,4-imidazolidinedione

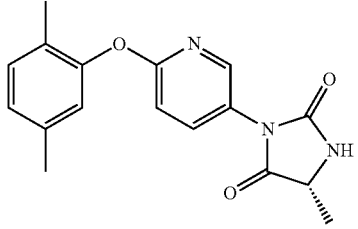 [SMILES: Cc1ccc(C)c(Oc2ccc(N3C(=O)N[C@H](C)C3=O)cn2)c1]

The title compound was made in a similar fashion to the preparation of Example 9 replacing N1-(6-{[3-(1-methylethyl)phenyl]oxy}-3-pyridinyl)-D-alaninamide with N1-{6-[(2,5-dimethylphenyl)oxy]-3-pyridinyl}-D-alaninamide (Intermediate 36, 48 mg) to afford the title compound as a yellow powder (31 mg).

$^1$H NMR (400 MHz, CDCl$_3$): δ ppm 8.25 (1H, d), 7.74-7.71 (1H, dd), 7.17 (1H, d), 6.98-6.88 (3H, m), 6.16 (1H, s), 4.25 (1H, q), 2.32 (3H, s), 2.14 (3H, s), 1.56 (3H, d); UPLC: 0.77 min, 312 [M+1]+

Example 12

(5R)-3-{6-[(2,3-dimethylphenyl)oxy]-3-pyridinyl}-5-methyl-2,4-imidazolidinedione

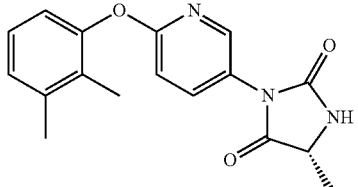 [SMILES: Cc1cccc(Oc2ccc(N3C(=O)N[C@H](C)C3=O)cn2)c1C]

N1-{6-[(2,3-dimethylphenyl)oxy]-3-pyridinyl}-D-alaninamide (Intermediate 40, 13 mg) was dissolved in dry dichloromethane (2 mL). The reaction mixture (under argon) was cooled down in an ice bath. Triethylamine (38.1 µl, 0.273 mmol) was added. Then a solution of triphosgene in dry dichloromethane (5.41 mg, 0.018 mmol, 0.40 equiv dissolved in 1 mL of DCM) was added dropwise. The reaction mixture was stirred at 0° C., under argon, during 10 min. A saturated aqueous solution of NaHCO3 was added (3 mL) and the aqueous layer was extracted with dichloromethane 4 times (4×4 mL). After drying over sodium sulphate, the solvents were removed under vacuum. The residue was purified by silica gel chromatography (Companion system, 4 g silica cartridge,) with a gradient cyclohexane/ethylacetate from 100:0 to 55:45 during 10 min and 55:45 during 20 min. This afforded the title compound (9 mg)

$^1$H NMR (400 MHz, CDCl$_3$): δ ppm 8.26 (1H, d), 7.75-7.54 (2H, m), 7.16-6.92 (3H, m), 5.63 (1H, s), 4.24 (1H, m), 2.34 (3H, s), 2.11 (3H, s), 1.60 (3H, d); UPLC: 0.70 min, 312 [M+H]+

Example 13

(5R)-3-{6-[(2,6-dimethylphenyl)oxy]-3-pyridinyl}-5-methyl-2,4-imidazolidinedione

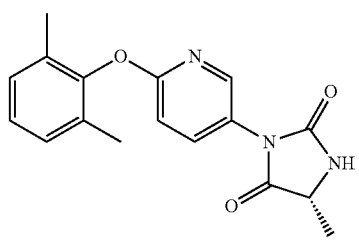 [SMILES: Cc1cccc(C)c1Oc1ccc(N2C(=O)N[C@H](C)C2=O)cn1]

In a 50 mL round-bottomed flask N$^1$-{6-[(2,6-dimethylphenyl)oxy]-3-pyridinyl}-D-alaninamide (Intermediate 44, 173.8 mg) was dissolved in dichloromethane (5 mL) to give a yellow solution. The reaction mixture was cooled at 0° C. N,N-dimethyl-4-pyridinamine (36.5 mg, 0.298 mmol), triethylamine (0.208 mL, 1.492 mmol) and triphosgene (89 mg, 0.298 mmol) were added. The reaction mixture was stirred at 0° C. After 20 min the solvent was evaporated under vacuum to afford a yellow solid. This residue was purified by silica gel chromatography (Biotage instrument, 10 g SNAP Silica column) eluting with Cyclohexane/EtOAc from 2:1 Cyclohexane/EtOAc to 1:3 Cyclohexane/EtOAc in 20 CV; then 1:3 Cyclohexane/EtOAc for 5 CV. The collected fractions afforded the title compound as a colourless oil (162 mg).

$^1$H NMR (400 MHz, CDCl$_3$) d ppm 8.26 (1H, d), 7.76 (1H, dd), 7.07-7.19 (3H, m), 6.95 (1H, d), 6.67 (1H, br. s), 4.32-4.22 (1H, m), 2.17 (6H, s), 1.57 (3H, d); UPLC_s: 0.80 min, 312 [M+H]+.

Example 14

(5R)-3-{6-[(2-ethylphenyl)oxy]-3-pyridinyl}-5-methyl-2,4-imidazolidinedione

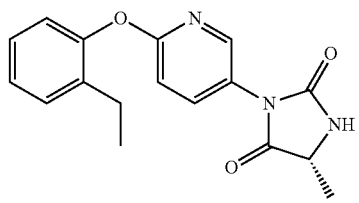 [SMILES: CCc1ccccc1Oc1ccc(N2C(=O)N[C@H](C)C2=O)cn1]

In a 50 mL round-bottomed flask N$^1$-{6-[(2-ethylphenyl)oxy]-3-pyridinyl}-D-alaninamide (Intermediate 48, 170.0 mg) was dissolved in dichloromethane (5 mL) to give a pale yellow solution. The reaction mixture was cooled at 0° C. N,N-dimethyl-4-pyridinamine (35.7 mg, 0.292 mmol), triethylamine (0.203 mL, 1.460 mmol) and triphosgene (87 mg, 0.292 mmol) were added. The reaction mixture was stirred at 0° C. After 20 min, the reaction mixture was evaporated in vacuo affording yellow solid that was purified by silica gel chromatography (Biotage system, 10 g SNAP column) eluting with a gradient Cyclohexane/EtOAc from 2:1 to 1:3 in 20 CV; then 1:3 for 5 CV. The collected fractions afforded the title compound as a colourless oil (153.2 mg).

$^1$H NMR (400 MHz, CDCl$_3$): δ ppm 8.29 (1H, d), 7.76 (1H, dd), 7.36 (1H, dd), 7.31-7.20 (2H, m), 7.08 (1H, dd), 6.99 (1H, d), 6.68-6.52 (1H, m), 4.32-4.23 (1H, m), 2.62 (2H, q), 1.57 (3H, d), 1.26-1.18 (3H, m); UPLC_B: 0.76 mins, 312 [M+H]+.

Example 15

(5R)-5-methyl-3-(6-{[4-methyl-3-(methyloxy)phenyl]oxy}-3-pyridinyl)-2,4-imidazolidinedione

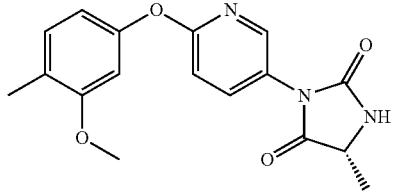 [SMILES: COc1cc(Oc2ccc(N3C(=O)N[C@H](C)C3=O)cn2)ccc1C]

To a solution of N1-(6-{[4-methyl-3-(methyloxy)phenyl]oxy}-3-pyridinyl)-D-alaninamide (Intermediate 52, 255 mg) in dry dichloromethane (15 mL), TEA (0.590 mL, 4.23 mmol) was added and the reaction mixture was cooled to 0° C. A solution of triphosgene (113 mg, 0.381 mmol) in dry dichloromethane (DCM) (5 mL) was slowly added and the reaction mixture was stirred for 30 minutes at the same temperature. The reaction was quenched with water (10 mL) and extracted with dichloromethane (20 mL). The organic layer was dried over sodium sulphate, filtered and evaporated and the residue was purified by silica gel chromatography (Biotage system, 10 g SNAP column) using as eluent a gradient cyclohexane/ethyl acetate from 70/30 to 30/70. This afforded the title compound as a white solid (172 mg, 0.525 mmol).

$^1$H NMR (400 MHz, DMSO-d$_6$): δ ppm 8.54 (1H, br. s), 8.13 (1H, d), 7.81-7.86 (1H, m), 7.17 (1H, d), 7.09 (1H, d), 6.79 (1H, d), 6.63 (1H, dd), 4.27 (1H, q), 3.77 (3H, s), 2.15 (3H, s), 1.37 (3H, d); UPLC_B: 0.75 min, 328 [M+1]+

Example 16

(5R)-5-methyl-3-(6-{[2-methyl-5-(methyloxy)phenyl]oxy}-3-pyridinyl)-2,4-imidazolidinedione

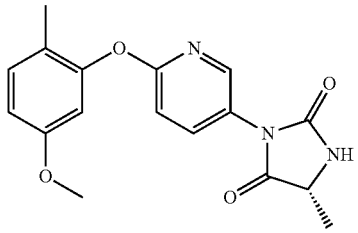 [SMILES: COc1ccc(C)c(Oc2ccc(N3C(=O)N[C@H](C)C3=O)cn2)c1]

The title compound was made in a similar fashion to the preparation of Example 7 replacing N$^1$-(4-{[2-methyl-5-(methyloxy)phenyl]oxy}phenyl)-D-alaninamide with N$^1$-(6-{[2-methyl-5-(methyloxy)phenyl]oxy}-3-pyridinyl)-D-alaninamide (Intermediate 56, 118 mg) to afford the title compound (78 mg)

$^1$H NMR (400 MHz, CDCl$_3$): δ ppm 8.26 (1H, d), 7.73 (1H, dd), 7.17 (1H, d), 6.94 (1H, d), 6.74 (1H, dd), 6.64 (1H, d), 5.88 (1H, s), 4.36-4.14 (1H, m), 3.82-3.71 (3H, s), 2.10 (3H, s), 1.57 (3H, d); UPLC_B: 0.71 min, 328 [M+1]+

Example 17

(5R)-5-methyl-3-(6-{[2-methyl-3-(methyloxy)phenyl]oxy}-3-pyridinyl)-2,4-imidazolidinedione

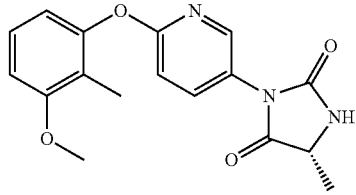 [SMILES: COc1cccc(Oc2ccc(N3C(=O)N[C@H](C)C3=O)cn2)c1C]

The title compound was made in a similar fashion to the preparation of Example 9 replacing N1-(6-{[3-(1-methylethyl)phenyl]oxy}-3-pyridinyl)-D-alaninamide with N-(6-{[2-methyl-3-(methyloxy)phenyl]oxy}-3-pyridinyl)-D-alaninamide (Intermediate 63, 200 mg) to afford the title compound (184 mg).

$^1$H NMR (400 MHz, CDCl$_3$): δ ppm 8.28 (1H, d), 7.77 (1H, m), 7.23 (1H, m), 6.98 (1H, d), 6.80-6.73 (2H, m), 6.49 (1H, s), 4.29-4.27 (1H, m), 3.89 (3H, s), 2.09 (3H, s), 1.58 (3H, d); UPLC_B: 0.72 min, 328 [M+1]+

Example 18

(5R)-5-ethyl-3-(4-{[3-(methyloxy)phenyl]oxy}phenyl)-2,4-imidazolidinedione

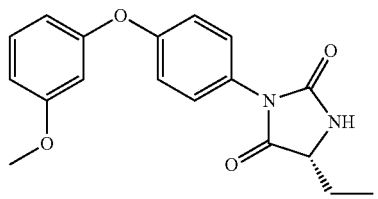 [SMILES: CC[C@H]1NC(=O)N(c2ccc(Oc3cccc(OC)c3)cc2)C1=O]

To D-2-aminobutyric acid (60.4 mg, 0.586 mmol) in dichloromethane (1 mL) was added DIPEA (0.236 mL, 1.352 mmol) and N-Methyl-N-trifluoroacetamide (269 mg, 1.352 mmol) and the suspension was shaken at 40° C. in a closed vial for 2.5 hours, resulting in a virtually clear solution (Solution 1).

To Boc-anhydride (138 mg, 0.631 mmol) in dichloromethane (1 mL) was added DMAP (55.1 mg, 0.451 mmol) followed by a solution of 4-{[3-(methyloxy)phenyl]oxy}aniline (97 mg, 0.451 mmol) in dichloromethane (1 mL). The mixture was stirred for 10 min. The brown solution thus obtained was added to Solution 1 via syringe with shaking at 35° C. and shaking was continued at this temperature for 2 hours. The solution was then kept at room temperature for ca. 64 hours. Conc. aq. HCl (ca. 0.8 mL) was added and the heterogenous mixture was heated at 100° C. for 2 hours with shaking, allowing the DCM to distill off through a glass capillary. After cooling to room temperature, the residue was diluted with water (ca. 3 mL) and extracted with dichloromethane (2 times ca. 2 mL). The dichloromethane extracts were concentrated under vacuum. The residue was purified by silica gel chromatography (Biotage system, 10 g column) eluting with a gradient cHex/EtOAc from 95/5 to 0/100 to give a brown viscous oil that was dissolved in Et2O (ca. 0.7 mL) and cHex (ca. 0.1 mL) and kept over night. The overstanding faint brown solution was decanted from a small quantity of a brown oil that had separated out. As the solvent was allowed to evaporate from this solution crystallisation initiated. The material thus obtained was allowed to dry and then triturated with Et2O (2 times ca. 0.5 mL) to afford, after drying, the title compound as a solid (28 mg).

$^1$H NMR (400 MHz, CDCl$_3$): δ ppm 7.40-7.33 (2H, m), 7.28-7.23 (1H, m), 7.15-7.07 (2H, m), 6.75-6.69 (1H, m), 6.67-6.61 (2H, m), 5.64 (1H, br. s), 4.25-4.18 (1H, m), 3.81 (3H, s), 2.10-1.88 (2H, m), 1.09 (3H, t); LC-MS_A: 2.43 min, 325 [M−H]−

Example 19

(5R)-5-ethyl-3-(6-{[4-methyl-3-(methyloxy)phenyl]oxy}-3-pyridinyl)-2,4-imidazolidinedione

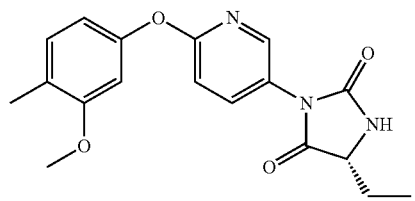 [SMILES: CC[C@H]1NC(=O)N(c2ccc(Oc3ccc(C)c(OC)c3)nc2)C1=O]

Method A

To a solution of (2R)-2-amino-N-(6-{[4-methyl-3-(methyloxy)phenyl]oxy}-3-pyridinyl)butanamide (Intermediate 65, 120 mg) in dry dichloromethane (8 mL) TEA (0.265 mL, 1.903 mmol) was added and the reaction mixture was cooled to 0° C. A solution of triphosgene (50.8 mg, 0.171 mmol) in dry dichloromethane (DCM) (2 mL) was slowly added and the reaction mixture was stirred for 30 minutes at the same temperature. The reaction was quenched with water (2 mL) and two phases were separated. The organic layer was dried over sodium sulphate, filtered and evaporated and the residue was purified by silica gel chromatography (Biotage system, 10 g SNAP column) with as eluent a gradient cyclohexane/ethyl acetate 80/20 to cyclohexane/ethyl acetate 50/50 to afford the title compound as a white solid (108 mg).

$^1$H NMR (400 MHz, DMSO-d$_6$): δ ppm 8.61 (1H, s), 8.12 (1H, d), 7.82 (1H, dd), 7.17 (1H, d), 7.08 (1H, d), 6.79 (1H, d), 6.63 (1H, dd), 4.25-4.18 (1H, m), 3.77 (3H, s), 2.15 (3H, s), 1.89-1.62 (2H, m), 0.95 (3H, t): UPLC_B: 0.79 min, 342 [M+H]+.

Method B (2R)-2-amino-N-(6-{[4-methyl-3-(methyloxy)phenyl]oxy}-3-pyridinyl)butanamide.2HCl (Intermediate 65b) (750 g) was suspended in dichloromethane (7.5 L) and 7.5% sodium carbonate aqueous solution (6 L) and stirred until dissolution. Two phases were separated, the organic one was washed with NaCl 10% aqueous solution (6 L) and concentrated under vacuum at 45° C. to about 3.75 L to remove water via the azeotrope (water ~0.05%). Dichloromethane was added up to 15 L and then Et$_3$N (1.35 L) was added. This solution was cooled to 0° C.

Triphosgene (201 g) was dissolved in dichloromethane (4.5 L) and this solution was added in about minutes to the previous solution maintaining the internal temperature at about 10° C. The line was washed with dichloromethane (375 mL). Work-up: the organic mixture was washed with a 28% aqueous solution of malic acid (7.5 L) then with a 2% w/w aqueous solution of sodium carbonate (7.5 L) and finally with a 20% aqueous solution of NaCl (7.5 L). The organic phase was concentrated to the lowest volume (about 3.75 L), toluene (2.25 L) was added and concentrated to low volume (3 L). Toluene (1 L) was further added, and concentrated to low volume (3 L) to remove all the DCM. A suspension was obtained and it was stirred for 3 hours then filtered and washed with toluene (2×1 L). The solid was dried under vacuum at 45° C. until constant weight (471 g) of the title compound. The solid was re-crystallised as follow: 459 g of the title compound was suspended in Isopropanol (1400 mL) and heated until complete dissolution (~70° C.) then cooled to 20° C., stirred for 3 hours then filtered and washed with IPA (2×700 mL). The solid was dried under vacuum at 45° C. until constant weight (412 g) of the title compound. The solid was further triturated as follow: 412 g of the title compound was suspended in toluene (1200 mL) at 20° C., stirred for 2 hours then filtered and washed with toluene (2×420 mL). The solid was dried under vacuum at 45° C. until constant weight (404 g) of the title compound as white solid.

$^{13}$C-NMR (150.81 MHz, DMSO-d$_6$): δ ppm 173.7, 162.7, 158.6, 155.9, 153.1, 145.8, 138.9, 131.1, 124.7, 122.6, 113.0, 111.3, 104.9, 58.0, 55.9, 24.9, 16.0, 9.3.

Chiral Chromatography: (Column type: Chiralpack OJ-H 4.6 mm×250 mm, 5 μm; Column temperature at 40° C.; Mobile phase: n-Hexane/Ethanol in the ratio 55/45% v/v; Flow Rate 0.8 mL/min; detector UV DAD @220 nm) 11.26 minutes, enantiomeric excess: 99.58%.

Example 20

(5S)-5-ethyl-3-(6-{[4-methyl-3-(methyloxy)phenyl]oxy}-3-pyridinyl)-2,4-imidazolidinedione

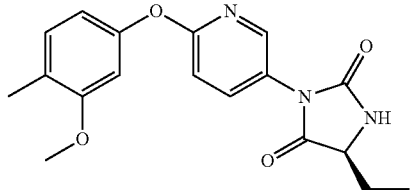 [SMILES: CC[C@@H]1NC(=O)N(c2ccc(Oc3ccc(C)c(OC)c3)nc2)C1=O]

To a solution of (2S)-2-amino-N-(6-{[4-methyl-3-(methyloxy)phenyl]oxy}-3-pyridinyl)butanamide (Intermediate 67, 43 mg) in dry dichloromethane (3 mL), triethylamine (0.095 mL, 0.682 mmol) was added. The reaction mixture was cooled down with an ice bath. A solution of triphosgene (18.21 mg, 0.061 mmol) in dichloromethane (0.750 mL) was then added dropwise and the reaction mixture was stirred during 30 minutes at 0° C. The reaction was quenched with water (10 mL). The organic phase was then separated, dried over sodium sulphate, filtered and evaporated. The residue was purified by flash chromatography on silica gel using a column SNAP 10 g and cyclohexane/ethyl acetate from 80/20 40/60 as eluent to afford the title compound as a white solid (37.2 mg).

$^1$H NMR (400 MHz, DMSO): δ ppm 8.60 (1H, s), 8.12 (1H, d), 7.82 (1H, dd), 7.16 (1H, d), 7.08 (1H, d), 6.78 (1H, d), 6.63 (1H, dd), 4.21-4.19 (1H, m), 3.76 (3H, s), 2.14 (3H, s), 1.84-1.66 (2H, m), 0.95 (3H, t): UPLC: 0.76 min, 342 [M+H]+

Example 21

(5R)-5-ethyl-3-(6-{[3-(1-methylethyl)phenyl]oxy}-3-pyridinyl)-2,4-imidazolidinedione

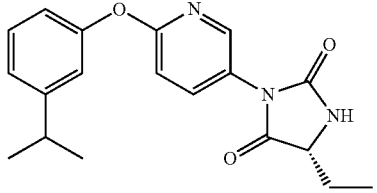 [SMILES: CC[C@H]1NC(=O)N(c2ccc(Oc3cccc(C(C)C)c3)nc2)C1=O]

(2R)-2-amino-N-(6-{[3-(1-methylethyl)phenyl]oxy}-3-pyridinyl)butanamide (Intermediate 70, 930 mg) was dissolved in dry dichloromethane (100 mL). The reaction mixture, under argon, was cooled down in an ice bath. Triethylamine (2.482 mL, 17.81 mmol) was added. Then a solution of triphosgene in dry dichloromethane (352 mg, 1.187 mmol dissolved in 40 mL of dichloromethane) was added dropwise. The reaction mixture was stirred at 0° C., under argon, during 10 min. A saturated aqueous solution of NaHCO3 was added (100 mL) and the aqueous layer was extracted with dichloromethane 4 times (4×80 mL). After drying over sodium sulphate, the solvent was removed under vacuum. The residue obtained was purified by silica gel chromatography (Companion system, 120 g silica cartridge,) with a gradient cyclohexane/ethyl acetate 100/0 to 55/45. The title compound (5R)-5-ethyl-3-(6-{[3-(1-methylethyl)phenyl]oxy}-3-pyridinyl)-2,4-imidazolidinedione was obtained as a beige powder (768 mg).

$^1$H NMR (400 MHz, CDCl$_3$): δ ppm 8.27 (1H, d), 7.74 (1H, dd), 7.32 (1H, t), 7.11 (1H, d), 7.01 (1H, t), 6.98-6.95 (2H, m), 6.40 (1H, s), 4.18 (1H, t), 2.96-2.89 (1H, m), 1.99-1.97 (1H, m), 1.93-1.63 (1H, m), 1.27 (3H, s), 1.25 (3H, s), 1.05 (3H, t); UPLC: 0.81 min, 340 [M+H]+.

Example 22

5,5-dimethyl-3-(4-{[3-(methyloxy)phenyl]oxy}phenyl)-2,4-imidazolidinedione

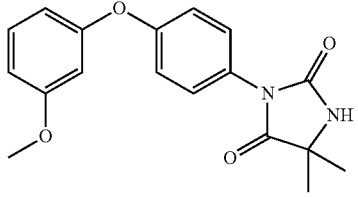 [SMILES: COc1cccc(Oc2ccc(N3C(=O)NC(C)(C)C3=O)cc2)c1]

To a solution of 2-methyl-N1-(4-{[3-(methyloxy)phenyl]oxy}phenyl)alaninamide (Intermediate 72, 1.33 g) and triethylamine (3.70 mL, 26.6 mmol) in dry dichloromethane (80 mL) at 0° C. was added dropwise a solution of triphosgene (600 mg, 2.022 mmol) in dry dichloromethane (20 mL) and the reaction mixture was stirred for 30 minutes at the same temperature. The reaction was quenched with a saturated solution of ammonium chloride (100 mL) and two phases were separated. Aqueous layer was extracted with dichloromethane (100 mL) and the two organic phases were collected, dried over sodium sulphate, filtered and evaporated. The residue was purified by silica gel chromatography (Biotage system, 100 g SNAP cartridge) using as eluent a gradient and cyclohexane/ethyl acetate from 80/20 to 40/60 to afford the title compound as a white solid (950 mg).

$^1$H NMR (400 MHz, DMSO-d$_6$): δ ppm 8.54 (1H, br. s), 7.34-7.40 (2H, m), 7.31 (1H, t), 7.09 (2H, m), 6.73-6.79 (1H, m), 6.65 (1H, t), 6.56-6.62 (1H, m), 3.75 (3H, s), 1.40 (6H, s); UPLC_B-MS: 0.79 min, 327 [M+H]+

The title compound was also obtained with the following alternative route. To 2-aminoisobutyric acid (120 mg, 1.164 mmol) in dichloromethane (2 mL) was added DIPEA (0.467 mL, 2.68 mmol) and N-methyl-N-trifluoroacetamide (533 mg, 2.68 mmol) and the suspension was shaken at 40° C. for 3.5 hours and then at 50° C. in a closed vial for 1 hour, resulting in a clear solution (Solution 1). To Boc2O (406 mg, 1.862 mmol) in dichloromethane (8 mL) was added with cooling in an ice bath DMAP (163 mg, 1.338 mmol) followed by slow addition (over ca. 5 min) via syringe of a solution of 4-{[3-(methyloxy)phenyl]oxy}aniline (288 mg, 1.338 mmol) in dichloromethane (2 mL). The mixture was stirred for 15 min at room temperature. The brown solution thus obtained was added to Solution 1 via syringe with stirring and stirring was continued for 1 hour. Volatiles were evaporated under vacuum.

Concentrated aqueous HCl (ca. 2 mL) was added and the heterogeneous mixture was heated at 100° C. for 2 hours. After cooling to room temperature the residue was diluted with water (ca. 10 mL) and extracted with dichloromethane (3 times ca. 5 mL). The dichloromethane extracts were concentrated under vacuum. The residue was purified by silica gel chromatography (Biotage system, 25 g column) eluting with a gradient cHex/EtOAc from 95/5 to 0/100. Fractions of good purity were collected, triturated with Et2O (2 times ca. 0.5 mL) and dried to give the title compound as a solid (40 mg)

Product containing but less pure fractions (by TLC) were combined to give 0.14 g brown material. This was again purified by silica gel chromatography (Biotage system, 95/5 to 40/60) and allowed to crystallize from Et2O (ca. 2 mL) and washed with some Et2O (2 times ca. 0.5 mL). This afforded after drying under vacuum an additional quantity of the title compound (15 mg).

$^1$H NMR (400 MHz, CDCl$_3$): δ ppm 7.43-7.35 (2H, m), 7.28-7.24 (1H, m), 7.11 (2H, d), 6.75-6.69 (1H, m), 6.67-6.61 (2H, m), 5.59-5.66 (1H, br, s), 3.81 (3H, s), 1.61-1.54 (6H, s); UPLC: 0.69 min, 325 [M–H]–

Example 23

3-{4-[(2,3-dimethylphenyl)oxy]phenyl}-5,5-dimethyl-2,4-imidazolidinedione

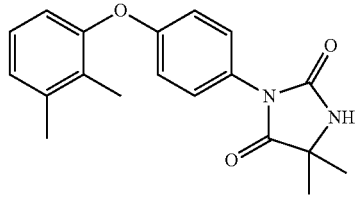 [SMILES: Cc1cccc(Oc2ccc(N3C(=O)NC(C)(C)C3=O)cc2)c1C]

N1-{4-[(2,3-dimethylphenyl)oxy]phenyl}-2-methylalaninamide (Intermediate 76, 68 mg) was solved in 2 mL of ethyl acetate under nitrogen atmosphere. TEA (0.070 mL, 0.50 mmol) was added followed by a solution of triphosgene (33.8 mg, 0.11 mmol) in 1.0 mL of ethyl acetate. After stirring for 5 minutes, DMAP (13.9 mg, 0.11 mmol) was added and the reaction mixture was stirred at room temperature for 10 minutes. After quenching with a saturated solution of NaHCO3,

Example 24

3-{6-[(2-ethylphenyl)oxy]-3-pyridinyl}-5,5-dimethyl-2,4-imidazolidinedione

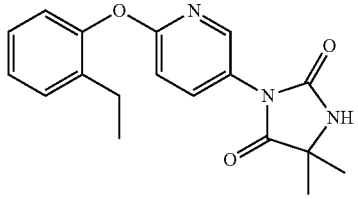 [SMILES: CCc1ccccc1Oc1ccc(N2C(=O)NC(C)(C)C2=O)cn1]

In a 50 mL round-bottomed flask N-{6-[(2-ethylphenyl)oxy]-3-pyridinyl}-2-methylalaninamide (Intermediate 78, 67.1 mg) was dissolved in dichloromethane (5 mL) to give a pale yellow solution. The reaction mixture was cooled at 0° C. N,N-dimethyl-4-pyridinamine (13.28 mg, 0.109 mmol), triethylamine (0.076 mL, 0.544 mmol) and triphosgene (32.3 mg, 0.109 mmol) were added. The reaction mixture was stirred at 0° C. After 20 minutes, the reaction mixture was evaporated under vacuum to afford a yellow solid which was purified by silica gel chromatography (Biotage system, 10 g SNAP column) eluting with a gradient Cyclohexane/EtOAc from 2:1 to 1:3 in 20 CV; then 1:3 for 5 CV. The collected fractions afforded the title compound as a white solid (60.9 mg).

$^1$H NMR (400 MHz, CDCl$_3$): δ ppm 8.30 (1H, d), 7.78 (1H, dd), 7.33-7.39 (1H, m), 7.20-7.31 (2H, m), 7.06-7.12 (1H, m), 6.98 (1H, d), 6.25 (1H, br. s), 2.62 (2H, q), 1.58 (6H, s), 1.22 (3H, t); UPLC_B: 0.80 min, 326 [M+H]+.

Example 25

3-{6-[(2,6-dimethylphenyl)oxy]-3-pyridinyl}-5,5-dimethyl-2,4-imidazolidinedione

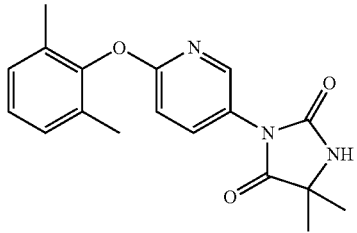 [SMILES: Cc1cccc(C)c1Oc1ccc(N2C(=O)NC(C)(C)C2=O)cn1]

In a 50 mL round-bottomed flask N-{6-[(2,6-dimethylphenyl)oxy]-3-pyridinyl}-2-methylalaninamide (Intermediate 80, 144.4 mg) was dissolved in dichloromethane (5 mL) to give a pale yellow solution. The reaction mixture was cooled at 0° C. N,N-dimethyl-4-pyridinamine (27.7 mg, 0.227 mmol), triethylamine (0.158 mL, 1.134 mmol) and triphosgene (67.3 mg, 0.227 mmol) were added. The reaction mixture was stirred at 0° C. After 20 min, the solvent was evaporated under vacuum to afford a yellow solid which was purified via silica gel chromatography (Biotage system, 10 g SNAP column) using as eluent a gradient Cyclohexane/EtOAc from 2:1 to 1:3 in 20 CV; then 1:3 for 5 CV. The collected fractions afforded the title compound as a white solid (139.7 mg).

$^1$H NMR (400 MHz, CDCl$_3$)): δ ppm 8.30-8.26 (1H, m), 7.78 (1H, dd), 7.20-7.07 (3H, m), 6.94 (1H, d), 6.33 (1H, br. s), 2.17 (6H, s), 1.58 (6H, s): UPLC_s: 0.84 min, 326 [M+H]+.

Example 26

(5R)-5-(1-methylethyl)-3-(4-{[4-methyl-3-(methyloxy)phenyl]oxy}phenyl)-2,4-imidazolidinedione

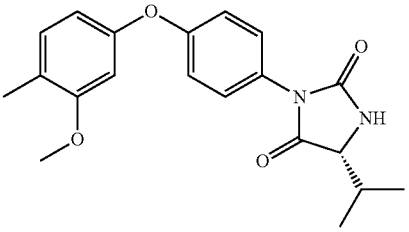 [SMILES: COc1cc(Oc2ccc(N3C(=O)N[C@H](C(C)C)C3=O)cc2)ccc1C]

To a solution of N1-(4-{[4-methyl-3-(methyloxy)phenyl]oxy}phenyl)-D-valinamide (Intermediate 83, 65 mg) in dry dichloromethane (10 mL), TEA (0.138 mL, 0.990 mmol) was added and the reaction mixture was cooled to 0° C. A solution of triphosgene (26.4 mg, 0.089 mmol) in dry dichloromethane (3 mL) was slowly added and the reaction mixture was stirred for 1 hour at 0° C. The reaction was quenched with water (2 mL) and a saturated aqueous solution of ammonium chloride (5 mL) and was extracted with dichloromethane (2 times 10 mL). The organic layer was dried over sodium sulphate, filtered and evaporated and the residue was purified by silica gel flash chromatography (Biotage system, 10 g SNAP column) using as eluent a gradient cyclohexane/ethyl from 100/0 to 60/40 to afford the title compound as a white solid (55 mg).

$^1$H-NMR (400 MHz, DMSO-d$_6$) δ ppm: 8.52 (1H, s), 7.29 (2H, m), 7.16 (1H, d), 7.05 (2H, m), 6.74 (1H, d), 6.52 (1H, dd), 4.13 (1H, dd), 3.77 (3H, s), 2.14 (4H, s), 1.02 (3H, d), 0.88 (3H, d); UPLC_B: 0.91 min, 355 [M+H]+.

Example 27

(5R)-5-methyl-3-(2-{[3-(1-methylethyl)phenyl]oxy}-5-pyrimidinyl)-2,4-imidazolidinedione

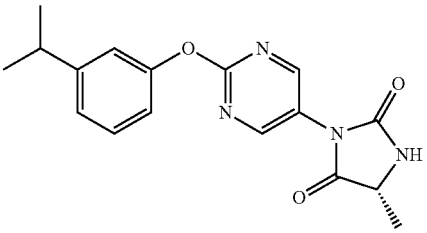 [SMILES: CC(C)c1cccc(Oc2ncc(N3C(=O)N[C@H](C)C3=O)cn2)c1]

To a solution of N-(2-{[3-(1-methylethyl)phenyl]oxy}-5-pyrimidinyl)-D-alaninamide (Intermediate 87, 100 mg) in dichloromethane (30 mL) were added triphosgene (40 mg, 0.133 mmol) and triethylamine (51 mg, 0.5 mmol). The resulting mixture was stirred at 0° C. for 30 minutes and water (30 mL) was added. It was extracted with dichloromethane (3 times 30 mL) and the combined organic layer was dried over sodium sulphate and evaporated to afford the title compound (100 mg). $^1$HNMR (400 MHz, CDCl$_3$): δ ppm 8.62 (2H, s), 7.26-7.30 (1H, t), 7.08-7.05 (2H, m), 6.99-6.92 (2H, m), 4.22-4.20 (1H, d), 2.88-2.84 (1H, m), 1.47-1.45 (3H, d), 1.19-1.18 (6H, d); MS_2 (ESI): 326 [M+H]+.

Example 28

(5R)-5-ethyl-3-(2-{[3-(ethyloxy)-4-methylphenyl]oxy}-5-pyrimidinyl)-2,4-imidazolidinedione

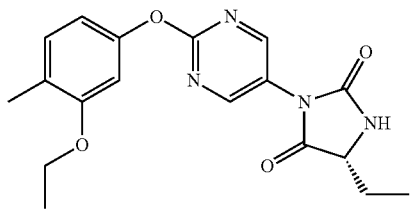 [SMILES: CCOc1cc(Oc2ncc(N3C(=O)N[C@H](CC)C3=O)cn2)ccc1C]

To a solution of ((2R)-2-amino-N-(2-{[3-(ethyloxy)-4-methylphenyl]oxy}-5-pyrimidinyl)butanamide (Intermediate 94, 62 mg) in dry dichloromethane (4 mL), TEA (158 μl, 1.13 mmol) was added and the reaction mixture was cooled to 0° C. A solution of triphosgene (25.2 mg, 0.085 mmol) in dry dichloromethane (2 mL) was then added dropwise and the reaction mixture was stirred at 0° C. for 20 minutes. The reaction mixture was evaporated under vacuum. The residue obtained was purified by silica gel chromatography chromatography (Companion system, 12 g silica cartridge) with Cyclohexane/EtOAc as eluents from 100/0 to 50/50 in 20 minutes and then 50/50 during 15 minutes to afford the title compound as a white solid (40 mg).

$^1$H NMR (400 MHz, CDCl$_3$): δ ppm 8.68 (1H, s), 7.16 (1H, d), 6.82-6.59 (2H, m), 6.29 (1H, s), 4.23 (1H, t), 4.12 (1H, q), 2.22 (3H, s), 2.04 (2H, s), 2.02-1.95 (1H, m), 1.96-1.80 (1H, m), 1.26 (3H, t), 1.06 (3H, t); UPLC: 0.72 min, 357 [M+H]+

Example 29

(5R)-5-(1,1-dimethylethyl)-3-(6-{[4-methyl-3-(methyloxy)phenyl]oxy}-3-pyridinyl)-2,4-imidazolidinedione

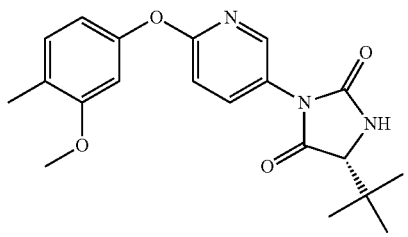 [SMILES: COc1cc(Oc2ccc(N3C(=O)N[C@H](C(C)(C)C)C3=O)cn2)ccc1C]

3-methyl-N$^1$-(6-{[4-methyl-3-(methyloxy)phenyl]oxy}-3-pyridinyl)-D-valinamide (Intermediate 97, 5.2 mg) was dissolved in dry dichloromethane (0.5 mL). The reaction mixture was cooled down in an ice bath. Triethylamine (12.6 μl, 0.091 mmol) was added at 0° C. Then 0.5 mL of a solution of triphosgene in dry dichloromethane (2.47 mg, 0.0083 mmol) was added dropwise. The reaction mixture was stirred under argon during 20 min at 0° C. Some water was added and the aqueous layer was extracted with dichloromethane 4 times. After drying over sodium sulphate, the solvents were removed under vacuum. The residue obtained was purified by flash chromatography on silica gel (Companion system, 4 g silica cartridge) with cyclohexane/ethylacetate as eluents from 100/0 to 60/40 during 15 min and 60/40 during 10 min. This afforded the title compound (5.9 mg).

$^1$H NMR (400 MHz, CDCl$_3$): δ ppm 8.24 (1H, d), 7.69 (1H, dd), 7.17 (1H, d), 7.00 (1H, d), 6.66 (2H, m), 6.46 (1H, br s), 3.89 (1H, s), 3.82 (3H, s), 2.23 (3H, s), 1.13 (9H, s); UPLC_ipqc: 1.11 min, 370 [M+H]+

Example 30

(5R)-5-ethyl-5-methyl-3-(6-{[4-methyl-3-(methyloxy)phenyl]oxy}-3-pyridinyl)-2,4-imidazolidinedione

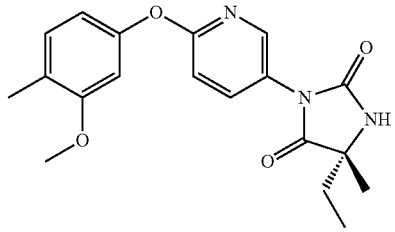 [SMILES: CC[C@@]1(C)NC(=O)N(c2ccc(Oc3ccc(C)c(OC)c3)nc2)C1=O]

To a solution of N1-(6-{[4-methyl-3-(methyloxy)phenyl]oxy}-3-pyridinyl)-D-isovalinamide (Intermediate 99, 42 mg) in dry dichloromethane (6 mL), TEA (0.089 mL, 0.638 mmol) was added. The mixture was cooled down to 0° C. and a solution of triphosgene (17.03 mg, 0.057 mmol) in dry dichloromethane (1.500 mL) was added dropwise. The mixture was stirred at that temperature for 1 hour, then a solution of triphosgene (17.03 mg, 0.057 mmol) in dry dichloromethane (DCM) (1.500 mL) was added dropwise again. The reaction was stirred for 30 minutes, it was maintained in the ice-bath and quenched with water (10 mL). The mixture was allowed to reach the room temperature then it was extracted with dichloromethane (3×7 mL). The combined organic layers were dried over sodium sulphate, filtered and evaporated. The residue obtained was purified by flash chromatography on silica gel using a 10 g SNAP column and cyclohexane/ethyl acetate as eluents from 80/20 to 50/50 (Biotage system). This afforded the title compound as a white solid (24 mg).

$^1$H NMR (400 MHz, DMSO-d$_6$): δ ppm 8.57 (1H, s), 8.13 (1H, d), 7.83 (1H, dd), 7.17 (1H, d), 7.07 (1H, d), 6.79 (1H, d), 6.62 (1H, dd), 3.76 (3H, s), 2.14 (3H, s), 1.57-1.86 (2H, m), 1.39 (3H, s), 0.86 (3H, t); UPLC_B: 0.83 min, 354 [M−H]+.

Example 31

7-(6-{[4-methyl-3-(methyloxy)phenyl]oxy}-3-pyridinyl)-5,7-diazaspiro[3,4]octane-6,8-dione

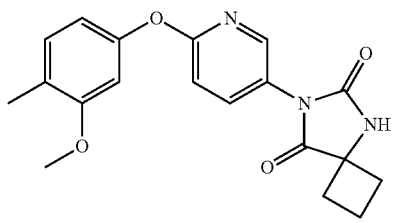 [SMILES: COc1cc(Oc2ccc(N3C(=O)NC4(CCC4)C3=O)cn2)ccc1C]

To a solution of 1-amino-N-(6-{[4-methyl-3-(methyloxy)phenyl]oxy}-3-pyridinyl)cyclobutanecarboxamide (Intermediate 102, 60 mg) in dry dichloromethane (2 mL) TEA (0.128 mL, 0.916 mmol) was added. The reaction mixture was cooled in an ice-bath, then a solution of triphosgene (24.47 mg, 0.082 mmol) in dry dichloromethane (0.500 mL) was added dropwise. The mixture was stirred at 0° C. for 30 minutes. The reaction was maintained at 0° C. and quenched with water (10 mL). The mixture was extracted with dichloromethane (3×4 mL). The combined organic layers were dried over sodium sulphate, filtered and evaporated. The residue was purified by flash chromatography on silica gel using a 25 g SNAP column and using as eluents cyclohexane/ethylacetate from 100:0 to 50:50. This afforded the title compound (52 mg) as a white solid.

$^1$H NMR (400 MHz, DMSO-$d_6$): δ ppm 8.96 (1H, s), 8.14 (1H, d), 7.84 (1H, dd), 7.17 (1H, d), 7.08 (1H, d), 6.79 (1H, d), 6.63 (1H, dd), 3.77 (3H, s), 2.61-2.72 (2H, m), 2.42-2.26 (3H, m), 2.15 (3H, s), 1.82-2.02 (1H, m); UPLC: 0.72 min, 354 [M+H]+.

Example 32

6-(6-{[4-methyl-3-(methyloxy)phenyl]oxy}-3-pyridinyl)-4,6-diazaspiro[2.4]heptane-5,7-dione

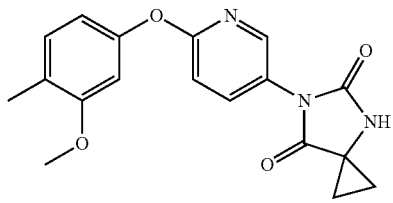 [SMILES: COc1cc(Oc2ccc(N3C(=O)NC4(CC4)C3=O)cn2)ccc1C]

To a solution of 1-amino-N-(6-{[4-methyl-3-(methyloxy)phenyl]oxy}-3-pyridinyl)cyclopropanecarboxamide (Intermediate 105, 58 mg) in dry dichloromethane (2 mL) TEA (0.129 mL, 0.925 mmol) was added. The reaction mixture was cooled in an ice-bath, then a solution of triphosgene (24.72 mg, 0.083 mmol) in dry dichloromethane (0.500 mL) was added dropwise. The reaction mixture was stirred at 0° C. for 30 minutes, then the solution of triphosgene (24.72 mg, 0.083 mmol) in dry dichloromethane (0.500 mL) was added again. The reaction mixture was stirred at 0° C. for 30 minutes. The reaction was maintained in the ice-bath and quenched with water (10 mL). The organic layer was separated, dried over sodium sulphate, filtered and evaporated. The residue was purified by flash chromatography on silica gel using a column 25 g SNAP column and cyclohexane/ethylacetate as eluents from 100:0 to 50:50. This afforded the title compound as a white solid (20 mg).

$^1$H NMR (400 MHz, DMSO-$d_6$): δ ppm 8.71 (1H, s), 8.18 (1H, d), 7.88 (1H, dd), 7.18 (1H, d), 7.09 (1H, d), 6.79 (1H, d), 6.64 (1H, dd), 3.77 (3H, s), 2.15 (3H, s), 1.20-1.47 (4H, m); UPLC: 0.68 min, 340 [M+H]+.

Example 33

5,5-dimethyl-3-(6-{[4-methyl-3-(methyloxy)phenyl]oxy}-3-pyridinyl)-2,4-imidazolidinedione

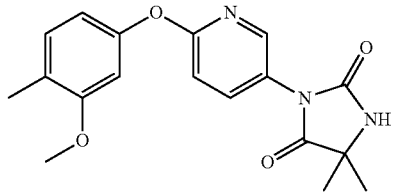 [SMILES: COc1cc(Oc2ccc(N3C(=O)NC(C)(C)C3=O)cn2)ccc1C]

Example 34

(5R)-5-(1-methylethyl)-3-(6-{[4-methyl-3-(methyloxy)phenyl]oxy}-3-pyridinyl)-2,4-imidazolidinedione

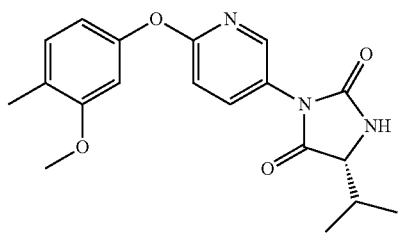 [SMILES: COc1cc(Oc2ccc(N3C(=O)N[C@H](C(C)C)C3=O)cn2)ccc1C]

Example 35

3-(6-{[2-(1,1-dimethylethyl)phenyl]oxy}-3-pyridinyl)-5,5-dimethyl-2,4-imidazolidinedione

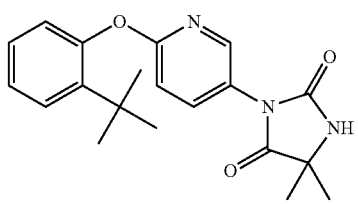

Example 36

3-(2-{[2-(1,1-dimethylethyl)phenyl]oxy}-5-pyrimidinyl)-5,5-dimethyl-2,4-imidazolidinedione

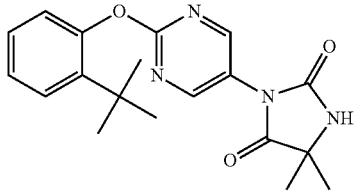 [SMILES: CC1(C)NC(=O)N(c2cnc(Oc3ccccc3C(C)(C)C)nc2)C1=O]

Example 37

(5R)-5-ethyl-5-methyl-3-(2-{[4-methyl-3-(methyloxy)phenyl]oxy}-5-pyrimidinyl)-2,4-imidazolidinedione

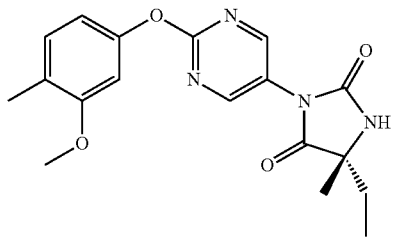 [SMILES: CC[C@@]1(C)NC(=O)N(c2cnc(Oc3ccc(C)c(OC)c3)nc2)C1=O]

Example 38

(5R)-5-ethyl-3-(2-{[3-(ethyloxy)-4-methylphenyl]oxy}-5-pyrimidinyl)-5-methyl-2,4-imidazolidinedione

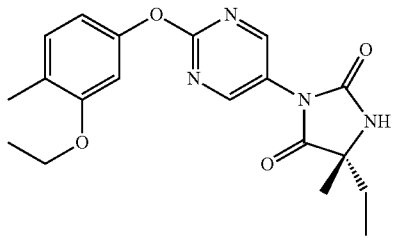 [SMILES: CCOc1cc(Oc2ncc(N3C(=O)N[C@](C)(CC)C3=O)cn2)ccc1C]

Example 39

4-{[5-(4,4-dimethyl-2,5-dioxo-1-imidazolidinyl)-2-pyridinyl]oxy}-2-(1-methylethyl)benzonitrile

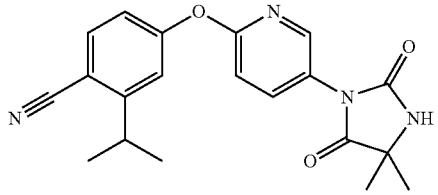 [SMILES: CC(C)c1cc(Oc2ccc(N3C(=O)NC(C)(C)C3=O)cn2)ccc1C#N]

4-hydroxy-2-(1-methylethyl)benzonitrile (30 mg) was dissolved in 1 mL of dimethylformamide. 3-(6-fluoro-3-pyridinyl)-5,5-dimethyl-2,4-imidazolidinedione (Intermediate 106, 41.5 mg) and potassium carbonate (51.4 mg, 0.372 mmol) were added. The reaction mixture was stirred at 120° C. during 40 hours. Some diethylether (4 mL) and water (4 mL) were added. The aqueous layer was extracted 4 times with diethylether. The gathered organic layers were dried over sodium sulphate and evaporated giving a residue which was purified by mass directed purification (METHOD H). After evaporation of the fraction, addition of a solution of saturated NaHCO3 (3 mL) and extraction with dichloromethane (four times 4 mL), evaporation afforded the title compound (13 mg).

$^1$H NMR (400 MHz, CDCl$_3$): δ ppm 8.32 (1H, d), 7.88 (1H, dd), 7.66 (1H, d), 7.17 (1H, dd), 7.08 (2H, m); 5.57 (s, 1H), 3.40 (1H, m), 1.57 (6H, s), 1.33 (6H, d); UPLC_ipqc: 1.01 min, 365 [M+H]+.

Example 40

5,5-dimethyl-3-[6-({3-[(trifluoromethyl)oxy]phenyl}oxy)-3-pyridinyl]-2,4-imidazoidinedione

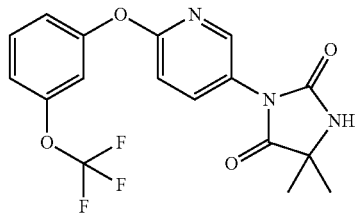 [SMILES: CC1(C)NC(=O)N(c2ccc(Oc3cccc(OC(F)(F)F)c3)nc2)C1=O]

3-[(trifluoromethyl)oxy]phenol (19.95 mg, 0.112 mmol) was dissolved in 1 mL of dimethylformamide. 3-(6-fluoro-3-pyridinyl)-5,5-dimethyl-2,4-imidazolidinedione (Intermediate 106, mg) and potassium carbonate (31.0 mg, 0.224 mmol) were added. The reaction mixture was stirred at 120° C. during 22 hours. Some diethylether (4 mL) and water (4 mL) were added. The aqueous layer was extracted 4 times with diethylether. The gathered organic layers were dried over sodium sulphate and evaporated giving a residue, which was purified by mass directed purification (METHOD I). After evaporation of the fraction, addition of a solution of saturated NaHCO3 (3 mL) and extraction with dichloromethane (four times 4 mL), evaporation afforded the title compound as a white solid (23 mg).

$^1$H NMR (400 MHz, CDCl$_3$): δ ppm 8.30 (1H, d), 7.83 (1H, dd), 7.42 (1H, t), 7.06 (4H, m), 6.36 (s br, 1H), 1.55 (6H, s); UPLC_ipqc: 1.01 min, 382 [M+H]+

Example 41

3-{6-[(4-fluoro-3-methylphenyl)oxy]-3-pyridinyl}-5,5-dimethyl-2,4-imidazolidinedione

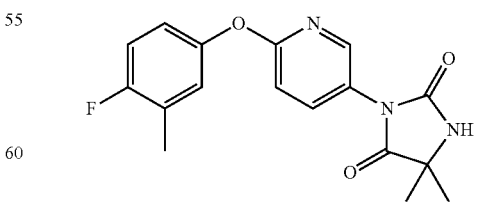

The title compound was made in a similar fashion to the preparation of Example 39 replacing 4-hydroxy-2-(1-methylethyl)benzonitrile with 4-fluoro-3-methylphenol (11.30 mg, 0.090 mmol)). For the mass directed purification METHOD J was used (instead of METHOD H). This afforded the title compound as a white solid (17 mg).
¹H NMR (400 MHz, CDCl₃): δ ppm 8.26 (1H, d), 7.77 (1H, dd), 7.03-6.92 (4H, m), 5.50 (1H, s br), 2.29 (3H, s), 1.57 (6H, s); UPLC_ipqc: 0.96 min, 330 [M+H]+.

Example 42

3-{6-[(4-fluoro-2-methylphenyl)oxy]-3-pyridinyl}-5,5-dimethyl-2,4-imidazolidinedione

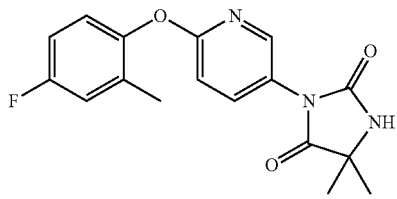 [SMILES: Cc1cc(F)ccc1Oc1ccc(N2C(=O)NC(C)(C)C2=O)cn1]

The title compound was made in a similar fashion to the preparation of Example 40 replacing 3-[(trifluoromethyl)oxy]phenol with 4-fluoro-2-methylphenol (14.13 mg, 0.112 mmol) to afford the title compound as a white solid (13 mg).
¹H NMR (400 MHz, CDCl₃): δ ppm 8.26 (1H, d), 7.77 (1H, dd), 7.03-6.93 (4H, m), 5.50 (1H, s br), 2.29 (3H, s), 1.57 (6H, s); UPLC_ipqc: 0.94 min, 330 [M+H]+.

Example 43

4-{[5-(4,4-dimethyl-2,5-dioxo-1-imidazolidinyl)-2-pyridinyl]oxy}-3-ethylbenzonitrile

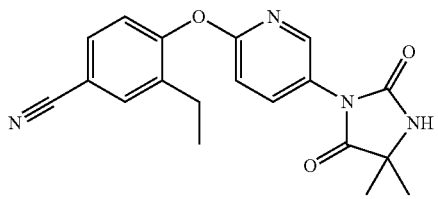 [SMILES: CCc1cc(C#N)ccc1Oc1ccc(N2C(=O)NC(C)(C)C2=O)cn1]

3-ethyl-4-hydroxybenzonitrile (Intermediate 115, 70 mg) was dissolved in 2 mL of dimethylformamide. 3-(6-fluoro-3-pyridinyl)-5,5-dimethyl-2,4-imidazolidinedione (Intermediate 106, 102 mg) and potassium carbonate (126 mg, 0.915 mmol) were added. The reaction mixture was stirred at 120° C. during 96 hours. Some diethyl ether (4 mL) and water (4 mL) were added. The aqueous layer was extracted 4 times with diethyl ether. The gathered organic layers were dried over sodium sulphate and evaporated giving a residue which was purified by flash chromatography on silica gel (companion system, 12 g Si cartridge) using as eluent a gradient cyclohexane/ethyl acetate 100/0, then from 100/0 to 55/45. Evaporation afforded the title compound (54 mg) as a white solid.
¹H NMR (400 MHz, CDCl₃): δ ppm 8.27 (1H, d), 7.87 (1H, dd), 7.62 (1H, d), 7.55 (1H, dd), 7.16 (1H, dd); 6.40 (1H, s), 5.58 (1H, s), 2.65 (2H, q), 1.56 (6H, s), 1.21 (3H, t); UPLC_ipqc: 0.97 min, 349 [M−H]−.

The following compounds were prepared using the foregoing methodology, reacting 3-(6-fluoro-3-pyridinyl)-5,5-dimethyl-2,4-imidazolidinedione (Intermediate 106) with the appropriately substituted phenol for a time ranging from 12 to 96 hrs, as described in the foregoing Reaction Schemes. Some final products were purified by flash-chromatography (Silica or NH cartridge; Cyclohexane/EtOAc or other appropriate solvent system) and were isolated as the free-base; alternatively, some products were purified by mass directed purification (METHOD K Chromatographic Acidic conditions: Column=Waters Sunfire OBD (150 mm×30 mm, 5 μm particle size) at room temperature; Mobile phase=A (water+0.1% formic acid in water), B (acetonitrile+0.1% formic acid in acetonitrile); Flow rate=40 mL/min; Gradient=from 1% (B) to 100% (B) in 8.5 min, 100% (B) during 6.5 min, return to 1% (B) in 0.5 min) and fractions containing the product were basified with NaHCO₃ and extracted with an appropriate organic solvent, dried and concentrated to provide the free-base. Finally in one case (Example 77) an additional purification by SCX (DCM and MeOH as solvents) was run.

| Ex. | Structure | Name | Phenol | NMR characterization | UPLC_ipqc characterization |
|---|---|---|---|---|---|
| 44 | 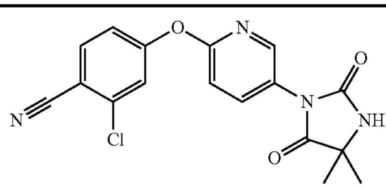 | 2-chloro-4-{[5-(4,4-dimethyl-2,5-dioxo-1-imidazolidinyl}-2-pyridinyl]oxy}benzonitrile | 2-chloro-4-hydroxy-benzonitrile | ¹H NMR (400 MHz, CDCl₃): δ ppm 8.35 (1H, d), 7.92 (1H, dd), 7.71 (1H, d), 7.38 (1H, d), 7.21 (1H, dd); 7.14 (1H, d), 5.58 (s, 1H), 1.59 (6H, s) | 1.94 min, 357 [M + H]+ |
| 45 | 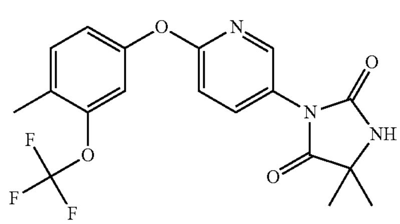 [SMILES: Cc1ccc(Oc2ccc(N3C(=O)NC(C)(C)C3=O)cn2)cc1OC(F)(F)F] | 5,5-dimethyl-3-[6-({4-methyl-3-[(trifluoromethyl)oxy]phenyl}oxy)-3-pyridinyl]-2,4-imidazolidinedione | 4-methyl-3-[(trifluoromethyl)oxy] phenol (Intermediate 116) | ¹H NMR (400 MHz, CDCl₃): δ ppm 8.28 (1H, d), 7.80 (1H, dd), 7.23-7.34 (1H, m), 7.00-7.09 (2H, m), 6.19 (1H, br. s.), 2.32 (3H, s), 1.56 (6H, s) | 1.13 min, 396 [M + H]+. |

| Ex. | Structure | Name | Phenol | NMR characterization | UPLC_ipqc characterization |
|---|---|---|---|---|---|
| 46 | 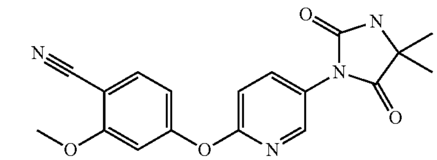 | 4-{[5-(4,4-dimethyl-2,5-dioxo-1-imidazolidinyl)-2-pyridinyl]oxy}-2-(methyloxy)benzonitrile | 4-hydroxy-2-(methyloxy)benzonitrile | ¹H NMR (400 MHz, CDCl₃): δ ppm 8.33 (1H, d) 7.88 (1H, dd) 7.58 (1H, d) 7.10 (1H, d) 6.76-6.83 (2H, m) 5.92 (1H, br. s.) 3.92 (3H, s) 1.58 (6H,s) | 0.86 min, 353 [M + H]+ |
| 47 | 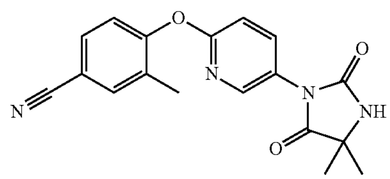 [SMILES: Cc1cc(C#N)ccc1Oc1ccc(N2C(=O)NC(C)(C)C2=O)cn1] | 4-{[5-(4,4-dimethyl-2,5-dioxo-1-imidazolidinyl)-2-pyridinyl]oxy}-3-methylbenzonitrile | 4-hydroxy-3-methyl-benzonitrile (Intermediate 118) | ¹H NMR (400 MHz, DMSO-d₆): δ ppm 8.66 (1H, s), 8.11-8.19 (1H, m), 7.91-8.00 (1H, m), 7.87 (1H, s), 7.76 (1H, d), 7.29 (2H, t), 2.17 (3H, s), 1.41 (6H, s) | 0.89 min, 337 [M + H]+, 335 [M − H]− |

Example 48

4-{[5-(4,4-dimethyl-2,5-dioxo-1-imidazolidinyl)-2-pyridinyl]oxy}-3-(trifluoromethyl)benzonitrile

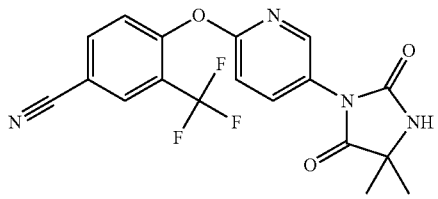 [SMILES: CC1(C)NC(=O)N(c2ccc(Oc3ccc(C#N)cc3C(F)(F)F)nc2)C1=O]

A solution of methyl N-{[(6-{[4-cyano-2-(trifluoromethyl)phenyl]oxy}-3-pyridinyl)amino]carbonyl}-2-methylalaninate (Intermediate 165, 49 mg) in MeOH (10 mL) was heated at reflux for 10 min. Sodium methoxide (4 mg) was added to the hot reaction mixture and it was left refluxing for 2.5 hours. The solvent was evaporated to dryness and the residue obtained was purified by flash-chromatography (companion system, 12 g Si cartridge), with Cyclohexane/EtOAc as eluents from 70/30 to 50/50, to give two batches. The second batch was purified again by mass directed purification (METHOD K), leading to the desired compound which was gathered to the first batch, to afford the title compound as a white solid (8.2 mg).

¹H NMR (400 MHz, CDCl₃): δ ppm 8.30 (1H, d), 8.02 (1H, s), 7.90-7.99 (1H, m), 7.87 (1H, d), 7.46 (1H, d), 7.21 (1H, d), 5.68 (1H, br. s.), 1.59 (6H, s); UPLC_ipqc: 0.98 min, 391 [M+H]+.

The following compounds were prepared using the foregoing methodology, replacing methyl N-{[(6-{[4-cyano-2-(trifluoromethyl)phenyl]oxy}-3-pyridinyl)amino]carbonyl}-2-methylalaninate (Intermediate 165) with the appropriate urea, as described in the foregoing Reaction Schemes. Final products were purified by flash-chromatography (Silica cartridge; Cyclohexane/EtOAc or other appropriate solvent system) and were isolated as the free-base.

| Ex. | Structure | Name | Urea | NMR characterization | UPLC_ipqc characterization |
|---|---|---|---|---|---|
| 49 | 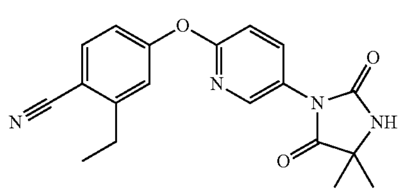 [SMILES: CCc1cc(Oc2ccc(N3C(=O)NC(C)(C)C3=O)cn2)ccc1C#N] | 4-{[5-(4,4-dimethyl-2,5-dioxo-1-imidazolidinyl)-2-pyridinyl]oxy}-2-ethylbenzonitrile | methyl N-[({6-[(4-cyano-3-ethylphenyl)oxy]-3-pyridinyl}amino)carbonyl]-2-methylalaninate (Intermediate 166) | ¹H NMR (400 MHz, CDCl₃): δ ppm 8.32 (1H, d), 7.84-7.90 (1H, m), 7.65 (1H, d), 7.04-7.16 (3H, m), 5.49 (1H, s), 2.90 (2H, q), 1.57-1.59 (6H, s), 1.32 (3H, t) | 0.97 min, 351 [M + H]+. |
| 50 | 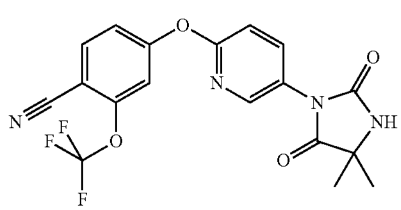 [SMILES: CC1(C)NC(=O)N(c2ccc(Oc3ccc(C#N)c(OC(F)(F)F)c3)nc2)C1=O] | 4-{(5-(4,4-dimethyl-2,5-dioxo-1-imidazolidinyl)-2-pyridinyl]oxy)-2-[(trifluoromethyl)oxy]benzonitrile | methyl N-({[6-({4-cyano-3-[(trifluoromethyl)oxy]phenyl}oxy)-3-pyridinyl]amino}carbonyl)-2-methylalaninate (Intermediate 167) | ¹H NMR (400 MHz, DMSO-d₆): δ ppm 8.66 (1H, s), 8.21-8.28 (1H, m), 8.13 (1H, d), 7.97-8.05 (1H, m), 7.64 (1H, s), 7.41-7.49 (1H, m), 7.35 (1H, d), 1.41 (6H, s) | 1.01 min, 407 [M + H]+, 405 [M − H]−. |

Example 51

4-{[5-(4,4-dimethyl-2,5-dioxo-1-imidazolidinyl)-2-pyrimidinyl]oxy}-2-ethylbenzonitrile

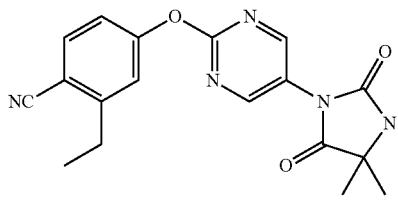 [SMILES: CCc1cc(Oc2ncc(N3C(=O)NC(C)(C)C3=O)cn2)ccc1C#N]

To a solution of triphosgene (20.8 mg, 0.07 mmol) in EtOAc (0.5 mL) at 0° C., a solution of 4-[(5-amino-2-pyrimidinyl)oxy]-2-ethylbenzonitrile (Intermediate 144, 35 mg)/TEA (0.037 mL, 0.27 mmol) in EtOAc (1.0 mL) was added dropwise under stirring. Then a solution of methyl 2-methylalaninate hydrochloride (Intermediate 107, 33.6 mg)/TEA (0.073 mL, 0.52 mmol) in 1.0 mL of EtOAc at 0° C. was slowly added and the reaction mixture was stirred at that temperature for 10 minutes. The mixture was quenched with an aqueous pH 3 buffer solution to pH 5-6 and extracted with EtOAc (three times). The collected organic were dried over Na$_2$SO$_4$, filtered and evaporated. The crude obtained was dissolved in MeOH (1.0 mL) and 3.0 mg (0.056 mmol) of sodium methoxide were added and the mixture was heated at 60° C. for 5 minutes. After cooling down to r.t., the mixture was evaporated, diluted with EtOAc and washed with NH$_4$Cl (aqueous saturated solution) and the aqueous phase was extracted with EtOAc (three times). The collected organic were dried over Na$_2$SO$_4$, filtered and evaporated. The crude obtained was charged on a silica gel column and eluted with Cyclohexane/EtOAc (from 70:30 Cyclohexane/EtOAc to 60:40 in 20 CV, plateau at 60:40 in 20 CV) affording 11.5 mg of the title compound.

$^1$H-NMR (400 MHz, CDCl$_3$): δ ppm 8.77 (2H, br. s), 7.69 (1H, d), 7.21 (1H, br. s), 7.16 (1H, d), 5.89 (1H, br. s), 2.91 (2H, q), 1.60 (6H, s), 1.33 (3H, t); UPLC_ipqc: 0.92 min, 352 [M+H]$^+$.

The following compounds were prepared using the foregoing methodology, replacing 4-[(5-amino-2-pyrimidinyl)oxy]-2-ethylbenzonitrile (Intermediate 144) with the appropriate aniline, as described in the foregoing Reaction Schemes. Final products were purified by flash-chromatography (Silica or NH cartridge; Cyclohexane/EtOAc, dichlorometane/methanol or other appropriate solvent system); alternatively, some products were purified by mass directed purification and fractions containing the product were basified with NaHCO$_3$ and extracted with an appropriate organic solvent, dried and concentrated to provide the desired product.

| Ex. | Structure | Name | Aniline | NMR characterization | UPLC_ipqc characterization |
|---|---|---|---|---|---|
| 52 | 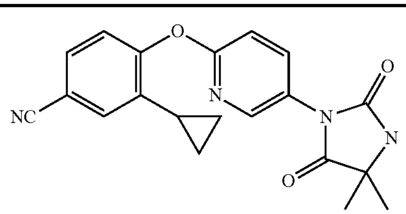 | 3-cyclopropyl-4-({5-(4,4-dimethyl-2,5-dioxo-1-imidazolidinyl)-2-pyridinyl]oxy}benzonitrile | 4-[(5-amino-2-pyridinyl)oxy]-3-cyclopropyl-benzonitrile (Intermediate 145) | $^1$H NMR (400 MHz, DMSO-d$_6$): δ ppm 8.65 (1H, br. s), 8.16 (1H, br. s), 7.99-7.91 (1H, m), 7.73-7.66 (1H, m), 7.52 (1H, br. s), 7.29 (2H. d), 1.97-1.86 (1H, m), 1.41 (6H, s), 0.91-0.83 (2H, m), 0.80-0.74 (2H, m) | 0.97 min, 363 [M + H]$^+$ |
| 53 | 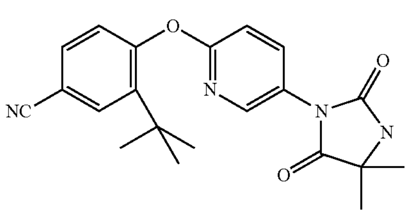 [SMILES: CC1(C)NC(=O)N(c2ccc(Oc3ccc(C#N)cc3C(C)(C)C)nc2)C1=O] | 4-{(5-(4,4-dimethyl-2,5-dioxo-1-imidazolidinyl)-2-pyridinyl]oxy}-3-(1,1-dimethylethyl)benzonitrile | 4-[(5-amino-2-pyridinyl)oxy]-3-(1,1-dimethylethyl)benzonitrile (Intermediate 146) | $^1$H NMR (400 MHz, DMSO-d$_6$): δ ppm 8.66 (1H, br. s), 8.25-8.19 (1H, m), 8.02-7.95 (1H, m), 7.83 (1H, br. s), 7.76-7.70 (1H, m), 7.31 (1H, d), 7.19 (1H, d), 1.42 (6H, s), 1.36 (9H, m) | 1.08 min, 379 [M + H]$^+$ |
| 54 | 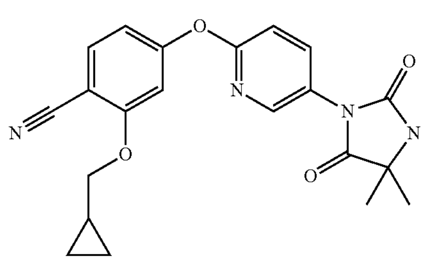 [SMILES: CC1(C)NC(=O)N(c2ccc(Oc3ccc(C#N)c(OCC4CC4)c3)nc2)C1=O] | 2-[(cyclopropyl-methyl)oxy]-{[5-(4,4-dimethyl-2,5-dioxo-1-imidazolidinyl)-2-pyridinyl]oxy}benzonitrile | 4-[(5-amino-2-pyridinyl)oxy]-2-[(cyclopropyl methyl)oxy]benzonitrile (Intermediate 151) | $^1$H NMR (400 MHz, CDCl$_3$): δ ppm 8.32 (1H, d), 7.86 (1H, dd), 7.58 (1H, d), 7.09 (1H, d), 6.74-6.79 (2H, m), 6.00 (1H, br. s.), 3.91 (2H, d), 1.58 (6H, s), 1.29-1.39 (1H, m), 0.63-0.72 (2H, m), 0.36-0.44 (2H, m) | 1.01 min, 393 [M + H]+ |

| Ex. | Structure | Name | Aniline | NMR characterization | UPLC_ipqc characterization |
|---|---|---|---|---|---|
| 55 | 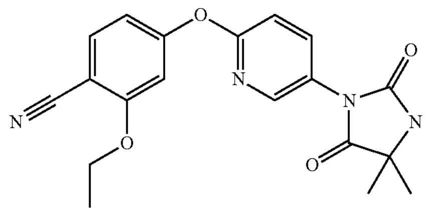 [SMILES: CCOc1cc(Oc2ccc(N3C(=O)NC(C)(C)C3=O)cn2)ccc1C#N] | 4-{[5-(4,4-dimethyl-2,5-dioxo-1-imidazolidinyl)-2-pyridinyl]oxy}-2-(ethyloxy)benzonitrile | 4-[(5-amino-2-pyridinyl)oxy]-2-(ethyloxy)benzonitrile (Intermediate 152) | $^1$H NMR (400 MHz, CDCl$_3$): δ ppm 8.32 (1H, dd), 7.87 (1H, dd), 7.58 (1H, d), 7.09 (1H, d), 6.74-6.80 (2H, m), 5.88 (1H, br. s.), 4.12 (2H, q), 1.58 (6H, s), 1.49 (3H, t) | 0.93 min, 367 [M + H]+ |
| 56 | 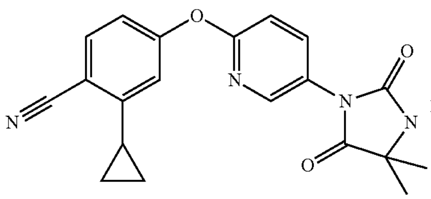 | 2-cyclopropyl-4-{[5-(4,4-dimethyl-2,5-dioxo-1-imidazolidinyl)-2-pyridinyl]oxy}benzonitrile | 4-[(5-amino-2-pyridinyl)oxy]-2-cyclopropyl-benzonitrile (Intermediate 153) | $^1$H NMR (400 MHz, DMSO-d$_6$): δ ppm 8.64 (1H, s), 8.22 (1H, d), 7.96 (1H, dd), 7.82 (1H, d), 7.25 (1H, d), 7.13 (1H, dd), 6.93 (1H, d), 2.16-2.26 (1H, m), 1.43 (6H,s), 1.09-1.18 (2 H, m), 0.86 (2H, dd) | 0.98 min, 363 [M + H]+ |
| 57 | 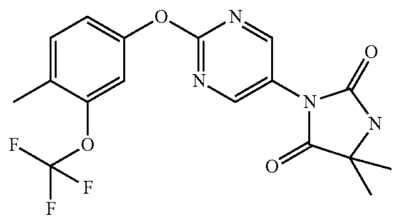 | 5,5-dimethyl-3-[2-({4-methyl-3-[(trifluoromethyl)oxy]phenyl}oxy)-5-pyrimidinyl]-2,4-imidazolidinedione | 2-({4-methyl-3-[(trifluoromethyl)oxy]phenyl}oxy)-5-pyrimidinamine (Intermediate 164) | $^1$H-NMR (400 MHz, CDCl$_3$): δ ppm 8.76 (2H, s), 7.33 (1H, d), 7.12-7.16 (1H, m), 7.12 (1H, dd), 4.68 (1H, br. s.), 2.36 (3H, s), 1.61 (6H,s). | 1.08 min, 397 [M + H]+. |
| 58 | 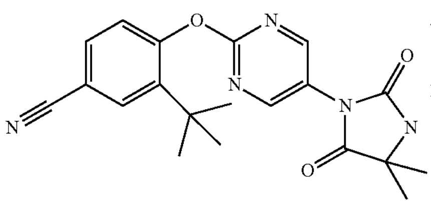 | 4-{[5-(4,4-dimethyl-2,5-dioxo-1-imidazolidinyl)-2-pyrimidinyl]oxy}-3-(1,1-dimethylethyl)benzonitrile | 4-[(5-amino-2-pyrimidinyl)oxy]-3-(1,1-dimethylethyl)benzonitrile (Intermediate 163) | $^1$H-NMR (400 MHz, DMSO-d$_6$): δ ppm 8.80 (2H, s) 7.79 (1H, d) 7.58 (1H, dd) 7.16 (1H, d) 5.59 (1H, br. s.) 1.62 (6H, s) 1.41 (9H, s) | 1.03 min. 380 [M + H]+. |
| 59 | 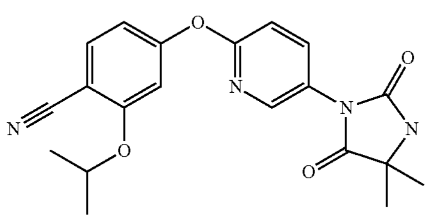 [SMILES: CC(C)Oc1cc(Oc2ccc(N3C(=O)NC(C)(C)C3=O)cn2)ccc1C#N] | 4-{[5-(4,4-dimethyl-2,5-dioxo-1-imidazolidinyl)-2-pyridinyl]oxy}-2-[(1-methylethyl)oxy]benzonitrile | 4-[(5-amino-2-pyridinyl)oxy]-2-[(1-methylethyl)oxy]benzonitrile (Intermediate 156) | $^1$H-NMR (400 MHz, DMSO-d$_6$): δ ppm 8.66 (1H, s), 8.23 (1H, d), 7.96 (1H, dd), 7.76 (1H, d), 7.27 (1H, d), 7.16 (1H, d), 6.83 (1H, dd), 4.74-4.85 (1H, m), 1.42 (6H, s), 1.31 (6H, d) | 0.98 min, 381 [M + H]+ |

Example 60

4-({5-[(4R)-4-ethyl-4-methyl-2,5-dioxo-1-imidazolidinyl]-2-pyridinyl}oxy)-2-[(1-methylethyl)oxy]benzonitrile

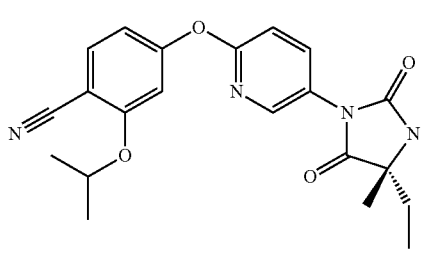 [SMILES: CC[C@@]1(C)NC(=O)N(c2ccc(Oc3ccc(C#N)c(OC(C)C)c3)nc2)C1=O]

In a 2-necked round bottomed flask, bis(trichloromethyl) carbonate (174.5 mg, 0.59 mmol) was dissolved in DCM (10 mL). N,N-diethylethanamine (0.651 mL, 3.74 mmol) was added therein. The obtained solution was cooled to 0° C. In a separate vial, 4-[(5-amino-2-pyridinyl)oxy]-2-[(1-methylethyl)oxy]benzonitrile (Intermediate 156, 145.4 mg) was dissolved in DCM (10 mL). The obtained solution was added dropwise in 5 min to the chilled bis(trichloromethyl)carbonate solution. At the end of addition, at 0° C., having checked that 4-[(5-amino-2-pyridinyl)oxy]-2-[(1-methylethyl)oxy] benzonitrile completely disappeared, a solution in DCM (5 mL) of N,N-diethylethanamine (0.280 mL, 1.60 mmol) and (2R)-2-methyl-1-(methyloxy)-1-oxo-2-butanaminium chloride (Tetrahedron 1988, 44(15), 4793-6, 179.2 mg, 1.07 mmol) was added to the reaction mixture and it was stirred for 25 min. The reaction mixture was quenched with 10 mL of water, diluted with 50 mL of DCM, and acidified to pH ~5-6 using an aqueous pH 3 buffer solution. Phases were separated. The organic layer was washed with 15 mL of brine, dried over dry sodium sulphate, filtered and evaporated in vacuo to obtain a white foam. This foam was dissolved in 8 mL of methanol and Sodium methoxide (17.3 mg, 0.32 mmol) was added to the reaction mixture. The vial was sealed and shaken on PLS at 60° C. After 15 min, further sodium methoxide (17.3 mg, 0.32 mmol) was added portionwise to the reaction mixture and it was shaken up to 1.5 hr. The reaction mixture was then evaporated in vacuo using a biotage V10 apparatus to obtain a pale yellow solid. This crude was purified by Biotage SP1 (Silica; from 100:0 to 50:50 Cyclohexane/EtOAc in 10 CV) to give the title compound (116.5 mg).

$^1$H NMR (400 MHz, CDCl$_3$) δ ppm 8.30 (1H, d), 7.84 (1H, dd), 7.56 (1H, d), 7.08 (1H, d), 6.78 (1H, d), 6.75 (1H, dd), 6.10 (1H, br. s.), 4.49-4.69 (1H, m), 1.91-2.04 (1H, m), 1.71-1.83 (1H, m), 1.55 (3H, s), 1.41 (3H, s), 1.40 (3H, s), 0.98 (3H, t); UPLC_ipqc: 1.03 min, 395 [M+H]+.

The following compounds were prepared using the foregoing methodology, replacing 4-[(5-amino-2-pyridinyl)oxy]-2-[(1-methylethyl)oxy]benzonitrile (Intermediate 156) with the appropriate aniline, as described in the foregoing Reaction Schemes.

| Ex. | Structure | Name | Aniline | NMR characterization | UPLC_ipqc characterization |
|---|---|---|---|---|---|
| 61 | 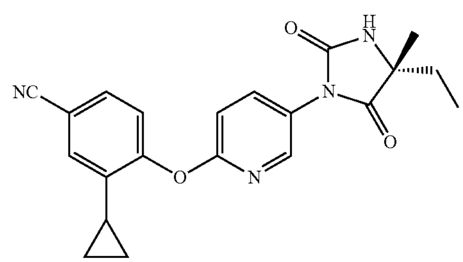 [SMILES: CC[C@@]1(C)NC(=O)N(c2ccc(Oc3ccc(C#N)cc3C3CC3)nc2)C1=O] | 3-cyclopropyl-4-({5-[(4R)-4-ethyl-4-methyl-2,5-dioxo-1-imidazolidinyl]-2-pyridinyl}oxy)benzonitrile | 4-[(5-amino-2-pyridinyl)oxy]-3-cyclopropyl-benzonitrile (Intermediate 145) | $^1$H NMR (400 MHz, CDCl$_3$) δ ppm 8.27 (1H, d), 7.85 (1H, dd), 7.52 (1H, dd), 7.30 (1H, d), 7.17 (1H, d), 7.11 (1H, d), 5.41 (1H, br. s.), 1.95-2.07 (2H, m), 1.73-1.84 (1H, m), 1.57 (3H, s), 1.00 (3H, t), 0.92-0.98 (2H, m), 0.68-0.75 (2H, m) | 1.02 min, 377 [M + H]+. |
| 62 | 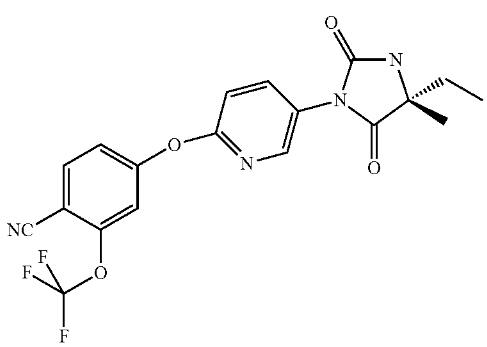 [SMILES: CC[C@@]1(C)NC(=O)N(c2ccc(Oc3ccc(C#N)c(OC(F)(F)F)c3)nc2)C1=O] | 4-({5-[(4R)-4-ethyl-4-methyl-2,5-dioxo-1-imidazolidinyl]-2-pyridinyl}oxy)-2-[(trifluoromethyl)oxy]benzonitrile | 4-[(5-amino-2-pyridinyl)oxy]-2-[(trifluoromethyl)oxy]benzonitrile (Intermediate 161) | $^1$H NMR (400 MHz, CDCl$_3$) δ ppm 8.34 (1H, d), 7.92 (1H, dd), 7.75 (1H, d), 7.29-7.32 (1H, m), 7.25 (1H, dd), 7.16 (1H, d), 5.49 (1H, br. s.), 1.96-2.08 (1H, m), 1.74-1.85 (1H, m), 1.58 (3H, s), 1.01 (3H, t) | 1.06 min, 421 [M + H]+. |
| 63 | 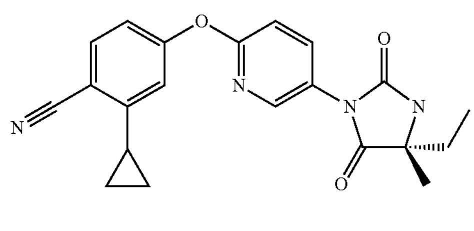 [SMILES: CC[C@@]1(C)NC(=O)N(c2ccc(Oc3ccc(C#N)c(C4CC4)c3)nc2)C1=O] | 2-cyclopropyl-4-({5-[(4R)-4-ethyl-4-methyl-2,5-dioxo-1-imidazolidinyl]-2-pyridinyl}oxy)benzonitrile | 4-[(5-amino-2-pyridinyl)oxy]-2-cyclopropyl-benzonitrile (Intermediate 153) | $^1$H NMR (400 MHz, CDCl$_3$) δ ppm 8.29 (1H, dd), 7.84 (1H, dd), 7.64 (1H, d), 7.08 (1H, d), 7.02 (1H, dd), 6.75 (1H, d), 5.47 (1H, br. s.), 2.28-2.37 (1H, m), 1.96-2.07 (1H, m), 1.73-1.84 (1H, m), 1.57 (3H, s), 1.14-1.21 (2H, m), 1.00 (3H, t), 0.79-0.85 (2H, m) | 1.02 min, 377 [M + H]+. |
| 64 | 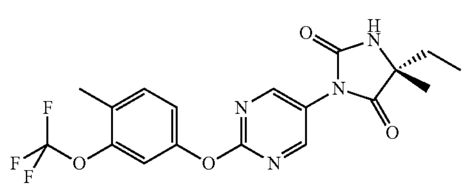 [SMILES: CC[C@@]1(C)NC(=O)N(c2cnc(Oc3ccc(C)c(OC(F)(F)F)c3)nc2)C1=O] | (5R)-5-ethyl-5-methyl-3-[2-({4-methyl-3-[(trifluoromethyl)oxy]phenyl}oxy)-5-pyrimidinyl]-2,4-imidazolidinedione | 2-({4-methyl-3-((trifluoromethyl)oxy)phenyl}oxy)-5-pyrimidin-amine (Intermediate 164) | $^1$H NMR (400 MHz, CDCl$_3$) δ ppm 8.73 (2H, s), 7.32 (1H, d), 7.12-7.16 (1H, m), 7.11 (1H, dd), 5.51 (1H, br. s.), 2.35 (3H, s), 1.95-2.07 (1H, m), 1.74-1.85 (1H, m), 1.00 (3H, t) | 1.12 min, 411 [M + H]+. |

| Ex. | Structure | Name | Aniline | NMR characterization | UPLC_ipqc characterization |
|---|---|---|---|---|---|
| 65 | 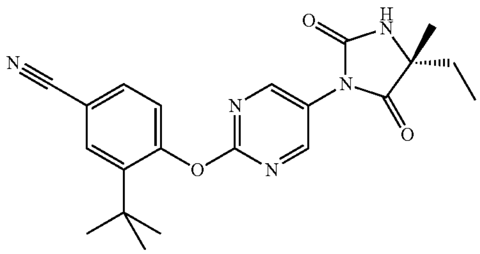 | 3-(1,1-dimethylethyl)-4-({5-[(4R)-4-ethyl-4-methyl-2,5-dioxo-1-imidazolidinyl]-2-pyrimidinyl}oxy)benzonitrile | 4-((5-amino-2-pyrimidinyl)oxy)-3-(1,1-dimethylethyl)benzonitrile (Intermediate 163) | $^1$H NMR (400 MHz, DMSO-$d_6$) δ ppm 8.78 (2H, s), 8.74 (1H, br. s.), 7.86 (1H, d), 7.78 (1H, dd), 7.41 (1H, d), 1.74-1.86 (1H, m), 1.62-1.74 (1H, m), 1.41 (3H, s), 1.33 (9H, s), 0.88 (3H, t) | 1.08 min, [M + H]+. |
| 66 | 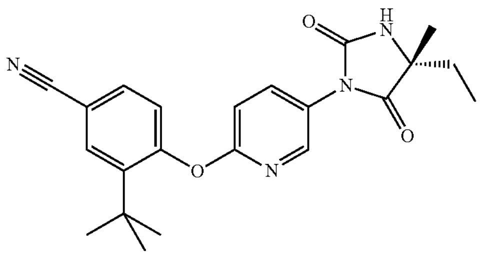 [SMILES: CC[C@@]1(C)NC(=O)N(c2ccc(Oc3ccc(C#N)cc3C(C)(C)C)nc2)C1=O] | 3-(1,1-dimethylethyl)-4-({5-[(4R)-4-ethyl-4-methyl-2,5-dioxo-1-imidazolidinyl]-2-pyridinyl}oxy)benzonitrile | 4-[(5-amino-2-pyridinyl)oxy]-3-(1,1-dimethylethyl)benzonitrile (Intermediate 146) | $^1$H NMR (400 MHz, DMSO-$d_6$) δ ppm 8.62 (1H, s), 8.21 (1H, d), 7.96 (1H, dd), 7.84 (1H, d), 7.74 (1H, dd), 7.31 (1H, d), 7.21 (1H, d), 1.74-1.86 (1H, m), 1.62-1.73 (1H, m), 1.41 (3H, s), 1.37 (9H, s), 0.88 (3H, t) | 1.13 min, 393 [M + H]+. |

Example 67

4-{[4-(4,4-dimethyl-2,5-dioxo-1-imidazolidinyl)phenyl]oxy}-2-(methyloxy)benzonitrile

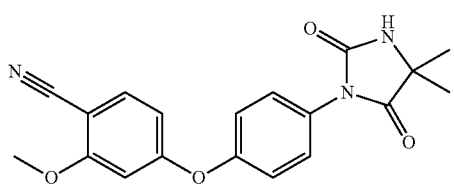 [SMILES: COc1cc(Oc2ccc(N3C(=O)NC(C)(C)C3=O)cc2)ccc1C#N]

N$^1$-(4-{[4-cyano-3-(methyloxy)phenyl]oxy}phenyl)-2-methylalaninamide (Intermediate 191, 77.0 mg) was dissolved in DCM (10 mL). Triethylamine (0.218 mL, 1.57 mmol) was added and the obtained mixture was cooled at 0° C. Bis(trichloromethyl)carbonate (68.1 mg, 0.22 mmol) was dissolved in 5 mL of DCM and the obtained solution was added dropwise to the reaction mixture. The reaction mixture was stirred at 0° C. After 15 min, the reaction mixture was evaporated in vacuo to obtain the crude product that was purified by silica gel chromatography (from 100:0 to 50:50 Cyclohexane/EtOAc in 10 CV; then 50:50 Cyclohexane/EtOAc for 10 CV) to obtain 65.1 mg of the title compound as a white solid $^1$H NMR (400 MHz, DMSO-$d_6$): δ ppm 8.56 (1H, br. s.) 7.72 (1H, d) 7.42-7.49 (2H, m) 7.19-7.29 (2H, m) 6.97 (1H, d) 6.57 (1H, dd) 3.89 (3H, s) 1.41 (6H, s); UPLC_ipqc: 0.93 min, 352 [M+H]+.

The following compounds were prepared using the foregoing methodology, replacing N$^1$-(4-{[4-cyano-3-(methyloxy)phenyl]oxy}phenyl)-2-methylalaninamide (Intermediate 191) with the appropriate amine, as described in the foregoing Reaction Schemes. Final products were purified by flash-chromatography (Silica cartridge; Cyclohexane/EtOAc or other appropriate solvent system).

| Ex. | Structure | Name | Amine | NMR characterization | UPLC_ipqc characterization |
|---|---|---|---|---|---|
| 68 | 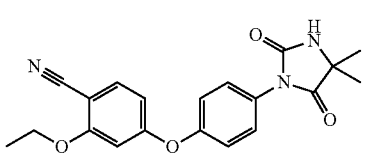 [SMILES: CCOc1cc(Oc2ccc(N3C(=O)NC(C)(C)C3=O)cc2)ccc1C#N] | 4-{[4-(4,4-dimethyl-2,5-dioxo-1-imidazolidinyl)phenyl]oxy}-2-(ethyloxy)benzonitrile | N$^1$-(4-{[4-cyano-3-(ethyloxy)phenyl]oxy}phenyl)-2-methylalaninamide (Intermediate 193) | $^1$H NMR (400 MHz, CDCl$_3$): δ ppm 7.50 (1H, d) 7.45-7.50 (2H, m) 7.12-7.17 (2H, m) 6.60 (1H, d) 6.55 (1H, dd) 5.77 (1H, br. s.) 4.08 (2H, q) 1.58 (6H,s) 1.47 (3H, t) | 1.00 min, 366 [M + H]+ |

| Ex. | Structure | Name | Amine | NMR characterization | UPLC_ipqc characterization |
|---|---|---|---|---|---|
| 69 | 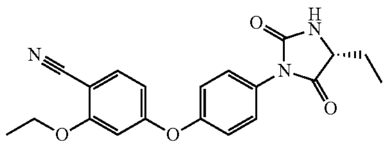 [SMILES: CCOc1cc(Oc2ccc(N3C(=O)N[C@H](CC)C3=O)cc2)ccc1C#N] | 4-({4-[(4R)-4-ethyl-2,5-dioxo-1-imidazolidinyl]phenyl}oxy)-2-(ethyloxy)benzonitrile | (2R)-2-amino-N-(4-{[4-cyano-3-(ethyloxy)phenyl]oxy}phenyl)butanamide (Intermediate 194) | $^1$H NMR (400 MHz, CDCl$_3$): δ ppm 7.49 (1H, d), 7.43-7.48 (2H, m), 7.12-7.18 (2H, m), 6.61 (1H, d), 6.55 (1H, dd), 5.64 (1H, br. s.), 4.22 (1H, ddd), 4.09 (2H, q), 1.98-2.09 (1H, m), 1.88-1.98 (1H, m), 1.48 (3H, t), 1.08 (3H, t) | 1.00 min, 366 [M + H]+. |
| 70 | 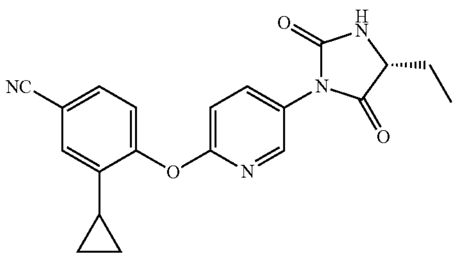 [SMILES: CC[C@H]1NC(=O)N(c2ccc(Oc3ccc(C#N)cc3C3CC3)nc2)C1=O] | 3-cyclopropyl-4-({5-[(4R)-4-ethyl-2,5-dioxo-1-imidazolidinyl]-2-pyridinyl}oxy)benzonitrile | (2R)-2-amino-N-{6-[(4-cyano-2-cyclopropyl-phenyl)oxy]-3-pyridinyl}butanamide (Intermediate 188) | $^1$H NMR (400 MHz, DMSO-d$_6$): δ ppm 8.64 (1H, br. s), 8.14-8.11 (1H, m), 7.96-7.84 (1H, m), 7.71-7.66 (1H, m), 7.52 (1H, br. s), 7.29 (2H, d), 4.24-4.18 (1H, m), 1.97-1.89 (1H, m), 1.86-1.78 (1H, m), 1.75-1.67 (1H, m), 0.95 (3H, t), 0.91-0.85 (2H, m), 0.81-0.75 (2H, m) | 0.98 min, 363 [M + H]+. |
| 71 | 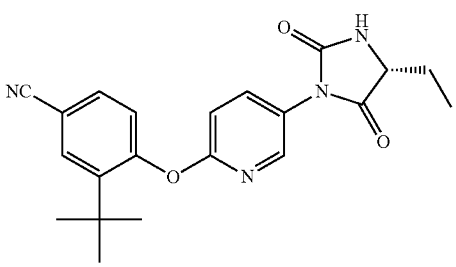 [SMILES: CC[C@H]1NC(=O)N(c2ccc(Oc3ccc(C#N)cc3C(C)(C)C)nc2)C1=O] | 3-(1,1-dimethylethyl)-4-({5-[(4R)-4-ethyl-2,5-dioxo-1-imidazolidinyl]-2-pyridinyl}oxy)benzonitrile | (2R)-2-amino-N-(6-{[4-cyano-2-(1,1-dimethylethyl)phenyl]oxy}-3-pyridinyl)butanamide (Intermediate 189) | $^1$H NMR (400 MHz, DMSO-d$_6$): δ ppm 8.64 (1H, br. s), 8.19 (1H, br. s), 7.96-7.90 (1H, m), 7.82 (1H, br. s), 7.76-7.68 (1H, m), 7.30 (1H, d), 7.19 (1H, d), 4.25-4.17 (1H, m), 1.86-1.77 (1H, m), 1.76-1.66 (1H, m), 1.35 (9H, s), 0.95 (3H, t) | 1.10 min, 379 [M + H]+. |
| 72 | 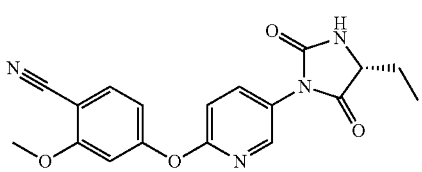 [SMILES: CC[C@H]1NC(=O)N(c2ccc(Oc3ccc(C#N)c(OC)c3)nc2)C1=O] | 4-({5-[(4R)-4-ethyl-2,5-dioxo-1-imidazolidinyl]-2-pyridinyl}oxy)-2-(methyloxy)benzonitrile | (2R)-2-amino-N-(6-{[4-cyano-3-(methyloxy)phenyl]oxy}-3-pyridinyl)butanamide (Intermediate 190) | $^1$H NMR (400 MHz, CDCl$_3$): δ ppm 8.30 (1H, dd) 7.85 (1H, dd) 7.58 (1H, dt) 7.10 (1H, dd) 6.74-6.84 (2H, m) 6.22 (1H, br. s.) 4.20-4.26 (1H, m) 3.92 (3H, s) 1.97-2.08 (1H, m) 1.85-1.97 (1H, m) 1.07 (3H, t) | 0.87 min, 353 [M + H]+. |
| 73 | 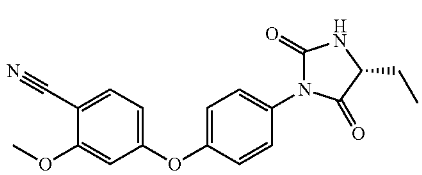 [SMILES: CC[C@H]1NC(=O)N(c2ccc(Oc3ccc(C#N)c(OC)c3)cc2)C1=O] | 4-({4-[(4R)-4-ethyl-2,5-dioxo-1-imidazolidinyl]phenyl}oxy)-2-(methyloxy)benzonitrile | (2R)-2-amino-N-[4-{[4-cyano-3-(methyloxy)phenyl]oxy}phenyl]butanamide (Intermediate 192) | $^1$H NMR (400 MHz, CDCl$_3$): δ ppm 7.50 (1H, d) 7.43-7.48 (2H, m) 7.12-7.19 (2H, m) 6.64 (1H, d) 6.56 (1H, dd) 6.08 (1H, br. s.) 4.18-4.24 (1H, m) 3.89 (3H, s) 1.98-2.08 (1H, m) 1.87-1.98 (1H, m) 1.08 (3H, t) | 0.94 min, 352 [M + H]+. |

| Ex. | Structure | Name | Amine | NMR characterization | UPLC_ipqc characterization |
|---|---|---|---|---|---|
| 74 | 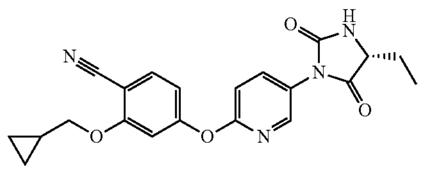 [SMILES: CC[C@H]1NC(=O)N(c2ccc(Oc3ccc(C#N)c(OCC4CC4)c3)nc2)C1=O] | 2-[(cyclopropyl-methyl)oxy]-4-({5-[(4R)-4-ethyl-2,5-dioxo-1-imidazolidinyl]-2-pyridinyl}oxy)benzonitrile | (2R)-2-amino-N-[6-({4-cyano-3-[(cyclopropyl-methyl)oxy]phenyl}oxy)-3-pyridinyl]butanamide (Intermediate 195) | ¹H NMR (400 MHz, CDCl₃): δ ppm 8.29 (1H, dd), 7.83 (1H, dd), 7.58 (1H, dd), 7.09 (1H, dd), 6.75-6.79 (2H, m), 6.07 (1H, br. s.), 4.23 (1H, ddd), 3.91 (2H, d), 1.97-2.08 (1H, m), 1.86-1.98 (1H, m), 1.25-1.37 (1H, m), 1.07 (3H, t), 0.62-0.72 (2H, m), 0.35-0.46 (2H, m) | 1.01 min. 393 [M + H]+. |
| 75 | 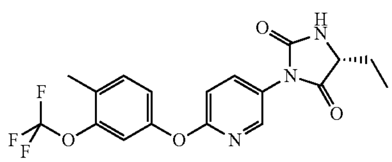 [SMILES: CC[C@H]1NC(=O)N(c2ccc(Oc3ccc(C)c(OC(F)(F)F)c3)nc2)C1=O] | (5R)-5-ethyl-3-[6-({4-methyl-3-[(trifluoromethyl)oxy]phenyl}oxy)-3-pyridinyl]-2,4-imidazolidinedione | (2R)-2-amino-N-[6-({4-methyl-3-[(trifluoromethyl)oxy]phenyl}oxy)-3-pyridinyl]butanamide (Intermediate 196) | ¹H NMR (400 MHz, CDCl₃): δ ppm 8.26 (1H, dd), 7.77 (1H, dd), 7.28 (1H, m), 7.05-7.10 (1H, m), 7.00-7.05 (2H, m), 6.36 (1H, br. s.), 4.21 (1H, ddd), 2.32 (3H, s), 1.96-2.05 (1H, m), 1.84-1.96 (1H, m), 1.06 (3H, t) | 1.14 min, 396 [M + H]+. |
| 76 | 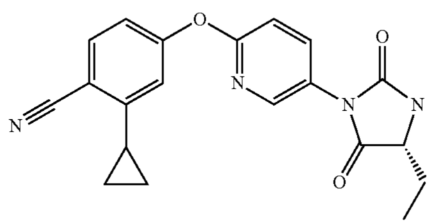 [SMILES: CC[C@H]1NC(=O)N(c2ccc(Oc3ccc(C#N)c(C4CC4)c3)nc2)C1=O] | 2-cyclopropyl-4-({5-[(4R)-4-ethyl-2,5-dioxo-1-imidazolidinyl]-2-pyridinyl}oxy)benzonitrile | (2R)-2-amino-N-{6-[(4-cyano-3-cyclopropyl-phenyl)oxy]-3-pyridinyl}butanamide (Intermediate 197) | ¹H-NMR (400 MHz, DMSO-d₆): δ ppm 8.63 (1H, br. s.), 8.19 (1H, d), 7.92 (1H, dd), 7.82 (1H, d), 7.25 (1H, d), 7.13 (1H, dd), 6.93 (1H, d), 4.19-4.26 (1H, m), 2.16-2.26 (1H, m), 1.78-1.88 (1H, m), 1.67-1.77 (1H, m), 1.09-1.18 (2H, m), 0.97 (3H, t), 0.82-0.90 (2H, m) | 0.99 min, 363 [M + H]+ |
| 77 | 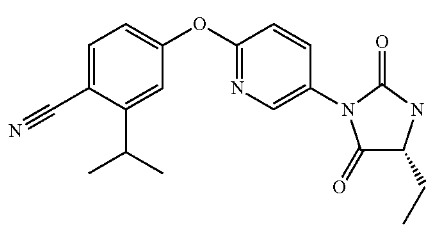 [SMILES: CC[C@H]1NC(=O)N(c2ccc(Oc3ccc(C#N)c(C(C)C)c3)nc2)C1=O] | 4-({5-[(4R)-4-ethyl-2,5-dioxo-1-imidazolidinyl]-2-pyridinyl}oxy)-2-(1-methylethyl)benzonitrile | (2R)-2-amino-N-(6-{[4-cyano-3-(1-methylethyl)phenyl]oxy}-3-pyridinyl)butanamide (Intermediate 198) | ¹H-NMR (400 MHz, DMSO-d₆): δ ppm 8.66 (1H, s) 8.19 (1H, d) 7.93 (1H, dd) 7.84 (1H, d) 7.36 (1H, d) 7.28 (1H, dd) 7.18 (1H, dd) 4.19-4.25 (1H, m) 3.21-3.30 (1H, m) 1.77-1.87 (1H, m) 1.65-1.76 (1H, m) 1.27 (6H, d) 0.96 (3H, t) | 1.03 min, 365 [M + H]+ |
| 78 | 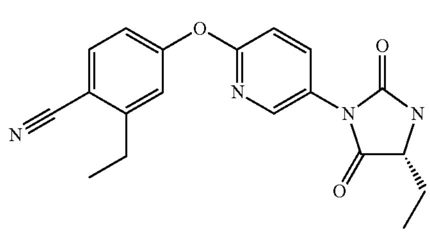 [SMILES: CCc1cc(Oc2ccc(N3C(=O)N[C@H](CC)C3=O)cn2)ccc1C#N] | 4-({5-[(4R)-4-ethyl-2,5-dioxo-1-imidazolidinyl]-2-pyridinyl}oxy)-2-(1-methylethyl)benzonitrile | (2R)-2-amino-N-{6-[(4-cyano-3-ethylphenyl)oxy]-3-pyridinyl}butanamide (Intermediate 199) | ¹H-NMR (400 MHz, DMSO-d₆): δ ppm 8.66 (1H, s) 8.19 (1H,dd) 7.93 (1H, dd) 7.85 (1H, d) 7.32 (1H, d) 7.28 (1H, dd) 7.19 (1H, dd) 4.19-4.25 (1H, m) 2.82 (2H, q) 1.77-1.88 (1H, m) 1.65-1.77 (1H, m) 1.23 (3H, t) 0.96 (3H, t) | 0.98 min, 351 [M + H]+ |

| Ex. | Structure | Name | Amine | NMR characterization | UPLC_ipqc characterization |
|---|---|---|---|---|---|
| 79 | 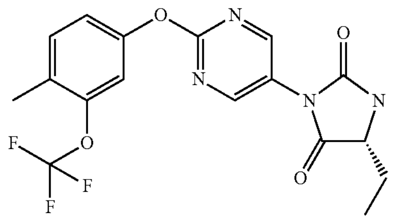 [SMILES: CC[C@H]1NC(=O)N(c2cnc(Oc3ccc(C)c(OC(F)(F)F)c3)nc2)C1=O] | (5R)-5-ethyl-3-[2-({4-methyl-3-[(trifluoromethyl)oxy]phenyl}oxy)-5-pyrimidinyl]-2,4-imidazolidinedione | (2R)-2-amino-N-[2-({4-methyl-3-[(trifluoromethyl)oxy]phenyl}oxy)-5-pyrimidinyl]butanamide (Intermediate 200) | ¹H-NMR (400 MHz. DMSO-d₆): δ ppm 8.76 (1 H, br. s.), 8.70 (2 H, s), 7.48 (1 H, d), 7.33-7.37 (1 H, m), 7.26 (1 H, dd), 4.20-4.27 (1 H, m), 2.31 (3 H, s), 1.77-1.90 (1 H, m), 1.65-1.77 (1 H, m), 0.98 (3H, t) | 1.08 min, 397 [M + H]+ |
| 80 | 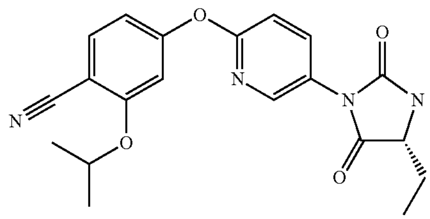 [SMILES: CC[C@H]1NC(=O)N(c2ccc(Oc3ccc(C#N)c(OC(C)C)c3)nc2)C1=O] | 4-({5-[(4R)-4-ethyl-2,5-dioxo-1-imidazolidinyl]-2-pyridinyl}oxy)-2-[(1-methylethyl)oxy]benzonitrile | (2R)-2-amino-N-[6-({4-cyano-3-[(1-methylethyl)oxy]phenyl}oxy)-3-pyridinyl]butanamide (Intermediate 201) | ¹H-NMR (400 MHz, DMSO-d₆): δ ppm 8.65 (1H, s), 8.20 (1H, d), 7.93 (1H, dd), 7.76 (1H, d), 7.27 (1H, d), 7.16 (1H, d), 6.84 (1H, dd), 4.74-4.85 (1H, m), 4.17-4.26 (1H, m), 1.76-1.89 (1H, m), 1.65-1.76 (1H, m), 1.31 (6H, d), 0.96 (3H, t) | 1.00 min, 381 [M + H]+. |
| 81 | 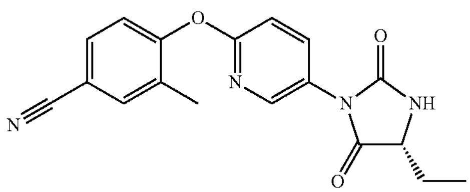 [SMILES: CC[C@H]1NC(=O)N(c2ccc(Oc3ccc(C#N)cc3C)nc2)C1=O] | 4-({5-[(4R)-4-ethyl-2,5-dioxo-1-imidazolidinyl]-2-pyridinyl}oxy)-3-methylbenzonitrile | (2R)-2-amino-N-{6-[(4-cyano-2-methylphenyl)oxy]-3-pyridinyl}butanamide (Intermediate 202) | ¹H NMR (400 MHz, DMSO-d₆): δ ppm 8.64 (1H, s), 8.08-8.14 (1H, m), 7.88-7.95 (1H, m), 7.86 (1H, s), 7.70-7.77 (1H, m), 7.28 (2H, t), 4.15-4.26 (1H, m), 2.17 (3H, s), 1.62-1.89 (2H, m), 0.95 (3H, t) | 0.90 min, 337 [M + H]+ |
| 82 | 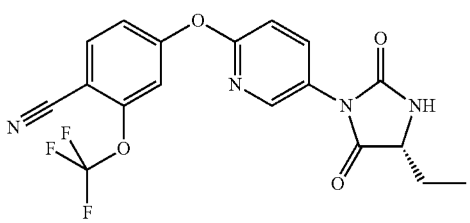 [SMILES: CC[C@H]1NC(=O)N(c2ccc(Oc3ccc(C#N)c(OC(F)(F)F)c3)nc2)C1=O] | 4-({5-[(4R)-4-ethyl-2,5-dioxo-1-imidazolidinyl]-2-pyridinyl}oxy)-2-[(trifluoromethyl)oxy]benzonitrile | (2R)-2-amino-N-[6-({4-cyano-3-[(trifluoromethyl)oxy]phenyl}oxy)-3-pyridinyl]butanamide (Intermediate 203) | ¹H NMR (400 MHz, DMSO-d₆): δ ppm 8.67 (1H, s), 8.19-8.26 (1H, m), 8.14 (1H, d), 7.94-8.02 (1H, m), 7.66 (1H, s), 7.43-7.51 (1H, m), 7.36 (1H, d), 4.18-4.27 (1H, m), 1.63-1.91 (2H, m), 0.96 (3H, t) | 1.02 min, 407 [M + H]+, 405 [M − H]− |
| 83 | 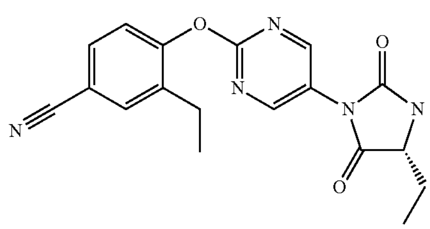 [SMILES: CCc1cc(C#N)ccc1Oc1ncc(N2C(=O)N[C@H](CC)C2=O)cn1] | 3-ethyl-4-({5-[(4R)-4-ethyl-2,5-dioxo-1-imidazolidinyl]-2-pyrimidinyl}oxy)benzonitrile | (2R)-2-amino-N-{2-[(4-cyano-2-ethylphenyl)oxy]-5-pyrimidinyl}butanamide (Intermediate 204) | ¹H-NMR (400 MHz, DMSO-d₆): δ ppm 8.78 (1H, s) 8.73 (2H, s) 7.91 (1H,d) 7.79 (1H, dd) 7.45 (1H, d) 4.21-4.27 (1H, m) 2.53-2.58 (2H, m) 1.77-1.88 (1H, m) 1.66-1.76 (1H, m) 1.12 (3H, t) 0.97 (3H, t) | 0.93 min, 352 [M + H]+ |
| 84 | 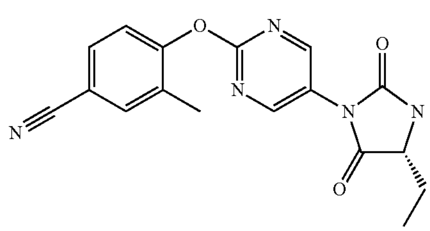 [SMILES: CC[C@H]1NC(=O)N(c2cnc(Oc3ccc(C#N)cc3C)nc2)C1=O] | 4-({5-[(4R)-4-ethyl-2,5-dioxo-1-imidazolidinyl]-2-pyrimidinyl}oxy)-3-methylbenzonitrile | (2R)-2-amino-N-{2-[(4-cyano-2-melhylphenyl)oxy]-5-pyrimidinyl}butanamide (Intermediate 205) | ¹H-NMR (400 MHz, DMSO-d₆): δ ppm 8.77 (1H, s) 8.73 (2H, s) 7.91 (1H,d) 7.79 (1H, dd) 7.45 (1H, d) 4.21-4.27 (1H, m) 2.16 (3H, s) 1.77-1.88 (1H, m) 1.65-1.77 (1H, m) 0.97 (3H,t) | 0.85 min. 338 [M + H]+ |

| Ex. | Structure | Name | Amine | NMR characterization | UPLC_ipqc characterization |
|---|---|---|---|---|---|
| 85 | 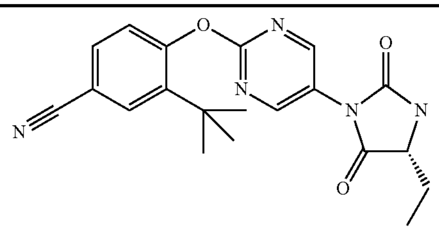 | 3-(1,1-dimethylethyl)-4-({5-[(4R)-4-ethyl-2,5-dioxo-1-imidazolidinyl]-2-pyrimidinyl}oxy)benzonitrile | (2R)-2-amino-N-(2-{[4-cyano-2-(1,1-dimethylethyl)phenyl]oxy}-5-pyrimidinyl)butanamide (Intermediate 206) | $^1$H-NMR (400 MHz. DMSO-$d_6$): δ ppm 8.78 (1H, br. s.), 8.75 (2H, s), 7.86 (1H, d), 7.79 (1H, dd), 7.42 (1H, d), 4.21-4.27 (1H, m), 1.78-1.89 (1H, m), 1.65-1.78 (1H, m), 1.33 (9H, s), 0.98 (3H, t) | 1.03 min, 380 [M + H]+ |

Example 86

4-({5-[(4R)-4-ethyl-4-methyl-2,5-dioxo-1-imidazolidinyl]-2-pyridinyl}oxy)-2-(1-methylethyl)benzonitrile

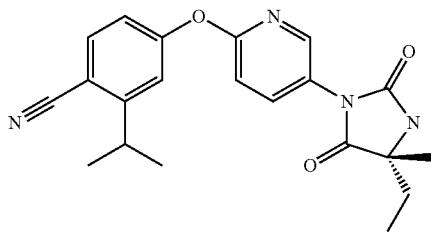 [SMILES: CC[C@@]1(C)NC(=O)N(c2ccc(Oc3ccc(C#N)c(C(C)C)c3)nc2)C1=O]

To a solution of 4-({5-[(4R)-4-ethyl-4-methyl-2,5-dioxo-1-imidazolidinyl]-2-pyridinyl}oxy)-2-(1-methylethenyl) benzonitrile (Intermediate 207, 98 mg) in MeOH (10 mL) Pd 10% w/w on activate carbon (10 mg) was added and the reaction mixture was stirred for 1 hour under H$_2$ atmosphere (P=1 atm). The catalyst was filtered off and the solvent removed under reduced pressure. The residue was purified by flash chromatography on silica gel (SNAP 10 g) eluting from 75:25 to 40:60 cyclohexane/ethyl acetate affording the title compound (80 mg) as white solid.

$^1$H NMR (400 MHz, DMSO-$d_6$) δ ppm 8.61 (1H, br. s.), 8.21 (1H, d), 7.94 (1H, dd), 7.84 (1H, d), 7.35 (1H, d), 7.27 (1H, d), 7.18 (1H, dd), 3.21-3.30 (1H, m), 1.73-1.85 (1H, m), 1.60-1.72 (1H, m), 1.40 (3H, s), 1.28 (6H, d), 0.88 (3H, t); UPLC_ipqc: 1.08 min, 379 [M+H]+.

Reference Intermediate 208

1,3-bis{[(methyloxy)methyl]oxy}benzene

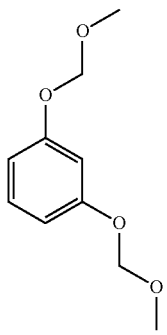

To a solution of 1,3-benzenediol (1.5 g, 13.62 mmol) in dry N,N-Dimethylformamide (13.62 ml) at 0° C. sodium hydride (0.981 g, 40.9 mmol) was added and the reaction mixture was stirred for 15 minutes at the same temperature. MOM-Cl (3.10 ml, 40.9 mmol) was quickly added and the reaction mixture was stirred for 1 hour while the temperature was allowed to reach room temperature. The reaction was quenched with brine (20 ml) and extracted with ethyl acetate (3×50 ml). The organic layer was washed with brine (2×30 ml), dried over sodium sulphate, filtered and evaporated and the residue was purified by flash chromatography (Biotage system) on silica gel using a 50 g SNAP column and cyclohexane to cyclohexane/ethyl acetate 8:2 as eluents affording the title compound (1.59 g, 8.02 mmol) as a colourless oil.

1H NMR (400 MHz, DMSO): δ ppm 7.16-7.23 (1H, d), 6.69-6.64 (3H, m), 5.17 (4H, s), 3.38 (6H, s).

Reference Intermediate 209 ethyl (2,6-bis{[(methyloxy)methyl]oxy}phenyl)(oxo)acetate

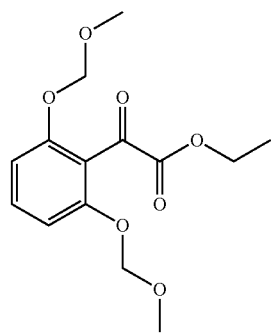 [SMILES: CCOC(=O)C(=O)c1c(OCOC)cccc1OCOC]

To a solution of 1,3-bis{[(methyloxy)methyl]oxy}benzene (Reference Intermediate 208, 2.19 g) in dry tetrahydrofuran (10 ml) at room temperature BuLi 1.6M in hexane (8.29 ml, 13.26 mmol) was added and the reaction mixture was stirred for 30 minutes at the same temperature. The mixture was cooled to −78° C. and it was added (via cannulation) to a solution of ethyl chloro(oxo)acetate (2.263 g, 16.57 mmol) in dry tetrahydrofuran (10 ml) at −78° C. The reaction mixture was stirred at −78° C. for 30 minutes. The reaction was quenched with an aqueous saturated solution of ammonium chloride (10 ml) and extracted with ethyl acetate (2×30 ml). Combined organic layers were dried over sodium sulphate, filtered and evaporated. The residue was purified by flash chromatography (Biotage system) on silica gel using a 100 g SNAP column and cyclohexane to cyclohexane/ethyl acetate 8:2 as eluent affording the title compound as a light yellow oil (1.75 g).

1H NMR (400 MHz, DMSO): δ ppm 7.46 (1H, t), 6.87 (2H, d), 5.20 (4H, s), 4.29 (2H, q), 3.34 (6H, s), 1.27 (3H, t).

Reference Intermediate 210 ethyl 2-(2,6-bis{[(methyloxy)methyl]oxy}phenyl)-2-propenoate

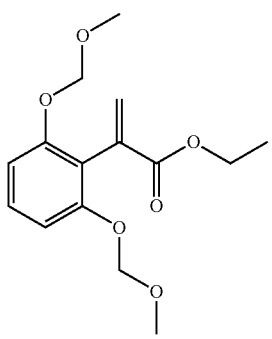 [SMILES: C=C(C(=O)OCC)c1c(OCOC)cccc1OCOC]

To a suspension of methyltriphenylphosphonium bromide (3.13 g, 8.75 mmol) in dry tetrahydrofuran (30 ml) at 0° C. KHMDS (1.745 g, 8.75 mmol) was slowly added and the reaction mixture was stirred for 15 minutes at 0° C. and for 45 minutes at room temperature. The reaction mixture was cooled to 0° C. and a solution of ethyl (2,6-bis{[(methyloxy)methyl]oxy}phenyl)(oxo)acetate (Reference Intermediate 209, 1.74 g) in dry tetrahydrofuran (10 mL) was slowly added and the reaction mixture was stirred for 2 hours at 0° C. The reaction was quenched with an aqueous saturated solution of ammonium chloride (10 ml), diluted with water (20 ml) and extracted with ethyl acetate (2×50 ml). The organic layer was dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound as a colourless oil (1.37 g).

1H NMR (400 MHz, DMSO-d6): δ ppm 7.21 (1H, t), 6.78 (2H, d), 6.44 (1H, d), 5.74 (1H, d), 5.12 (4H, s), 4.12 (2H, q), 3.32 (6H, s), 1.17 (3H, t).

Reference Intermediate 211 ethyl 1-(2,6-bis{[(methyloxy)methyl]oxy}phenyl)cycloproanecarboxylate

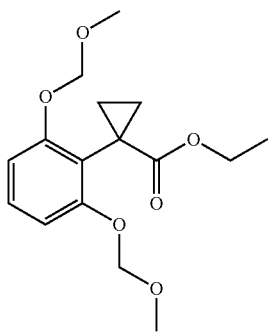 [SMILES: CCOC(=O)C1(c2c(OCOC)cccc2OCOC)CC1]

To a solution of trimethylsulfoxonium iodide (1.805 g, 8.20 mmol) in dry dimethyl sulfoxide (20 mL) sodium hydride 60% dispersion in mineral oil (0.310 g, 7.75 mmol) was added and the reaction mixture was stirred for 1 hour at room temperature. A solution of ethyl 2-(2,6-bis{[(methyloxy)methyl]oxy}phenyl)-2-propenoate (Reference Intermediate 210, 1.35 g) in dry dimethyl sulfoxide (10 mL) was slowly added and the reaction mixture was stirred for 1 hour at room temperature. The reaction was quenched with an aqueous saturated solution of ammonium chloride (10 ml), diluted with water (20 ml) and extracted with ethyl acetate (2×50 ml). The organic layer was washed with water (50 ml), dried over sodium sulphate, filtered and evaporated. The residue was purified by flash chromatography (Biotage system) on silica gel using a 50 g SNAP column and cyclohexane to cyclohexane/ethyl acetate 8:2 as eluents affording the title as a colourless oil (1.14 g).

1H NMR (400 MHz, DMSO): δ ppm 7.15 (1H, t), 6.71 (2H, d), 5.18 (4H, s), 3.97 (2H, q), 3.36 (6H, s), 1.53-1.58 (2H, m), 1.09-1.14 (2H, m), 1.04 (3H, t).

Reference Intermediate 212

2-[1-(hydroxymethyl)cyclopropyl-3-{(methyloxy)methyl]oxy}phenol

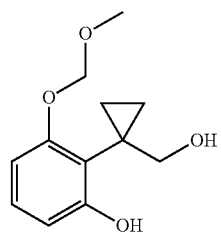 [SMILES: COCOc1cccc(O)c1C1(CO)CC1]

To a solution of ethyl 1-(2,6-bis{[(methyloxy)methyl]oxy}phenyl)cyclopropanecarboxylate (Reference Intermediate 211, 490 mg) in ethanol (10 ml) HCl 2N in water (0.789 mL, 1.579 mmol) was added and the reaction mixture was stirred overnight at 50° C. Toluene (20 mL) was added and the combined solvents were removed under reduced pressure. The residue was re-suspended in toluene (20 ml) and the solvent evaporated. The obtained residue was dissolved in dry tetrahydrofuran (20 ml), the mixture was cooled to 0° C. and NaH 60% dispersion in mineral oil (126 mg, 3.16 mmol) was added and the reaction mixture was stirred for 30 minutes at the same temperature. MOM-Cl (0.120 mL, 1.579 mmol) was then added and the reaction mixture was stirred for 2 hours at 0° C. LiAlH4 (1M in THF, 1.579 ml, 1.579 mmol) was added and the reaction mixture was further stirred for 1 hour at the same temperature. The reaction was quenched with an aqueous saturated solution of ammonium chloride (10 ml), diluted with water (10 ml) and extracted with ethyl acetate (2×50 ml). Combined organic layers were dried over sodium sulphate, filtered and evaporated and the residue was purified by flash chromatography (Biotage system) on silica gel using a 25 g SNAP column and cyclohexane to cyclohexane/ethyl acetate 7:3 as eluents affording the title compound as a colourless oil (191 mg).

1H NMR (400 MHz, DMSO): δ ppm 8.90 (1H, br.s) 6.96 (1H, t), 6.50 (1H, d), 6.45 (1H, d), 5.16 (2H, s), 4.93 (1H, br.s), 3.45 (2H, s), 3.40 (3H, s), 0.86-0.93 (2H, m), 0.56-0.62 (2H, m); UPLC: 0.59 min, 225 [M+H]+.

Reference Intermediate 213

4-{[(methyloxy)methyl]oxy}spiro[1-benzofuran-3,1'-cyclopropane]

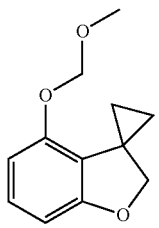

To a solution of 2-[1-(hydroxymethyl)cyclopropyl]-3-{[(methyloxy)methyl]oxy}phenol (Reference Intermediate 212, 190 mg) in dry tetrahydrofuran (10 ml) triphenylphosphine (333 mg, 1.271 mmol) was added and the reaction mixture was stirred until complete dissolution of PPh3. DIAD (0.198 ml, 1.017 mmol) was then added dropwise and the reaction mixture was stirred for 30 minutes at room temperature The solvent was removed under reduced pressure. The residue was purified by flash chromatography (Biotage system) on silica gel using a 25 g SNAP column and cyclohexane to cyclohexane/ethyl acetate 9:1 as eluents affording the title compound as a light yellow oil (120 mg).

1H NMR (400 MHz, DMSO): δ ppm 6.97 (1H, t), 6.51 (1H, d), 6.43 (1H, d), 5.12 (2H, s), 4.40 (2H, s), 3.35 (3H, s), 1.43-1.48 (2H, m), 0.85-0.90 (2H, m); UPLC_B: 0.88 min, 207 [M+H]+.

Reference Intermediate 214 spiro[1-benzofuran-3,1'-cyclopropan]-4-ol

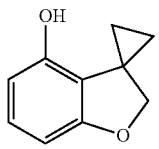

To a solution of 4-{[(methyloxy)methyl]oxy}spiro[1-benzofuran-3,1'-cyclopropane] (Reference Intermediate 213, 118 mg) in methanol (5 ml), HCl 2N in water (0.286 mL, 0.572 mmol) was added and the reaction mixture was stirred overnight at 50° C. Combined solvents were removed under reduced pressure and the residue was re-dissolved in toluen (10 ml) and the solvent was removed. The residue was purified by flash chromatography (Biotage system) on silica gel using a 10 g SNAP column and cyclohexane to cyclohexane/ethyl acetate 7:3 as eluents affording the title compound as a white solid (70 mg).

1H NMR (400 MHz, DMSO): δ ppm 9.28 (1H, s), 6.81 (1H, t), 6.24 (1H, d), 6.22 (1H, d), 4.34 (2H, s), 1.40-1.45 (2H, m), 0.77-0.82 (2H, m).

Reference Intermediate 215

5-nitro-2-(spiro[1-benzofuran-3,1'-cyclopropan]-4-yloxy)pyridine

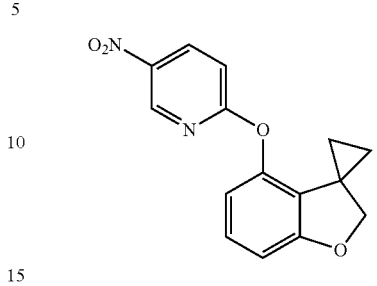

To a solution of spiro[1-benzofuran-3,1'-cyclopropan]-4-ol (Reference Intermediate 214, 70 mg) in dry N,N-dimethylformamide (2 ml) potassium carbonate (89 mg, 0.647 mmol) and then 2-chloro-5-nitropyridine (75 mg, 0.475 mmol) were added and the reaction mixture was stirred for 3 hours at 100° C. The reaction was quenched with brine (1 ml), diluted with water (2 ml) and extracted with ethyl acetate (3×10 ml). The organic layer was dried over sodium sulphate, filtered and evaporated. The residue was purified by flash chromatography (Biotage system) on silica gel using a 10 g SNAP column and cyclohexane to cyclohexane/ethyl acetate 9:1 as eluents affording the title compound as a white solid (100 mg).

1H NMR (400 MHz, DMSO): δ ppm 9.05 (1H, d), 8.63 (1H, dd), 7.23 (1H, d), 7.13 (1H, t), 6.73 (1H, d), 6.60 (1H, d), 4.45 (2H, s), 1.05-1.10 (2H, m), 0.88-0.93 (2H, m); UPLC: 0.79 min, 285 [M+H]+.

Reference Intermediate 216

6-(spiro[1-benzofuran-3,1'-cyclopropan]-4-yloxy)-3-pyridinamine

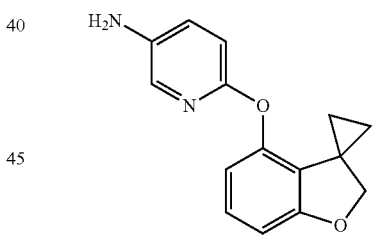

To a solution of 5-nitro-2-(spiro[1-benzofuran-3,1'-cyclopropan]-4-yloxy)pyridine (Reference Intermediate 215, 99 mg) in tetrahydrofuran (5 ml)/water (2.5 ml) iron (97 mg, 1.741 mmol) and then ammonium chloride (93 mg, 1.741 mmol) were added and the reaction mixture was stirred for 4 hours at room temperature. The catalyst was filtered off and the residue was diluted with an aqueous saturated solution of NaHCO3 (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound as a light yellow solid (85 mg).

1H NMR (400 MHz, DMSO): δ ppm 7.52 (1H, d), 7.06 (1H, dd), 6.97 (1H, t), 6.70 (1H, d), 6.53 (1H, d), 6.23 (1H, d), 5.08 (2H, s), 4.43 (2H, s), 1.28-1.33 (2H, m), 0.86-0.91 (2H, m); UPLC: 0.62 min, 255 [M+H]+.

Reference Intermediate 217

1,1-dimethylethyl[(1R)-1-({[6-(spiro[1-benzofuran-3,1'-cyclopropan]-4-yloxy)-3-pyridinyl]amino}carbonyl)propyl]carbamate

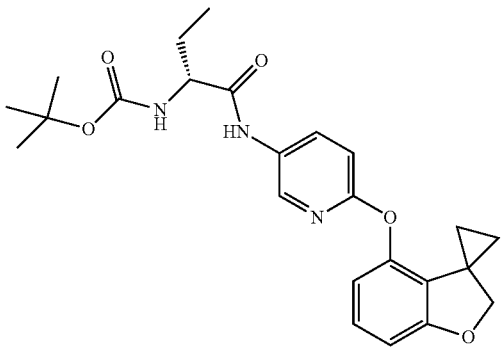 [SMILES: CC[C@@H](NC(=O)OC(C)(C)C)C(=O)Nc1ccc(Oc2cccc3c2C2(CC2)CO3)nc1]

To a solution of (2R)-2-({[(1,1-dimethylethyl)oxy]carbonyl}amino)butanoic acid (94 mg, 0.462 mmol) in dry N,N-Dimethylformamide (2 mL) DIPEA (0.115 mL, 0.661 mmol) and then TBTU (159 mg, 0.496 mmol) were added and the reaction mixture was stirred for 15 minutes at room temperature. 6-(spiro[1-benzofuran-3,1'-cyclopropan]-4-yloxy)-3-pyridinamine (Reference Intermediate 216, 84 mg) was added and the reaction mixture was stirred for 6 hours at the same temperature. The reaction was quenched with brine (2 ml), diluted with water (5 ml) and extracted with ethyl acetate (2×10 ml). The organic layer was washed with ice cold brine (2×5 ml), dried over sodium sulphate, filtered and evaporated. The residue was purified by flash chromatography (Biotage system) on silica gel using a 10 g SNAP column and cyclohexane to cyclohexane/ethyl acetate 7:3 as eluents affording the title compound as a colourless oil (130 mg).

1H NMR (400 MHz, DMSO): δ ppm 10.14 (1H, br.s), 8.32 (1H, d), 8.08 (1H, dd), 7.02-7.09 (2H, m), 6.96 (1H, d), 6.63 (1H, d), 6.42 (1H, d), 4.44 (2H, s), 3.93-4.01 (1H, m), 1.52-1.75 (2H, m), 1.39 (9H, s), 1.15-1.22 (2H, m), 0.85-0.95 (5H, m); UPLC: 0.80 min, 440 [M+H]+.

Reference Intermediate 218

(2R)-2-amino-N-[6-(spiro[1-benzofuran-3,1'-cyclopropan]-4-yloxy)-3-pyridinyl]butanamide

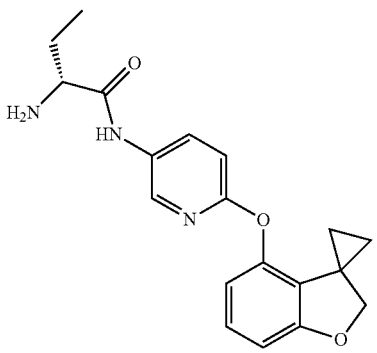 [SMILES: CC[C@@H](N)C(=O)Nc1ccc(Oc2cccc3c2C2(CC2)CO3)nc1]

To a solution of 1,1-dimethylethyl[(1R)-1-({[6-(spiro[1-benzofuran-3,1'-cyclopropan]-4-yloxy)-3-pyridinyl]amino}carbonyl)propyl]carbamate (Reference Intermediate 217, 128 mg) in dry dichloromethane (3 ml) at 0° C. TFA (0.9 mL, 11.68 mmol) was slowly added and the reaction mixture was stirred for 2 hours at the same temperature. The reaction was diluted with dichloromethane (10 ml) and an aqueous saturated solution of NaHCO3 was added while the pH was allowed to reach ~8. Two phases were separated and the aqueous layer was re-extracted with dichloromethane (10 ml). The organic layers were combined, dried over sodium sulphate, filtered and evaporated affording the title compound as a colourless oil (92 mg).

1H NMR (400 MHz, DMSO): δ ppm 8.37 (1H, d), 8.13 (1H, dd), 7.05 (1H, t), 6.95 (1H, d), 6.63 (1H, d), 6.42 (1H, d), 4.44 (2H, s), 3.24 (1H, m), 1.61-1.72 (1H, m), 1.44-1.55 (1H, m), 1.16-1.21 (2H, m), 0.91 (3H, t), 0.86-0.91 (2H, m); UPLC_B: 0.74 min, 340 [M+H]+.

Reference Intermediate 219

1,1-dimethylethyl (1,1-dimethyl-2-oxo-2-{[6-(spiro[1-benzofuran-3,1'-cyclopropan]-4-yloxy)-3-pyridinyl]amino}ethyl)carbamate

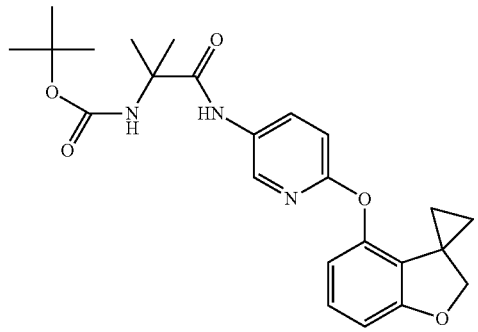 [SMILES: CC(C)(C)OC(=O)NC(C)(C)C(=O)Nc1ccc(Oc2cccc3c2C2(CC2)CO3)nc1]

To a solution of N-{[(1,1-dimethylethyl)oxy]carbonyl}-2-methylalanine (80 mg, 0.393 mmol) in dry N,N-dimethylformamide (1.5 mL) DIPEA (0.096 mL, 0.551 mmol) and then HATU (150 mg, 0.393 mmol) were added and the reaction mixture was stirred for 15 minutes at room temperature. This solution was added to a solution of 6-(spiro[1-benzofuran-3,1'-cyclopropan]-4-yloxy)-3-pyridinamine (Reference Intermediate 218, 40 mg) in dry N,N-dimethylformamide (0.5 ml) and the reaction mixture was stirred overnight at room temperature. The reaction was quenched with water (2 ml), diluted with brine (10 ml) and extracted with ethyl acetate (2×20 ml). The organic layer was dried over sium sulphqte, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound as a white solid (52 mg).

1H NMR (400 MHz, DMSO): δ ppm 9.62 (1H, br.s), 8.24-8.42 (1H, br. m), 8.05 (1H, d), 6.98-7.10 (2H, m), 6.92 (1H, d), 6.61 (1H, d), 6.40 (1H, d), 4.44 (2H, s), 1.42 (6H, s), 1.36 (9H, s), 1.15-1.21 (2H, m), 0.85-0.91 (2H, m); UPLC: 0.81 min, 440 [M+H]+.

Reference Intermediate 219

2-methyl-N¹-[6-(spiro[1-benzofuran-3,1'-cyclopropan]-4-yloxy)-3-pyridinyl]alaninamide

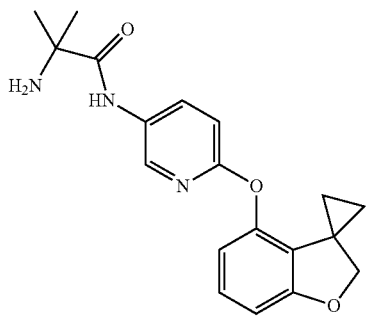 [SMILES: CC(C)(N)C(=O)Nc1ccc(Oc2cccc3c2C2(CC2)CO3)nc1]

To a solution of 1,1-dimethylethyl (1,1-dimethyl-2-oxo-2-{[6-(spiro[1-benzofuran-3,1'-cyclopropan]-4-yloxy)-3-pyridinyl]amino}ethyl)carbamate (Reference Intermediate 219, 50 mg) in dry dichloromethane (4 mL) at 0° C. TFA (1 ml, 12.98 mmol) was slowly added and the reaction mixture was stirred for 2 hours at the same temperature. The reaction was diluted with dichloromethane (10 ml) and an aqueous saturated solution of NaHCO3 was added while the pH was allowed to reach ~8. Two phases were separated and the organic layer was dried over sodium sulphate, filtered and evaporated affording the title compound (35 mg) as a colourless oil.

1H NMR (400 MHz, DMSO): δ ppm 8.40 (1H, d), 8.15 (1H, dd), 7.04 (1H, t), 6.94 (1H, d), 6.62 (1H, d), 6.41 (1H, d), 4.43 (2H, s), 1.28 (6H, s), 1.15-1.20 (2H, m), 0.86-0.91 (2H, m); UPLC: 0.56 min, 340 [M+H]+.

Reference Example 87

(5R)-5-ethyl-3-[6-(spiro[1-benzofuran-3,1'-cyclopropan]-4-yloxy)-3-pyridinyl]-2,4-imidazolidinedione

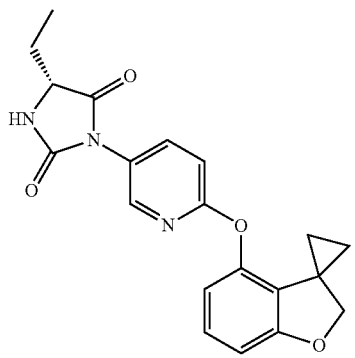 [SMILES: CC[C@H]1NC(=O)N(c2ccc(Oc3cccc4c3C3(CC3)CO4)nc2)C1=O]

To a solution of (2R)-2-amino-N-[6-(spiro[1-benzofuran-3,1'-cyclopropan]-4-yloxy)-3-pyridinyl]butanamide (Reference Intermediate 218, 90 mg) in dry dichloromethane (15 ml) TEA (0.185 ml, 1.326 mmol) was added and the reaction mixture was cooled to 0° C. A solution of triphosgene (35.4 mg, 0.119 mmol) in dry dichloromethane (5 mL) was slowly added and the reaction mixture was stirred for 30 minutes at the same temperature. The reaction was quenched with water (10 ml) and two phases were separated. The organic layer was dried over sodium sulphate, filtered and evaporated. The residue was purified by flash chromatography (Biotage system) on silica gel using a 10 g SNAP column and cyclohexane/ethyl acetate 8:2 to cyclohexane/ethyl acetate 1:1 as eluents affording the title compound (65 mg, 0.178 mmol) as a white solid.

1H NMR (400 MHz, DMSO): δ ppm 8.63 (1H, s), 8.14 (1H, d), 7.85 (1H, dd), 7.11 (1H, s), 7.09 (1H, t), 6.68 (1H, dd), 6.52 (1H, dd), 4.45 (2H, s), 4.18-1.24 (1H, m), 1.76-1.88 (1H, m), 1.64-1.76 (1H, m), 1.13-1.18 (2H, m), 0.96 (3H, t), 0.89-0.94 (2H, m); UPLC_B: 0.78 min, 366 [M+H]+.

Reference Example 88

5,5-dimethyl-3-[6-(spiro[1-benzofuran-3,1'-cyclopropan]-4-yloxy)-3-pyridinyl]-2,4-imidazolidinedione

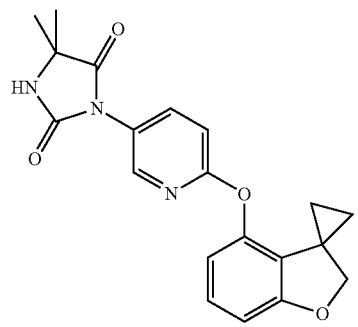 [SMILES: CC1(C)NC(=O)N(c2ccc(Oc3cccc4c3C3(CC3)CO4)nc2)C1=O]

To a solution of 2-methyl-N1-[6-(spiro[1-benzofuran-3,1'-cyclopropan]-4-yloxy)-3-pyridinyl]alaninamide (Reference Intermediate 219, 34 mg) in dry dichloromethane (6 mL) TEA (0.070 mL, 0.501 mmol) was added and the mixture was cooled to 0° C. A solution of triphosgene (13.38 mg, 0.045 mmol) in dry dichloromethane (2 mL) was slowly added and the reaction mixture was stirred for 1 hour at the same temperature. The reaction was quenched with water (3 ml) and two phases were separated. The organic layer was dried over sodium sulphate, filtered and evaporated. The residue was purified by flash chromatography (Biotage system) on silica gel using a 10 g SNAP column SNAP and cyclohexane/ethyl acetate 7:3 to cyclohexane/ethyl acetate 3:7 as eluents affording the title as a white solid (23 mg).

1H NMR (400 MHz, DMSO): δ ppm 8.63 (1H, s), 8.17 (1H, d), 7.88 (1H, d), 7.06-7.12 (2H, m), 6.67 (1H, d), 6.51 (1H, d), 4.45 (2H, s), 1.41 (6H, s), 1.12-1.17 (2H, m), 0.88-0.93 (2H, m); UPLC: 0.73 min, 366 [M+H]+.

Example 89

Biological Assay

The ability of the compounds of the invention to modulate the voltage-gated potassium channel subtypes Kv3.2/3.1 may be determined using the following assay.

Cell Biology

A stable cell line expressing human Kv3.2 channels (hKv3.2) was created by transfecting Chinese Hamster Ovary (CHO)-K1 cells with a pCIH5-hKv3.2 vector. Cells were cultured in DMEM/F12 medium supplemented by 10% Foetal Bovine Serum, 1× non-essential amino acids (Invitrogen)

and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pcDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml. All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. From the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. In all experiments, the test pulses protocol was performed in the absence (pre-read) and presence (post-read) of the test compound. Pre- and post-reads were separated by the compound addition followed by a 3 minute incubation.

Solutions and Drugs

The intracellular solution contained the following (in mM): K-gluconate 100, KCl 54, $MgCl_2$ 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): $CaCl_2$ 0.90, KCl 2.67, $KH_2PO_4$ 1.47, $MgCl.6H_2O$ 0.493, NaCl 136.9, $Na_3PO_4$ 8.06, with a pH of 7.4.

Compounds of the invention (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the invention was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MΩ) and peak current amplitude (>500pA at the voltage step of 40 mV) in the absence of compound to eliminate unsuitable cells from further analysis. Paired comparisons between pre- and post-drug additions measured for the −15 mV voltage step were used to determine the positive modulation effect of each compound. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase software. The concentration of compound required to increase currents by 50% (pEC50) was determined by fitting of the concentration-response data using a four parameter logistic function in ActivityBase.

N-cyclohexyl-N-[(7,8-dimethyl-2-oxo-1,2-dihydro-3-quinolinyl)methyl]-N'-phenylurea was obtained from ASINEX (Registry Number: 552311-06-5).

All the Example compounds were tested in the above assay and demonstrated potentiation of Kv3.1 or Kv3.2 or Kv3.1 and Kv 3.2 (herein "Kv-3.1 and/or Kv3.2") whole-cell currents of, on average, at least 20% of that observed with 50 microM N-cyclohexyl-N-[(7,8-dimethyl-2-oxo-1,2-dihydro-3-quinolinyl)methyl]-N'-phenylurea. Thus, in the recombinant cell assays of Example x, all of the Examples act as positive modulators. As used herein, a Kv3.1 and/or Kv3.2 positive modulator is a compound which has been shown to produce at least 20% potentiation of whole-cell currents mediated by human Kv3.1 and/or human Kv3.2 channels recombinantly expressed in mammalian cells, as determined using the assays described in Example 89 (Biological Assays).

A secondary analysis of the data from the assays described in Example 89 investigates the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1 or Kv3.2 currents following the start of the depolarising voltage pulse.

$$Y=(Y0-Y\max)*\exp(-K*X)+Y\max$$

Where:
Y0 is the current value at the start of the depolarising voltage pulse;
Ymax is the plateau current;
K is the rate constant, and $Tau_{act}$ is the activation time constant, which is the reciprocal of K.

Similarly, the effect of the compounds on the time taken for Kv3.1 and Kv3.2 currents to decay on closing of the channels at the end of the depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

The time constant for activation ($Tau_{act}$) has been determined for several of the compounds of the Examples. FIG. 1 shows the data for two compounds of the invention. Table 1 provides the $Tau_{act}$ data for all of the Examples analysed in this way.

FIG. 1a shows hKv3.2 currents recorded using the assay described in Example 89. Data shown are the individual currents over the period of the depolarising voltage step to −15 mV recorded from 4 different cells at two concentrations of compound (Example 19). The data are fitted by a single exponential curve (solid lines) using the fitting procedure in Prism version 5 (Graphpad Software Inc).

FIG. 1b shows hKv3.2 currents recorded using the assay described in Example 89. Data shown are the individual currents over the period of the depolarising voltage step to −15 mV recorded from 2 different cells at two concentrations of the compound of Example 71. The data are fitted by a single exponential curve (solid lines) using the fitting procedure in Prism version 5 (Graphpad Software Inc).

TABLE 1

Summary hKv3.2 data from the analysis of activation time ($Tau_{act}$). To allow for comparison between compounds, the compound concentration chosen was that which produced a similar current (~0.3 nA) at the end of the voltage pulse, with the exception of the vehicle, where maximum currents were <0.1 nA.

| Example | Concentration (µM) | $Tau_{act}$ mean (ms) | Standard Deviation | Number of experiments |
| --- | --- | --- | --- | --- |
| Vehicle | — | 7.1 | 1.7 | 6 (cells) |
| 19 | 6.25 | 9.9 | 2.2 | 5 |
| 30 | 12.5 | 7.3 | 1.8 | 4 |
| 87 | 0.2 | 50.1 | 7.5 | 5 |
| 88 | 0.4 | 19.3 | 1.0 | 4 |
| 71 | 0.2 | 23.0 | 6.2 | 4 |
| 77 | 0.8 | 9.2 | 2.3 | 2 |
| 70 | 3.1 | 13.0 | 2.3 | 2 |
| 76 | 3.1 | 7.6 | 1.9 | 2 |
| 78 | 3.1 | 8.2 | 2.0 | 2 |
| 82 | 3.1 | 10.4 | 2.8 | 2 |
| 80 | 3.1 | 9.7 | 1.0 | 2 |

As can be seen from Table 1, Examples 87, 88 and 71 markedly increase the value of $Tau_{act}$. Whereas the other compounds analysed had no marked effect on $Tau_{act}$ compared to the vehicle control (DMSO 0.5%).

Kv3.1 and Kv3.2 channels must activate and deactivate very rapidly in order to allow neurons to fire actions potentials at high frequency (Rudy and McBain, 2001, Trends in Neurosciences 24, 517-526). Slowing of activation will delay the onset of action potential repolarisation; slowing of deactivation will lead to hyperpolarising currents that reduce the excitability of the neuron and delay the time before the neuron can fire a further action potential. Together these two slowing effects will lead to a reduction rather than a facilitation of the neurons ability to fire at high frequencies. Thus compounds that have this slowing effect on the Kv3.1 and/or Kv3.2 channels will effectively behave as negative modulators of the channels, leading to a slowing of neuronal firing. This latter effect can be observed from recordings made from "fast-firing" interneurons in the cortex of rat brain, using electrophysiological techniques, in vitro (FIG. 2).

FIG. 2 shows recordings made from identified "fast-firing" interneurons in the somatosensory cortex of the mouse. The neurons are induced to fire at high frequencies by trains of high frequency depolarising current pulses at 100, 200, and 300 Hz. The ability of the neuron to fire an action potential on each pulse is determined. A spike probability of 1 on the y-axis of the graph indicates that an action potential is generated by the neuron on each of the depolarising current pulses. In the absence of drug (closed circles, n=9), the neurons maintained a spike probability of 1 up to 300 Hz. However, in the presence of Example 87 (1 microM; open circles, n=6), the neurons were unable to follow trains at the highest frequency. * p<0.05, ANOVA for repeated measures.

Therefore, although all the Examples herein identified act as positive modulators in the recombinant cell assay of Example 89, those compounds which markedly increase the value of $Tau_{act}$ reduce the ability of neurons in native tissue to fire at high speeds, and as a result act as negative modulators.

Compounds which act as positive modulators include Examples 19, 30, 77, 70, 76, 78, 82 and 80

Compounds which act as negative modulators include Examples 87, 88, and 71.

In one aspect of the invention, there is provided a Kv3 potentiating compound which is associated with a mean tau value that is not more that 2 standard deviations greater than the mean value obtained in the presence of vehicle (DMSO 0.5%), for use in the treatment of disorders where positive modulation of Kv3.1 and/or Kv3.2 channel function is beneficial, including schizophrenia, bipolar disorder, hearing disorders, sleep disorders, substance-related disorders, and epilepsy.

In one aspect of the invention, there is provided a Kv3 potentiating compound which is associated with a mean tau value that is more that 2 standard deviations greater than the mean value obtained in the presence of vehicle (DMSO 0.5%), for use in the treatment of disorders where inhibition of Kv3.1 and/or Kv3.2 channel function is beneficial, including hyperacusis, Fragile-X, and autism.

Preclinical Experiments

All in vivo studies were conducted in compliance with Project Licences obtained according to Italian law (art. 7, Legislative Decree no. 116, 27 Jan. 1992), which acknowledged the European Directive 86/609/EEC, and with the GlaxoSmithKline company policy on the care and use of laboratory animals and related codes of practice.

In the studies that follow, Compound 19 is the compound of Example 19.

Example 90

Evaluation of Compound Effects on the Firing of Interneurons in the Somatosensory Cortex of Mice, In Vitro Animals Transgenic mice [CB6-Tg (Gad1-EGFP) G42Zjh/J] were purchased from The Jackson Laboratory (Maine, USA). These mice selectively express enhanced green fluorescent protein (EGFP) in the calcium-binding protein parvalbumin (Pv)-expressing subclass of basket interneurons. EGFP expression is not reported in other interneuron classes positive for somatostatin (SOM), cholecystokinin (CCK), calretinin (CR), and VIP. These mice are therefore useful for the identification of the Pv-expressing subset of GABAergic neurons that express Kv3.1 and Kv3.2 channels and are able to fire at high frequency.

Slice Preparation

Experiments were performed on 250-μm-thick brain slices containing the somatosensory cortex. Briefly, brains were removed from deeply anaesthetized (isofluorane) 25-35 day-old Gad1-EGFP mice. Slices were cut using a DTK 1000 microslicer (DSK, Japan) in the following solution (in mM): KCl (2.5), $CaCl_2$ (0.1), $NaH_2PO_4$ (1.2), $MgCl_2$ (5), $NaHCO_3$ (26), sucrose (189) and glucose (10), kept at 2-6° C. and gassed with 95% $O_2$-5% $CO_2$. After cutting, the slices were left to equilibrate in a recovery chamber for at least one hour in an artificial cerebrospinal fluid (ACSF) containing (in mM): NaCl (120), KCl (2.5), $CaCl_2$ (2), $NaH_2PO_4$ (2.5), $MgCl_2$ (1.5), $NaHCO_3$ (26), and glucose (10), at room temperature and saturated with 95% $O_2$-5% $CO_2$.

Electrophysiological Recordings

For electrophysiological recordings, a slice was transferred to a submersion chamber mounted on the stage of an upright microscope (Axioskop, Carl Zeiss, Germany) and superfused with oxygenated ACSF. Visualization of neurons in the slices was accomplished with a 40× objective using infrared-differential interference contrast (IR-DIC) video microscopy (Hamamatsu C5985, Hamamatsu City, Japan). Parvalbumin-positive interneurons were identified by illuminating the preparation with a fluorescence lamp with a GFP-filter and switching between fluorescence and IR-DIC video microscopy. Only GFP-positive neurons were recorded. Whole-cell recordings were made using borosilicate-glass patch pipettes pulled using a Sutter P-97 electrode puller and filled with an internal solution containing (in mM): KGluconate (125), EGTA (10), HEPES (10), $MgCl_2$ (1), KCl (10) and MgATP (2); pH 7.3 adjusted with KOH. When filled with this internal solution, patch electrodes had a tip resistance of 4-7 MΩ. Recordings were carried out at room temperature (20-22° C.) using a Multiclamp 700B amplifier (Axon Instruments, Foster City, Calif., USA). Current-command protocols (indicated below) and data acquisition were performed using pClamp 10.0 software and a Digidata 1320A interface (Axon Instruments, Foster City, Calif., USA). Capacitive transients were neutralised and series-resistance was monitored continuously throughout the experiment. If it changed by >20% the cell was discarded. Data were filtered at 3 kHz and sampled at 10 kHz.

Drugs

Compounds of the invention were dissolved in DMSO (100%), tetraethylammonium (TEA) and tetrodotoxin (TTX), (both from Sigma, Italy) were dissolved in distilled water and stored at −20° C. until use. Drugs were diluted to the final concentration on the day of the experiment. The highest final concentration of DMSO used was 0.1%.

Experimental Procedure

The firing activity of the recorded interneurons was evaluated by applying long current steps at different intensities. Thus, after the formation of a giga-seal, the amplifier was switched to current-clamp mode, allowing the neuron to reach its resting membrane 45 potential. A negative current was then injected into the cell in order to obtain a resting potential close to −80 mV. From this condition, step current injections (50 pA increments, 600 ms) were applied to elicit action potentials. This protocol was repeated at least 2 times for each cell.

Online bridge-balance compensation was carried out and $R_m$ value was monitored continuously throughout the experiment.

Drug Application

Slices were incubated in the recovery chamber for at least 1 hour in the presence of either vehicle (0.1% DMSO), TEA (0.5 mM)+0.1% DMSO, or TEA (0.5 mM)+Example 19 (1 or 10 microM). After transfer of a slice to the recording chamber, the same drug condition was maintained by superfusion of the appropriate drugs in the circulating ACSF.

Data Acquisition and Analysis

Raw data were acquired using Clampex 10.0 (Molecular Devices, USA). Data were analyzed using Clampfit 10.0 software (Molecular Devices, USA). The frequency of action potential firing (expressed in Hz) in response to step current injections was calculated from the number of action potentials detected over the 600 ms step current. Values of frequency obtained for each current step in the same experimental condition and in the same cell were averaged. Since the threshold to evoke action potentials differed from one cell to another, current step intensity was expressed as pA from the current threshold for action potential generation, rather than in absolute values.

Action potential half-width was calculated for each action potential using Clampfit. The values of the $2^{nd}$-$5^{th}$ or the last ten action potentials evoked by a non-saturating current step (typically 100-150 pA from threshold) were averaged for each experimental condition in each analyzed cell.

Statistical Analysis

Statistical differences between the effect of treatments on action firing frequency were evaluated using a two-way ANOVA for repetitive measurements and, if necessary, post hoc planned comparisons (differences were considered significant where p<0.05). The effect of drug treatment on action potential half-width and on the first derivative amplitude was evaluated using an ANOVA. All statistical analyses were conducted using Statistica Software (StatSoft version 8). When appropriate, results were reported as mean±SEM.

Criteria for Data Inclusion/Exclusion

The criteria used to include or exclude a cell from the analysis were based on accurate current-clamp conditions and the stability of the recording throughout the experiment. Online evaluation allowed the exclusion of a cell when the $R_s$ and/or $R_m$ values changed by >20%.

Results

Interneurons recorded from slices incubated with 0.5 mM TEA fired at a lower maximal frequency in response to step currents compared to neurons recorded from control slices (Figure X). This effect was significantly reversed in slices incubated with TEA (0.5 mM) plus Example 19 at 1 μM or 10 μM (one-way ANOVA for repeated measurements, * p<0.05 with respect to TEA alone).

Figure 3:
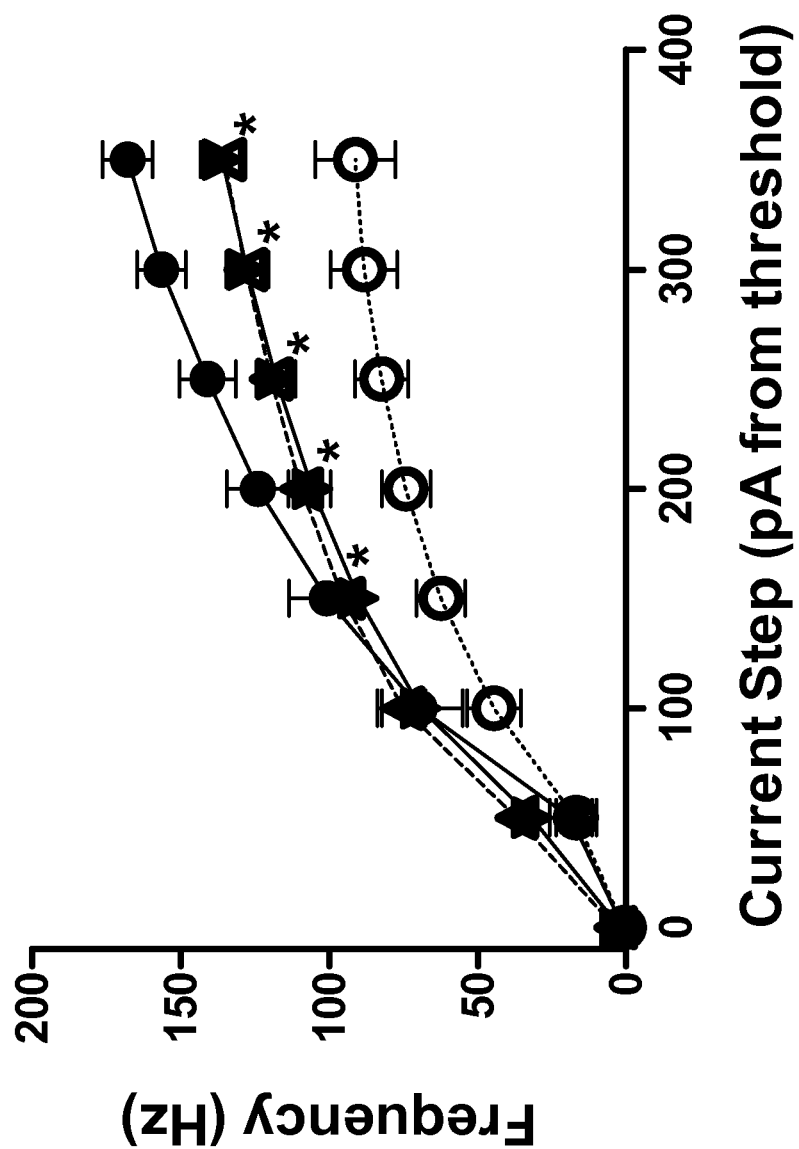
FIG. 3 The frequency of action potentials recorded from parvalbumin-positive interneurons in the somatosensory cortex of the mouse, evoked by depolarizing current steps FIG. 4 The half-width of evoked action potentials from parvalbumin-positive interneurons in the somatosensory cortex of the mouse FIG. 5 High-voltage activated potassium currents recorded from visually identified MNTB neurons in the mouse, in vitro

FIG. 3. The frequency of action potentials recorded from parvalbumin-positive interneurons in the somatosensory cortex of the mouse, evoked by depolarizing current steps (600 ms duration and Δ-increment of 50pA) after at least 1 hour with either vehicle (0.1% DMSO; filled circles, n=6), TEA (0.5 mM)+0.1% DMSO (open circles, n=7), TEA (0.5 mM)+Example 19 (1 M; filled triangles, n=9), or TEA (0.5 mM)+Example 19 (10 μM; open triangles, n=5). * p<0.05; One-way ANOVA for repeated measurements.

Furthermore, the action potential half-width and was significantly increased in cells recorded from slices incubated with TEA (0.5 mM) compared to control slices (0.1% DMSO) (Figure Y). In slices incubated with TEA (0.5 mM) plus Example 19 at 1 M or 10 μM, the mean action potential half-width was significantly decreased by 24% and 36%, respectively, compared to slices incubated with TEA (0.5 mM) only (ANOVA and Dunnett test, * p<0.05, n=9; ** p<0.01, n=5, respectively).

Figure 4:
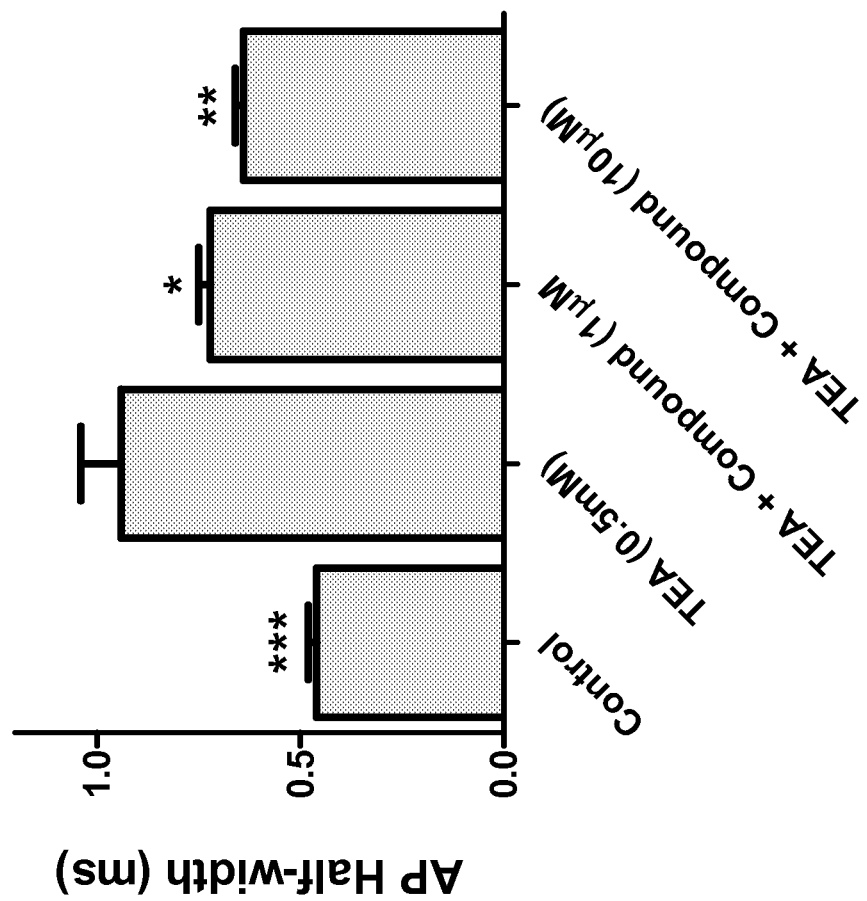

FIG. 4. The half-width of evoked action potentials from parvalbumin-positive interneurons in the somatosensory cortex of the mouse. Prior to recordings, slices were incubated for at least 1 hour with either vehicle (Control; 0.1% DMSO, n=6), TEA (0.5 mM)+0.1% DMSO (n=7), TEA (0.5 mM)+Example 19 (1 μM; n=9), or TEA (0.5 mM)+EXAMPLE 19 (10 μM; n=5). * p<0.05;  p<0.01, * p<0.001, ANOVA followed by Dunnett test.

These results demonstrate the ability of compounds of the invention to modulate the behaviour of fast-firing interneurons in the mouse brain in a manner consistent with positive modulation of Kv3 channels. The ability to enhance Kv3 function in cortical brain areas is also consistent with the potential of these compounds to treat schizophrenia, bipolar disorder, and epilepsy.

Example 91

Evaluation of Compound Effects on Potassium Currents Recorded from Neurons in the Medial Nucleus of the Trapezoid Body in Mice, In Vitro Animals Male CBA/Ca mice (aged 12-16 days) were used in these experiments (in accordance with the UK Animals Scientific Procedures Act, 1986). Brain slices containing the medial nucleus of the trapezoid body (MNTB) were prepared as described previously (Brew and Forsythe, 2005).

Drugs

Chemicals and reagents were purchased from Sigma, (Poole, UK) unless otherwise noted. EXAMPLE 19 was dissolved in DMSO and diluted in ACSF to the required concentration.

Electrophysiological Recording

Recordings from identified MNTB neurons were conducted as previously described (Brew and Forsythe, 2005). Slices was placed in a superfusion chamber on an inverted microscope stage and continuously perfused with gassed (95% $O_2$-5% $CO_2$) ACSF at a rate of 1 ml $min^{-1}$ at room temperature. Whole-cell recordings were made from visually identified MNTB neurons using an Axopatch 700B amplifier (Molecular Devices, Union City, Calif., USA). Patch solution comprised (in mM) potassium gluconate (97.5), KCl (32.5), Hepes (40), EGTA (5), $MgCl_2$ (1), $Na_2$ phosphocreatin (5), pH 7.2 with KOH. Pipettes had resistances of 3-5 MΩ and series resistances were 6-10 MΩ (compensated by 70%, 10 μs lag). Access resistance was frequently monitored and the recording discarded if increases were more than 2 MΩ.

Once a whole-cell confirguration had been obtained, cells were held at −60 mV prior to application of voltage protocols as follows: cells were stepped from the holding potential to −90 for 700 ms and stepped to −40 mV for 25 ms and then a voltage pulse to a range of voltages from −100 to +40 mV (10 mV increments) was applied for 220 ms before returning to the holding potential. Following completion of this protocol, TEA (1 mM) was added to the superfusion medium. After 5 minutes, a second set of recordings using the same voltage protocol was carried out. Following this, Compound 19 (10 microM) was added to the ACSF, in the continuing presence of TEA (1 mM), and after a further 5 minutes, a final set of recordings with the voltage protocol was made.

Statistical Analysis

Currents evoked by the voltage step to +40 mV were compared across drug treatments for each cell using an unpaired t-test.

Results

Figure 5:
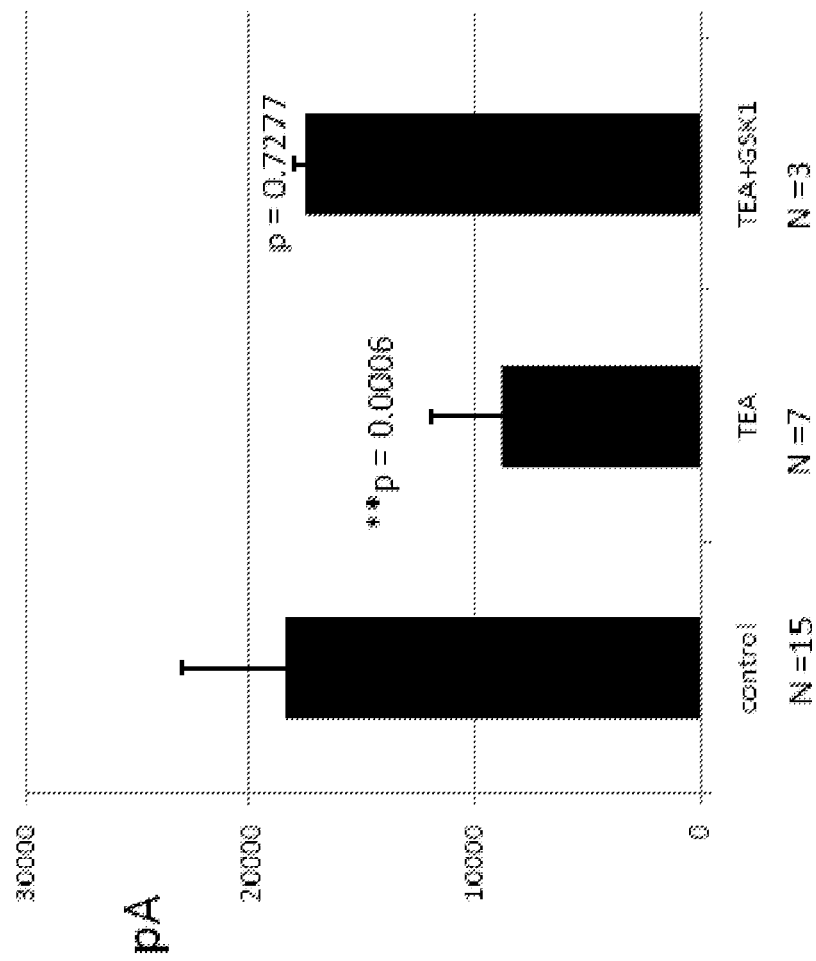

TEA (1 mM) significantly reduced the amplitude of outward, high voltage-activated potassium currents evoked by voltage steps to +40 mV (FIG. 5). This effect was reversed by the subsequent application of EXAMPLE 19 (10 microM).

FIG. 5. High-voltage activated potassium currents recorded from visually identified MNTB neurons in the mouse, in vitro. Data shown are the mean (+/−s.d.) of the current amplitude evoked by voltage steps to +40 mV under different drug conditions. TEA (1 mM), TEA (1 mM)+EXAMPLE 19 (10 microM). Statistical analysis was conducted using an unpaired t-test.

These data indicate that compounds of the invention can modulate high voltage-activated potassium currents (presumed to be mediated by Kv3.1 channels; Brew and Forsythe, 2005) in neurons of the MNTB, a region of the brainstem that processes auditory information. This result supports the utility of compounds of the invention for the treatment of hearing disorders.

Example 92

Electroshock Seizure Model in Rats

Experimental Preparation

Male CD rats (85-130 g) were supplied by Charles River, Italy. Animals were group housed with free access to food (Standard rodent chow) and water under a 12 h light/dark cycle (lights on at 0600 h). A period of at least 5 days between arrival at GSK and the study was allowed in all cases.

Experimental Protocol

Animals were administered a test compound at the appropriate dose, route and pre-treatment time and returned to their home cage. Testing occurred in a separate room from that used for housing. Testing involved determining the threshold for tonic hindlimb extensor seizures using a Hugo Sachs Electronik stimulator which delivers a constant current of 0.3 second duration, 50 Hz, sinewave form, fully adjustable between 1 and 300 mA. Stimuli were delivered via corneal electrodes (Stean T O, Atkins A R, Heidbreder C A, Quinn L P, Trail B K, Upton N. (2005) Br J. Pharmacol. 144(5):628-35). Seizure threshold was determined using the 'up and down' method of Kimball et al. (1957)(Kimball A W, Burnett W T Jr, Doherty D G. (1957) Radiat Res. 7(1):1-12). The first animal tested in each group was stimulated with a current that might be expected to be close to the threshold for induction of a seizure. If a tonic seizure was not induced, then the next animal in the group received a stimulus 5 mA higher. If a tonic seizure was induced, then the next animal received a stimulus 5 mA lower. This is repeated for all animals within the control (vehicle) group. In the case of groups treated with a test compound steps of 5 to 10 mA were used. At the end of the study, blood samples were taken for analysis of the drug concentrations in this compartment (n=4/group).

Drugs and Materials

All doses were calculated as base. Sodium valproate was suspended in Methocell 1% (w/v) and dosed via the oral (p.o.) route at 5 mL/kg 1 hour before test. Compound 19 was dissolved in DMSO and then suspended in Methocell 1% (w/v) to a final DMSO concentration of 5% (v/v). Compound 19 was then dosed p.o. at 5 mL/kg 2 hours before test.

Data Analysis

Induction of seizure is measured as an all-or-nothing effect scored as either present (+) or absent (0) for each animal. The data for each treatment group were recorded as the number of +'s and 0's at each current level employed and this information was then used to calculate the CC50 value (current required for 50% of animals to show seizure behaviour)+ standard error of the mean according to the method of Kimball et al. (1957). Drug effects were calculated as the % change in CC50. Significant differences between drug-treated animals and appropriate vehicle treated groups were assessed according to the methods of Litchfield and Wilcoxon (1949).

Results

Pretreatment with Compound 19 was associated with a significant increase in seizure threshold at both doses tested: At the dose of 30 mg/kg p.o., Compound 19 produced a 91% increase in seizure threshold, whereas at the dose of 60 mg/kg p.o., the increase in seizure threshold was +218%. The increase produced by the higher dose of Compound 19 was similar to the increase produced by the positive control, sodium valproate at 300 mg/kg p.o. (+258%).

Blood concentrations of Compound 19 measured in satellite animals 2 hours after dosing were 5.3 and 9.1 μg/mL following the doses of 30 and 60 mg/kg p.o., respectively. These concentrations are equivalent to unbound concentrations in blood of 1.3 and 2.2 μM, respectively, and thus are consistent with concentrations of Compound 19 that produce a significant increase in Kv3-mediated currents observed in the in vitro recombinant human Kv3 electrophysiology assay, described above.

Conclusions

These results suggest that Compound 19 has anticonvulsant efficacy, and that this effect is likely to be mediated by the positive modulation of Kv3 potassium channels.

Example 93

Psychostimulant-Induced Hyperactivity in Mice

Experimental Preparation

Male CD-1 mice (25-35 g) were supplied by Charles River, Italy. Animals were group housed with free access to food (Standard rodent chow) and water under a 12 h light/dark cycle (lights on at 0600 h). A period of at least 5 days between arrival at GSK and the study was allowed in all cases.

Experimental Protocol

Animals were administered a test compound at the appropriate dose, route and pre-treatment time, and then returned to their home cage. Testing occurred in a separate room from that used for housing. Mice were treated orally (p.o.) with the test compound and placed individually into a Perspex box (length 20.5 cm, width 20.5 cm, height 34 cm) covered with a perforated lid. Infrared monitoring sensors were located around the perimeter walls (horizontal sensors). Two additional sensors were located 2.5 cm above the floor on opposite sides (vertical sensors). Data were collected and analysed using a VersaMax System (Accuscan Instruments Inc., Columbus, Ohio) which in turn transferred information to a computer. After 30 minutes of habituation, mice were treated with amphetamine dosed intraperitoneally (i.p.) at 2 mg/kg at 10 mL/kg, and subsequent locomotor activity in the test arena was assessed over a further 60 minutes. Locomotor activity was determined as the total distance (cm) travelled by each mouse in the test arena over the 60 minute test period.

Drugs and Materials

All doses were calculated as base. Clozapine was dissolved in distilled water and dosed at 3 mg/kg intraperitoneum (i.p.) at 10 mL/kg. Compound 19 (10, 30 or 60 mg/kg) or vehicle (HPMC 0.5% w/v, Tween80 0.1% v/v in water) was administered p.o. at 10 mL/kg. Both clozapine and Compound 19 were dosed immediately before placing the animal in the test arena (30 minutes before amphetamine administration).

Results

Amphetamine alone produced a large and significant increase in total distance travelled. A dose of 30 mg/kg p.o. of Compound 19 significantly reduced the increase in total distance travelled produced by amphetamine. A higher dose of 60 mg/kg p.o. of Compound 19 further reduced the increase in locomotor activity induced by amphetamine in a manner similar to the positive control, clozapine (3 mg/kg i.p.). Data are summarised in Table 1.

TABLE 1

Effects of Compound 19 on amphetamine induced hyperlocomotion in the mouse.

| Treatment | Total Distance Travelled (cm) |
|---|---|
| Vehicle | 1049 ± 522** |
| Amphetamine (AMPH) 2.0 mg/kg | 16304 ± 3309 |
| AMPH 2 mg/kg + Compound 19 10 mg/kg | 15267 ± 3166 |
| AMPH 2 mg/kg + Compound 19 30 mg/kg | 5790 ± 1436** |
| AMPH 2 mg/kg + Compound 19 60 mg/kg | 1494 ± 378** |
| AMPH 2 mg/kg + Clozapine 3 mg/kg | 932 ± 362** |

Compound 19 was administered p.o. 30 minutes before amphetamine (2 mg/kg i.p.).
Clozapine was administered i.p. 30 minutes before amphetamine (2 mg/kg i.p.).
Total distance was assessed over 60 minutes starting immediately after amphetamine administration.
Data are expressed as mean ± sem.
Data were subjected to one-way analysis of variance (ANOVA) followed by Dunnett's test (**= $p < 0.01$ vs amphetamine treatment alone).

Conclusions

These results show that Compound 19, at doses similar to those that show anticonvulsant efficacy, is able to prevent hyperactivity induced by the psychostimulant, amphetamine. Compound 19 and other compounds that positively modulate Kv3.1 and/or Kv3.2 channels may thus be useful in the treatment of disorders associated with hyperactivity, such as bipolar mania, or disruption of the dopamine system, such that may occur in drug dependence, attention deficit hyperactivity disorder (ADHD), or schizophrenia.

Example 94

Behaviour of the Common Marmoset

Central anxiolytic effects of a test compound can be assessed from the ability of the compound to reduce the characteristic defensive postures of marmosets in response to a threatening approach by a human. The test can also be used to assess the sedative or hypnotic effects of a test compound from its ability to reduce the number of jumps made by the animals. The study was based on the method described in Costall, B. et al (1988) Br. J. Pharmac. 95 p 475P. Laboratory-bred (GSK SpA, Italy) male and female common marmosets over 2 years of age, weighing 300-500 g were used in the study. The animals were caged in couples in a housing room maintained at 25±1° C., 60% humidity, and a 12 hour light/dark cycle (lights on at 0600, with 30 minutes simulated dawn and twilight). Both animals in each pair were involved in the test, which was carried out with the animals in their home cage.

As there can be variability in the behavioural response between different marmosets, the "responder" animals were pre-selected to meet the baseline criteria of at least 10 postures exhibited in the 2 minutes test period following the approach of the human operator. The postures recorded in the test were those described by Costall et al supra;

Genital presenting ("Tail Posture"): the animal's back is turned to the observer with elevation of the tail to expose the genital region;

Scent-marking: the animal scent-marks the cage surfaces using circum-anal and circum-genital scent glands;

Slit-stare: the animal stares at the observer with flattened ear tufts and eyes reduced to "slits"

Arch-piloerection: the animal moves around the cage with arched back and full-body piloerection, failing to make eye contact with the observer The number of jumps from the back of the cage to the cage front provided an index of locomotor activity, which could be used to assess the potential for a hypnotic effect, sedation, or locomotor stimulation produced by the test compound.

Drugs and Materials

A single dose of Compound 19 (0.3, 1 or 3 mg/kg) or vehicle (HPMC 0.5% (w/v), Tween80 0.1% (v/v) in water) was administered orally (p.o.) 2 hours prior to the test (n=5-6 animals per group).

Results

Compound 19 (1 and 3 mg/kg p.o.) significantly reduced the number of jumps made by the animals over the 2 minute test period, without any effects on postures at any dose, indicative of a sedative or hypnotic effect. Data are summarised in Table 2.

TABLE 2

Effects of Compound 19 on marmoset behaviour.

| Treatment | Number of postures | Number of Jumps |
| --- | --- | --- |
| Vehicle | 12.2 ± 0.3 | 22.3 ± 2.5 |
| Compound 19 0.3 mg/kg | 12.2 ± 1.03 | 21.3 ± 2.7 |
| Compound 19 1 mg/kg | 10.0 ± 1.2 | 15.3 ± 2.5* |
| Compound 19 3 mg/kg | 9.7 ± 1.1 | 11.5 ± 1.9** |

Compound 19 was administered p.o. 2 hours before the test.
Data are expressed as mean ± sem.
Data were subjected to a one-way analysis of variance (ANOVA) followed by Dunnett's test, comparing each compound dose with the related vehicle treatment (*= $p < 0.05$ vs vehicle treated animals; **= $p < 0.01$ vs vehicle treated animals).

Conclusions

These results suggest that Compound 19 has a hypnotic or sedative profile in non-human primates, and thus indicates that Compound 19 and other compounds that positively modulate Kv3.1 and/or Kv3.2 channels could be useful in the treatment of sleep disorders.

Example 95

Pharmaco-Electroencephalography (PHEEG) in the Common Marmoset

Animals and Surgery

Laboratory bred male (vasectomised) and female common marmosets (*Callithrix jacchus*) over 2 years of age, weighing 250-500 g were used in this study. The animals were caged in couples, in a housing room maintained at 25±1° C., 60% humidity and a 12 hour light/dark cycle (lights on at 0600, with 30 min simulated dawn and twilight). Animals received a standard diet and drinking water ad libitum. Only one animal of each pair was involved in the test, which was carried out with the animal situated in the home cage.

The effect of compounds of the invention was assessed using telemetric recording of cortical EEG (ECoG). A multichannel telemetric transmitter (DSI model TL11M2-F40-EET) is implanted intraperitoneally using standard surgical techniques in anaesthetised marmosets. Recording electrodes were permanently fixed, with dental cement, to the skull directly in contact with the dura mater through two drilled holes in the fronto-parietal region. Following surgery, animals were housed in pairs (one implanted, one unoperated partner) in their home cage with access to food and water ad libitum. Animals demonstrated a normal behavioural repertoire immediately after recovery from surgery; however, phEEG was assessed at least 3 weeks later. All in vivo studies were conducted in accordance with the Italian laws and conformed to GlaxoSmithkline ethical standards.

Experimental Procedure

The animals were placed in the nest-boxes in their room cages and EEG traces were recorded using Dataquest ART software for a 5-min period for each time-point and analyzed using Spike2 software (CED, UK). The spectral power in each frequency band was determined for each 2 sec epoch during the pre-treatment period and averaged; similarly spectral power in each band was determined for successive 2 sec epochs of each 5-min period of recording following vehicle or drug treatment. Change in the absolute spectral power, for each of the different bands (delta, theta, alpha and beta) was calculated offline.

Drug treatments were assigned according to a complete crossover design: All treatments were randomly distributed between animals, in separate experimental sessions, each animal received vehicle and each dose of drug, after an appropriate wash-out period.

Six animals were treated orally with EXAMPLE 30 at the doses of 0.3, 1 and 3 mg/kg (1 ml/kg) and the EEG traces were recorded at +15, 30, 60, 90, 120 and 180 minutes following treatment. EXAMPLE 30 was suspended in 12.5% (w/v) aqueous captisol containing 0.1% (w/v) Tween80 and 0.5% (w/v) HPMC.

Data Analysis

Four different frequency bands were considered: delta (1.50-6.00 Hz), theta (6.00-8.00 Hz), alpha (8.00-12.00 Hz) and beta (12.00-30.00 Hz). Values for spectral power in each band at each time point were first 10 g transformed and then analysed with a mixed effect model with time as fixed effect, the baseline level as covariate, and animal as random term. Data are summarised as mean of the percentage changes from baseline and standard error.

Results

The pharmaco-EEG changes observed in these studies show that, compared to vehicle, EXAMPLE 30 at the highest dose (3 mg/kg) induced a statistically significant increase of the absolute power in the delta band between 30 and 120 minutes ($p<0.05$) and a statistically significant increase in theta band power at 60 minutes ($p<0.05$). At the intermediate dose (1 mg/kg) EXAMPLE 30 induced a marginally significant ($p<0.10$) increase in the absolute power in delta band at 30 minutes and a concomitant significant reduction in the beta band ($p<0.05$). No significant effects were observed in the alpha band at any dose of EXAMPLE 30.

These results suggest that compounds of the invention may have an antipsychotic-like profile, since a similar pattern of EEG changes can be observed with antipsychotic agents in humans.

The invention claimed is:

1. A compound of formula (Ia)

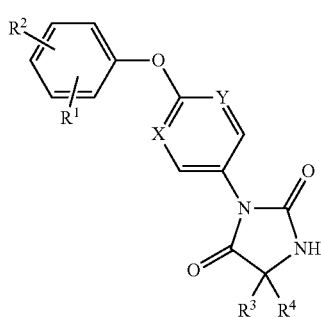

(Ia)

wherein:
$R^1$ is halo, $C_{1-4}$ alkyl, $C_{1-4}$ alkoxy, halo-$C_{1-4}$alkyl, halo-$C_{1-4}$alkoxy, or cyano;
$R^2$ is H, halo, cyano, $C_{1-4}$ alkyl or $C_{1-4}$ alkoxy; with the proviso that when $R_2$ is H, $R_1$ is not in the para position;
X is CH or N;
Y is CH or N;
$R^3$ is $C_{1-4}$ alkyl;
$R^4$ is H, deuterium, or $C_{1-4}$alkyl; or $R_3$ and $R_4$ can be fused to form a $C_{3-4}$ spiro carbocyclyl group;
or a pharmaceutically acceptable salt thereof.

2. A compound according to claim 1 wherein $R^1$ is halo, $C_{1-4}$ alkyl, $C_{1-4}$ alkoxy, halo-$C_{1-4}$alkoxy or cyano and $R^2$ is H, halo, $C_{1-4}$ alkyl or $C_{1-4}$ alkoxy; with the proviso that when R2 is H, R1 is not in the para position; or a pharmaceutically acceptable salt thereof.

3. A compound according to claim 1 wherein $R^1$ is halo, $C_{1-4}$ alkyl or $C_{1-4}$ alkoxy; or a pharmaceutically acceptable salt thereof.

4. A compound according to claim 1 wherein $R^1$ is $C_{1-4}$alkyl, $C_{1-4}$ alkoxy, or halo-$C_{1-4}$ alkoxy; $R^2$ is H, cyano or alkyl; X is N, Y is N or CH, $R_3$ is $C_{1-4}$ alkyl, and $R^4$ is $C_{1-4}$ alkyl or H; or a pharmaceutically acceptable salt thereof.

5. A compound according to claim 1 wherein $R^1$ is propyl, butyl, methoxy, propoxy, or trifluoromethoxy; $R^2$ is H, cyano or methyl; X is N, Y is N or CH, $R^3$ is ethyl, and $R^4$ is methyl or H; or a pharmaceutically acceptable salt thereof.

6. A compound selected from the group consisting of:
(5R)-5-methyl-3-{4-[(3-methylphenyl)oxy]phenyl}-2,4-imidazolidinedione;
(5R)-5-methyl-3-(4-{[3-(methyloxy)phenyl]oxy}phenyl)-2,4-imidazolidinedione;
(5R)-3-(4-{[3-(ethyloxy)phenyl]oxy}phenyl)-5-methyl-2,4-imidazolidinedione;
(5R)-3-{4-[(3-chloro-5-fluorophenyl)oxy]phenyl}-5-methyl-2,4-imidazolidinedione;
(5R)-3-{4-[(3-chloro-4-fluorophenyl)oxy]phenyl}-5-methyl-2,4-imidazolidinedione;
(5S)-3-{4-[(3-chloro-4-fluorophenyl)oxy]phenyl}-5-methyl-2,4-imidazolidinedione;
(5R)-5-methyl-3-(4-{[2-methyl-5-(methyloxy)phenyl]oxy}phenyl)-2,4-imidazolidinedione;
(5R)-5-methyl-3-(4-{[4-methyl-3-(methyloxy)phenyl]oxy}phenyl)-2,4-imidazolidinedione;
(5R)-5-methyl-3-(6-{[3-(1-methylethyl)phenyl]oxy}-3-pyridinyl)-2,4-imidazolidinedione;
(5R)-5-methyl-3-[6-({3-[(1-methylethyl)oxy]phenyl}oxy)-3-pyridinyl]-2,4-imidazolidinedione;
(5R)-3-{6-[(2,5-dimethylphenyl)oxy]-3-pyridinyl}-5-methyl-2,4-imidazolidinedione;
(5R)-3-{6-[(2,3-dimethylphenyl)oxy]-3-pyridinyl}-5-methyl-2,4-imidazolidinedione;
(5R)-3-{6-[(2,6-dimethylphenyl)oxy]-3-pyridinyl}-5-methyl-2,4-imidazolidinedione;
(5R)-3-{6-[(2-ethylphenyl)oxy]-3-pyridinyl}-5-methyl-2,4-imidazolidinedione;
(5R)-5-methyl-3-(6-{[4-methyl-3-(methyloxy)phenyl]oxy}-3-pyridinyl)-2,4-imidazolidinedione;
(5R)-5-methyl-3-(6-{[2-methyl-5-(methyloxy)phenyl]oxy}-3-pyridinyl)-2,4-imidazolidinedione;
(5R)-5-methyl-3-(6-{[2-methyl-3-(methyloxy)phenyl]oxy}-3-pyridinyl)-2,4-imidazolidinedione;
(5R)-5-ethyl-3-(4-{[3-(methyloxy)phenyl]oxy}phenyl)-2,4-imidazolidinedione;
(5R)-5-ethyl-3-(6-{[4-methyl-3-(methyloxy)phenyl]oxy}-3-pyridinyl)-2,4-imidazolidinedione;
(5S)-5-ethyl-3-(6-{[4-methyl-3-(methyloxy)phenyl]oxy}-3-pyridinyl)-2,4-imidazolidinedione;
(5R)-5-ethyl-3-(6-{[3-(1-methylethyl)phenyl]oxy}-3-pyridinyl)-2,4-imidazolidinedione;
5,5-dimethyl-3-(4-{[3-(methyloxy)phenyl]oxy}phenyl)-2,4-imidazolidinedione;
3-{4-[(2,3-dimethylphenyl)oxy]phenyl}-5,5-dimethyl-2,4-imidazolidinedione;
3-{6-[(2-ethylphenyl)oxy]-3-pyridinyl}-5,5-dimethyl-2,4-imidazolidinedione;
3-{6-[(2,6-dimethylphenyl)oxy]-3-pyridinyl}-5,5-dimethyl-2,4-imidazolidinedione;
(5R)-5-(1-methylethyl)-3-(4-{[4-methyl-3-(methyloxy)phenyl]oxy}phenyl)-2,4-imidazolidinedione;
(5R)-5-methyl-3-(2-{[3-(1-methylethyl)phenyl]oxy}-5-pyrimidinyl)-2,4-imidazolidinedione;
(5R)-5-ethyl-3-(2-{[3-(ethyloxy)-4-methylphenyl]oxy}-5-pyrimidinyl)-2,4-imidazolidinedione;
(5R)-5-(1,1-dimethylethyl)-3-(6-{[4-methyl-3-(methyloxy)phenyl]oxy}-3-pyridinyl)-2,4-imidazolidinedione;
(5R)-5-ethyl-5-methyl-3-(6-{[4-methyl-3-(methyloxy)phenyl]oxy}-3-pyridinyl)-2,4-imidazolidinedione;
7-(6-{[4-methyl-3-(methyloxy)phenyl]oxy}-3-pyridinyl)-5,7-diazaspiro[3.4]octane-6,8-dione;
6-(6-{[4-methyl-3-(methyloxy)phenyl]oxy}-3-pyridinyl)-4,6-diazaspiro[2.4]heptane-5,7-dione;
4-{[5-(4,4-dimethyl-2,5-dioxo-1-imidazolidinyl)-2-pyridinyl]oxy}-2-(1-methylethyl)benzonitrile;
4-{[5-(4,4-dimethyl-2,5-dioxo-1-imidazolidinyl)-2-pyridinyl]oxy}-2-[(trifluoromethyl)oxy]benzonitrile;
3-{6-[(4-fluoro-3-methylphenyl)oxy]-3-pyridinyl}-5,5-dimethyl-2,4-imidazolidinedione;
3-{6-[(4-fluoro-2-methylphenyl)oxy]-3-pyridinyl}-5,5-dimethyl-2,4-imidazolidinedione;
5,5-dimethyl-3-(6-{[4-methyl-3-(methyloxy)phenyl]oxy}-3-pyridinyl)-2,4-imidazolidinedione;
(5R)-5-(1-methylethyl)-3-(6-{[4-methyl-3-(methyloxy)phenyl]oxy}-3-pyridinyl)-2,4-imidazolidinedione;
3-(6-{[2-(1,1-dimethylethyl)phenyl]oxy}-3-pyridinyl)-5,5-dimethyl-2,4-imidazolidinedione;
3-(2-{[2-(1,1-dimethylethyl)phenyl]oxy}-5-pyrimidinyl)-5,5-dimethyl-2,4-imidazolidinedione;
(5R)-5-ethyl-5-methyl-3-(2-{[4-methyl-3-(methyloxy)phenyl]oxy}-5-pyrimidinyl)-2,4-imidazolidinedione;

(5R)-5-ethyl-3-(2-{[3-(ethyloxy)-4-methylphenyl]oxy}-5-pyrimidinyl)-5-methyl-2,4-imidazolidinedione;
5,5-dimethyl-3-[6-({3-[(trifluoromethyl)oxy]phenyl}oxy)-3-pyridinyl]-2,4-imidazolidinedione;
4-{[5-(4,4-dimethyl-2,5-dioxo-1-imidazolidinyl)-2-pyridinyl]oxy}-3-ethylbenzonitrile;
2-chloro-4-{[5-(4,4-dimethyl-2,5-dioxo-1-imidazolidinyl)-2-pyridinyl]oxy}benzonitrile;
5,5-dimethyl-3-[6-({4-methyl-3-[(trifluoromethyl)oxy]phenyl}oxy)-3-pyridinyl]-2,4-imidazolidinedione;
4-{[5-(4,4-dimethyl-2,5-dioxo-1-imidazolidinyl)-2-pyridinyl]oxy}-2-(methyloxy)benzonitrile;
4-{[5-(4,4-dimethyl-2,5-dioxo-1-imidazolidinyl)-2-pyridinyl]oxy}-3-methylbenzonitrile;
4-{[5-(4,4-dimethyl-2,5-dioxo-1-imidazolidinyl)-2-pyridinyl]oxy}-3-(trifluoromethyl)benzonitrile;
4-{[5-(4,4-dimethyl-2,5-dioxo-1-imidazolidinyl)-2-pyridinyl]oxy}-2-ethylbenzonitrile;
4-{[5-(4,4-dimethyl-2,5-dioxo-1-imidazolidinyl)-2-pyrimidinyl]oxy}-2-ethylbenzonitrile;
3-cyclopropyl-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-3-(1,1-dimethylethyl)benzonitrile;
2-[(cyclopropylmethyl)oxy]-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-2-(ethyloxy)benzonitrile;
2-cyclopropyl-4-{[5-(4,4-dimethyl-2,5-dioxo-1-imidazolidinyl)-2-pyridinyl]oxy}benzonitrile;
5,5-dimethyl-3-[2-({4-methyl-3-[(trifluoromethyl)oxy]phenyl}oxy)-5-pyrimidinyl]-2,4-imidazolidinedione;
4-{[5-(4,4-dimethyl-2,5-dioxo-1-imidazolidinyl)-2-pyrimidinyl]oxy}-3-(1,1-dimethylethyl)benzonitrile;
4-{[5-(4,4-dimethyl-2,5-dioxo-1-imidazolidinyl)-2-pyridinyl]oxy}-2-[(1-methylethyl)oxy]benzonitrile;
4-({5-[(4R)-4-ethyl-4-methyl-2,5-dioxo-1-imidazolidinyl]-2-pyridinyl}oxy)-2-[(1-methylethyl)oxy]benzonitrile;
3-cyclopropyl-4-({5-[(4R)-4-ethyl-4-methyl-2,5-dioxo-1-imidazolidinyl]-2-pyridinyl}oxy)benzonitrile;
4-({5-[(4R)-4-ethyl-4-methyl-2,5-dioxo-1-imidazolidinyl]-2-pyridinyl}oxy)-2-[(trifluoromethyl)oxy]benzonitrile;
2-cyclopropyl-4-({5-[(4R)-4-ethyl-4-methyl-2,5-dioxo-1-imidazolidinyl]-2-pyridinyl}oxy)benzonitrile;
(5R)-5-ethyl-5-methyl-3-[2-({4-methyl-3-[(trifluoromethyl)oxy]phenyl}oxy)-5-pyrimidinyl]-2,4-imidazolidinedione;
3-(1,1-dimethylethyl)-4-({5-[(4R)-4-ethyl-4-methyl-2,5-dioxo-1-imidazolidinyl]-2-pyrimidinyl}oxy)benzonitrile;
3-(1,1-dimethylethyl)-4-({5-[(4R)-4-ethyl-4-methyl-2,5-dioxo-1-imidazolidinyl]-2-pyridinyl}oxy)benzonitrile;
4-{[4-(4,4-dimethyl-2,5-dioxo-1-imidazolidinyl)phenyl]oxy}-2-(methyloxy)benzonitrile;
4-{[4-(4,4-dimethyl-2,5-dioxo-1-imidazolidinyl)phenyl]oxy}-2-(ethyloxy)benzonitrile;
4-({4-[(4R)-4-ethyl-2,5-dioxo-1-imidazolidinyl]phenyl}oxy)-2-(ethyloxy)benzonitrile;
3-cyclopropyl-4-({5-[(4R)-4-ethyl-2,5-dioxo-1-imidazolidinyl]-2-pyridinyl}oxy)benzonitrile;
3-(1,1-dimethylethyl)-4-({5-[(4R)-4-ethyl-2,5-dioxo-1-imidazolidinyl]-2-pyridinyl}oxy)benzonitrile;
4-({5-[(4R)-4-ethyl-2,5-dioxo-1-imidazolidinyl]-2-pyridinyl}oxy)-2-(methyloxy)benzonitrile;
4-({4-[(4R)-4-ethyl-2,5-dioxo-1-imidazolidinyl]phenyl}oxy)-2-(methyloxy)benzonitrile;
2-[(cyclopropylmethyl)oxy]-4-({5-[(4R)-4-ethyl-2,5-dioxo-1-imidazolidinyl]-2-pyridinyl}oxy)benzonitrile;
(5R)-5-ethyl-3-[6-({4-methyl-3-[(trifluoromethyl)oxy]phenyl}oxy)-3-pyridinyl]-2,4-imidazolidinedione;
2-cyclopropyl-4-({5-[(4R)-4-ethyl-2,5-dioxo-1-imidazolidinyl]-2-pyridinyl}oxy)benzonitrile;
4-({5-[(4R)-4-ethyl-2,5-dioxo-1-imidazolidinyl]-2-pyridinyl}oxy)-2-(1-methylethyl)benzonitrile;
(5R)-5-ethyl-3-[2-({4-methyl-3-[(trifluoromethyl)oxy]phenyl}oxy)-5-pyrimidinyl]-2,4-imidazolidinedione;
4-({5-[(4R)-4-ethyl-2,5-dioxo-1-imidazolidinyl]-2-pyridinyl}oxy)-2[(1-methylethyl)oxy]benzonitrile;
4-({5-[(4R)-4-ethyl-2,5-dioxo-1-imidazolidinyl]-2-pyridinyl}oxy)-3-methylbenzonitrile;
4-({5-[(4R)-4-ethyl-2,5-dioxo-1-imidazolidinyl]-2-pyridinyl}oxy)-2-[(trifluoromethyl)oxy]benzonitrile;
3-ethyl-4-({5-[(4R)-4-ethyl-2,5-dioxo-1-imidazolidinyl]-2-pyrimidinyl}oxy)benzonitrile;
4-({5-[(4R)-4-ethyl-2,5-dioxo-1-imidazolidinyl]-2-pyrimidinyl}oxy)-3-methylbenzonitrile;
3-(1,1-dimethylethyl)-4-({5-[(4R)-4-ethyl-2,5-dioxo-1-imidazolidinyl]-2-pyrimidinyl}oxy)benzonitrile, and
4-({5-[(4R)-4-ethyl-4-methyl-2,5-dioxo-1-imidazolidinyl]-2-pyridinyl}oxy)-2-(1-methylethyl)benzonitrile;
or a pharmaceutically acceptable salt thereof.

7. A compound according to claim 6, wherein the compound is selected from the group consisting of:

(5R)-5-ethyl-3-(6-{[4-methyl-3-(methyloxy)phenyl]oxy}-3-pyridinyl)-2,4-imidazolidinedione;
(5R)-5-ethyl-5-methyl-3-(6-{[4-methyl-3-(methyloxy)phenyl]oxy}-3-pyridinyl)-2,4-imidazolidinedione;
4-({5-[(4R)-4-ethyl-4-methyl-2,5-dioxo-1-imidazolidinyl]-2-pyridinyl}oxy)-2-[(trifluoromethyl)oxy]benzonitrile;
(5R)-5-ethyl-5-methyl-3-[2-({4-methyl-3-[(trifluoromethyl)oxy]phenyl}oxy)-5-pyrimidinyl]-2,4-imidazolidinedione;
3-(1,1-dimethylethyl)-4-({5-[(4R)-4-ethyl-4-methyl-2,5-dioxo-1-imidazolidinyl]-2-pyridinyl}oxy)benzonitrile;
(5R)-5-ethyl-3-[6-({4-methyl-3-[(trifluoromethyl)oxy]phenyl}oxy)-3-pyridinyl]-2,4-imidazolidinedione;
4-({5-[(4R)-4-ethyl-2,5-dioxo-1-imidazolidinyl]-2-pyridinyl}oxy)-2-(1-methylethyl)benzonitrile;
(5R)-5-ethyl-3-[2-({4-methyl-3-[(trifluoromethyl)oxy]phenyl}oxy)-5-pyrimidinyl]-2,4-imidazolidinedione;
4-({5-[(4R)-4-ethyl-2,5-dioxo-1-imidazolidinyl]-2-pyridinyl}oxy)-2[(1-methylethyl)oxy]benzonitrile;
4-({5-[(4R)-4-ethyl-2,5-dioxo-1-imidazolidinyl]-2-pyridinyl}oxy)-2-[(trifluoromethyl)oxy]benzonitrile; and
3-(1,1-dimethylethyl)-4-({5-[(4R)-4-ethyl-2,5-dioxo-1-imidazolidinyl]-2-pyrimidinyl}oxy)benzonitrile;
or a pharmaceutically acceptable salt thereof.

8. A compound according to claim 1, selected from the group consisting of
(5R)-5-ethyl-3-(6-{[4-methyl-3-(methyloxy)phenyl]oxy}-3-pyridinyl)-2,4-imidazolidinedione

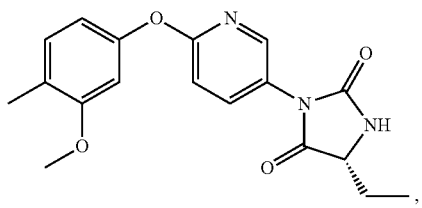 [SMILES: CC[C@H]1NC(=O)N(c2ccc(Oc3ccc(C)c(OC)c3)nc2)C1=O]

(5R)-5-ethyl-3-(2-{[3-(ethyloxy)-4-methylphenyl]oxy}-5-pyrimidinyl)-2,4-imidazolidinedione

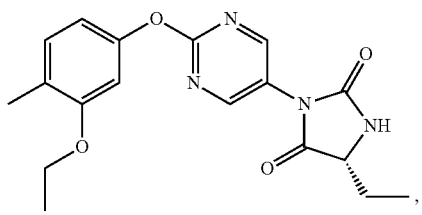 [SMILES: CCOc1cc(Oc2ncc(N3C(=O)N[C@H](CC)C3=O)cn2)ccc1C]

(5R)-5-ethyl-5-methyl-3-(6-{[4-methyl-3-(methyloxy)phenyl]oxy}-3-pyridinyl)-2,4-imidazolidinedione

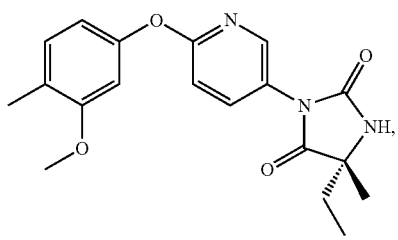 [SMILES: CC[C@@]1(C)NC(=O)N(c2ccc(Oc3ccc(C)c(OC)c3)nc2)C1=O]

5,5-dimethyl-3-[6-({4-methyl-3-[(trifluoromethyl)oxy]phenyl}oxy)-3-pyridinyl]-2,4-imidazolidinedione

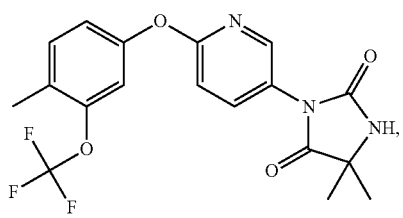 [SMILES: Cc1ccc(Oc2ccc(N3C(=O)NC(C)(C)C3=O)cn2)cc1OC(F)(F)F]

5,5-dimethyl-3-[2-({4-methyl-3-[(trifluoromethyl)oxy]phenyl}oxy)-5-pyrimidinyl]-2,4-imidazolidinedione

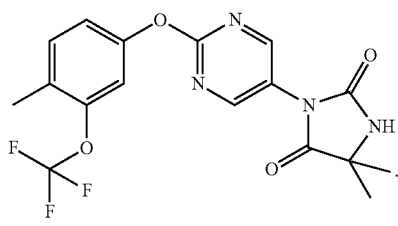

(5R)-5-ethyl-5-methyl-3-[2-({4-methyl-3-[(trifluoromethyl)oxy]phenyl}oxy)-5-pyrimidinyl]-2,4-imidazolidinedione

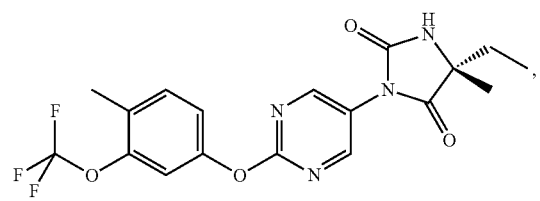 [SMILES: CC[C@@]1(C)NC(=O)N(c2cnc(Oc3ccc(C)c(OC(F)(F)F)c3)nc2)C1=O]

(5R)-5-ethyl-3-[6-({4-methyl-3-[(trifluoromethyl)oxy]phenyl}oxy)-3-pyridinyl]-2,4-imidazolidinedione

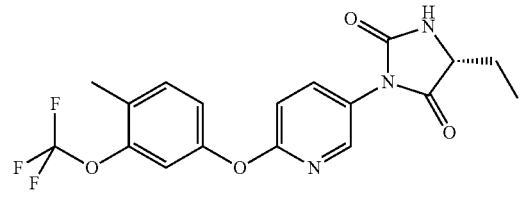 [SMILES: CC[C@H]1NC(=O)N(c2ccc(Oc3ccc(C)c(OC(F)(F)F)c3)nc2)C1=O]

and
(5R)-5-ethyl-3-[2-({4-methyl-3-[(trifluoromethyl)oxy]phenyl}oxy)-5-pyrimidinyl]-2,4-imidazolidinedione

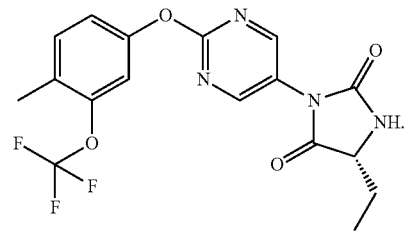 [SMILES: CC[C@H]1NC(=O)N(c2cnc(Oc3ccc(C)c(OC(F)(F)F)c3)nc2)C1=O]

9. A compound which is:
(5R)-5-ethyl-3-(6-{[4-methyl-3-(methyloxy)phenyl]oxy}-3-pyridinyl)-2,4-imidazolidinedione

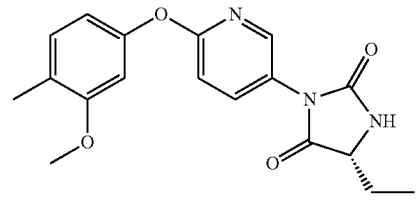

10. A compound which is:
(5R)-5-ethyl-5-methyl-3-[2-({4-methyl-3-[(trifluoromethyl)oxy]phenyl}oxy)-5-pyrimidinyl]-2,4-imidazolidinedione

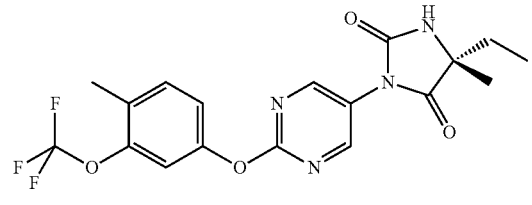

11. A compound which is:

(5R)-5-ethyl-3-[2-({4-methyl-3-[(trifluoromethyl)oxy]phenyl}oxy)-5-pyrimidinyl]-2,4-imidazolidinedione

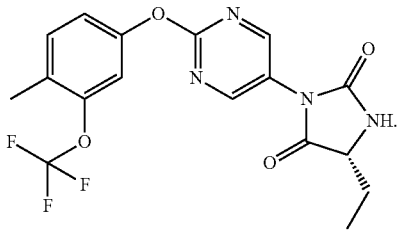 [SMILES: CC[C@H]1NC(=O)N(c2cnc(Oc3ccc(C)c(OC(F)(F)F)c3)nc2)C1=O]

12. A pharmaceutical composition comprising a compound of formula (Ia)

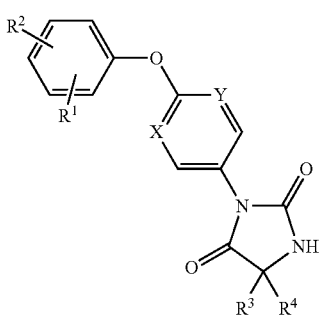

(Ia)

wherein:

$R^1$ is halo, $C_{1-4}$ alkyl, $C_{1-4}$ alkoxy, halo-$C_{1-4}$alkyl, halo-$C_{1-4}$alkoxy, or cyano;

$R^2$ is H, halo, cyano, $C_{1-4}$ alkyl or $C_{1-4}$ alkoxy; with the proviso that when $R_2$ is H, $R_1$ is not in the para position;

X is CH or N;

Y is CH or N;

$R^3$ is $C_{1-4}$ alkyl;

$R^4$ is H, deuterium, or $C_{1-4}$alkyl; or $R_3$ and $R_4$ can be fused to form a $C_{3-4}$ spiro carbocyclyl group;

or a pharmaceutically acceptable salt thereof;

and a pharmaceutically acceptable carrier.

13. A pharmaceutical composition according to claim 12, comprising a compound selected from the group consisting of:

(5R)-5-ethyl-3-(6-{[4-methyl-3-(methyloxy)phenyl]oxy}-3-pyridinyl)-2,4-imidazolidinedione

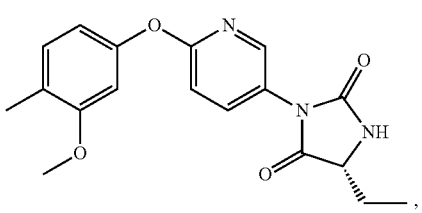 [SMILES: CC[C@H]1NC(=O)N(c2ccc(Oc3ccc(C)c(OC)c3)nc2)C1=O]

(5R)-5-ethyl-3-(2-{[3-(ethyloxy)-4-methylphenyl]oxy}-5-pyrimidinyl)-2,4-imidazolidinedione

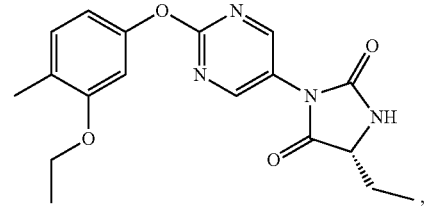 [SMILES: CCOc1cc(Oc2ncc(N3C(=O)N[C@H](CC)C3=O)cn2)ccc1C]

(5R)-5-ethyl-5-methyl-3-(6-{[4-methyl-3-(methyloxy)phenyl]oxy}-3-pyridinyl)-2,4-imidazolidinedione

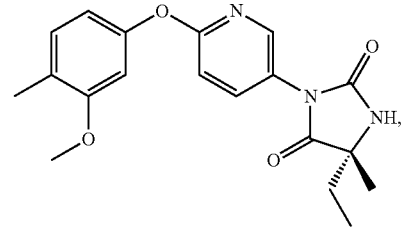 [SMILES: CC[C@@]1(C)NC(=O)N(c2ccc(Oc3ccc(C)c(OC)c3)nc2)C1=O]

5,5-dimethyl-3-[6-({4-methyl-3-[(trifluoromethyl)oxy]phenyl}oxy)-3-pyridinyl]-2,4-imidazolidinedione

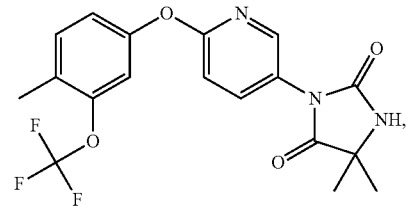 [SMILES: Cc1ccc(Oc2ccc(N3C(=O)NC(C)(C)C3=O)cn2)cc1OC(F)(F)F]

5,5-dimethyl-3-[2-({4-methyl-3-[(trifluoromethyl)oxy]phenyl}oxy)-5-pyrimidinyl]-2,4-imidazolidinedione

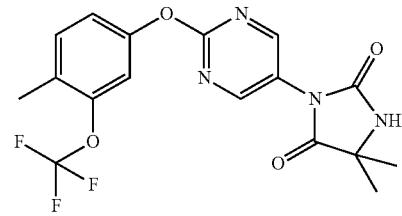

(5R)-5-ethyl-5-methyl-3-[2-({4-methyl-3-[(trifluoromethyl)oxy]phenyl}oxy)-5-pyrimidinyl]-2,4-imidazolidinedione

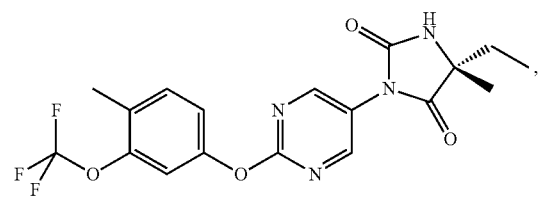 [SMILES: CC[C@@]1(C)NC(=O)N(c2cnc(Oc3ccc(C)c(OC(F)(F)F)c3)nc2)C1=O]

(5R)-5-ethyl-3-[6-({4-methyl-3-[(trifluoromethyl)oxy]phenyl}oxy)-3-pyridinyl]-2,4-imidazolidinedione

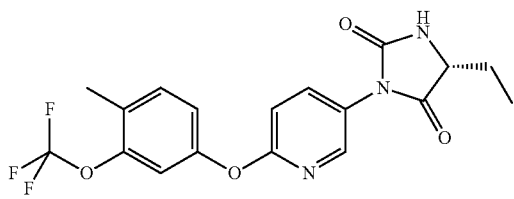 [SMILES: CC[C@H]1NC(=O)N(c2ccc(Oc3ccc(C)c(OC(F)(F)F)c3)nc2)C1=O]

and
(5R)-5-ethyl-3-[2-({4-methyl-3-[(trifluoromethyl)oxy]phenyl}oxy)-5-pyrimidinyl]-2,4-imidazolidinedione

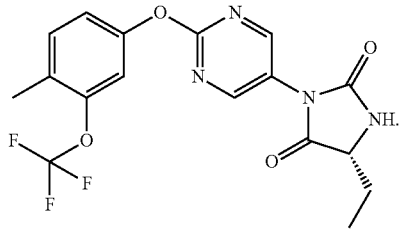 [SMILES: CC[C@H]1NC(=O)N(c2cnc(Oc3ccc(C)c(OC(F)(F)F)c3)nc2)C1=O]

14. A pharmaceutical composition according to claim 13, wherein the compound is:
(5R)-5-ethyl-3-(6-{[4-methyl-3-(methyloxy)phenyl]oxy}-3-pyridinyl)-2,4-imidazolidinedione

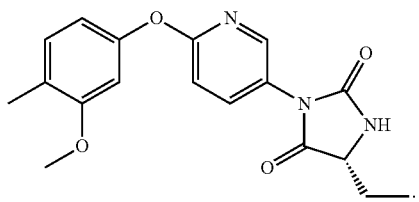 [SMILES: CC[C@H]1NC(=O)N(c2ccc(Oc3ccc(C)c(OC)c3)nc2)C1=O]

15. A pharmaceutical composition according to claim 13, wherein the compound is:

(5R)-5-ethyl-5-methyl-3-[2-({4-methyl-3-[(trifluoromethyl)oxy]phenyl}oxy)-5-pyrimidinyl]-2,4-imidazolidinedione

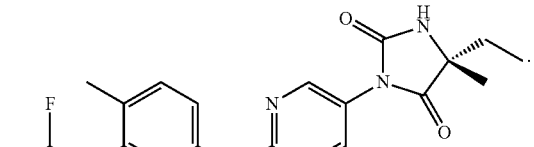

16. A pharmaceutical composition according to claim 13, wherein the compound is:

(5R)-5-ethyl-3-[2-({4-methyl-3-[(trifluoromethyl)oxy]phenyl}oxy)-5-pyrimidinyl]-2,4-imidazolidinedione

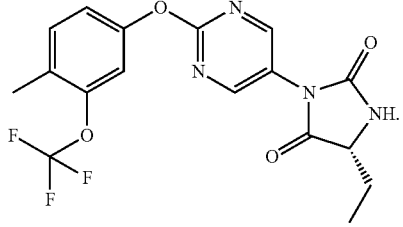 [SMILES: CC[C@H]1NC(=O)N(c2cnc(Oc3ccc(C)c(OC(F)(F)F)c3)nc2)C1=O]

\* \* \* \* \*